(12) United States Patent
Thompson et al.

(10) Patent No.: US 10,527,629 B2
(45) Date of Patent: Jan. 7, 2020

(54) ISOBARIC MASS LABELS

(71) Applicant: Electrophoretics Limited, Surrey (GB)

(72) Inventors: Andrew Hugin Thompson, Surrey (GB); Stefan Kienle, Frankfurt (DE); Karsten Kuhn, Frankfurt (DE); Nikolai Woellmer, Frankfurt (DE)

(73) Assignee: ELECTROPHORETICS LIMITED, Surrey (GB)

( * ) Notice: Subject to any disclaimer, the term of this patent is extended or adjusted under 35 U.S.C. 154(b) by 120 days.

(21) Appl. No.: 15/318,247

(22) PCT Filed: Jun. 12, 2015

(86) PCT No.: PCT/EP2015/063224
§ 371 (c)(1),
(2) Date: Dec. 12, 2016

(87) PCT Pub. No.: WO2015/189413
PCT Pub. Date: Dec. 17, 2015

(65) Prior Publication Data
US 2017/0146549 A1  May 25, 2017

(30) Foreign Application Priority Data
Jun. 12, 2014 (GB) .................................. 1410523.3

(51) Int. Cl.
*G01N 33/00* (2006.01)
*G01N 33/68* (2006.01)
(Continued)

(52) U.S. Cl.
CPC ....... *G01N 33/6848* (2013.01); *C07B 59/008* (2013.01); *C07K 5/0202* (2013.01); *C12Q 1/6872* (2013.01); *C07B 2200/05* (2013.01)

(58) Field of Classification Search
CPC .................................................. G01N 33/6848
(Continued)

(56) References Cited

U.S. PATENT DOCUMENTS 7,294,456 B2  11/2007  Schmidt et al.
7,355,045 B2   4/2008  Dey et al.
(Continued)

FOREIGN PATENT DOCUMENTS

WO   WO2001/68664 A2   9/2001
WO   WO2007/012849 A2  2/2007
(Continued)

OTHER PUBLICATIONS

Gygi, S.P. et al., "Quantitative analysis of complex protein mixtures using isotope-coded affinity tags", Nature Biotechnology, vol. 17, Oct. 1999, pp. 994-999.
(Continued)

*Primary Examiner* — Christine T Mui
*Assistant Examiner* — Emily R. Berkeley
(74) *Attorney, Agent, or Firm* — Arent Fox LLP

(57) ABSTRACT

The present invention relates to a set of two or more mass labels. Each mass label comprises: X-L-M-Re; X is a reporter moiety having exact mass; L is a bond cleavable by collision in a mass spectrometer; M is a mass modifier; Re is a) a reactive functionality for attaching the mass label to an analyte or b) the analyte. Each mass label in the set has the same integer mass; wherein the set comprises two or more subsets of mass labels, each subset comprising one or more mass labels; wherein, when the subset comprises two or more mass labels, the exact mass of the reporter moiety X of each mass label in the subset is different from the exact mass of the reporter moiety X of the mass labels in the same subset and in all other subsets; each mass label is distinguishable by mass spectrometry.

31 Claims, 15 Drawing Sheets

(51) Int. Cl.
C12Q 1/6872 (2018.01)
C07B 59/00 (2006.01)
C07K 5/02 (2006.01)

(58) Field of Classification Search
USPC .......................................................... 436/86
See application file for complete search history.

(56) References Cited

U.S. PATENT DOCUMENTS

| | | | |
|---|---|---|---|
| 7,947,513 B2 | 5/2011 | Pappin et al. | |
| 8,273,706 B2 | 9/2012 | Pappin et al. | |
| 2004/0220412 A1* | 11/2004 | Pappin .................. | C07D 401/12 548/542 |
| 2010/0178710 A1* | 7/2010 | Hamon .............. | C07D 207/404 436/173 |
| 2013/0309689 A1 | 11/2013 | Rogers et al. | |

FOREIGN PATENT DOCUMENTS

| | | |
|---|---|---|
| WO | WO2008/064239 A2 | 5/2008 |
| WO | WO2008/110581 A2 | 9/2008 |
| WO | WO2009/141310 A1 | 11/2009 |
| WO | WO2011/036059 A1 | 3/2011 |
| WO | WO2014/184320 A1 | 11/2014 |
| WO | WO2015/091876 A2 | 6/2015 |

OTHER PUBLICATIONS

Hu, Q. et al., "The Orbitrap: a new mass spectrometer", Journal of Mass Spectrometry, vol. 40, 2005, pp. 430-443.
Makarov, A., "Electrostatis Axially Harmonic Orbital Trapping: A High-Performance Technique of Mass Analysis", Analytical Chemistry, vol. 72, No. 6, Mar. 15, 2000, pp. 1156-1162.
Marshall, A.G. et al., Fourier Transform Ion Cyclotron Resonance Mass Spectrometry: A Primer, Mass Spectrometry Reviews, vol. 17, Jan. 1998, pp. 1-35.
Andrews, G.L. et al., "Performance Characteristics of a New Hybrid Triple Quadrupole Time-Of-Flight Tandem Mass Spectrometer", Analytical Chemistry, vol. 83, No. 13, Jul. 1, 2011, pp. 5442-5446.
McAlister, G.C. et al., "Increasing the multiplexing capacity of TMT using reporter ion isotopologues with isobaric masses", Analytical Chemistry, vol. 84, No. 17, Sep. 4, 2012, pp. 7469-7478.
Werner, T. et al, "High-Resolution Enabled TMT 8-plexing", Analytical Chemistry, vol. 84, 2002, pp. 7188-7194.
Hebert, A.S. et al., "Neutron-encoded mass signatures for multiplexed proteome quantification", Nature Methods, vol. 10, No. 4, Apr. 2013, pp. 332-334.
Zhang, J. et al., "Deuterium Isobaric Amine-Reactive Tags for Quantitative Proteomics", Analytical Chemistry, vol. 82, No. 18, Sep. 15, 2010, pp. 7588-7595.
Thompson, A. et al., "Tandem Mass Tags: A Novel Quantification Strategy for Comparative Analysis of Complex Protein Mixtures by MS/MS", Analytical Chemistry, vol. 75, No. 8, Apr. 15, 2003, pp. 1895-1904.
Rostovtsev, V.V.; et al., "A Stepwise Huisgen Cycloaddition Process: Copper(I)-Catalyzed Regioselective 'Litigation' of Azides and Terminal Alkynes", Angew. Chem., Int. Ed. 2002, 41, pp. 2596-2599.
Goddard-Borger, E.D. et al., An Efficient, Inexpensive, and Shelf-Stable Diazotransfer Reagent: Imidazole-1-sulfonyl Azide Hydrochloride, Organic Letters, vol. 9, No. 19, 2007, pp. 3797-3800.
Okumura, D. et al., High-resolution time-of-flight spectra obtained using the MULTUM II multi-turn type time-of-flight mass spectrometer with an electron ionization ion source, European Journal of Mass Spectrometry, vol. 11, pp. 2005, 261-266.
Shimma, S. et al., "Detailed Structural Analysis of Lipids Directly on Tissue Specimens Using a MALDI-SprialTOF-Reflectron TOF Mass Spectrometer", PLoS One, vol. 7, No. 5, e37107, 2012.
Marshall, A.G. et al., "High-Resolution Mass Spectrometers", Annual Review of Analytical Chemistry vol. 1, 2008, pp. 579-599.
Schaub, T.M. et al., "High-Performance Mass Spectrometry: Fourier Transform Ion Cyclotron Resonance at 14.5 Tesla", Analytical Chemistry, vol. 80, No. 11, Jun. 1, 2008, pp. 3985-3990.
Da Silva, R.A. et al., "Reductive methylation of primary and secondary amines and amino acids by aqueous formaldehyde and zinc", Tetrahedron Letters, vol. 48, 2007, pp. 7680-7682.
Kuhn, K. et al., "TMT labelling for the quantitative analysis of adaptive responses in the meningococcal proteome", Methods in Molecular Biology, Chapter 8, vol. 799, 2012, pp. 127-141.
Evans, D.A. et al., "Directed Reduction of β-Hydroxy Ketones Employing Tetramethylammonium Triacetoxyborohydride", Journal of American Chemical Society, vol. 110, 1988, pp. 3560-3578.
Vogt, T., International Search Report, dated Aug. 6, 2015, 3 pages.
Communication pursuant to Article 94(3) EPC received from European Patent Office, for EP Application 15 730 112.8, dated Jun. 26, 2019, 5 pages.

* cited by examiner

ISOBARIC MASS LABELS

CROSS-REFERENCE TO RELATED APPLICATIONS

This application is the U.S. National Stage Application of international Patent Application No. PCT/EP2015/063224, filed on Jun. 12, 2015, which claims priority to GB Application No. 1410523.3, filed on Jun. 12, 2014, the contents of each of which is incorporated herein by reference in its entirety.

This invention relates to useful reactive labels for labelling peptides and to methods for using these reactive labels, to identify and quantify peptides particularly peptides derived from complex protein mixtures. These reactive labels are of particular value for the analysis of peptides by high resolution and high mass accuracy mass analysers such as orbitraps, time-of-flight and ion cyclotron resonance mass analysers.

BACKGROUND OF THE INVENTION

The study of biological systems and particularly the understanding of human disease is dependent on the ability to detect changes caused in biological systems by or in response to a disease. Such changes provide means of diagnosis and offer insights into the targets for therapeutic compounds such as vaccines and medicines. A wide range of biological molecules need to be measured quantitatively to understand disease processes including nucleic acids, proteins, steroids, sugars and lipids. In this context, the ability to quantitatively detect such biomolecules using mass spectrometers has provided considerable advances in their study and application to human and also to veterinary disease. The same advances have also occurred in environmental analysis and monitoring, and in food and beverage manufacturing. In particular the use of stable isotopes to provide synthetic quantitative references has been developed in isotope dilution mass spectrometry for monitoring of all classes of biomolecules. However, these methods have traditionally required an available synthetic standard, which is not always possible.

Recently, a range of chemical mass tags bearing heavy isotope substitutions have been developed to further improve the quantitative analysis of biomolecules by mass spectrometry. Depending on the tag design, members of tag sets are either isotopic having the same chemical structure but different absolute masses, or isobaric and isotopomeric, having both identical structure and absolute mass. Isotopic tags are typically used for quantification in MS mode whilst isobaric tags must be fragmented in MS/MS mode to release reporter fragments with a unique mass.

An early example of isotopic mass tags were the Isotope-Coded Affinity Tags (ICAT) (Gygi, S. P. et al., (1999) *Nat Biotechnol,* 17, 994-999). The ICAT reagents are a pair of mass tags bearing a differential incorporation of heavy isotopes in one (heavy) tag with no substitutions in the other (light) tag. Two samples are labelled with either the heavy or light tag and then mixed prior to analysis by LC-MS. A peptide present in both samples will give a pair of precursor ions with masses differing in proportion to the number of heavy isotope atomic substitutions.

The ICAT method also illustrates 'sampling' methods, which are useful as a way of reconciling the need to deal with small populations of peptides to reduce the complexity of the mass spectra generated while retaining sufficient information about the original sample to identify its components. The 'isotope encoded affinity tags' used in the ICAT procedure comprise a pair of biotin linker isotopes, which are reactive to thiols, for the capture peptides comprising cysteine. Typically 90 to 95% or proteins in a proteome will have at least one cysteine-containing peptide and typically cysteine-containing peptides represent about 1 in 10 peptides overall so analysis of cysteine-containing peptides greatly reduces sample complexity without losing significant information about the sample. Thus, in the ICAT method, a sample of protein from one source is reacted with a 'light' isotope biotin linker while a sample of protein from a second source is reacted with a 'heavy' isotope biotin linker, which is typically 4 to 8 Daltons heavier than the light isotope. The two samples are then pooled and cleaved with an endopeptidase. The biotinylated cysteine-containing peptides can then be isolated on avidinated beads for subsequent analysis by mass spectrometry. The two samples can be compared quantitatively: corresponding peptide pairs act as reciprocal standards allowing their ratios to be quantified. The ICAT sampling procedure produces a mixture of peptides that still accurately represents the source sample while being less complex than MudPIT, but large numbers of peptides are still isolated and their analysis by LC-MS/MS generates complex spectra. With 2 ICAT tags, the number of peptide ions in the mass spectrum is doubled compared to a label-free analysis.

Further examples of isotopic tags include the ICPL reagents that provide up to four different reagents, and with ICPL the number of peptide ions in the mass spectrum is quadrupled compared to a label-free analysis. For this reason, it is unlikely to be practical to develop very high levels of multiplexing with simple heavy isotope tag design.

Whilst isotopic tags allow quantification in proteomic studies and assist with experimental reproducibility, this is achieved at the cost of increasing the complexity of the mass spectrum. To overcome this limitation, and to take advantage of greater specificity of tandem mass spectrometry isobaric mass tags were developed. Since their introduction in 2000 (WO01/68664), isobaric mass tags have provided improved means of proteomic expression profiling by universal labelling of amines and other reactive functions in proteins and peptides prior to mixing and simultaneous analysis of multiple samples. Because the tags are isobaric, having the same mass, they do not increase the complexity of the mass spectrum since all precursors of the same peptide will appear at exactly the same point in the chromatographic separation and have the same aggregate mass. Only when the molecules are fragmented prior to tandem mass spectrometry are unique mass reporters released, thereby allowing the relative or absolute amount of the peptide present in each of the original samples to be determined.

WO01/68664 sets out the underlying principles of isobaric mass tags and provides specific examples of suitable tags wherein different specific atoms within the molecules are substituted with heavy isotope forms including $^{13}C$ and $^{15}N$ respectively. WO01/68664 further describes the use of offset masses to make multiple isobaric sets to increase the overall multiplexing rates available without unduly increasing the size of the individual tags.

WO2007/012849 describes further sets of isobaric mass tags including 3-[2-(2,6-Dimethyl-piperidin-1-yl)-acetylamino]-propanoic acid-(2,5-dioxo-pyrrolidine-1-yl)-ester (DMPip-βAla-OSu).

Recently, with dramatic improvements in mass accuracy and mass resolution enabled by high mass resolution mass spectrometers such as the Orbitrap (Hu, Q. et al., (2005) *J Mass Spectrom,* 40, 430-443 & Makarov, A. (2000) *Anal*

Chem, 72, 1156-1162), Fourier Transform Ion Cyclotron Resonance (FT-ICR) mass spectrometers (Marshall, A. G. et al., (1998) *Mass Spectrom Rev*, 17, 1-35) and high resolution Time-of-Flight (TOF) mass spectrometers (Andrews, G. L. et al., (2011) *Anal Chem*, 83, 5442-5446), it has become possible to resolve millidalton differences between ion mass-to-charge ratios. This high resolution capability has been exploited to increase multiplexing of Isobaric Tandem Mass Tags using heavy nucleon substitutions of $^{13}$C for $^{15}$N in the reporter region which results in 6.32 millidalton differences between the respective reporter fragments upon analysis by MS/MS (McAlister, G. C. et al., (2012) *Anal Chem*, 84, 7469-7478 & Werner, T. et al., (2012) *Anal Chem*, 84, 7188-7194). Similarly, it has been shown that metabolic labelling with lysine isotopes comprising millidalton mass differences can be resolved by high-resolution mass spectrometry enabling multiplexing and relative quantification of samples in yeast (Hebert, A. S. et al., (2013) *Nat Methods*, 10, 332-334).

Despite the significant benefits of previously disclosed isobaric mass tags, the multiplexing rate has been limited to 10-plex in commercial reagents to date. In addition, tags comprising very small mass differences would be useful because labelled ions that are related to each other, e.g. corresponding peptides from different samples, would cluster closely in the same ion envelope with very distinctive and unnatural isotope patterns that would be readily recognisable and which will be much less likely to interfere with the identification of other different peptides.

Hence, there still remains the need for sets of tags, where each tag differs from the others by millidalton mass differences, for labelling peptides and biomolecules with multiplexing rates greatly in excess of 10-fold.

STATEMENT OF INVENTION

Accordingly, in a first aspect the present invention provides for a set of two or more mass labels, wherein each mass label comprises the formula:

X-L-M-Re wherein X is a reporter moiety having an exact mass, L is a bond cleavable by collision in a mass spectrometer, M is a mass modifier, and Re is a) a reactive functionality for attaching the mass label to an analyte or b) the analyte, wherein each mass label in the set has an integer mass, wherein each mass label in the set has the same integer mass, and wherein the set comprises two or more subsets of mass labels, each subset comprising one, two or more mass labels, and wherein, when the subset comprises two or more mass labels, the exact mass of the reporter moiety X of each mass label in the subset is different from the exact mass of the reporter moiety X of the mass labels in the same subset and in all other subsets, and wherein each mass label is distinguishable by mass spectrometry.

In a second aspect, the present invention provides for a set of two or more mass labels, wherein each label comprises the formula:

X-L-M-Re wherein X is a reporter moiety having an exact mass, L is a bond cleavable by collision in a mass spectrometer, M is a mass modifier, and Re is a reactive functionality for attaching the mass label to an analyte or the analyte, and X comprises the following general formula:

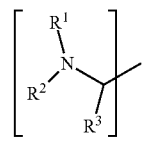

wherein:
i) $R^1$ is a substituted or unsubstituted straight or branched $C_1$-$C_{10}$ alkyl group, a substituted or unsubstituted aliphatic cyclic group, a substituted or unsubstituted aromatic group or a substituted or unsubstituted heterocyclic group; or a structure selected from methyl, ethyl, propyl, isopropyl, butyl, isobutyl, sec-butyl, pentyl or neopentyl.

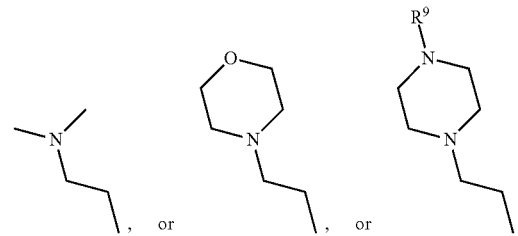

and $R^9$ is selected from a substituted or unsubstituted straight or branched $C_1$-$C_{10}$ alkyl group or hydrogen and $R^2$ and $R^3$ together comprise:

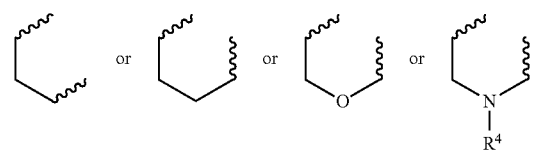

wherein $R^4$ is a H or a substituted or unsubstituted linear or branched $C_1$-$C_{10}$ alkyl group; or ii) $R^3$ is H; and $R^1$ and $R^2$ together comprise:

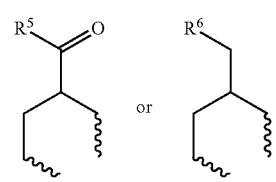

and wherein $R^5$ and $R^6$ are each independently a substituted or unsubstituted straight or branched $C_1$-$C_{10}$ alkyl group, a substituted or unsubstituted aliphatic cyclic group, a substituted or unsubstituted aromatic group or a substituted or unsubstituted heterocyclic group, or a substituted or unsubstituted amine group, or

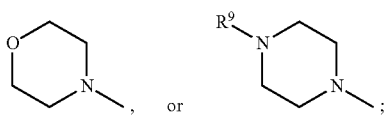

and each $R^9$ is independently selected from a substituted or unsubstituted straight or branched $C_1$-$C_{10}$ alkyl group or hydrogen.

In one embodiment of the first aspect, the mass labels have structures as defined in the second aspect of the invention.

In one embodiment of the first and second aspect of the invention, each mass label comprises a mass series modifying group, wherein the mass series modifying group is part of the reporter moiety X or part of the mass modifier M; preferably the mass series modifying group is part of the reporter moiety X.

In another embodiment of the first and second aspect of the invention, the mass series modifying group is selected from:

a) a heavy isotope $^2H$, $^{13}C$, $^{15}N$ or $^{18}O$; or b) a substituted or unsubstituted straight or branched $C_1$-$C_{10}$ alkyl group optionally comprising one or more heavy isotope substitutions; or c) or a combination of a) and b).

In one embodiment, the mass series modifying group is selected from —$CH_3$, —$^{13}CH_3$, —$^{13}CD_3$ or —$CD_3$.

In another embodiment of the first and second aspect of the invention, each mass label comprises a mass series modifying group having the following structure:

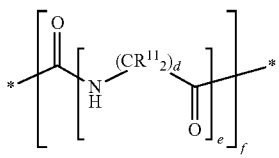

wherein, each $R^{11}$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain; and f is an integer from 0-10; and wherein d and e are at least 1.

In another embodiment of the first and second aspect of the invention, Re is the analyte, wherein the analyte comprises one or more analytes selected from the group of amino acids, peptides, polypeptides, nucleotides, oligonucleotides, polynucleotides, carbohydrates, lipids, phospholipids or combination thereof.

In yet another embodiment of the first and second aspect of the invention, each mass label has a reporter moiety with general formula i), wherein $R^1$ is selected from:

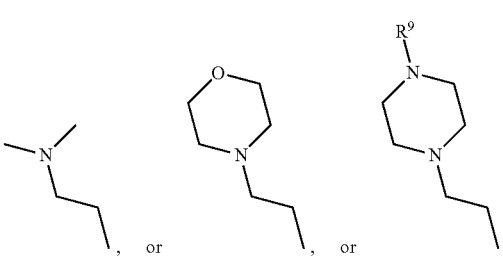

and $R^9$ is selected from a substituted or unsubstituted straight or branched $C_1$-$C_{10}$ alkyl group, preferably an alkyl chain selected from methyl, ethyl, propyl, isopropyl, butyl, isobutyl, sec-butyl, pentyl or neopentyl, or hydrogen;

or alternatively each mass label has a the reporter moiety with general formula ii) and $R^5$ and $R^6$ are each independently

where $R^7$ and $R^8$ are each independently a substituted or unsubstituted straight or branched $C_1$-$C_{10}$ alkyl group or hydrogen.

Preferably when R4 is present, $R^4$ is methyl, ethyl, propyl, isopropyl, butyl, isobutyl, sec-butyl, pentyl, neopentyl or (dimethylamino)methyl.

In some embodiments of the first and second aspect of the invention, each mass label has a reporter moiety X selected from:

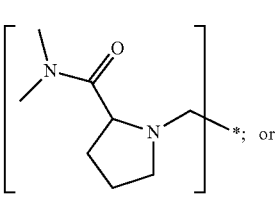

a)

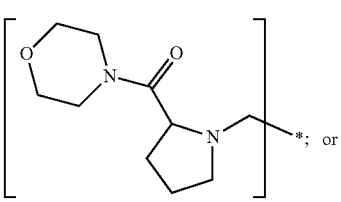

b)

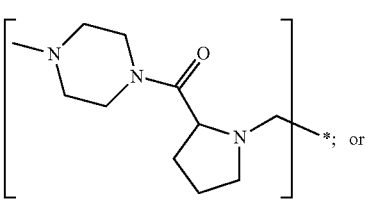

c)

d)
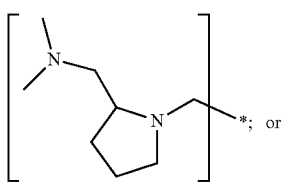
e)
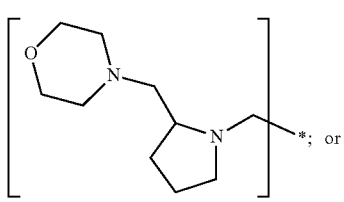
f)
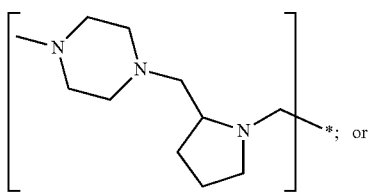
g)
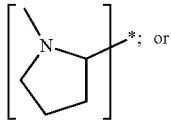
h)
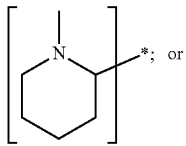
i)
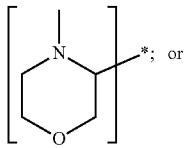
j)
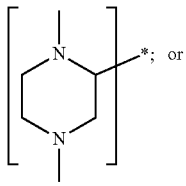
k)
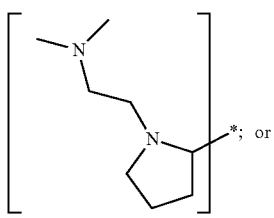
l)
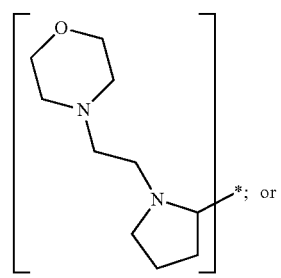
m)
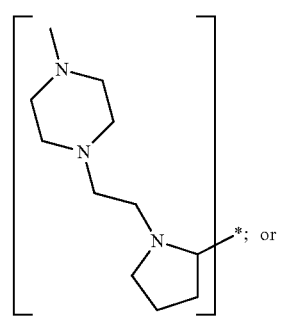
n)
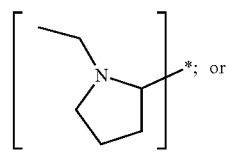
o)
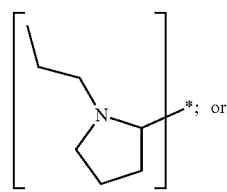
p)
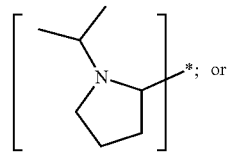
q)
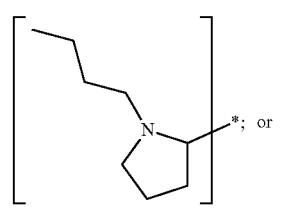
r)
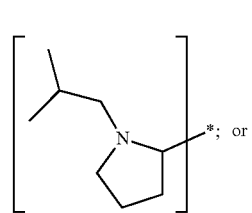

s)

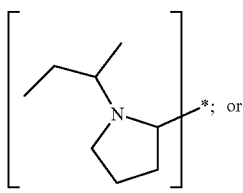

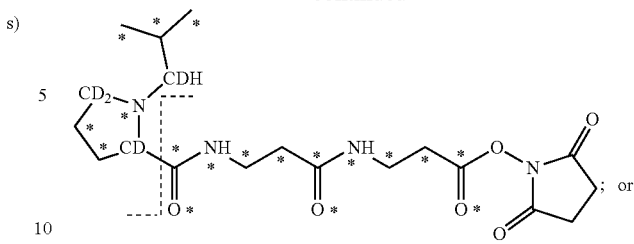

t)

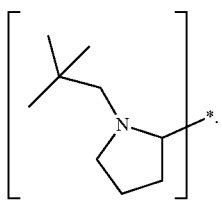

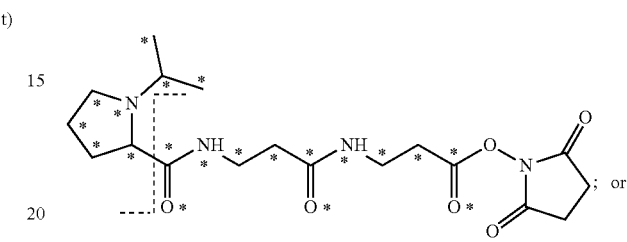

In yet some other embodiments of the first and second aspect of the invention, each mass label comprises a mass modifier M comprising or having the following structure:

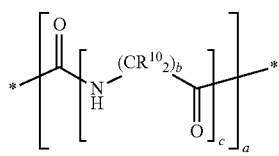

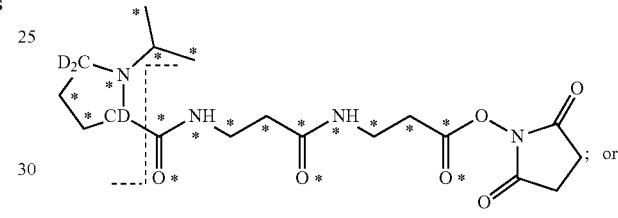

wherein each $R^{10}$ is independently selected from H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain; and a is an integer from 0-10; wherein b and c are integer and at least 1.

The mass label according to the invention may have one of the following structures:

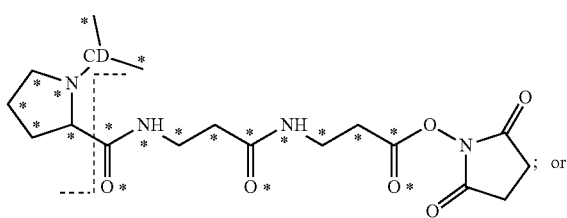

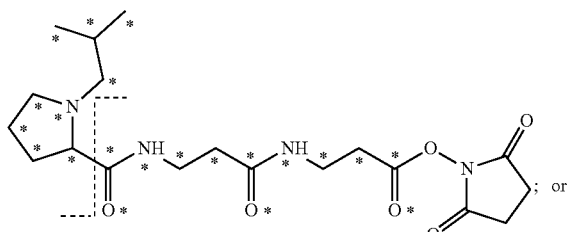

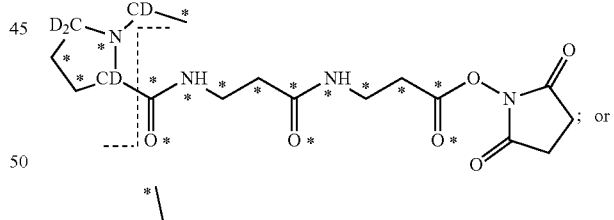

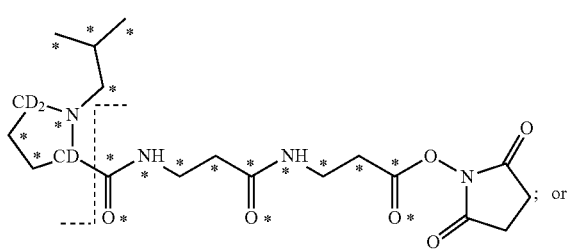

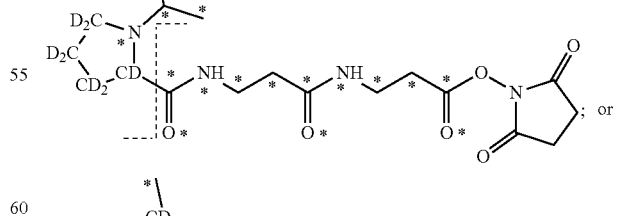

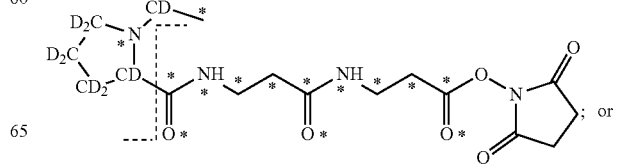

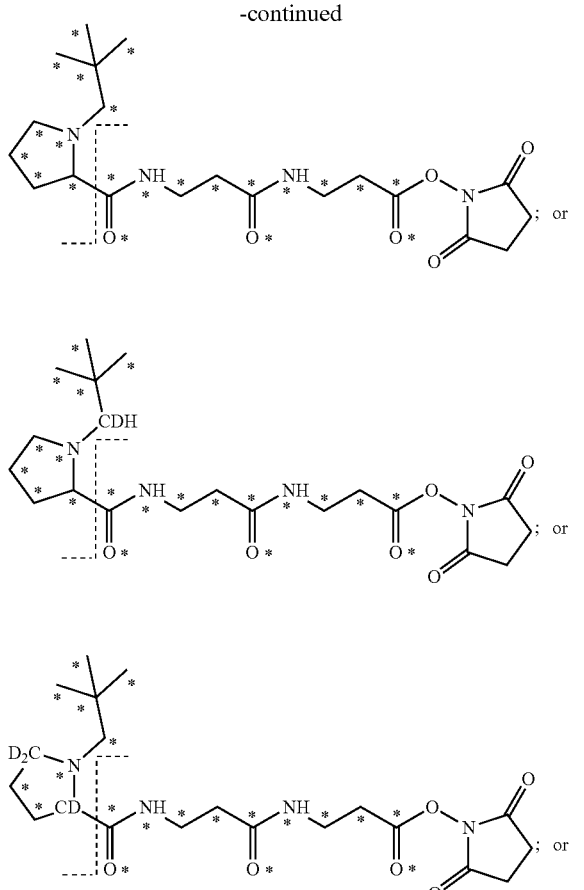
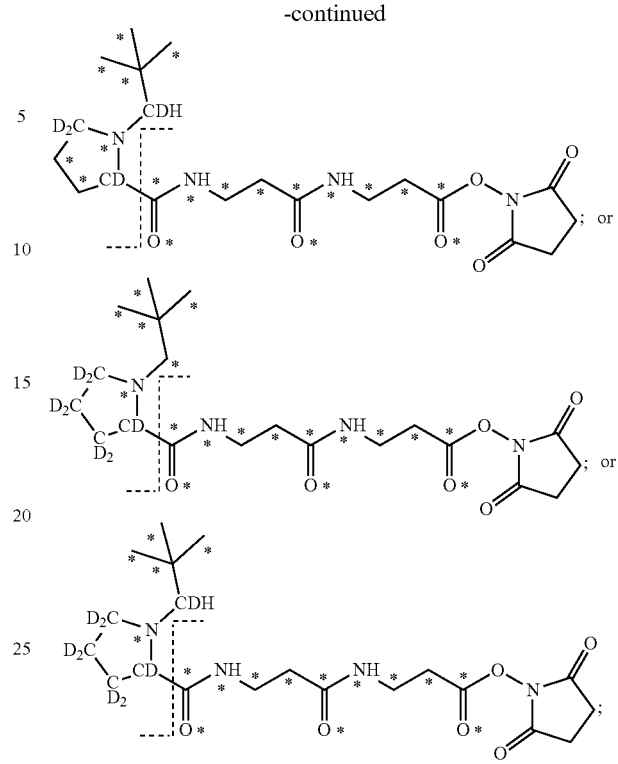
wherein * represents that oxygen is $^{18}O$, carbon is $^{13}C$, nitrogen is $^{15}N$ or hydrogen is $^{2}H$, and wherein one or more * may be present.
The mass label may also have one of the following structures:
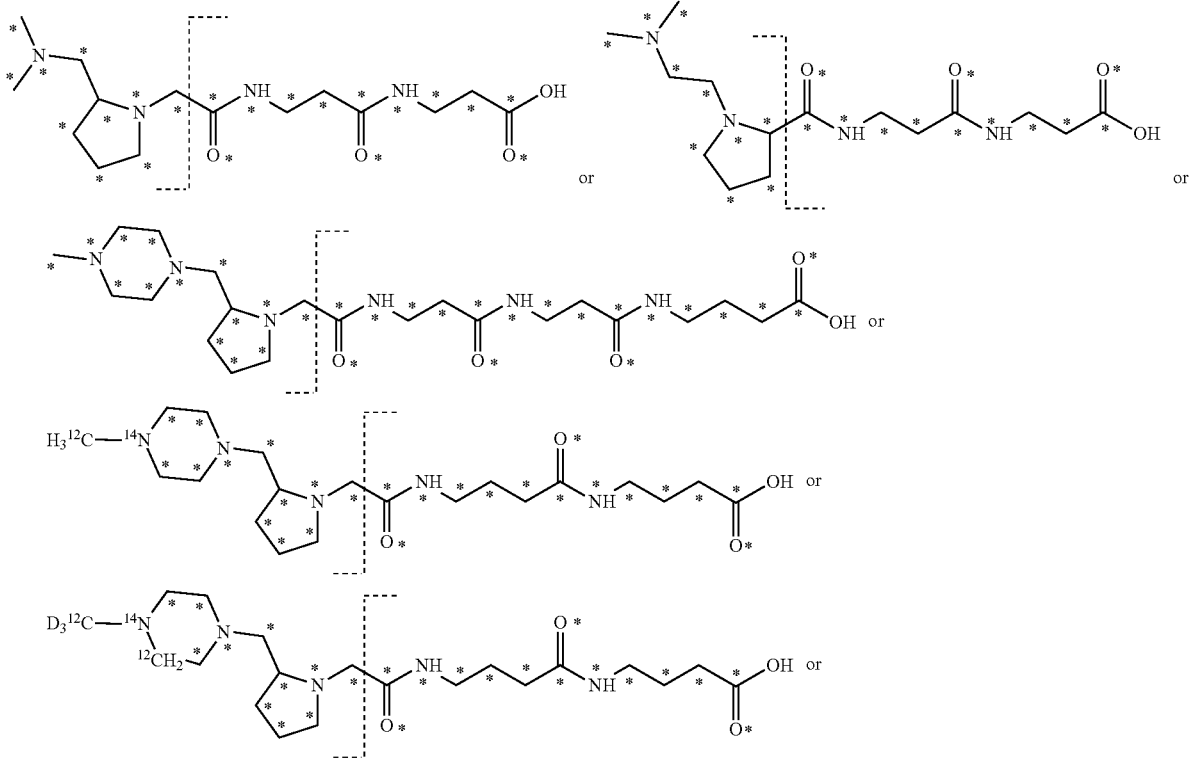

-continued

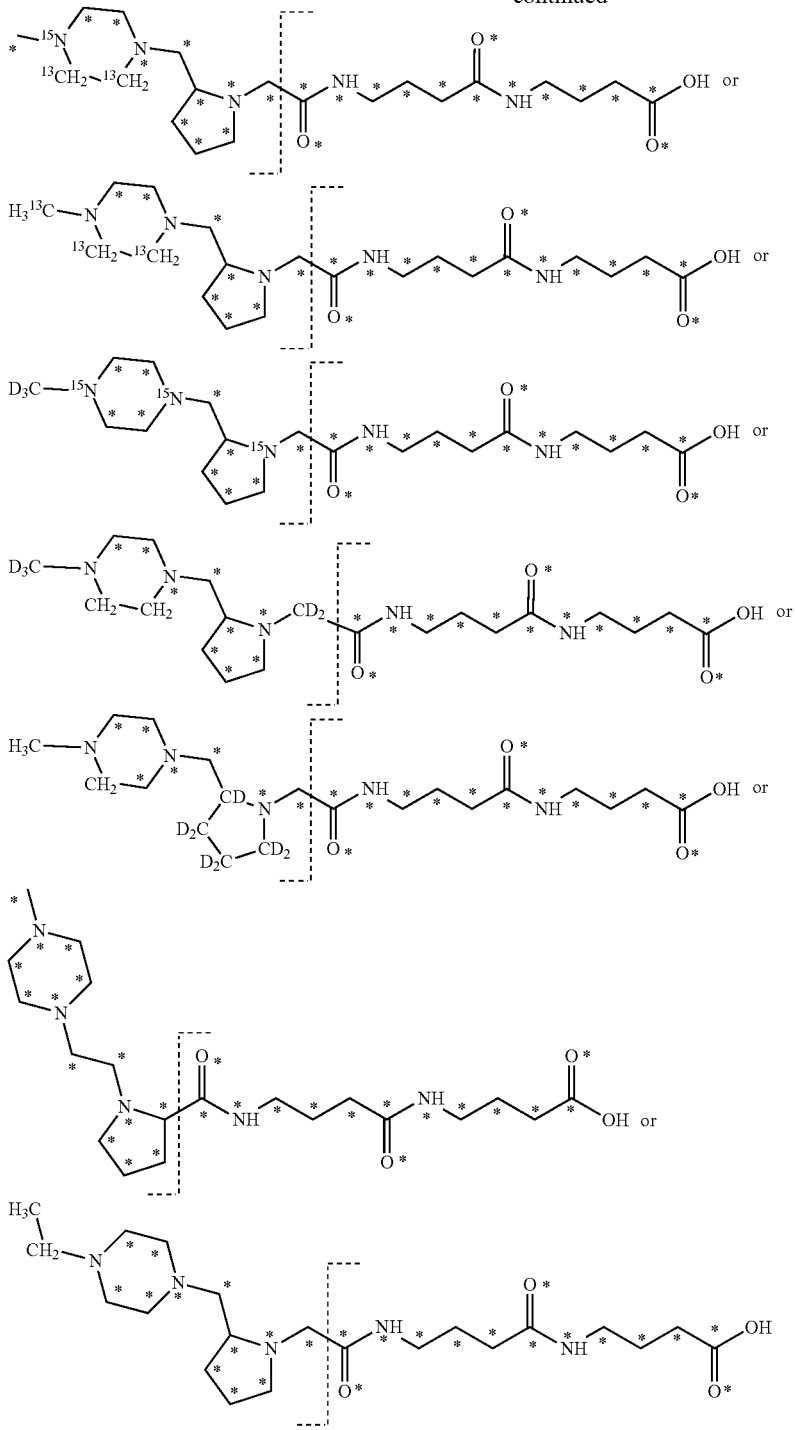

wherein * represents that oxygen is $^{18}O$, carbon is $^{13}C$, nitrogen is $^{15}N$ or hydrogen is $^{2}H$, and wherein one or more * may be present.

In a third aspect the present invention provides for an array of mass labels, comprising two or more sets of mass labels as defined in the first and second aspects of the invention and their embodiments.

In one embodiment of this third aspect, the integer mass of each of the mass labels of any one set in the array is different from the integer mass of each of the mass labels of every other set in the array.

Preferably, each mass label in a set comprises:
a) a mass series modifying group having the same integer mass as every other mass label in the set and
b) a different integer mass to the mass labels of all the other sets of the array.

In another embodiment of the third aspect of the invention, each mass label in a set comprises a mass series modifying group which is:
a. the same; or
b. an isotopologue of the mass series modifying group of all other mass labels of the array.

In a fourth aspect the present invention provides for a method of mass spectrometry analysis, which method comprises detecting an analyte by identifying by mass spectrometry a mass label or combination of mass labels relatable to the analyte, wherein the mass label is a mass label from a set or array of mass labels as defined herein.

In one embodiment of this fourth aspect the method comprises:
a) providing a plurality of samples, each sample comprising one or more analytes, wherein each sample is differentially labelled with a mass label or a combination of mass labels, obtaining one or more labelled analytes; wherein the mass label(s) are from a set or an array of mass labels as defined herein;
b) mixing the plurality of differentially labelled samples to form an analysis mixture comprising labelled analytes;
c) optionally detecting the labelled analytes in a mass spectrometer;
d) dissociating the labelled analytes in the mass spectrometer to form mass labels and/or analyte fragments comprising intact mass labels;
e) detecting the mass labels and/or analyte fragments comprising intact mass labels;
f) optionally dissociating the mass labels in the mass spectrometer to release the reporter moieties, and detecting the reporter moieties;
g) optionally dissociating the reporter moieties formed in step f to form fragments, and detecting the fragments;
h) identifying the analytes on the basis of the mass spectrum of the labelled analytes; and/or the mass spectrum of the mass labels and/or analyte fragments comprising an intact mass label; and/or the mass spectrum of the reporter moieties or fragments of reporter moieties.

The analytes may be identified on the basis of i) the mass spectrum of the labelled analytes; or ii) the mass spectrum of the mass labels and/or analyte fragments comprising an intact mass label; or iii the mass spectrum of the reporter moieties or fragments of reporter moieties. When identification according to ii) occurs, the analyte fragment preferably comprises an intact mass label is a b-series ion comprising an intact mass label, preferably a b1 ion.

In another embodiment, the method of mass spectrometry analysis comprises:
a) providing a plurality of samples, each sample comprising one or more analytes, wherein each sample is differentially labelled with a mass label or a combination of mass labels; obtaining one or more labelled analytes; wherein the mass label(s) are from a set or an array of mass labels as defined herein;
b) mixing the plurality of differentially labelled samples to form an analysis mixture comprising labelled analytes;
c) detecting the labelled analytes in a mass spectrometer;
d) dissociating the labelled analytes in the mass spectrometer to release the reporter moieties, and detecting complement ions comprising the remainder of the mass label attached to the analyte or a fragment of the analyte;
e) optionally one or more further steps of dissociating the complement ions formed in step d to form fragments, and detecting the fragments;
f) identifying the analytes on the basis of the mass spectrum of the labelled analytes and/or the mass spectrum of the complement ions and/or fragments thereof.

Preferably, the dissociation is collision induced dissociation in a mass spectrometer.

The method may be performed in a mass spectrometer with a resolution of greater than 60,000 at a mass-to-charge ratio of 400, preferably a resolution of greater than 100,000 at a mass-to-charge ratio of 400, most preferably greater than 250,000 at a mass-to-charge ratio of 400.

Preferably, step d) in the methods according to the invention, the complement ion is formed by neutral loss of carbon monoxide from the bond L.

In a further alternative embodiment, there is provided a set of two or more mass labels, wherein each mass label comprises the formula:

X-L-M wherein X is a reporter moiety, L is a linker cleavable by collision in a mass spectrometer, and M is a mass modifier, and wherein each mass label further comprises a reactive functionality Re for attaching the mass label to an analyte, each mass label in the set having the same integer mass, and wherein the set comprises two or more subsets of mass labels, each subset comprising one or more mass labels, and wherein if the subset comprises two or more mass labels, each mass label in the subset has a reporter moiety with an exact mass different from that of the reporter moiety of all other mass labels in the subset; and wherein the integer mass of the reporter moiety of each mass label in the subset is different from the integer mass of the reporter moiety of the mass label in all other subsets, and wherein each mass label is distinguishable by mass spectrometry.

DETAILED DESCRIPTION

Figure 1:
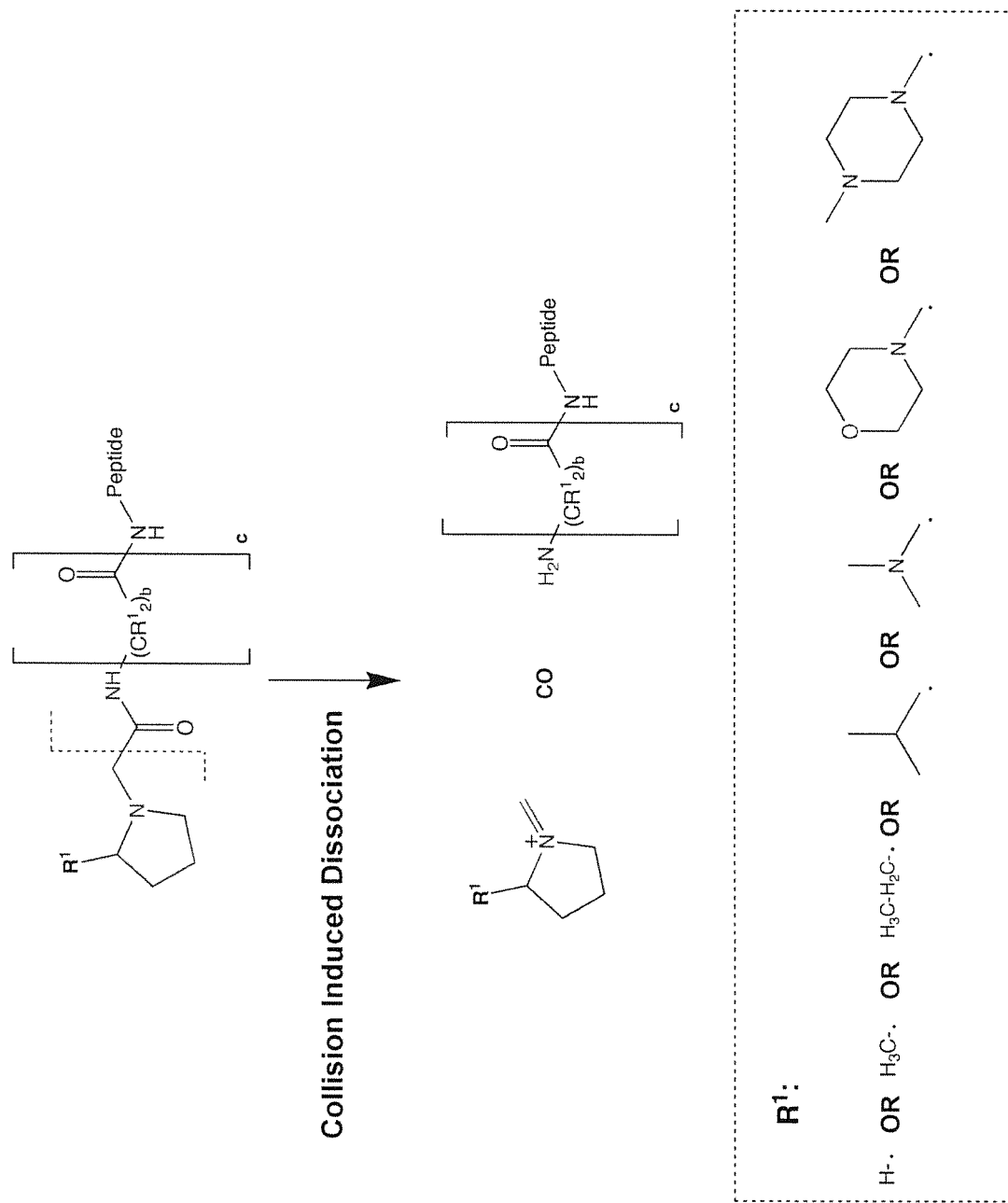
FIG. 1 is a schematic of the predicted fragmentation pathway of a first class of mass labels according to this invention (depicted structure is hypothetical and illustrated only for the purpose of predicting the mass-to-charge ratio of expected reporter ions).

The present invention provides sets of isotopomeric reactive tags for the purposes of labelling peptides and other biomolecules with multiplexing rates greatly in excess of 10-plex. Co-selectable isotopologue arrays of isotomoperic reactive tags have masses differences in the range of millidalton which supports even higher levels of multiplexing.

The present invention also provides for methods of use of co-selectable isotopologue arrays of isotopomeric reactive tags that enable novel forms of analysis of labelled peptides and proteins particularly for the discovery of biologically significant differences between sets of biological samples.

The present invention provides for a set of two or more mass labels, wherein each mass label comprises the formula:

X-L-M-Re wherein X is a reporter moiety having an exact mass, L is a bond cleavable by collision in a mass spectrometer, M is a mass modifier, and Re is a) a reactive functionality for attaching the mass label to an analyte or b) the analyte, wherein each mass label in the set has an integer mass, wherein each mass label in the set has the same integer mass, and wherein the set comprises two or more subsets of mass labels, each subset comprising one, two or more mass labels, and wherein, when the subset comprises two or more mass labels, the exact mass of the reporter moiety X of each mass label in the subset is different from the exact mass of the reporter moiety X of the mass labels in the same subset and in all other subsets, and wherein each mass label is distinguishable by mass spectrometry. The term mass label used in the present context is intended to refer to a reagent suitable to label an analyte for mass spectroscopy determination. The term label is synonymous with the term tag.

In preferred embodiments of the present invention, the set of two or more mass labels has a reporter moiety X comprising the following general formula:

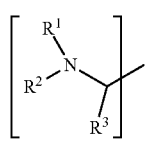

wherein:
i) $R^1$ is a substituted or unsubstituted straight or branched $C_1$-$C_{10}$ alkyl group, a substituted or unsubstituted aliphatic cyclic group, a substituted or unsubstituted aromatic group or a substituted or unsubstituted heterocyclic group; or a structure selected from methyl, ethyl, propyl, isopropyl, butyl, isobutyl, sec-butyl, pentyl or neopentyl.

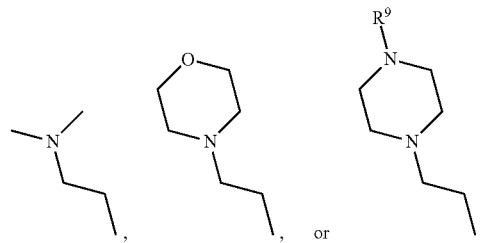

and $R^9$ is selected from a substituted or unsubstituted straight or branched $C_1$-$C_{10}$ alkyl group or hydrogen and $R^2$ and $R^3$ together comprise:

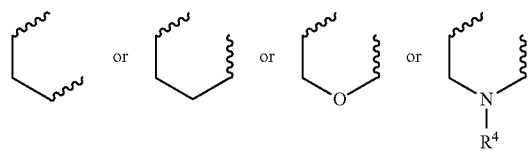

wherein $R^4$ is a H or a substituted or unsubstituted linear or branched $C_1$-$C_{10}$ alkyl group; or ii) $R^3$ is H; and $R^1$ and $R^2$ together comprise:

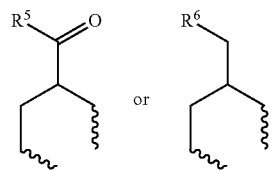

and wherein $R^5$ and $R^6$ are each independently a substituted or unsubstituted straight or branched $C_1$-$C_{10}$ alkyl group, a substituted or unsubstituted aliphatic cyclic group, a substituted or unsubstituted aromatic group or a substituted or unsubstituted heterocyclic group, or a substituted or unsubstituted amine group, or

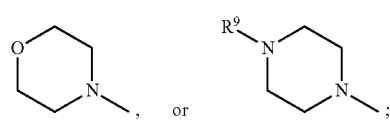

and each $R^9$ is independently selected from a substituted or unsubstituted straight or branched $C_1$-$C_{10}$ alkyl group or hydrogen.

In some preferred embodiments the mass label X-L-M have a reporter moiety X comprising the formula:

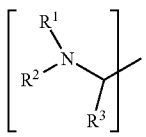

wherein $R^2$ and $R^3$ together comprises

and $R^1$ is selected from isopropyl or butyl or isobutyl or neopentyl.

Preferably, each mass label comprises a mass series modifying group, wherein the mass series modifying group is part of the reporter moiety X or of the mass modifier M or both. More preferably, the mass series modifying group is part of the reporter moiety X.

The mass series modifying group may be selected from:
d) a heavy isotope $^2H$, $^{13}C$, $^{15}N$ or $^{18}O$;
e) a substituted or unsubstituted straight or branched $C_1$-$C_{10}$ alkyl group optionally comprising one or more heavy isotope substitutions;
f) or a combination of a) and b).

In one embodiment, the mass series modifying group is selected from —$CH_3$, —$^{13}CH_3$, —$^{13}CD_3$ or —$CD_3$.

In other embodiments, each mass label comprises a mass series modifying group having the following structure:

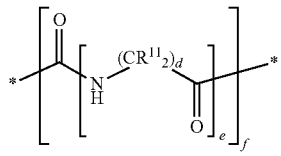

wherein, each $R^{11}$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain; and f is an integer from 0-10; and wherein d and e are at least 1.

In the mass labels according to the invention, Re may either be a reactive functionality for attaching the mass label to an analyte or be an analyte.

Preferably the mass tags additionally comprise a reactive functionality to allow the mass label to be conjugated to an analyte. The reactive functionality for attaching the mass label to the analyte is not especially limited and may comprise any appropriate reactive group.

The reactive functionality may react with an amino group on the biological molecule, for example the ε-amino group of a lysine residue. In the simplest embodiments this may be an N-hydroxysuccinimide ester. Other reactive functionalities are contemplated herein such as those which react with thiol groups in biological molecules. In particular these reactive functionalities are designed to react with the thiol group of a cysteine residue. Examples of reactive groups of the present invention which are able to react with cysteine residues are the maleimido, haloacetyl and 2-dithiopyridine groups. The thiol group of cysteine undergoes nucleophilic addition across the double bond of the maleimido group and undergoes nucleophilic substitution with the haloacetyl or 2-dithiopyridine group.

Reactive functionalities which are capable of reacting with carbonyl or hydroxyl groups in biological molecules are also contemplated herein. In particular, these reactive functionalities are designed to react with the carbonyl or hydroxyl groups of steroid hormones. Reactive groups of the present invention which are able to react with carbonyl or hydroxyl groups in a biological molecule are hydrazide or —CONH—$(CH_2)_n$—$ONH_2$, wherein n is from 1 to 6, and preferably n is 3 i.e. aminoxypropyl amide. These groups react with carbonyl groups to form hydrazones or O-alkyloximes respectively. Examples of reactive functionalities are shown in WO2011/036059, which reference is incorporated herein.

Preferably, the reactive functionality is an N-hydroxysuccinimide ester, a 2,3,5,6-tetrafluorophenyl ester or a sulphodichlorophenyl ester.

When Re is the analyte, the analyte preferably comprises amino acids, peptides, polypeptides, nucleotides, oligonucleotides, polynucleotides, carbohydrates, lipids, phospholipids or combination thereof.

To achieve the desired integer masses, one or both of the moieties X and M, the reactive functionality Re or the analyte may be modified with heavy isotopes t.

Typically the heavy isotopes are selected from $^2H$, $^{13}C$, $^{15}N$ or $^{18}O$.

The term "exact mass" refers to the theoretical mass of the mass label or of the reporter moiety and is the sum of the exact masses of the individual isotopes of the entire mass label or reporter moiety, e.g. $^{12}C$=12.000000, $^{13}C$=13.003355 $H^1$=1.007825, $^{16}O$=15.994915. The "exact mass" takes account of mass defects.

The term "integer mass" is the sum of the integer masses of each isotope of each nucleus that comprises the molecule, e.g. $^{12}C$=12, $^{13}C$=13, $^1H$=1, $^{16}O$=16. The integer mass of an isotope is the sum of protons and neutrons that make up the nucleus of the isotope, i.e. $^{12}C$ comprises 6 protons and 6 neutrons while $^{13}C$ comprises 6 protons and 7 neutrons. This is often also referred to as the nominal mass, or atomic mass number or nucleon number of an isotope.

In the literature the term "isobaric" often refers to species that have the same integer mass and are co-selectable for MS/MS but in the context of this invention we will use the term "isobaric" refer to species that have the same exact mass and we will use the term "pseudo-isobaric" for species that have the same integer mass but may have slightly differing exact masses.

The difference in exact mass between at least two of the mass labels in a subset is usually less than 100 millidaltons, preferably less than 50 millidaltons, most preferably less than 20 millidaltons (mDa). Preferably, the difference in exact mass between at least two of the mass labels in a set is 2.5 mDa, 2.9 mDa, 6.3 mDa, 8.3 mDa, 9.3 mDa, or 10.2 mDa due to common isotope substitutions. For example, if a first label comprises a $^{13}C$ isotope, and in a second label this $^{13}C$ isotope is replaced by $^{12}C$ but a $^{14}N$ isotope is replaced by a $^{15}N$ isotope, the difference in exact mass between the two labels will be 6.3 mDa.

Preferably, the reporter moiety of each mass label in a subset is an isotopologue of the reporter moiety of all other mass labels in the subset. Isotopologues are chemical species that differ only in the isotopic composition of their molecules. For example, water has three hydrogen-related isotopologues: HOH, HOD and DOD, where D stands for deuterium ($^2$H). Isotopologues are distinguished from isotopomers (isotopic isomers) which are isotopic isomers having the same number of each isotope but in different positions. More preferably, the set of two or more mass labels comprises at least one subset comprising two or more mass labels.

Usually, the difference in exact mass is provided by a different number or type of heavy isotope substitution(s).

The term reporter moiety X is used to refer to a moiety of the mass label to be detected independently, typically after cleavage, by mass spectrometry, however, it will be understood that the remainder of the mass label attached to the analyte as a complement ion may also be detected in methods of the invention. The mass modifier X is a moiety which is incorporated into the mass label to ensure that the mass label has a desired integer mass. The reporter moiety X of each mass label may in some embodiments comprise no heavy isotopes.

The mass modifier M ensures that each mass label in the set has a desired integer mass. The mass modifier M is not necessarily to be detected by mass spectrometry. However, the mass modifier M may be detected as part of a complement ion (see below). The mass modifier M is not particularly limited structurally, but merely serves to vary the overall mass of the mass label.

In some embodiments, the set of two or more mass labels, each mass label has a reporter moiety X comprising the following general formula i) as defined above and wherein $R^1$ is selected from:

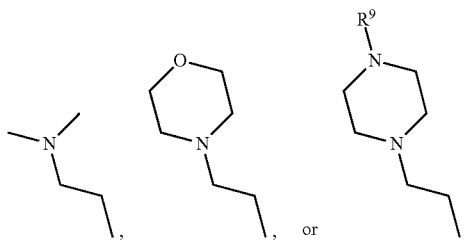

and $R^9$ is selected from a substituted or unsubstituted straight or branched $C_1$-$C_{10}$ alkyl group preferably an alkyl chain selected from methyl, ethyl, propyl, isopropyl, butyl, isobutyl, sec-butyl, pentyl or neopentyl, or hydrogen In some other embodiment the set of two or more mass labels, each mass label has a reporter moiety X comprising the following general formula ii) as defined above and $R^5$ and $R^6$ are each independently

where $R^7$ and $R^8$ are each independently a substituted or unsubstituted straight or branched $C_1$-$C_{10}$ alkyl group or hydrogen.

In some other embodiment, $R^4$ is methyl, ethyl, propyl, isopropyl, butyl, isobutyl, sec-butyl, pentyl, neopentyl or (dimethylamino)methyl. More preferably, $R^4$ is (dimethylamino)methyl.

The components of the reporter moiety according to the invention are preferably fragmentation resistant so that the site of fragmentation of the reporter moiety can be controlled by the introduction of a cleavable bond L that is easily broken by Collision Induced Dissociation (CID), Surface Induced Dissociation, Electron Capture Dissociation (ECD), Electron Transfer Dissociation (ETD), or Fast Atom Bombardment. In the most preferred embodiment, the linkage is easily broken by CID.

In a preferred embodiment the cleavable bond L comprises an amide bond.

In one embodiment, the mass labels are isotopologues of Tandem Mass Tags as defined in WO01/68664.

In a preferred embodiment the aggregate molecular weight of the mass label is 600 Daltons or less, more preferably 500 Daltons or less, still more preferably 400 Daltons or less, most preferably from 300 to 500 Daltons.

In another preferred embodiment, the molecular weight of the reporter moiety is 400 Daltons or less, preferably 250 Daltons or less, more preferably 100 to 250 Daltons, most preferably 100-220 Daltons. A reporter moiety of small size is particularly advantageous because it produces a peak in the silent region of a mass spectrum, which allows the reporter moiety to be easily identified from the mass spectrum and also allows sensitive quantification.

The term silent region of a mass spectrum used in the present context is intended to refer to the region of a mass spectrum with low background "noise" caused by peaks relating to the presence of fragments generated by fragmentation of the labelled peptides. Thus, the term silent region is intended to refer to the region of the mass spectrum with low "noise" caused by peaks relating to the peptide to be detected. For a peptide or protein, the silent region of the mass spectrum is less than 220, preferably less than 200 Daltons.

The mass labels according to the invention are designed to be reacted with a biomolecule, such as a protein to form a labelled biomolecule, e.g. a labelled protein.

In one embodiment, the sets of two or more mass labels comprise mass labels with reporter moieties X comprising the following general formula:

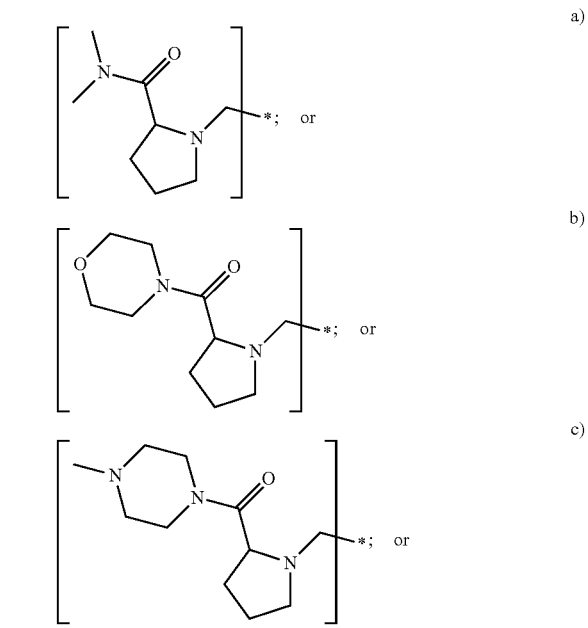

d)
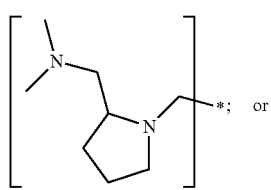
e)
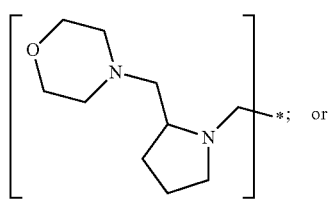
f)
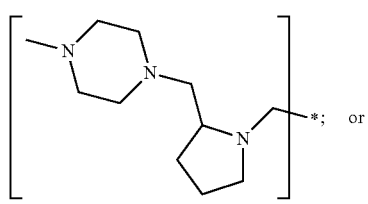
g)
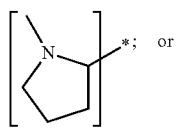
h)
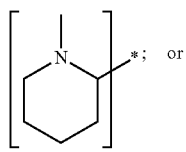
i)
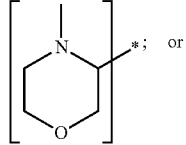
j)
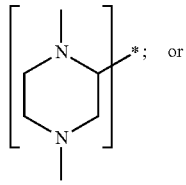
k)
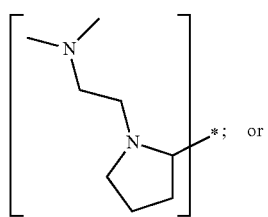
l)
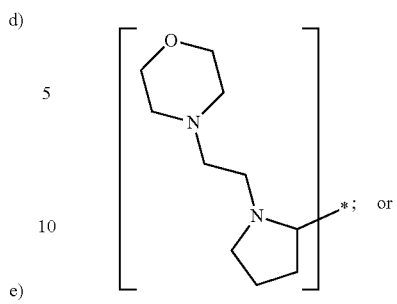
m)
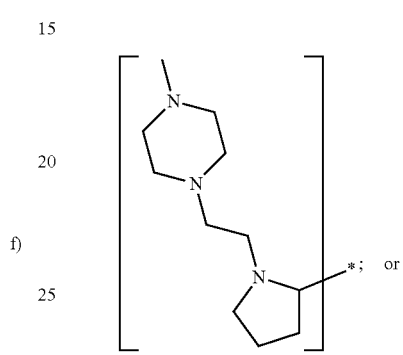
n)
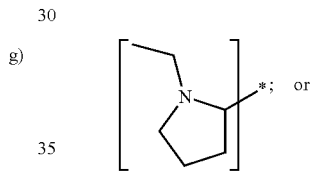
o)
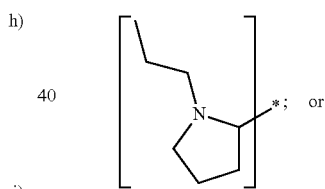
p)
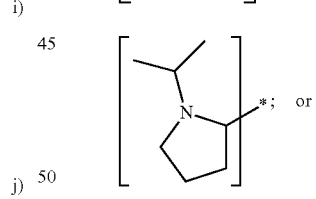
q)
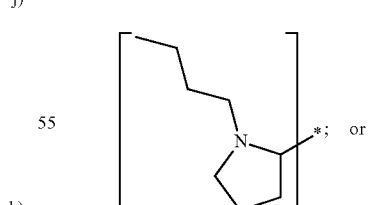
r)
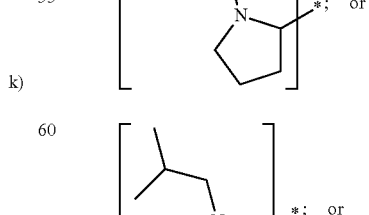

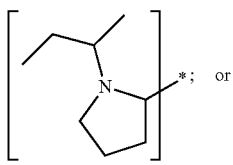 ; or

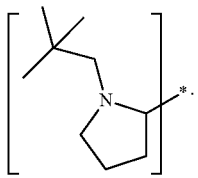

In another preferred embodiment the mass labels according to the invention have a mass modifier M comprising or having the following structure:

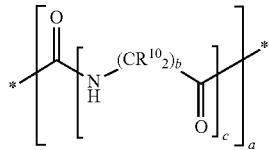

wherein each $R^{10}$ (on the carbon atom) is independently (i.e. may be the same or different) H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group or an amino acid side chain; and a is an integer from 0-10; and b and c are integer and at least 1. For example, the $C(R^{10})_2$ group includes groups such as $CH(R^{10})$, wherein one $R^{10}$ is H and the other $R^{10}$ is another group selected from the above definition of $R^{10}$.

In the most preferred embodiments the mass label X-L-M have a reporter moiety X comprising the formula:

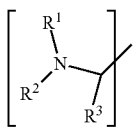

wherein $R^2$ and $R^3$ together comprises

and $R^1$ is selected from isopropyl or isobutyl or neopentyl; the mass modifier M comprises the structure s) 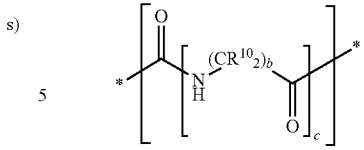

t) wherein $R^{10}$ is H, a=1, b=2 and c=2; the mass modifying group is one or more heavy isotope selected from $^2H$, $^{13}C$, $^{15}N$ or $^{18}O$; and wherein optionally, the mass label X-L-M is connected through M to a reactive functionality Re selected from an N-hydroxysuccinimide ester, a 2,3,5,6-tetrafluorophenyl ester, a sulpho-dichlorophenyl ester, an iodacetamide group, a maleimide group or an aminoxy group.

Even more preferably, the mass labels X-L-M according to the invention have reporter moieties X comprising one of the following formula:

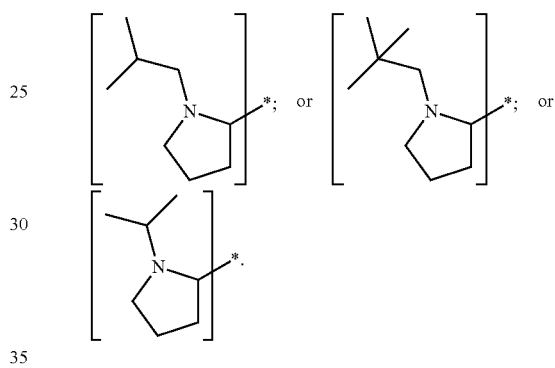

The most preferred mass labels according to the invention together with examples of sets of two or more mass labels comprising heavy isotopes mass series modifying groups are described in details herein below in Embodiments 1 to 6.

Embodiment 1

The mass label has structure:

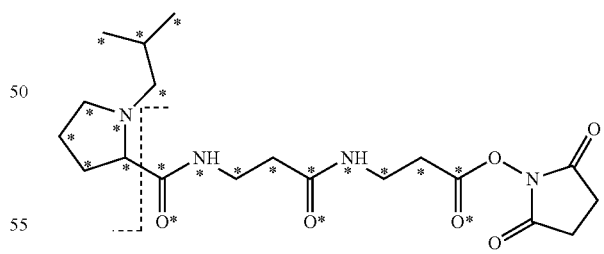

wherein * represents that oxygen is $^{18}O$, carbon is $^{13}C$, nitrogen is $^{15}N$ or hydrogen is $^2H$, and wherein one or more * may be present.

Figure 2:
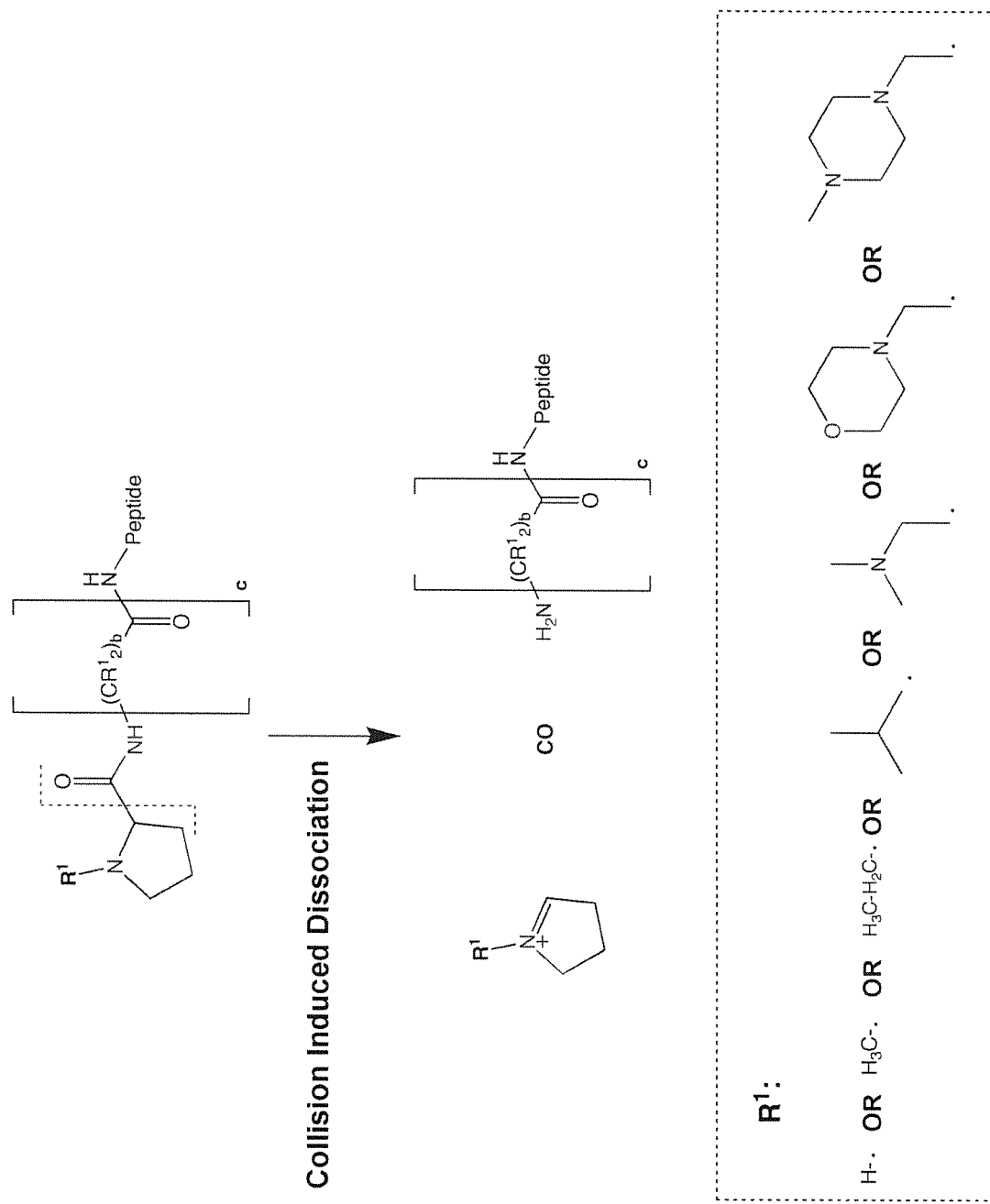
FIG. 2 is a schematic of the predicted fragmentation pathway of an N-alkyl proline mass label (depicted structure is hypothetical and illustrated only for the purpose of predicting the mass-to-charge ratio of expected reporter ions).

The synthesis of the mass label of Embodiment 1 is described in detail in the examples below (Example 2). The fragmentation of this mass label is shown in FIG. 2, where R is an isobutyl group.

An example of a set of n=18 mass labels comprising the mass series modifying groups $^{13}C$ or $^{15}N$ is shown below:

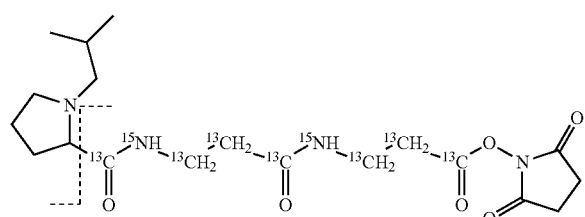
TMT-10-18-126.12773 (Subset 1)
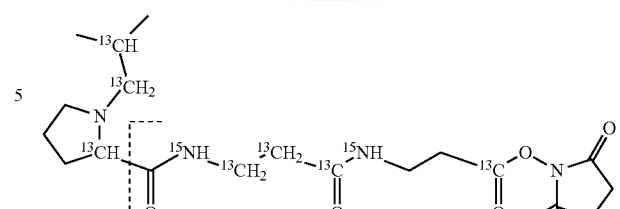
TMT-10-18-129.13724 (Subset 4)
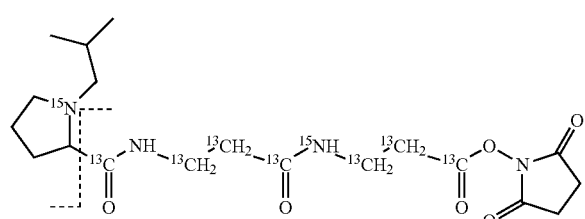
TMT-10-18-127.12476 (Subset 2)
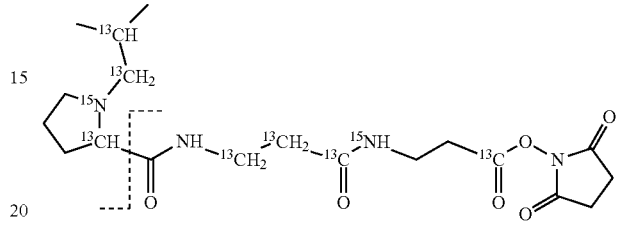
TMT-10-18-130.13483 (Subset 5)
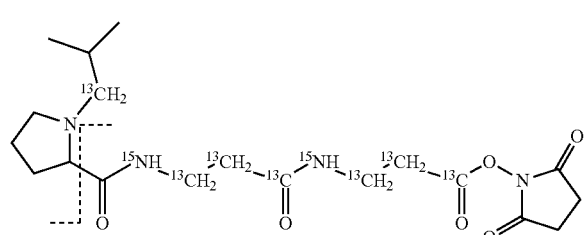
TMT-10-18-127.13053 (Subset 2)
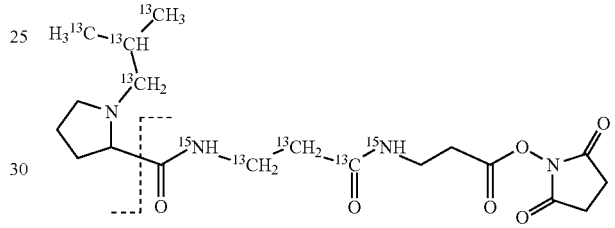
TMT-10-18-130.1406 (Subset 5)
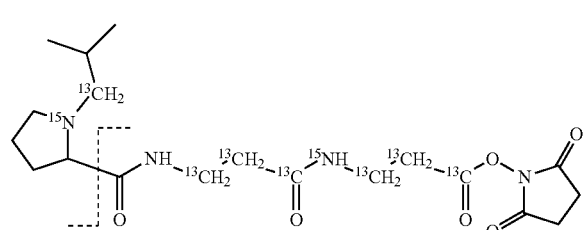
TMT-10-18-128.12812 (Subset 3)
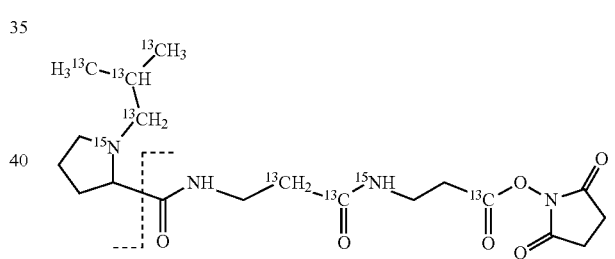
TMT-10-18-131.13818 (Subset 6)
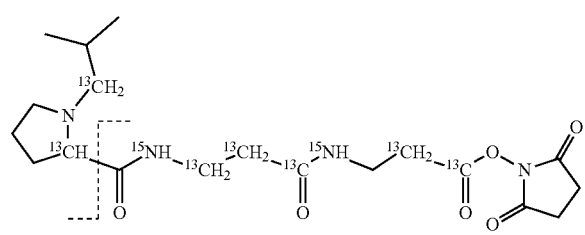
TMT-10-18-128.13389 (Subset 3)
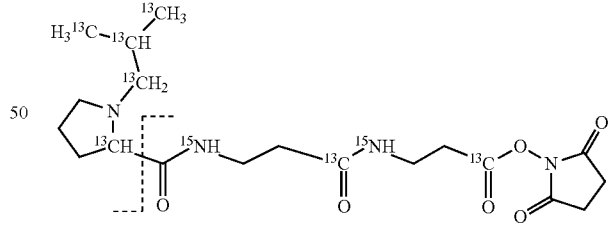
TMT-10-18-131.14395 (Subset 6)
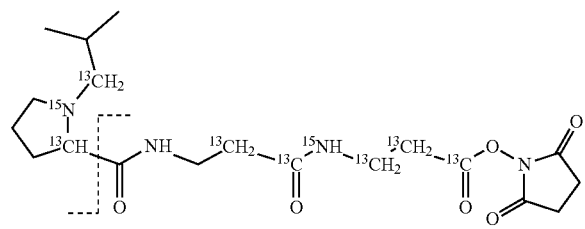
TMT-10-18-129.13147 (Subset 4)
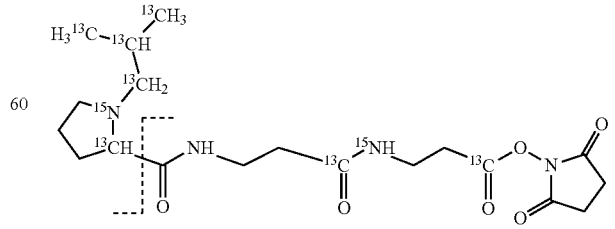
TMT-10-18-132.14154 (Subset 7)

-continued

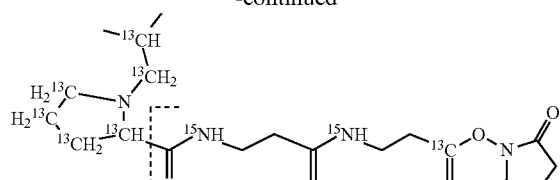

TMT-10-18-132.14731 (Subset 7)

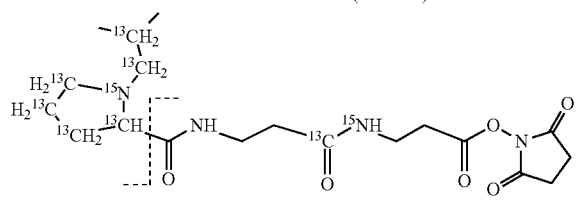

TMT-10-18-133.14489 (Subset 8)

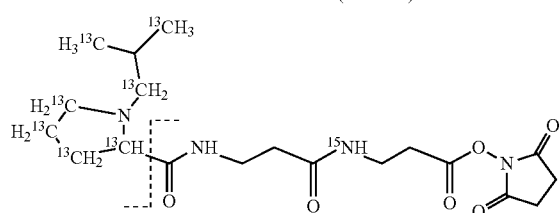

TMT-10-18-133.15066 (Subset 8)

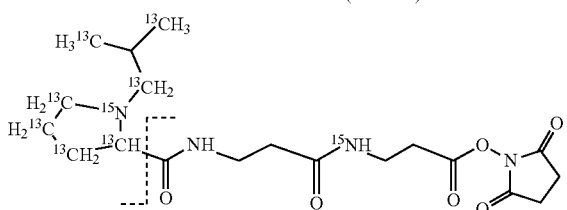

TMT-10-18-134.14824 (Subset 9)

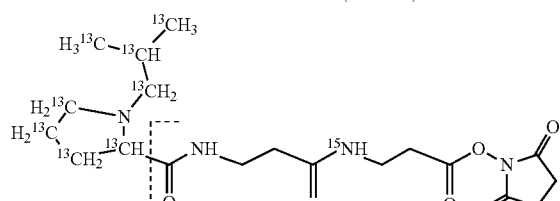

TMT-10-18-134.15402 (Subset 9)

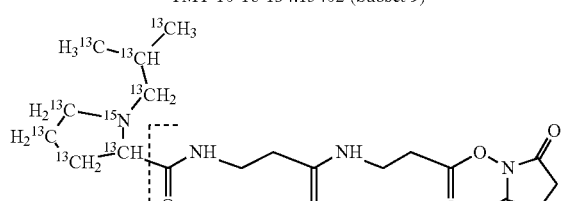

TMT-10-18-135.1516 (Subset 10)

It should be noted that although the substitutions of $^1$H, $^{12}$C and $^{14}$N are shown in a particular location in the example set of Embodiment 1, this has been done as a convenience for the purposes of explanation and the substitutions in example set of Embodiment 1 could located at any suitable position within the reporter moiety X or mass modifier M linker if it is more convenient or cost-effective to locate them elsewhere.

Further mass labels can be constructed with fixed substitutions of hydrogen, deuterium, $^{12}$C, $^{13}$C, $^{14}$N and $^{15}$N as shown in Embodiment 2 below.

Embodiment 2

The mass label has structure:

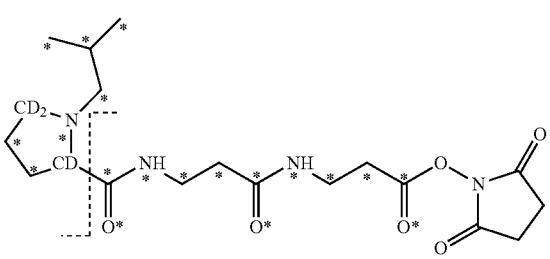

wherein * represents that oxygen is $^{18}$O, carbon is $^{13}$C, nitrogen is $^{15}$N or hydrogen is $^2$H, and wherein one or more * may be present.

The synthesis of the mass label of Embodiment 2 is described in detail in the examples below (Example 2). The fragmentation of this mass label is shown in FIG. 2, where R is an isobutyl group.

An example of a set of n=5 mass labels comprising the mass series modifying groups $^2$H (i.e. D)$^{13}$C or $^{15}$N is shown below:

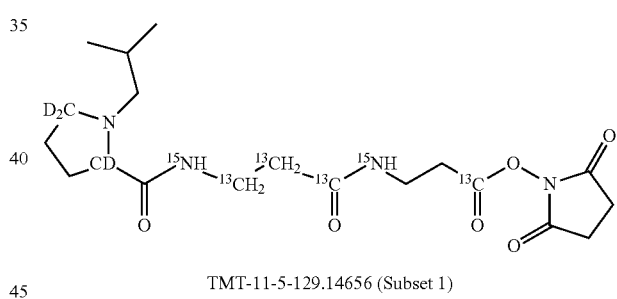

TMT-11-5-129.14656 (Subset 1)

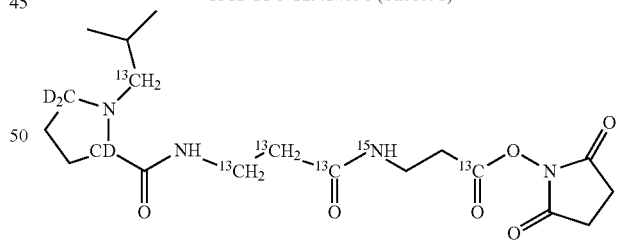

TMT-11-5-130.14881 (Subset 2)

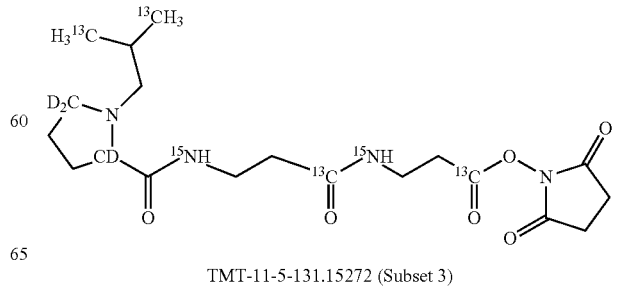

TMT-11-5-131.15272 (Subset 3)

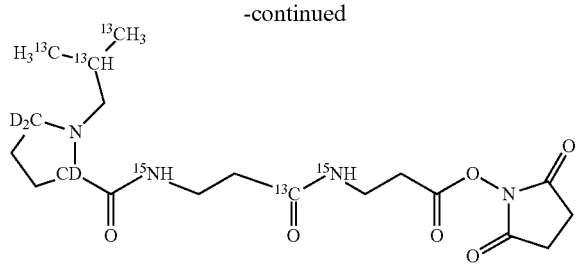

TMT-11-5-132.15662 (Subset 4)

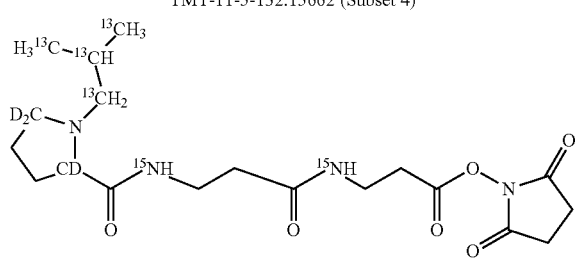

TMT-11-5-133.15888 (Subset 5)

It should be apparent that the mass labels of Embodiment 11 are pseudo-isobaric with the mass labels of Embodiment 10. These sets could thus be used simultaneously to support 23-plex multiplexing.

Further mass labels pseudo-isobaric with the sets of mass labels of Embodiments 1 and 2 can also be synthesized based on the structure of Embodiment 3 below.

Embodiment 3

The mass label has structure:

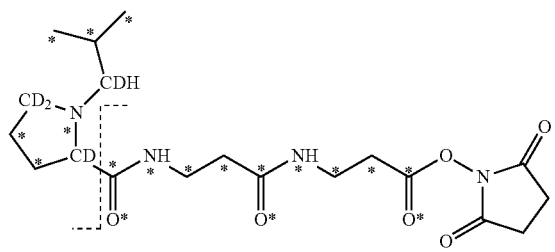

wherein * represents that oxygen is $^{18}O$, carbon is $^{13}C$, nitrogen is $^{15}N$ or hydrogen is $^{2}H$, and wherein one or more * may be present.

An example of a set of n=2 mass labels comprising the mass series modifying groups $^{2}H$ (i.e. D) $^{13}C$ or $^{15}N$ is shown below:

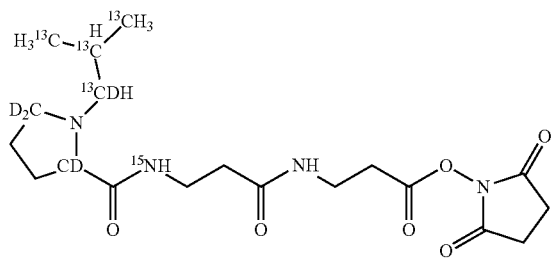

TMT-12-2-134.16625 (Subset 1)

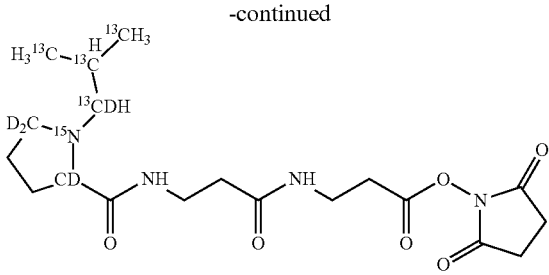

TMT-12-2-135.16329 (Subset 2)

The sets of mass labels according to Embodiments 1, 2 and 3 are pseudo-isobaric with each other since the parent mass label exact masses are 419.24041, 419.24285 and 419.2521 respectively. Thus, these mass labels are isotopes and pseudo-isobaric within 11.7 millidaltons of each other. Peptides labelled with these reagents will thus co-separate and will be co-selected for MS/MS-based sequencing together. Hence, these reagents form a pseudo-isobaric array of 25 tags.

It should also be apparent to one of ordinary skill in the art, that corresponding tag sets based on a linear butyl chain substitution of the proline nitrogen or sec-butyl chain substitution of the proline nitrogen can be readily synthesised from the corresponding linear butyraldehyde and butanone isotopes respectively.

Embodiment 4

The mass label has the structure:

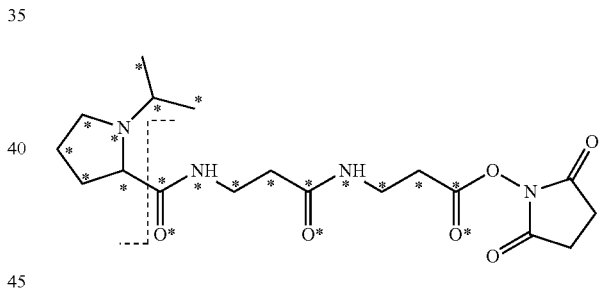

wherein * represents that oxygen is $^{18}O$, carbon is $^{13}C$, nitrogen is $^{15}N$ or hydrogen is $^{2}H$, and wherein one or more * may be present.

The synthesis of the mass label of Embodiment 4 is described in detail in the examples below (Example 3). The fragmentation of this mass label is shown in FIG. 2, where R is an isopropyl group.

An example of a set of n=16 mass labels comprising the mass series modifying groups $^{13}C$ or $^{15}N$ is shown below:

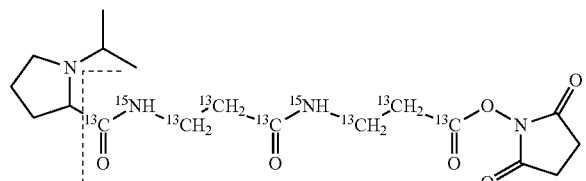

TMT-13-16-112.11208 (Subset 1)

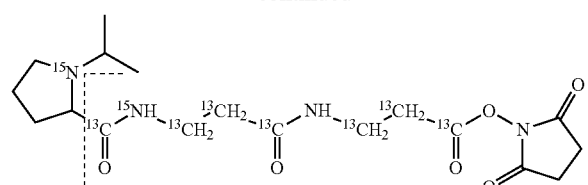
TMT-13-16-113.10911 (Subset 2)
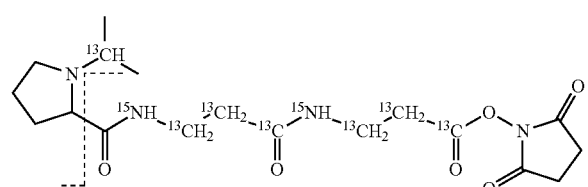
TMT-13-16-113.11543 (Subset 2)
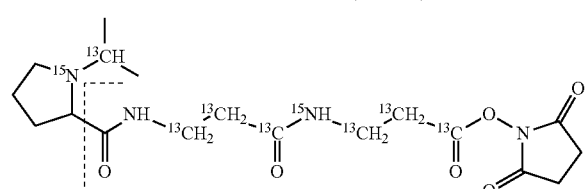
TMT-13-16-114.11247 (Subset 3)
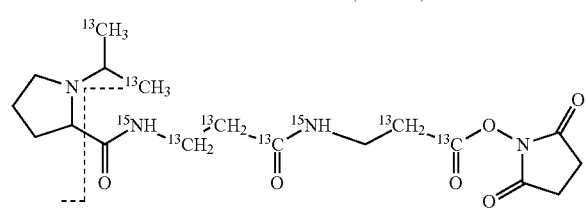
TMT-13-16-114.11879 (Subset 3)
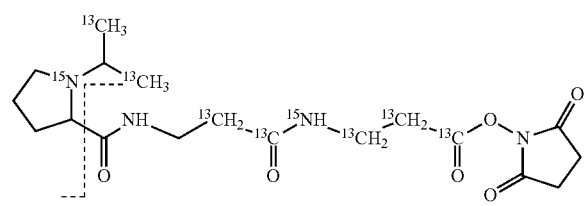
TMT-13-16-115.11582 (Subset 4)
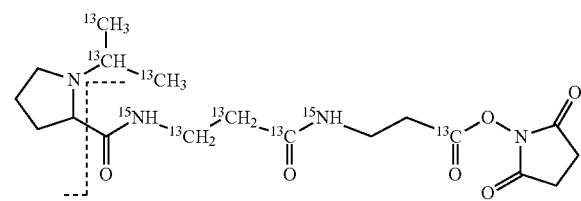
TMT-13-16-115.12214 (Subset 4)
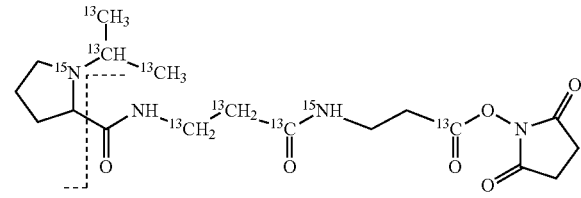
TMT-13-16-116.11918 (Subset 5)
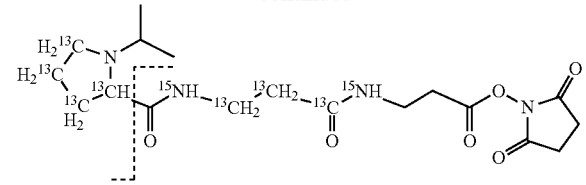
TMT-13-16-116.1255 (Subset 5)
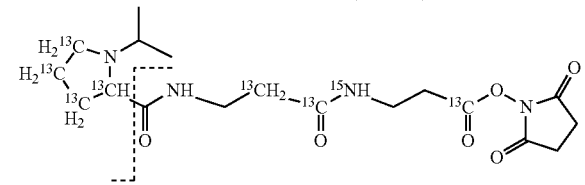
TMT-13-16-117.12253 (Subset 6)
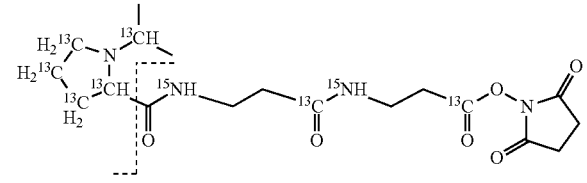
TMT-13-16-117.12885 (Subset 6)
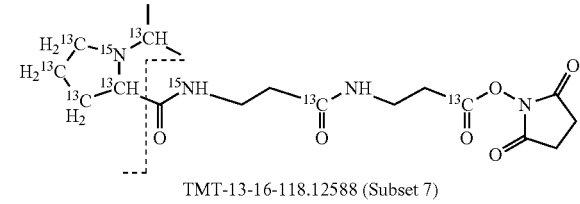
TMT-13-16-118.12588 (Subset 7)
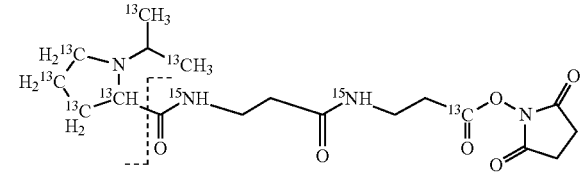
TMT-13-16-118.1322 (Subset 7)
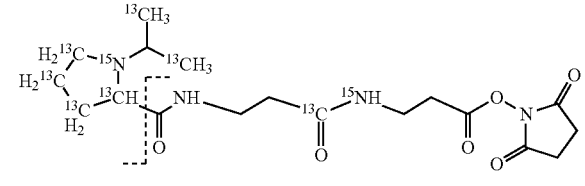
TMT-13-16-119.12924 (Subset 8)
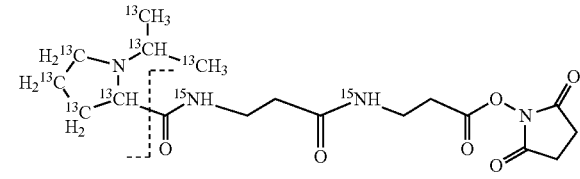
TMT-13-16-119.13556 (Subset 8)
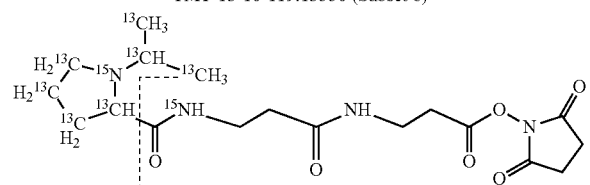
TMT-13-16-120.13259 (Subset 9)

Embodiment 5

The mass label has structure:

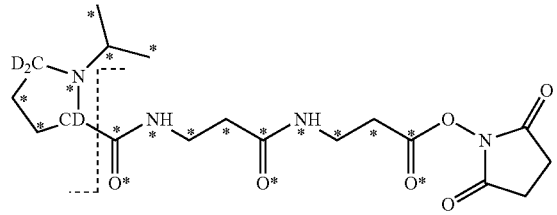

wherein * represents that oxygen is $^{18}$O, carbon is $^{13}$C, nitrogen is $^{15}$N or hydrogen is $^2$H, and wherein one or more * may be present.

The marked deuterium sites (D) may be regarded as a fixed mass series modifier groups, thus shifting the reporter moiety masses of Embodiment 5 relative to those of Embodiment 4.

The synthesis of the mass label of Embodiment 5 is described in detail in the examples below (Example 3). The fragmentation of this mass label is shown in FIG. 2, where R is an isopropyl group.

An example of a set of n=4 mass labels comprising the mass series modifying groups $^2$H (i.e. D) $^{13}$C or $^{15}$N is shown below:

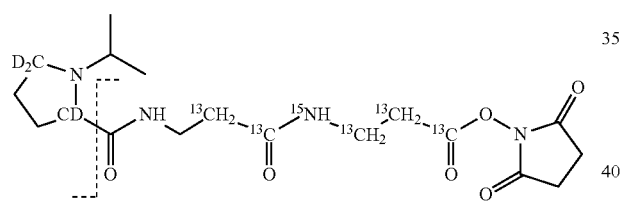

TMT-14-4-115.13091 (Subset 1)

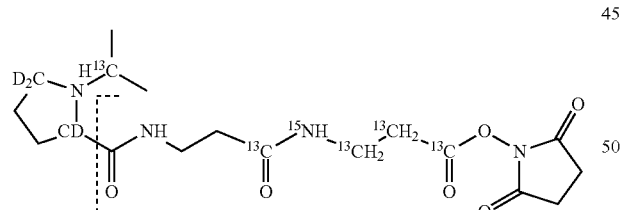

TMT-14-4-116.13426 (Subset 2)

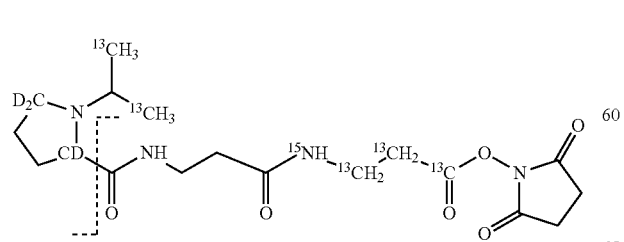

TMT-14-4-117.13762 (Subset 3)

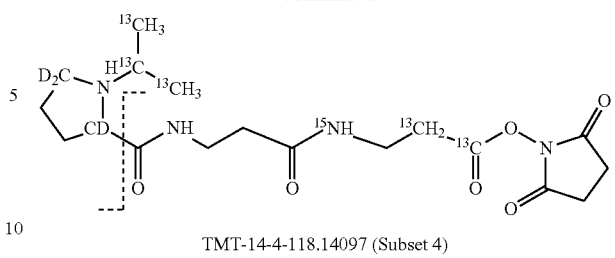

TMT-14-4-118.14097 (Subset 4)

The mass label of Embodiment 5 is pseudo-isobaric with the mass label of Embodiment 4 because the exact masses of these mass labels are 405.23352 and 405.21844 respectively. Together, these two sets would provide an array of 20 resolvable mass labels.

Alternative heavy isotope substitutions could also be introduced as illustrated below:

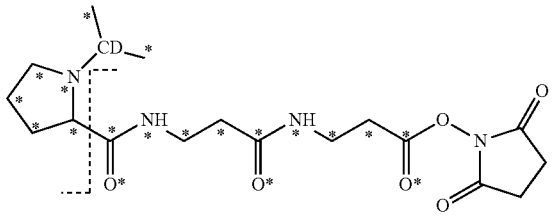

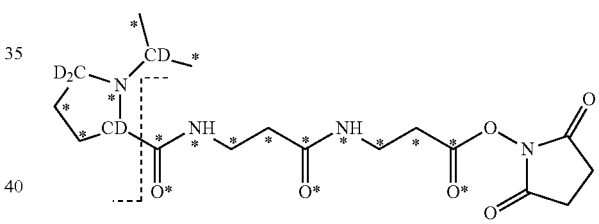

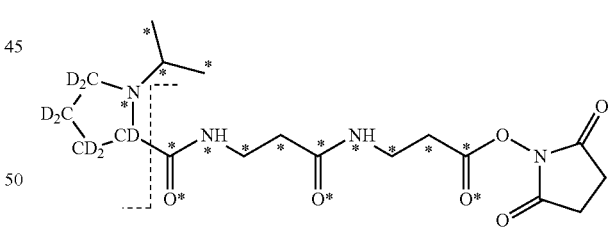

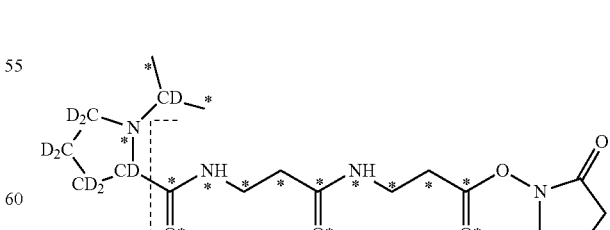

wherein * represents that oxygen is $^{18}$O, carbon is $^{13}$C, nitrogen is $^{15}$N or hydrogen is $^2$H, and one or more * may be present.

Embodiment 6

The mass label has structure:

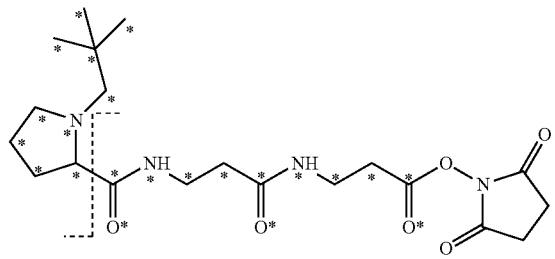

wherein * represents that oxygen is $^{18}O$, carbon is $^{13}C$, nitrogen is $^{15}N$ or hydrogen is $^{2}H$, and wherein one or more * may be present.

The synthesis of the mass label of Embodiment 6 is described in detail in the examples below (Example 6). The fragmentation of this mass label is shown in FIG. 2, where R is a neopentyl group.

An example of a set of n=18 mass labels comprising the mass series modifying groups $^{13}C$ or $^{15}N$ is shown below:

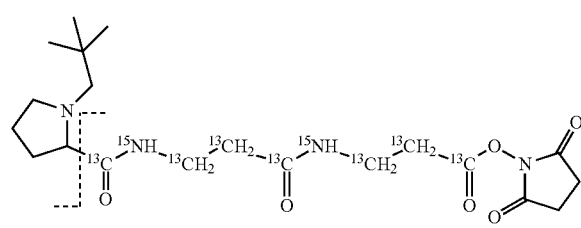

TMT-15-18-140.14338 (Subset 1)

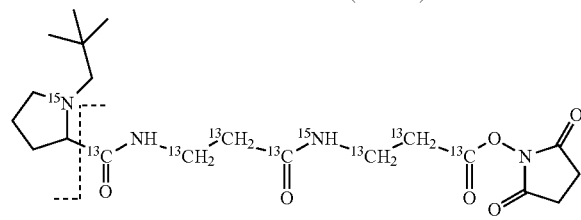

TMT-15-18-141.14041 (Subset 2)

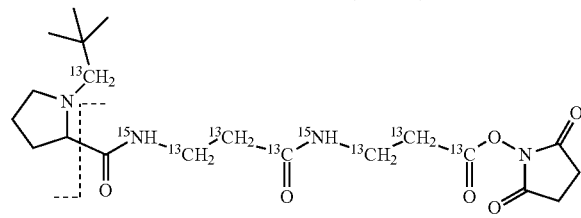

TMT-15-18-141.14673 (Subset 2)

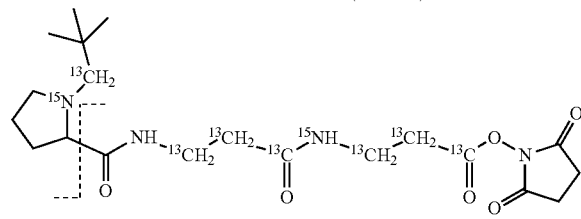

TMT-15-18-142.14377 (Subset 3)

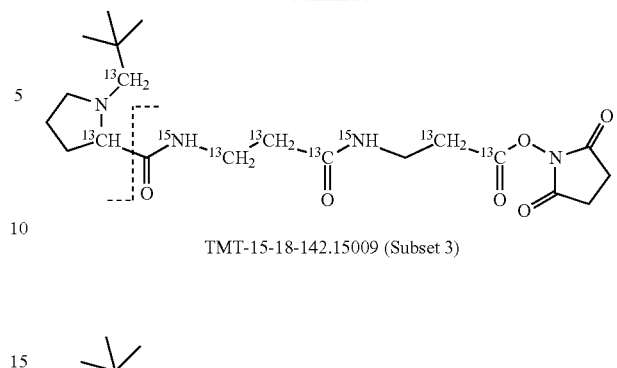

TMT-15-18-142.15009 (Subset 3)

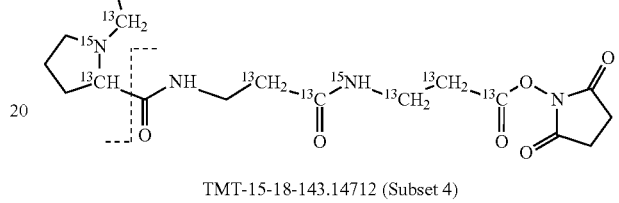

TMT-15-18-143.14712 (Subset 4)

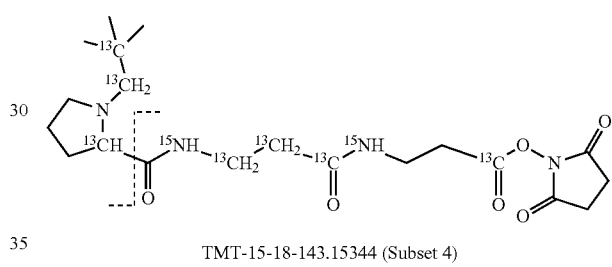

TMT-15-18-143.15344 (Subset 4)

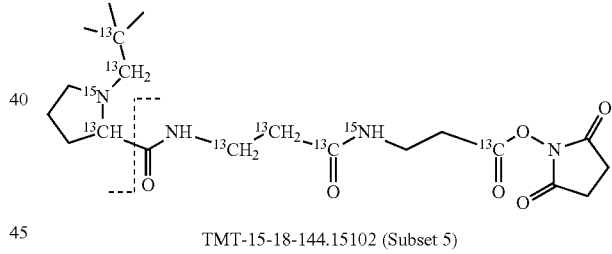

TMT-15-18-144.15102 (Subset 5)

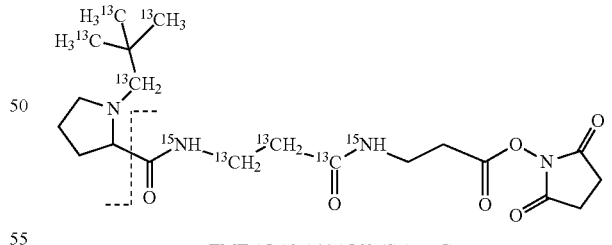

TMT-15-18-144.1568 (Subset 5)

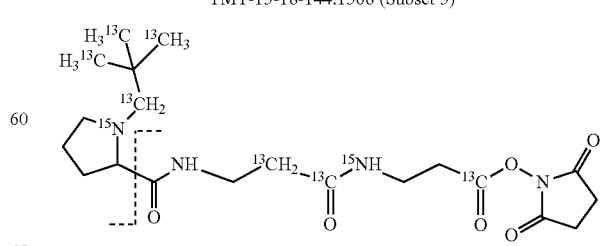

TMT-15-18-145.15383 (Subset 6)

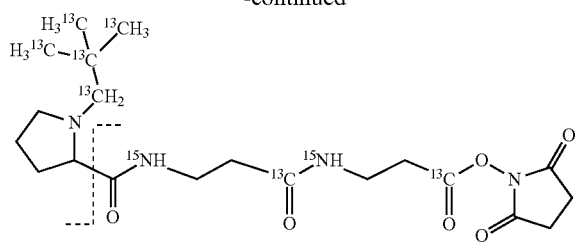
TMT-15-18-145.16015 (Subset 6)
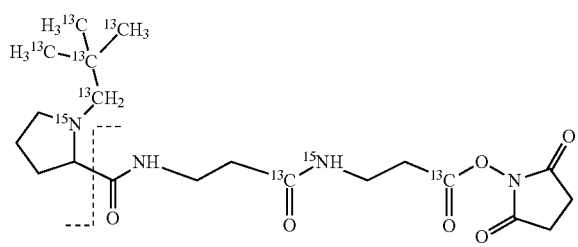
TMT-15-18-146.15719 (Subset 7)
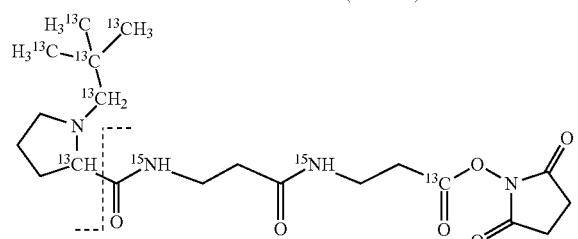
TMT-15-18-146.16351 (Subset 7)
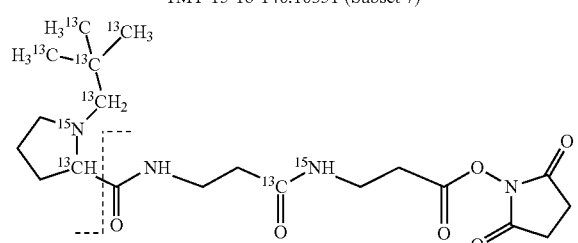
TMT-15-18-147.16054 (Subset 8)
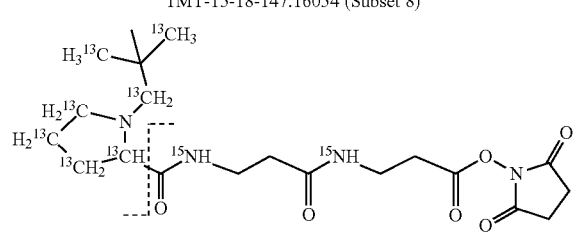
TMT-15-18-147.16686 (Subset 8)
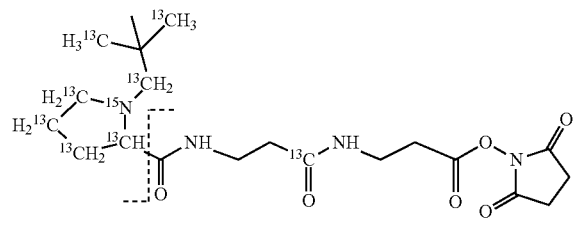
TMT-15-18-148.16389 (Subset 9)
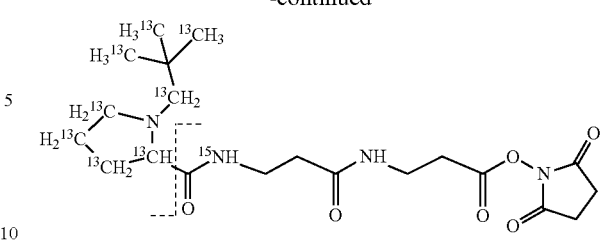
TMT-15-18-148.17021 (Subset 9)
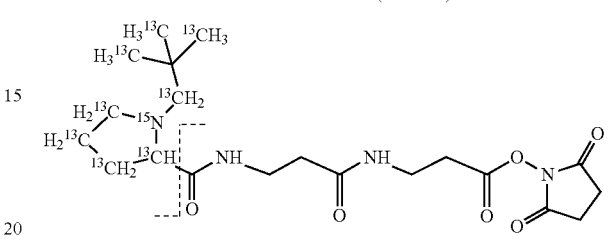
TMT-15-18-149.16725 (Subset 10)
Alternative heavy isotope substitutions could be introduced as shown below:
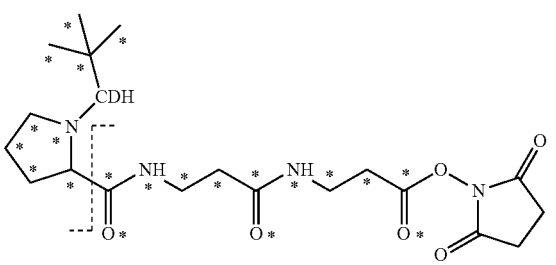
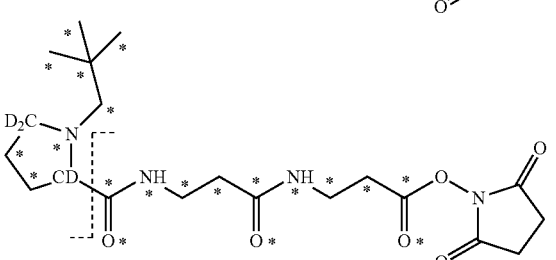
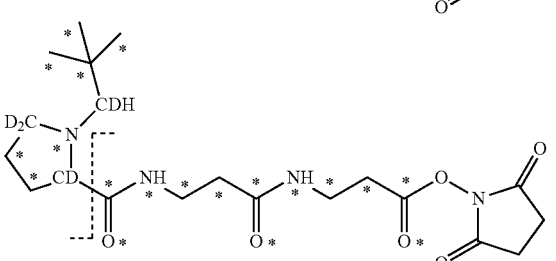
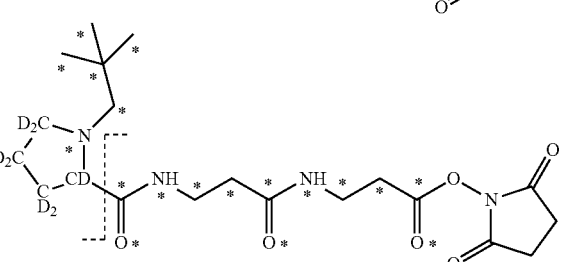

-continued

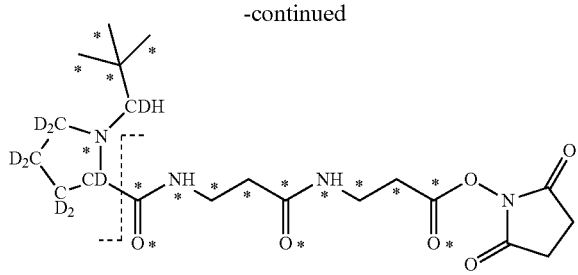

wherein * represents that oxygen is $^{18}O$, carbon is $^{13}C$, nitrogen is $^{15}N$ or hydrogen is $^{2}H$, and one or more * may be present.

The marked deuterium sites (D) may be regarded as a fixed mass series modifier groups, thus shifting these reporter moiety masses relative to those of Embodiment 6.

Further embodiments of the mass labels according to the present invention are described below. As for the preferred embodiments described above, the mass labels are identified by the set number, parent set size and the reporter ion mass, e.g. in Set 1 below, each mass label is named TMT-1-24-"reporter mass", where TMT stands for Tandem Mass Tag, i.e. tags for tandem mass spectrometry, the digit 1 refers to the Set number, the 24 refers to the number of mass labels in the set and the reporter mass is the mass-to-charge ratio of the expected reporter ion under Collision Induced Dissociation conditions. Different reporter ions may be obtained by Electron Transfer Dissociation (ETD) or Electron Capture Dissociation (ECD).

Set 1:

The isobaric mass labels may have the following structure:

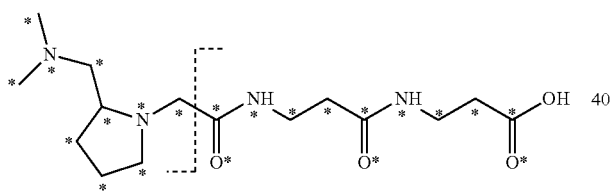

wherein the mass series modifying group * represents that oxygen is replaced (or substituted) by $^{18}O$, carbon by $^{13}C$ or nitrogen by $^{15}N$ or at sites where the hydrogen is present * represents $^{2}H$. One or more positions may be substituted in single label. Preferably more than one position is substituted.

Figure 3:
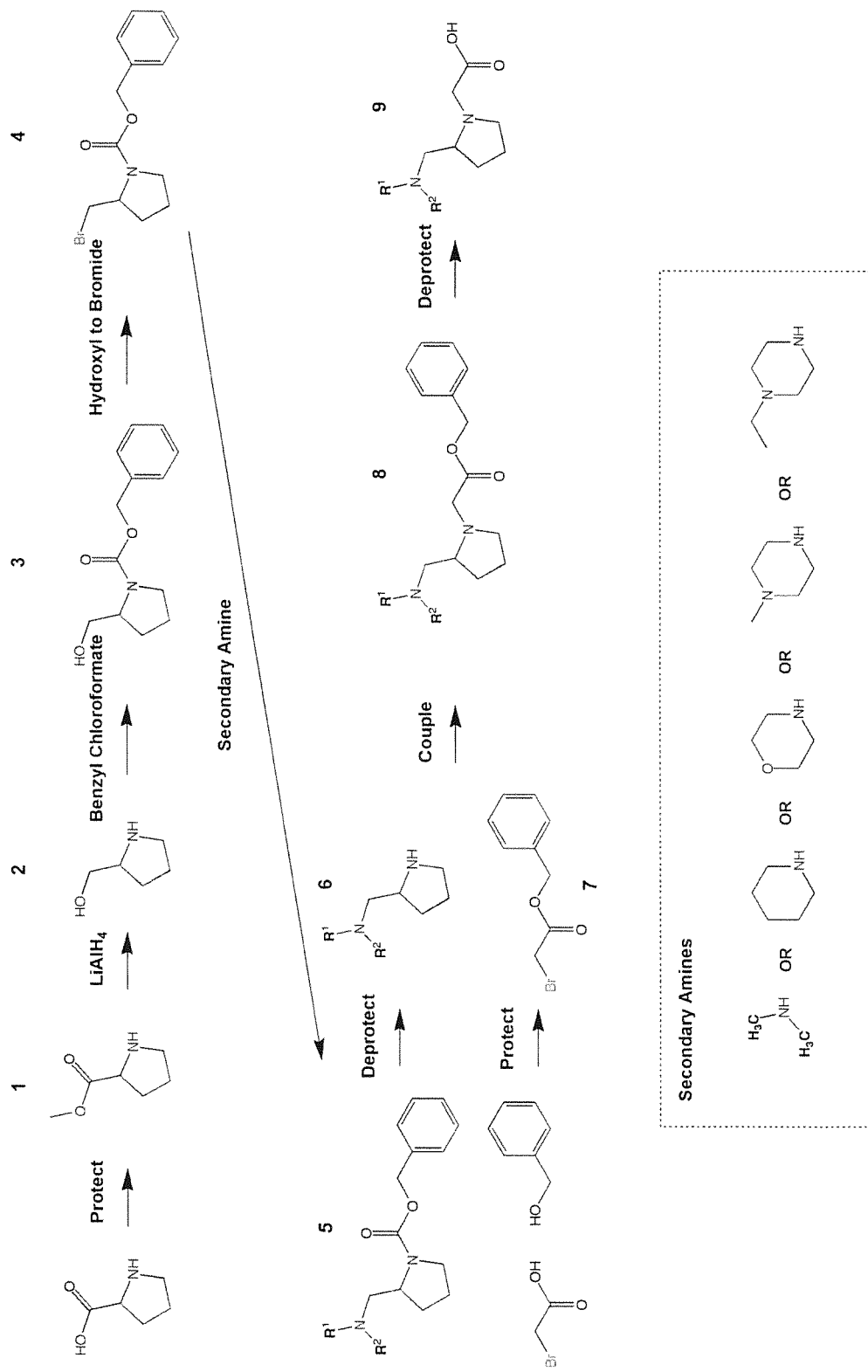
FIG. 3 shows a schematic representation of the synthesis method for the reporter moiety of the mass labels of Set 1.

The synthesis of the reporter moiety (indicated at the left of the dashed line representing the cleavable bond L in the general structure of set 1) is shown in FIG. 3. FIG. 3 shows a schematic diagram of a generalised synthetic route for producing a variety of reporter groups according to this invention. Methanol is used to protect the proline carboxylic acid as the methyl ester (1). The ester is reduced to prolinol (2) by Lithium Aluminium Hydride. The proline amino group is then protected by reaction with benzylchloroformate to afford the benzyloxycarbonyl protected amine (3). The alcohol is then converted to the corresponding bromide (4) by reaction with a mixture of either sodium or potassium bromide and concentrated sulphuric acid. A secondary amine is then coupled to the bromide (4) to give the tertiary amine (5). A number of different secondary amines can be used at this stage with preferred examples shown at the bottom of FIG. 3. The protected amine is then deprotected, typically by reduction with hydrogen in the presence of palladium catalyst to liberate the pyrolidine amine (6). In parallel, bromacetic acid is protected as a benzyl ester (7). The pyrolidine amine (6) is then coupled to the protected bromoacetic acid to give the di-tertiary amine (8), which is then deprotected, typically by reduction with hydrogen in the presence of palladium catalyst to liberate the free carboxylic acid (9).

Figure 4:
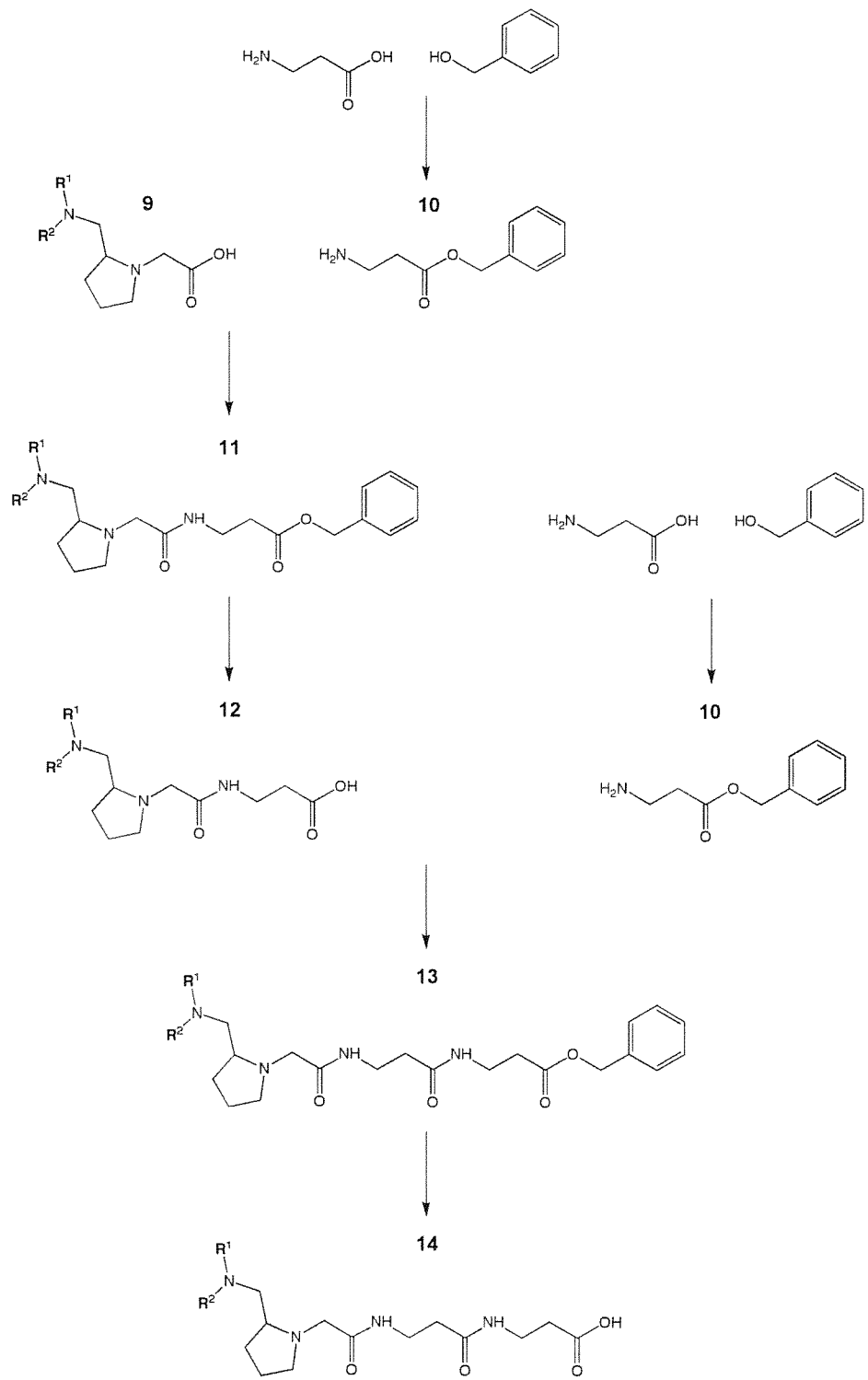
FIG. 4 shows a schematic representation of the coupling of the reporter ion structure shown in FIG. 3 to two consecutive beta-alanine residues.

Coupling of this reporter moiety to two consecutive beta-alanine residues (the mass modifier M) is shown in FIG. 4. FIG. 4 shows a schematic diagram of a generalised synthetic route for coupling of amino acid linkers to the reporter groups of this invention. Beta-alanine, or an isotope thereof, is protected as a benzyl ester (10). The protected beta-alanine (10) can then be coupled to the free carboxylic acid of the reporter group from FIG. 3 (9) to give the singly extended reporter structure (11). The benzyl ester protecting group is then removed, typically by reduction with hydrogen in the presence of palladium catalyst, to liberate the free carboxylic acid (12). Structure 12 is then coupled to a further benzyl ester protected beta-alanine (10) to give the protected double-beta alanine extended reporter group (13). Finally, the benzyl ester protecting group is removed as explained for FIG. 3 to yield the finished tag as a free acid (14).

In a preferred embodiment of an isobaric set of mass tags according to this set 1, the mass series modifying group * is $^{13}C$ or $^{15}N$ and the set comprises n=24 mass labels having the following structures:

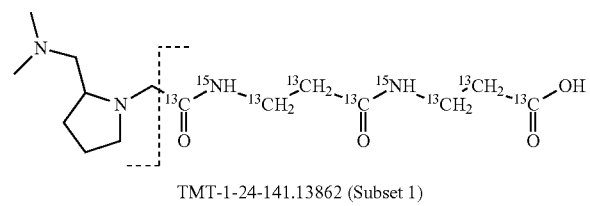

TMT-1-24-141.13862 (Subset 1)

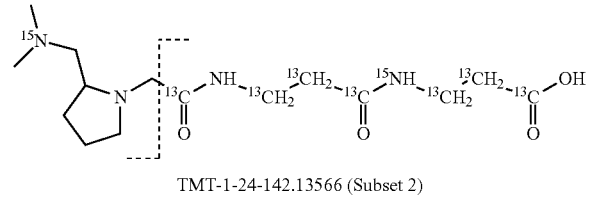

TMT-1-24-142.13566 (Subset 2)

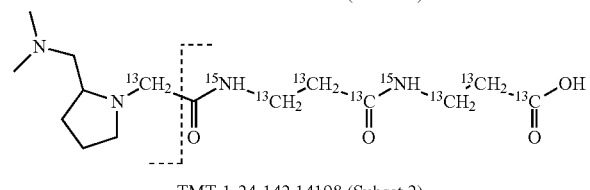

TMT-1-24-142.14198 (Subset 2)

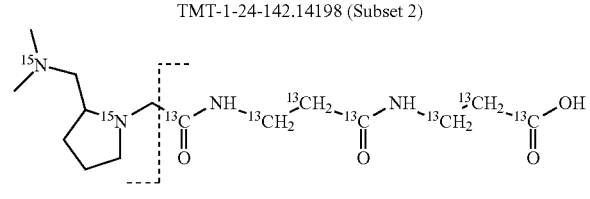

TMT-1-24-143.13269 (Subset 3)

-continued

TMT-1-24-143.13901 (Subset 3)

TMT-1-24-143.14533 (Subset 3)

TMT-1-24-144.13605 (Subset 4)

TMT-1-24-144.14237 (Subset 4)

TMT-1-24-144.14869 (Subset 4)

TMT-1-24-145.1394 (Subset 5)

TMT-1-24-145.14572 (Subset 5)

TMT-1-24-1-145.15204 (Subset 5)

-continued

TMT24-1-146.14276 (Subset 6)

TMT-1-24-146.14908 (Subset 6)

TMT-1-24-146.1554 (Subset 6)

TMT-1-24-147.14611 (Subset 7)

TMT-1-24-147.15243 (Subset 7)

TMT-1-24-147.15875 (Subset 7)

TMT-1-24-148.14947 (Subset 8)

TMT-1-24-148.15579 (Subset 8)

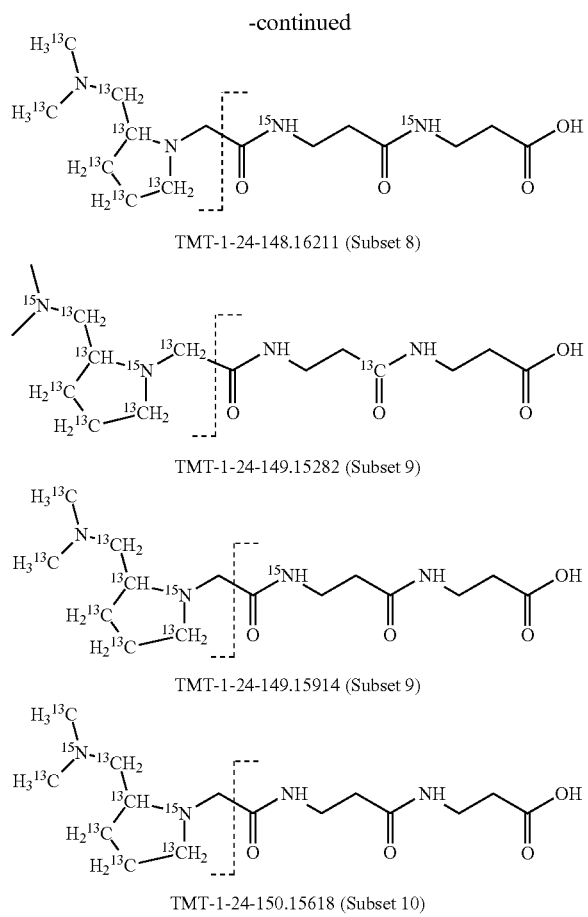

TMT-1-24-148.16211 (Subset 8)

TMT-1-24-149.15282 (Subset 9)

TMT-1-24-149.15914 (Subset 9)

TMT-1-24-150.15618 (Subset 10)

The cleavable bond L, which is marked with the dashed line in the structures above, would split in a mass spectrometer between the reporter moiety and the mass modifier (M) and generate a reporter ion (reporter moiety X split from the remaining part of the mass label, structure at the left of the dash line in the general structure). In Set 1, there are 10 subsets of mass labels based on the mass of the reporter ions, i.e. the reporter ions in subset 2 are approximately 1 Dalton heavier than the reporter ions in subset 1. Similarly, the reporter ions in subset 3 are approximately 1 Dalton heavier than the reporter ions in subset 2, etc. Within each subset of mass labels, it can be seen from the calculated exact masses that each mass label differs from the next by 6.32 Millidaltons.

In subset 1, there are no heavy isotope mass adjusters in the reporter ion and there is only one way in which this reporter can be constructed so there is only 1 tag in subset 1. In subset 2, there is one heavy isotope in the reporter ion, shifting the mass of the reporter by approximately 1 Dalton relative to subset 1. There are 2 ways to introduce the heavy isotope, by introduction of a single $^{15}$N nucleus or by introduction of a single $^{13}$C nucleus and hence there are two tags in subset 2 differing in mass from each other by 6.3 millidaltons. In subset 3, there are two heavy isotope mass adjusters in the reporter ion, shifting the mass of the reporter by approximately 1 Dalton relative to subset 2. There are 3 ways to introduce the 2 mass adjusters into subset 3, by introduction of two $^{15}$N nuclei or by introduction of a single $^{15}$N nucleus and a single $^{13}$C nucleus or by introduction of two $^{13}$C nuclei and hence there are 3 tags in subset 3. In subset 4, there are three heavy isotope mass adjusters in the reporter ion, shifting the mass of the reporter by approximately 1 Dalton relative to subset 3. There are again only 3 ways to introduce the 3 mass adjusters into subset 3, by introduction of two $^{15}$N nuclei and a single $^{13}$C or by introduction of a single $^{15}$N nucleus and a two $^{13}$C nuclei or by introduction of three $^{13}$C nuclei and hence there are 3 tags in subset 4. In general, the number of tags in each subset is limited by which of the mass adjuster nuclei is present less frequently in the structure.

It should be clear to one of ordinary skill in the art that the mass modifier M, which comprises two beta-alanine residues in this specific mass label, could be varied considerably. Possible substitutions include replacement with other amino acids such as alanine, valine, leucine or with longer amino acids such as gamma-aminobutyric acid, aminopentanoic acid or aminohexanoic acid. Poly-ethylene glycol linkers might also be appropriate with an amino and a carboxylic acid terminus. The preparation of benzyl esters and use of these esters for all these alternatives would be essentially the same as shown in FIG. 4 for beta-alanine.

Set 2:

The isobaric mass labels may also have the following structure:

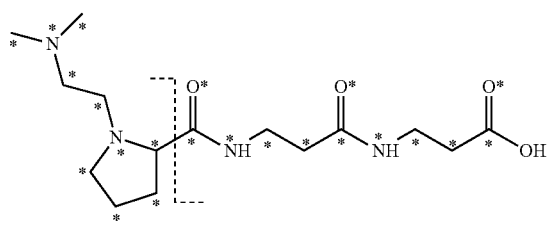

wherein the mass series modifying group * represents that oxygen is replaced (or substituted) by $^{18}$O, carbon by $^{13}$C or nitrogen by $^{15}$N or at sites where the hydrogen is present * represents $^{2}$H. One or more positions may be substituted in single label. Preferably more than one position is substituted.

Figure 5:
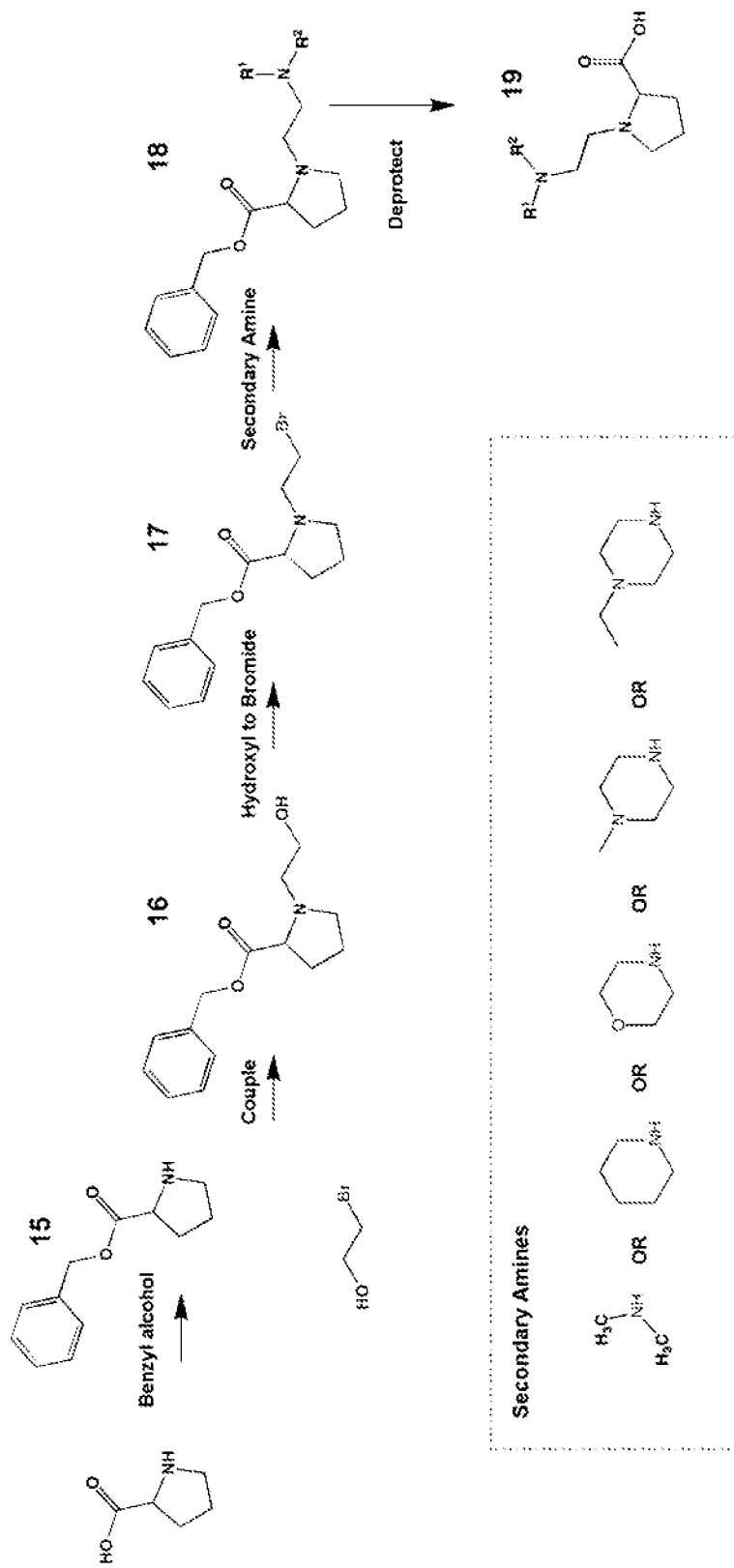
FIG. 5 shows a schematic representation of the synthesis method for the reporter moiety of the mass labels of Set 2.

The synthesis of the reporter moiety structure of Set 2 is shown in FIG. 5. FIG. 5 shows a schematic diagram of a generalised synthetic route that can produce a variety of reporter groups according to this invention. In FIG. 5, proline is protected to give the proline benzyl ester (15), the protected proline is then coupled to bromoethanol (or an isotope thereof) to give the tertiary amine (16) with a free hydroxyl group. The free hydroxyl group is then converted to the bromide (17) by reaction with a mixture of either sodium or potassium bromide and concentrated sulphuric acid. A secondary amine is then coupled to the bromide (17) to give the di-tertiary amine (18). A number of different secondary amines can be used at this stage with preferred examples shown at the bottom of FIG. 5. The protected amine is then deprotected, typically by reduction with hydrogen in the presence of palladium catalyst to liberate the proline carboxylic acid reporter structure (19).

Figure 6:
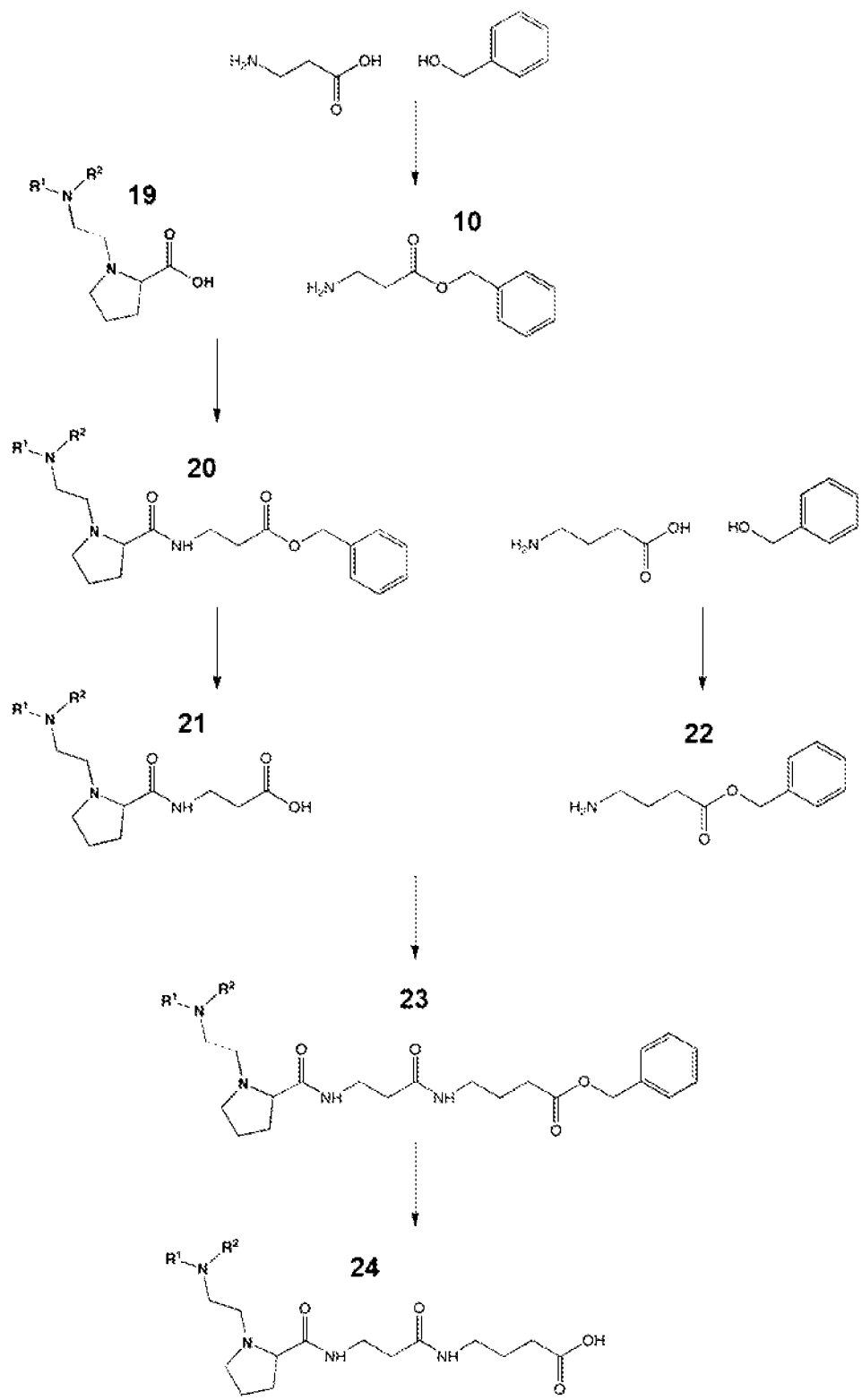
FIG. 6 shows a schematic of the coupling of the reporter ion structure shown in FIG. 5 to two consecutive beta-alanine residues

Coupling of this reporter moiety to a beta-alanine residue and a gamma-aminobutyric acid residue (the mass modifier M) is shown in FIG. 6. FIG. 6 shows a schematic diagram of a generalised synthetic route for coupling of amino acid linkers to the reporter groups of this invention. In short, beta-alanine, or an isotope thereof, is protected as a benzyl ester (10). The protected beta-alanine (10) can then be coupled to the free carboxylic acid of the reporter group from FIG. 5, (19), to give the singly extended reporter structure (20). The benzyl ester protecting group is then removed, typically by reduction with hydrogen in the presence of palladium catalyst, to liberate the free carboxylic acid (21). Gamma-aminobutyric acid (GABA) is also protected to give a benzyl ester (22). Structure 21 is then coupled to the benzyl ester protected GABA linker (22) to give the protected beta alanine and GABA extended reporter (23). Finally, the benzyl ester protecting group is then removed as above to yield the finished tag as a free acid (24).

In a preferred embodiment of an isobaric set of mass labels according to this invention, mass series modifying group * is $^{13}C$ or $^{15}N$ and the set comprises n=24 mass labels having the following structures:

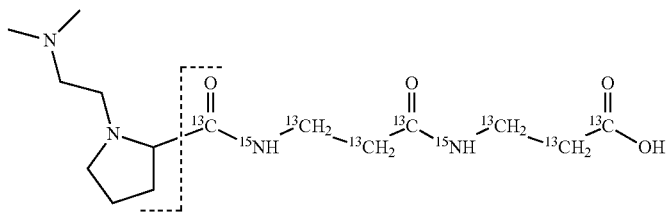

TMT-2-24-141.13862 (Subset 1)

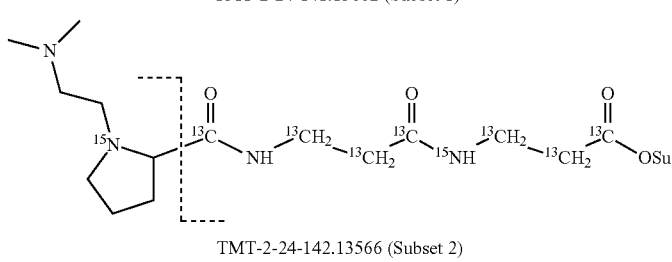

TMT-2-24-142.13566 (Subset 2)

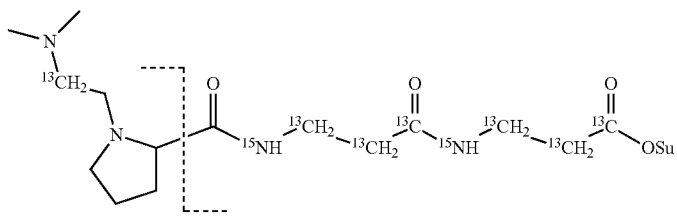

TMT-2-24-142.14198 (Subset 2)

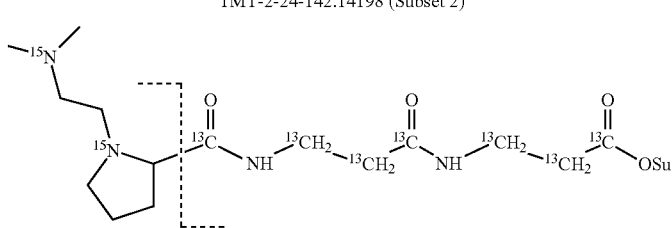

TMT-2-24-143.13269 (Subset 3)

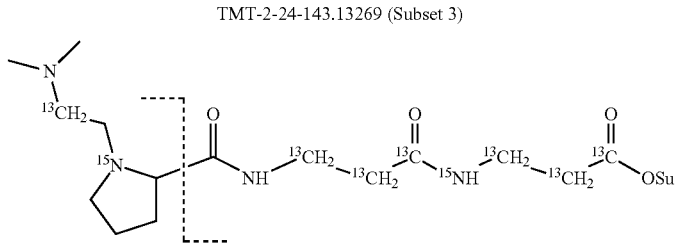

TMT-2-24-143.13901 (Subset 3)

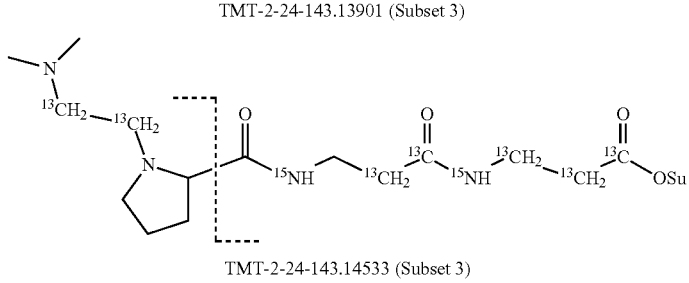

TMT-2-24-143.14533 (Subset 3)

-continued
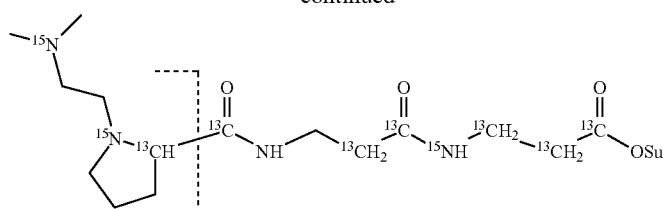
TMT-2-24-144.13605 (Subset 4)
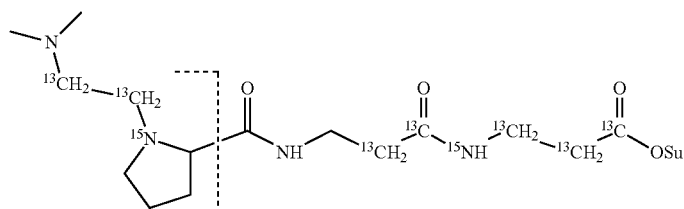
TMT-2-24-144.14237 (Subset 4)
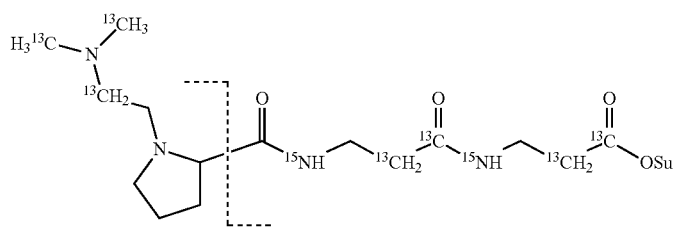
TMT-2-24-144.14869 (Subset 4)
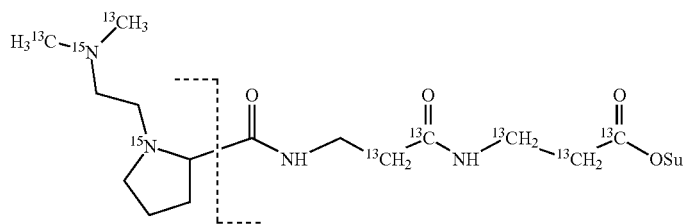
TMT-2-24-145.1394 (Subset 5)
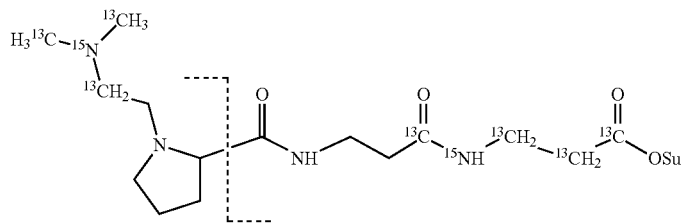
TMT-2-24-145.14572 (Subset 5)
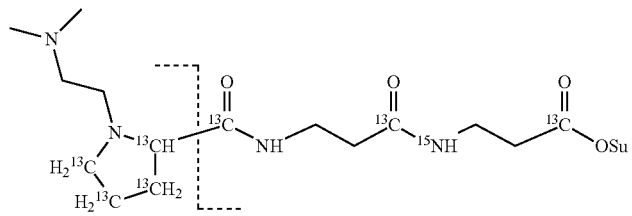
TMT-2-24-145.15204 (Subset 5)

-continued
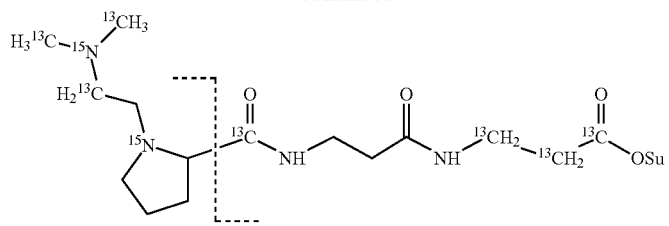
TMT-2-24-146.14276 (Subset 6)
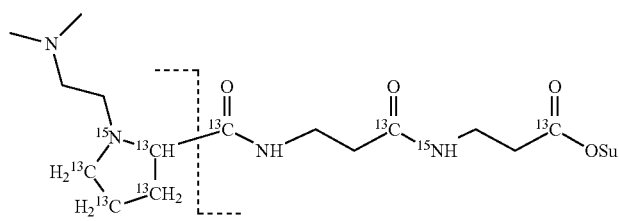
TMT-2-24-146.14908 (Subset 6)
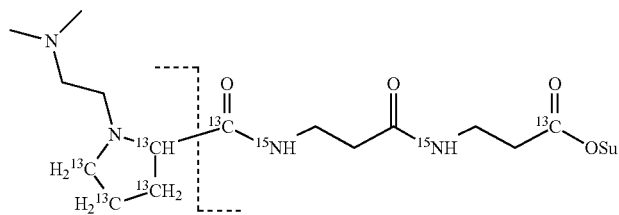
TMT-2-24-146.1554 (Subset 6)
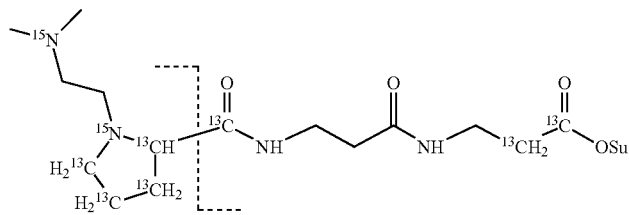
TMT-2-24-147.14611 (Subset 7)
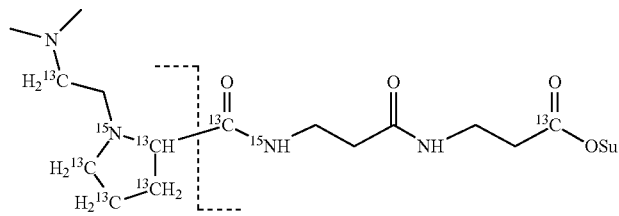
TMT-2-24-147.15243 (Subset 7)
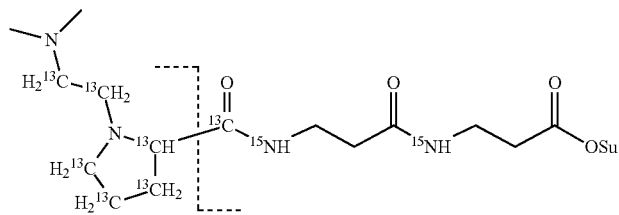
TMT-2-24-147.15875 (Subset 7)

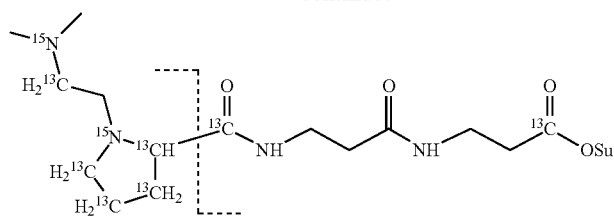
TMT-2-24-148.14947 (Subset 8)
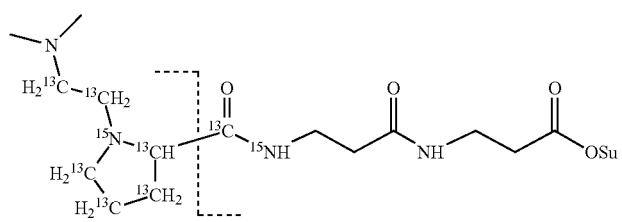
TMT-2-24-148.15579 (Subset 8)
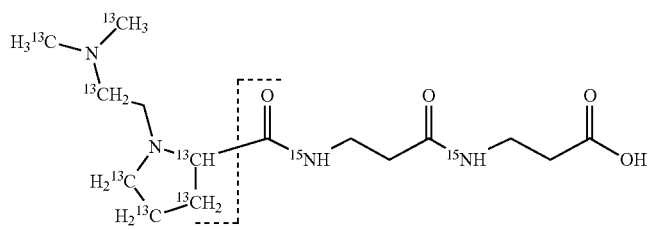
TMT-2-24-148.16211 (Subset 8)
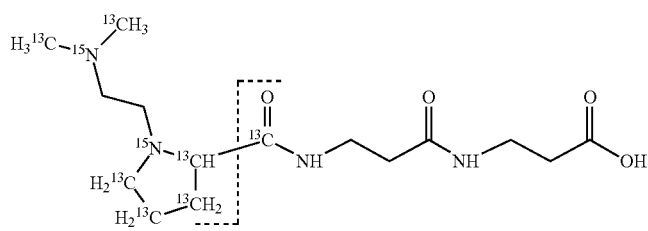
TMT-2-24-149.15282 (Subset 9)
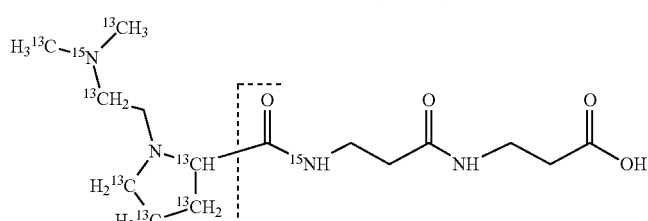
TMT-2-24-149.15914 (Subset 9)
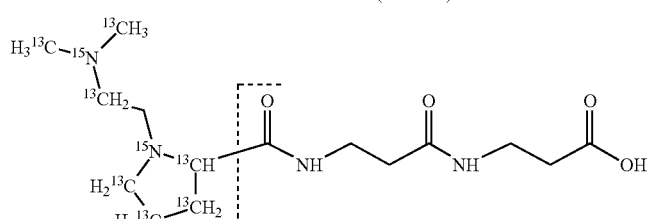
TMT-2-24-150.15618 (Subset 10)

The mass label structure in Set 2 is an isomer of the mass label structure in Set 1 and both give rise in a mass spectrometer to reporter ions with the same masses although with different structures.

Set 3:

The isobaric mass labels may also have the following structure:

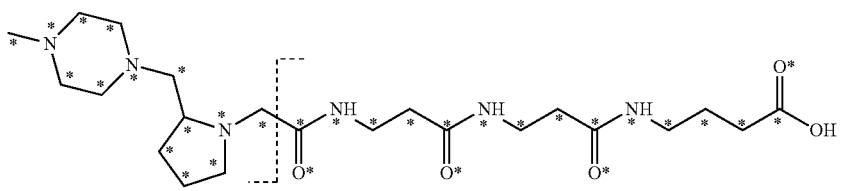

wherein the mass series modifying group * represents that oxygen is replaced (or substituted) by $^{18}O$, carbon by $^{13}C$ or nitrogen by $^{15}N$ or at sites where the hydrogen is present * represents $^{2}H$. One or more positions may be substituted in single label. Preferably more than one position is substituted.

Figure 14:
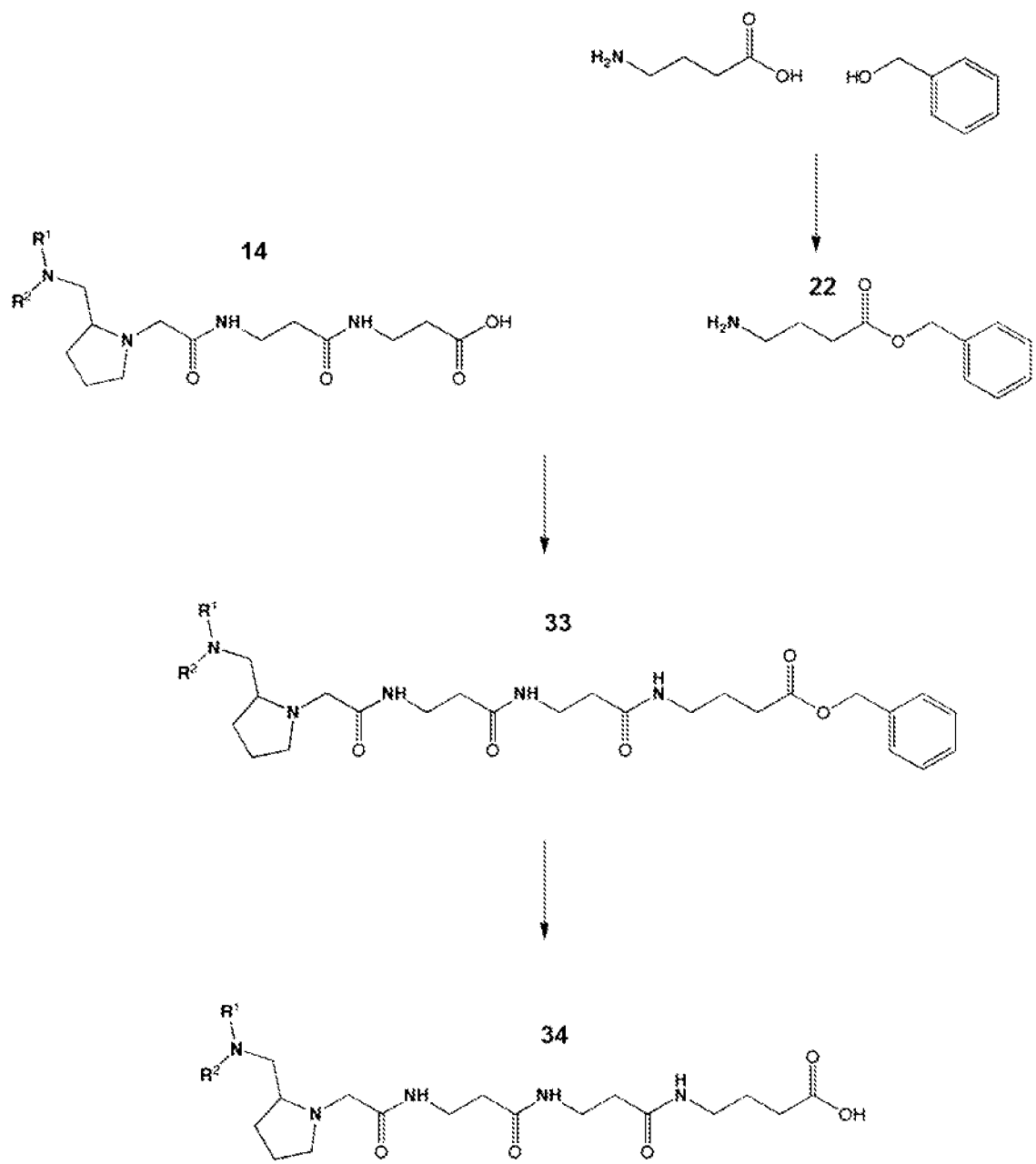
FIG. 14 shows a scheme for the formation of a mass label according to the present invention.

The synthesis of the reporter moiety structure is shown in FIG. 3 using N-methylpiperazine as the secondary amine. Coupling of this reporter moiety structure to two consecutive beta-alanine residues and a Gamma-Amino Butyric Acid (GABA) residue is shown in FIG. 4 and FIG. 14. The scheme shown in FIG. 4 shows the coupling of a reporter moiety according to this invention to two consecutive beta-alanine linkers to give Product 14 in FIG. 4. FIG. 14 shows the further coupling of the double beta-alanine tag (Product 14) from FIG. 4 to a benzyl ester protected GABA linker (22) to give the protected GABA extended product (33). The benzyl ester protecting group is then removed by reduction to yield the free acid form of the tag (34). Set 3 is a specific example of Product 33 where R1 and R2 together form the N-methylpiperazine ring of Set 3. The synthesis of N-methyl piperazine ring is described herein below in the Examples of synthesis section.

In a specific preferred embodiment of an isobaric set of mass labels according to this invention, the mass series modifying group* is $^{13}C$ or 15N and the set comprises n=48 mass labels having the following structures:

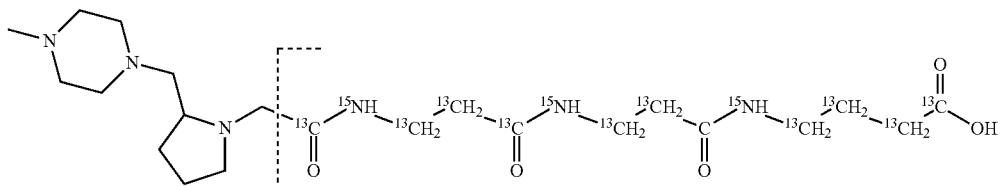

TMT-3-48-196.18082 (Subset 1)

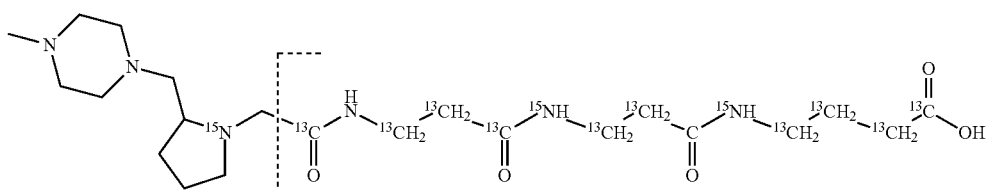

TMT-3-48-197.17786 (Subset 2)

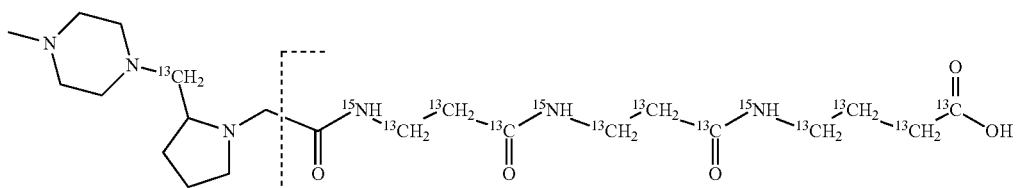

TMT-3-48-197.18418 (Subset 2)

-continued
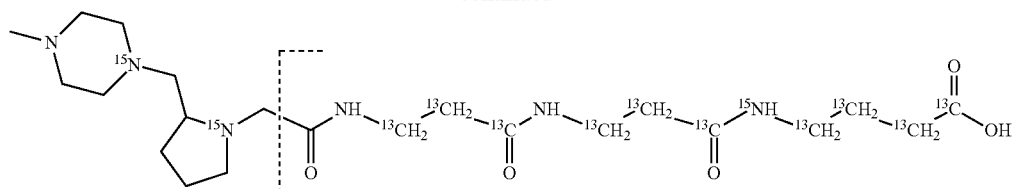
TMT-3-48-198.17489 (Subset 3)
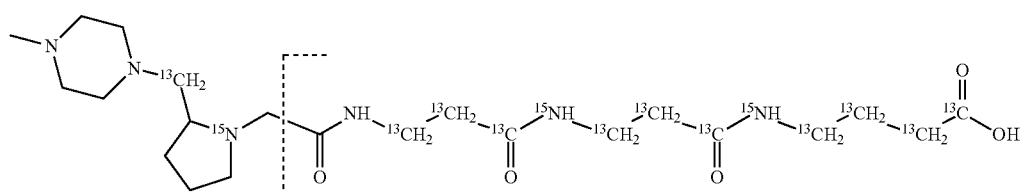
TMT-3-48-198.18121 (Subset 3)
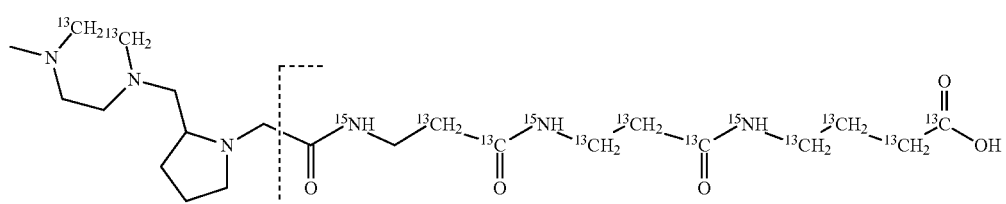
TMT-3-48-198.18753 (Subset 3)
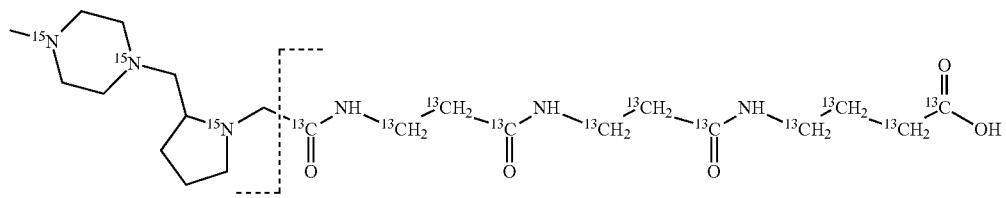
TMT-3-48-199.17193 (Subset 4)
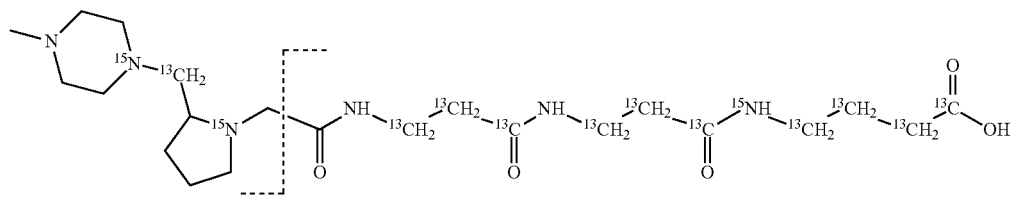
TMT-3-48-199.17825 (Subset 4)
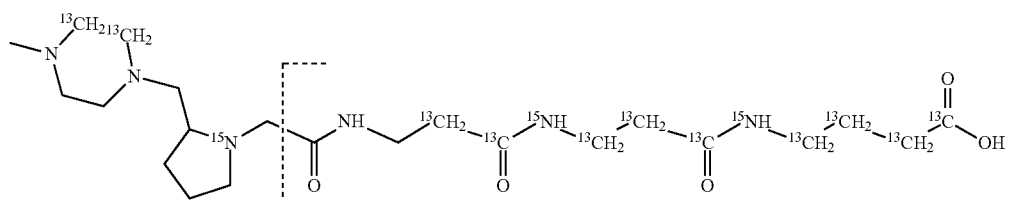
TMT-3-48-199.18457 (Subset 4)
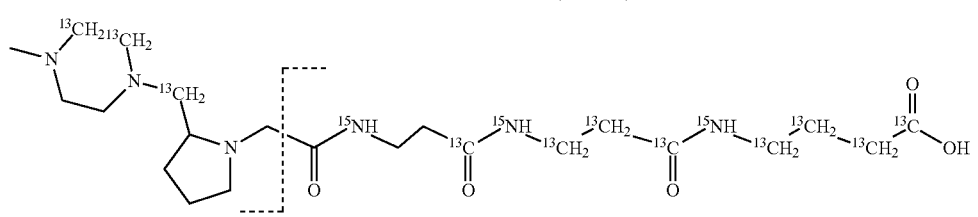
TMT-3-48-199.19089 (Subset 4)

-continued
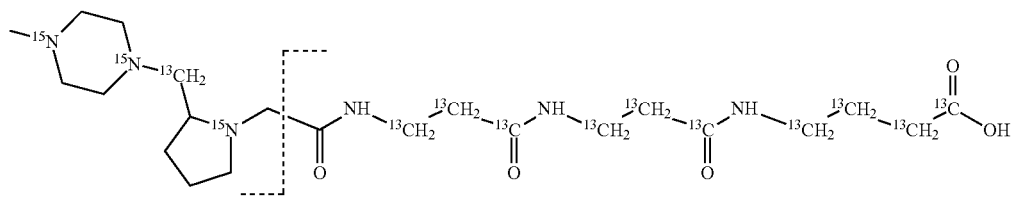
TMT-3-48-200.17528 (Subset 5)
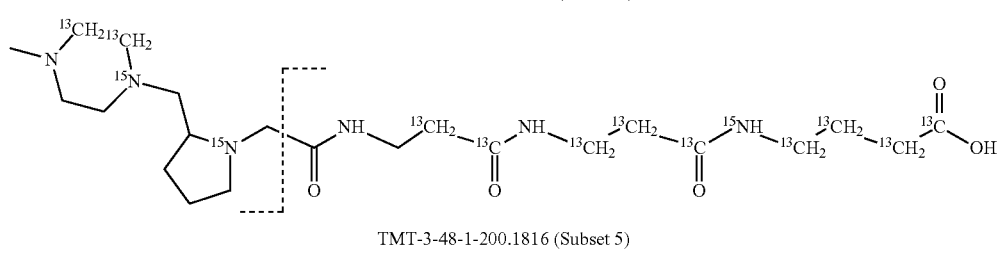
TMT-3-48-1-200.1816 (Subset 5)
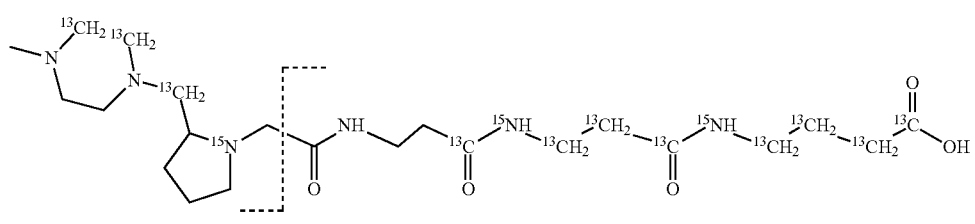
TMT-3-48-200.18792 (Subset 5)
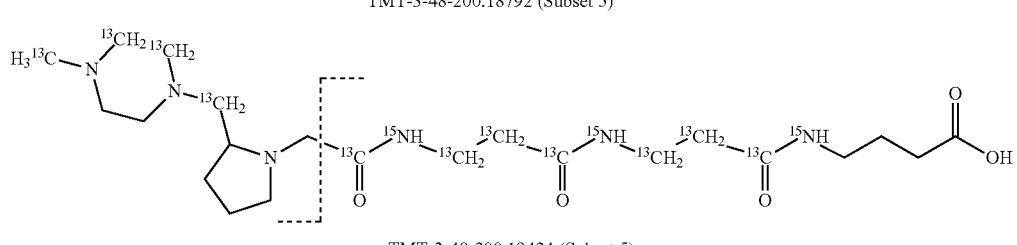
TMT-3-48-200.19424 (Subset 5)
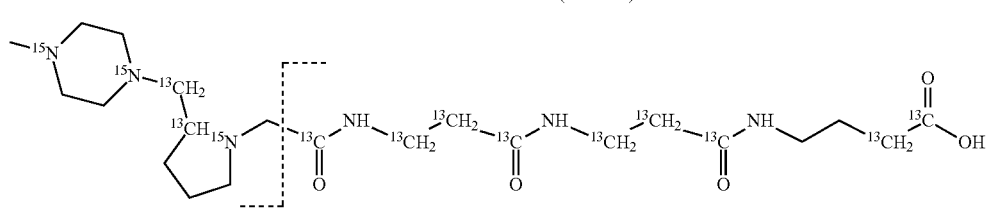
TMT-3-48-201.17864 (Subset 6)
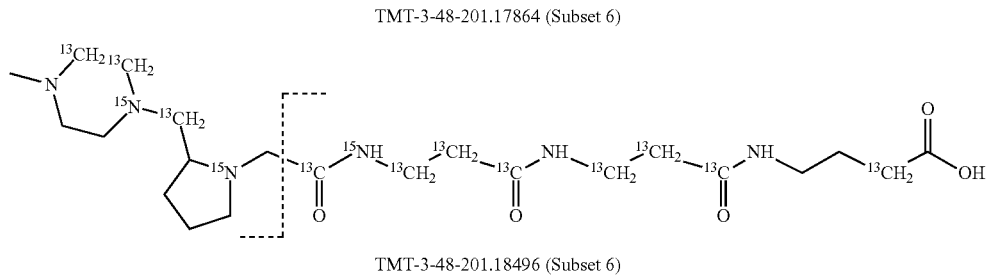
TMT-3-48-201.18496 (Subset 6)
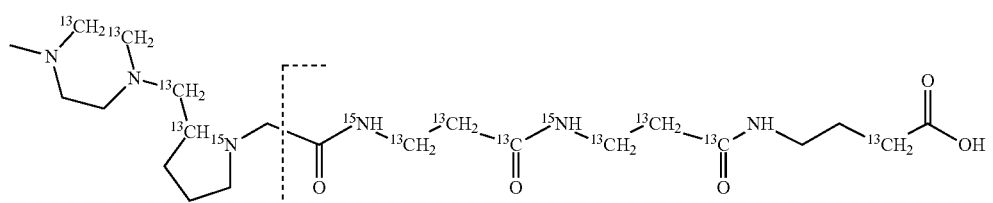
TMT-3-48-201.19128 (Subset 6)

-continued
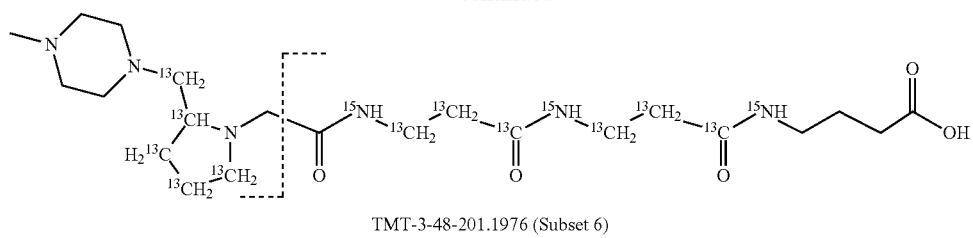
TMT-3-48-201.1976 (Subset 6)
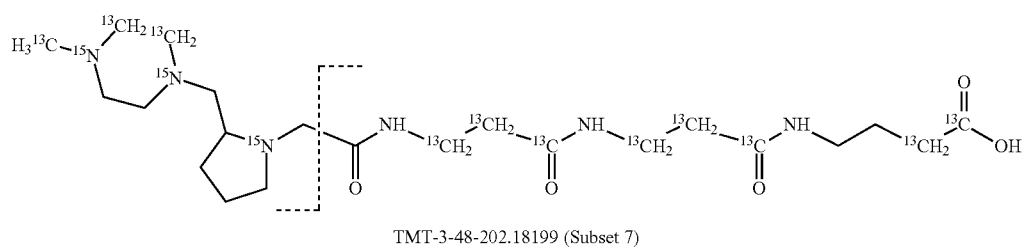
TMT-3-48-202.18199 (Subset 7)
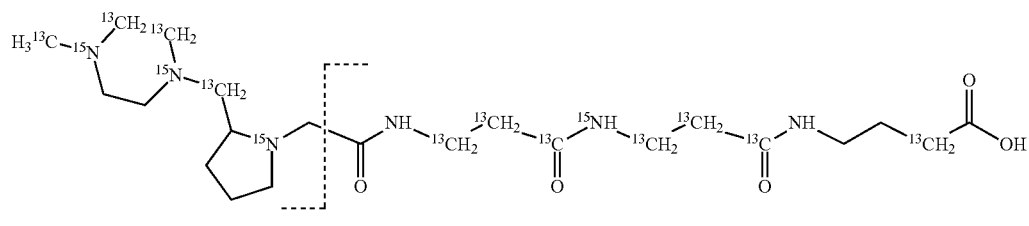
TMT-3-48-202.18831 (Subset 7)
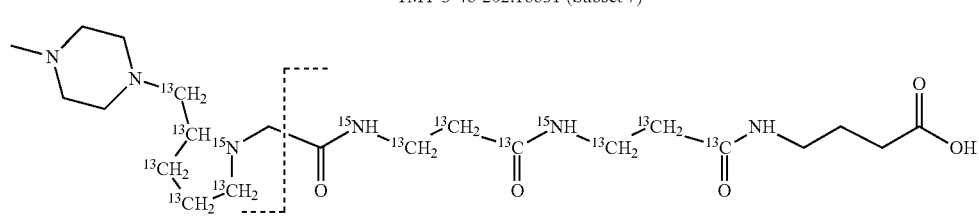
TMT-3-48-202.19463 (Subset 7)
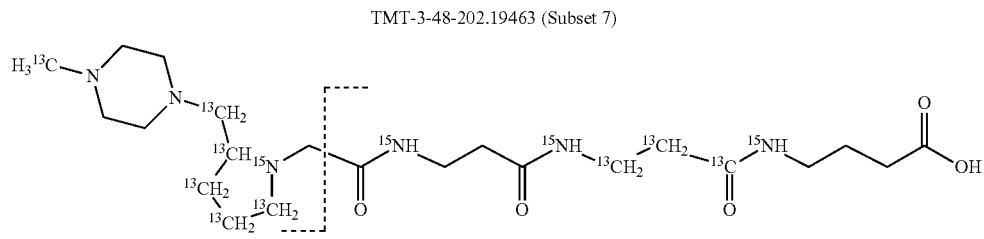
TMT-3-48-202.20095 (Subset 7)
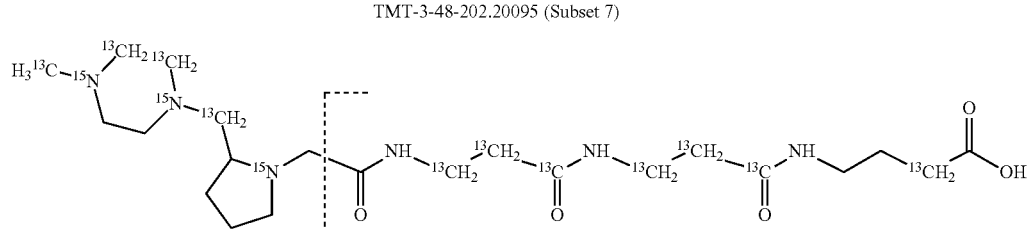
TMT-3-48-203.18535 (Subset 8)
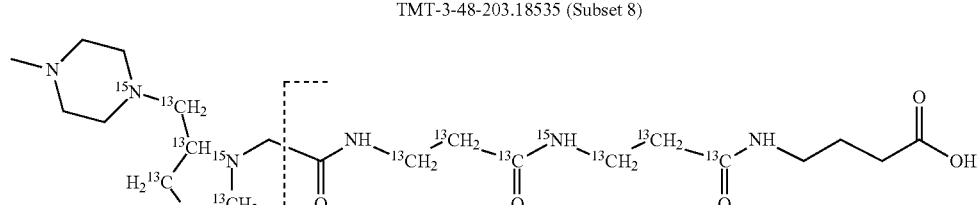
TMT-3-48-203.19167 (Subset 8)

-continued
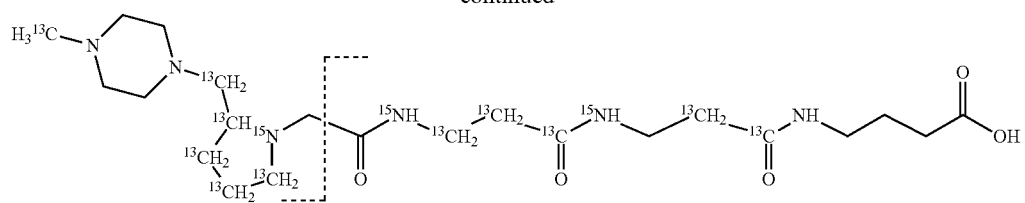
TMT-3-48-203.19799 (Subset 8)
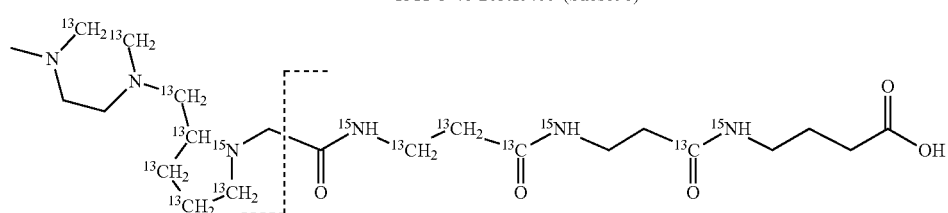
TMT-3-48-203.20431 (Subset 8)
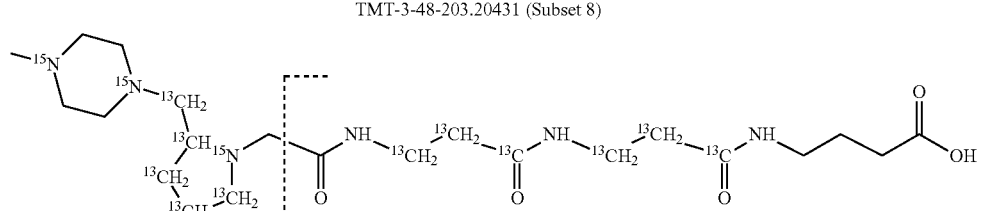
TMT-3-48-204.1887 (Subset 9)
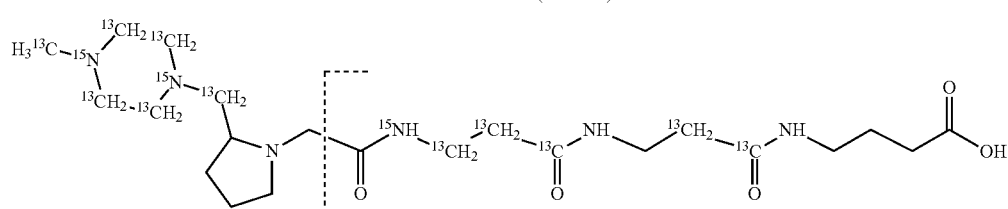
TMT-3-48-204.19502 (Subset 9)
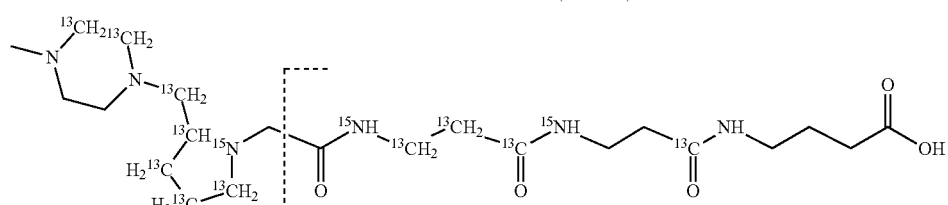
TMT-3-48-204.20134 (Subset 9)
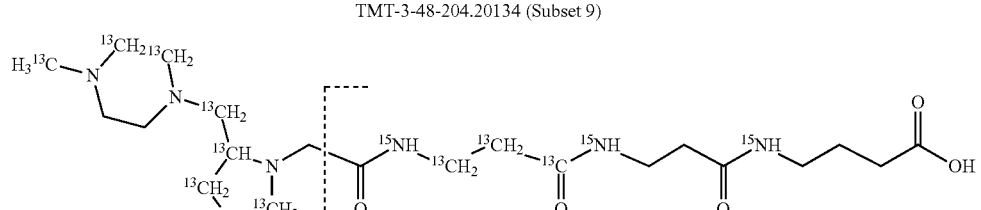
TMT-3-48-204.20766 (Subset 9)
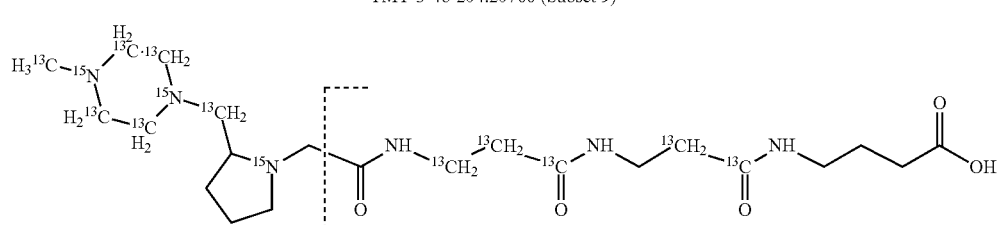
TMT-3-48-205.19206 (Subset 10)

-continued
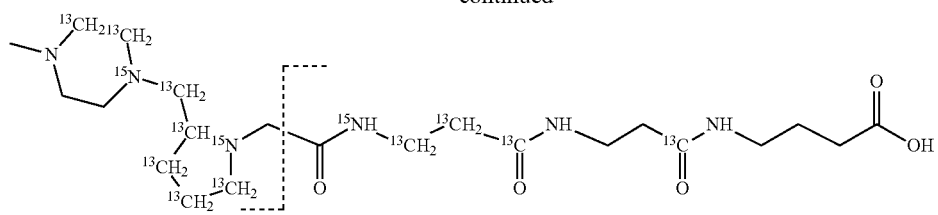
TMT-3-48-205.19838 (Subset 10)
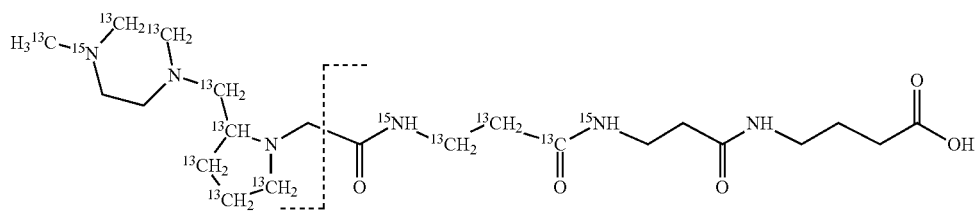
TMT-3-48-205.2047 (Subset 10)
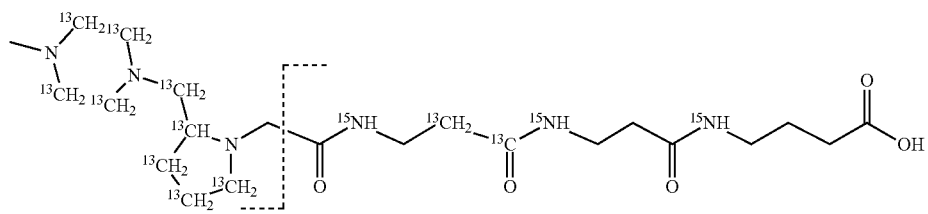
TMT-3-48-205.21102 (Subset 10)
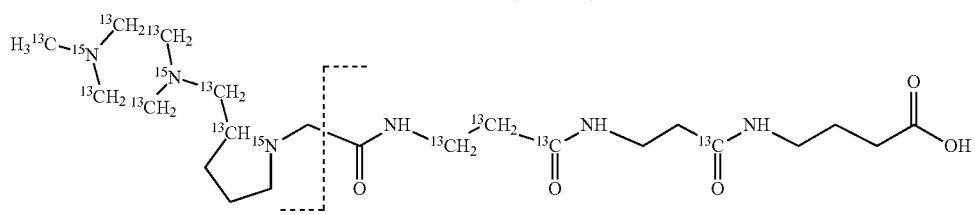
TMT-3-48-206.19541 (Subset 11)
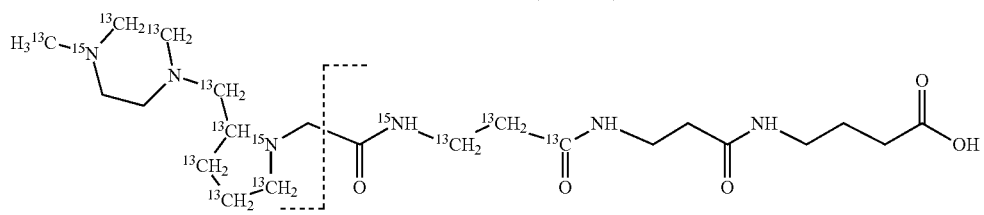
TMT-3-48-206.20173 (Subset 11)
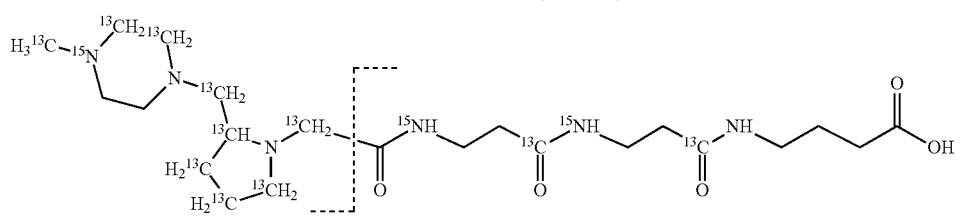
TMT-3-48-206.20805 (Subset 11)
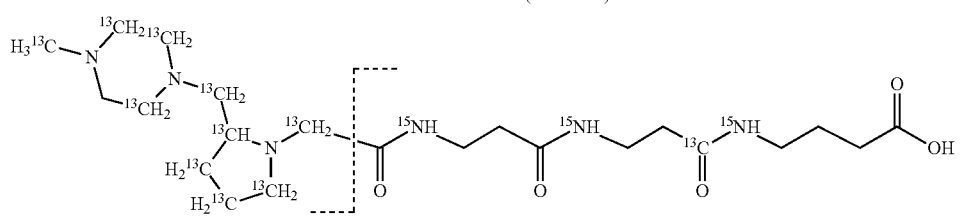
TMT-3-48-206.21437 (Subset 11)

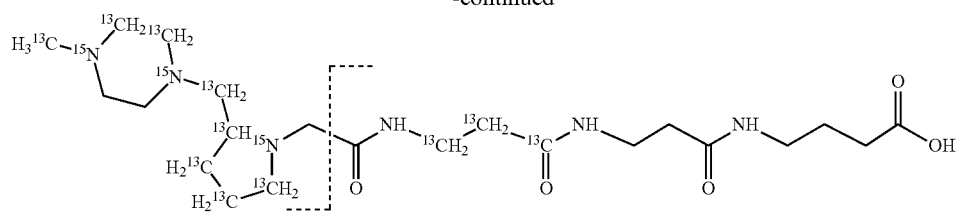
TMT-3-48-207.19877 (Subset 12)
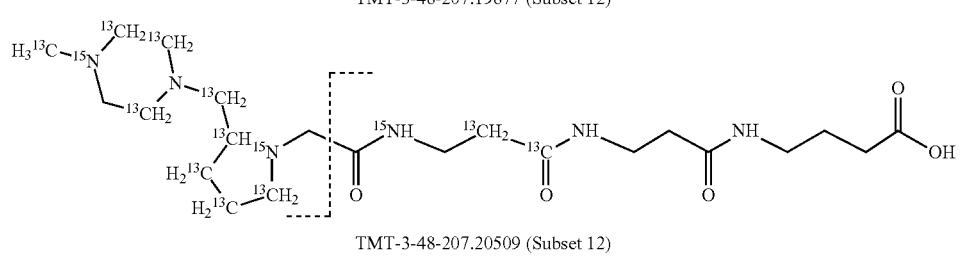
TMT-3-48-207.20509 (Subset 12)
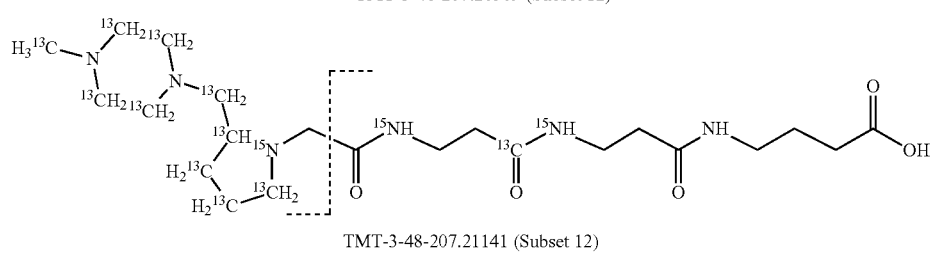
TMT-3-48-207.21141 (Subset 12)
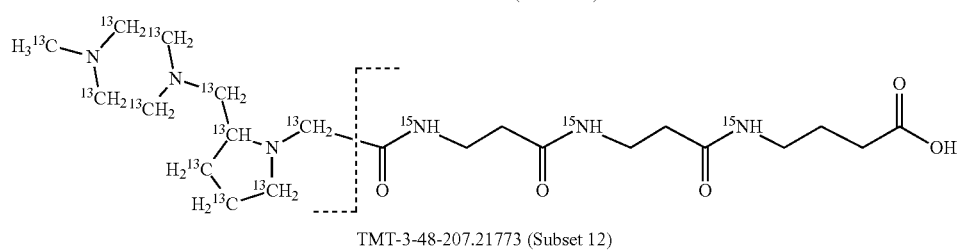
TMT-3-48-207.21773 (Subset 12)
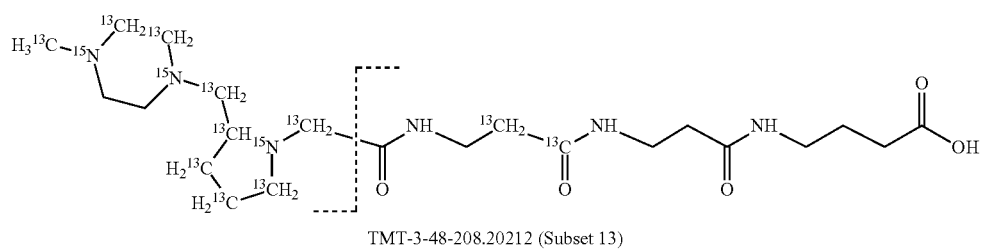
TMT-3-48-208.20212 (Subset 13)
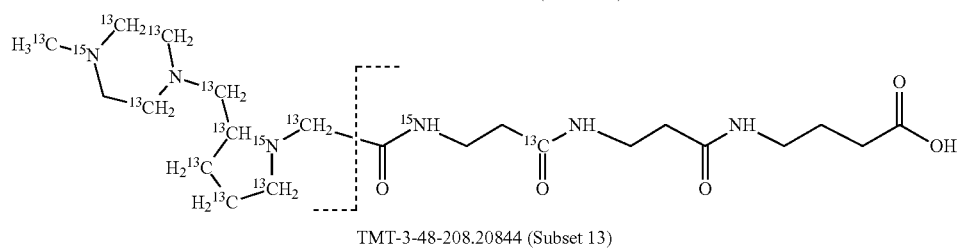
TMT-3-48-208.20844 (Subset 13)
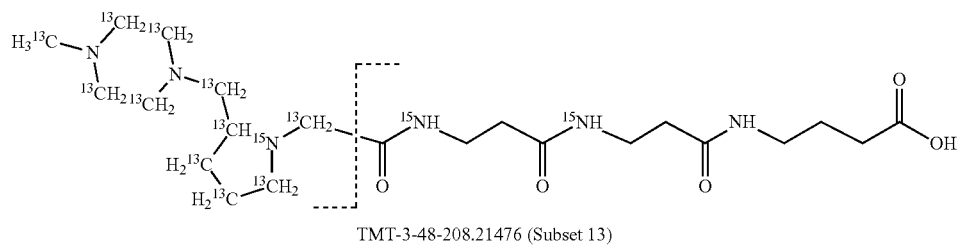
TMT-3-48-208.21476 (Subset 13)

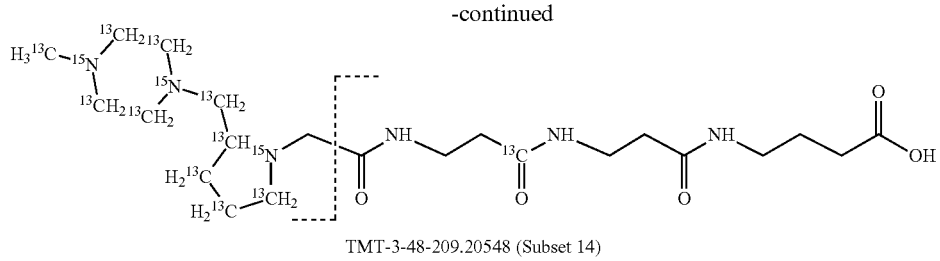

TMT-3-48-209.20548 (Subset 14)

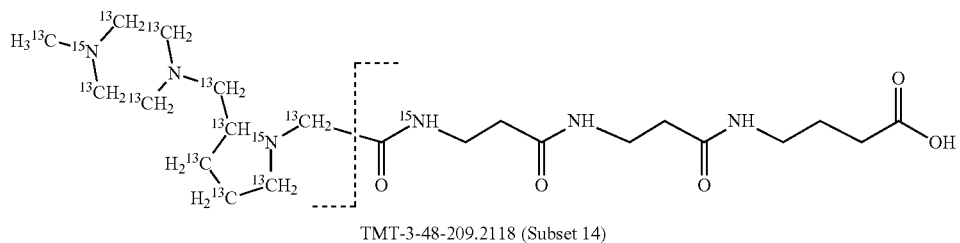

TMT-3-48-209.2118 (Subset 14)

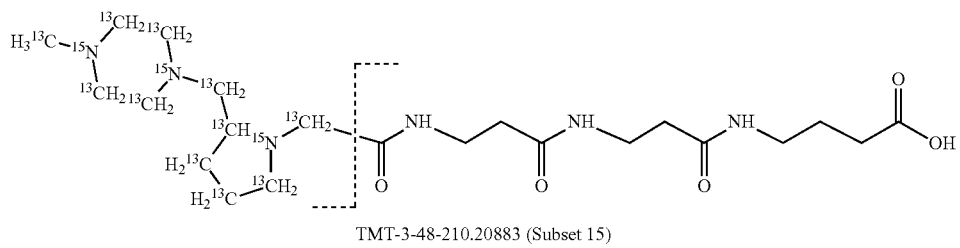

TMT-3-48-210.20883 (Subset 15)

The corresponding isomer of the reporter moiety (left of the dashed line) in Set 3 can be synthesized according to the scheme in FIG. 5 and would also give rise to an isobaric 48-plex set of tags having the general structure:

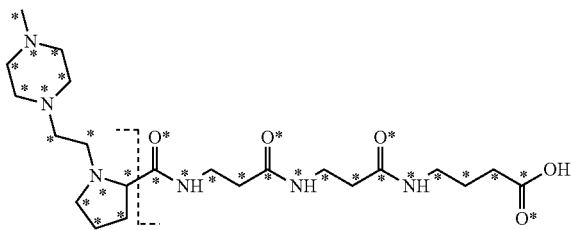

The limitation on the multiplexing rate for a single isobaric mass labels set, such as Sets 1, 2 and 3 described above can be overcome by providing multiple sets each carrying a unique additional mass, for example in the form of one or more beta-alanine moieties. The additional mass is provided by a mass series modifying group according to the present invention. The concept of introducing a unique additional mass series modifying group into the mass modifier M is described in U.S. Pat. No. 7,294,456 and in WO2011036059 which references are both incorporated herein. It is, thus, possible to develop arrays of isobaric mass label sets by adding additional beta-alanine moieties into the linker L of commercially available 6-plex Tandem Mass Tag Dimethylpiperazine-Beta-Alanine tag structures. Such a unitary approach provides a rapid and inexpensive means of increasing the multiplexing rate from 6 to 12, 18, 24 or more samples. The isobaric mass label sets of this invention may also be modified by introduction of additional linkers.

For example, the synthesis of the mass labels of Set 1 can be modified by introduction of a further undoped gamma amino butyric acid (GABA) molecule in the linker L as shown in FIG. 14 to give a different set of 24 mass labels that is differentiated from the mass labels in Set 1 by the mass of a GABA molecule. Clearly, a further set of 24 mass labels can be created by adding an undoped beta-alanine to the structure of the mass labels in Set 1. Moreover, a further set of 24 mass labels can be created by adding a doped beta-alanine linker to every mass labels in Set 1, where the additional beta-alanine comprises a fixed substitution of three $^{13}C$ nuclei and a $^{15}N$ nucleus.

Introducing additional masses to the mass labels disclosed herein and alternate means are contemplated within the scope of the present invention.

Surprisingly, it has been found that modifications of the mass of a mass label may be applied to the reporter moiety via a highly advantageous novel method as discussed below for the mass labels of Sets 4 to 9, in particular, that a mass series modifying group can be added to the reporter moiety. It has been found by the present inventors that these modifications of the reporter moiety already discussed for Embodiments 1-6 are highly advantageous and they will be further discussed in reference to Sets 4 to 9 below.

Set 4:

The isobaric mass labels may also have the following structure:

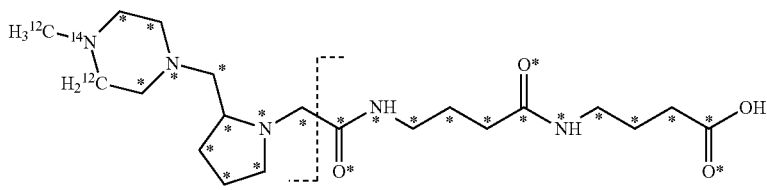

wherein the mass series modifying group * represents that oxygen is replaced (or substituted) $^{18}O$, carbon by $^{13}C$ or nitrogen by $^{15}N$ or at sites where the hydrogen is present * represents $^2H$. One or more positions may be substituted in single label. Preferably more than one position is substituted.

The N-methyl group substituted into the piperazine ring in the reporter moiety has a fixed substitution of 3 hydrogen atoms and a single $^{12}C$ atom. Furthermore the methyl-substituted nitrogen atom in the piperazine ring has a fixed substitution of $^{14}N$. There is a further fixed substitution of a single $^{12}C$ atom into the piperazine ring. The term 'fixed substitution' means that every mass label in this Set has this substitution in the reporter moiety, although the precise location of the substitution in the reporter moiety can vary.

Figure 15:
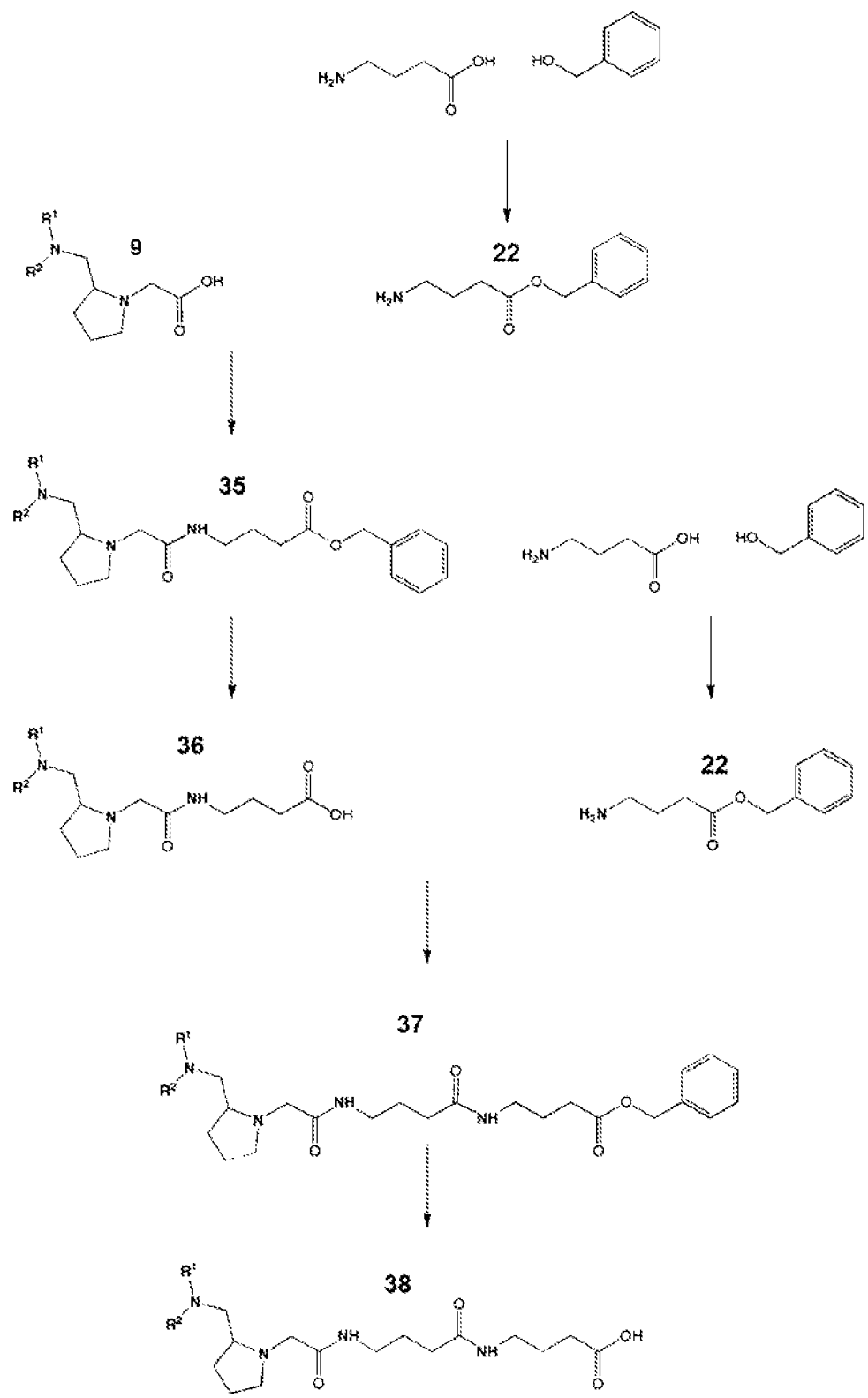
FIG. 15 shows a scheme for the formation of a mass label according to the present invention.

The synthesis of the reporter moiety structure is shown in FIG. 3 using N-methylpiperazine as the secondary amine and as described herein below in the Examples of synthesis section. Coupling of this reporter moiety structure to two consecutive gamma-amino butyric acid residues is shown in FIG. 15. FIG. 15 shows a schematic diagram of a generalised synthetic route for coupling of amino acid linkers to the reporter groups of this invention. In short, gamma-amino butyric acid (GABA), or an isotope thereof, is protected as a benzyl ester (22). The carboxyl-protected GABA linker (22) can then be coupled to the free carboxylic acid of the reporter group from FIG. 3 (9) to give the singly extended reporter structure (35). The benzyl ester protecting group is then removed, typically by reduction with hydrogen in the presence of palladium catalyst, to liberate the free carboxylic acid (36), which is then coupled to a further benzyl ester protected GABA linker (22) to give the protected double-GABA extended reporter (37). Finally, the benzyl ester protecting group is removed as described above for FIG. 3 to yield the finished tag as a free acid (38).

In a preferred embodiment of an isobaric set of mass labels, the set comprises n=30 mass labels having the following structures:

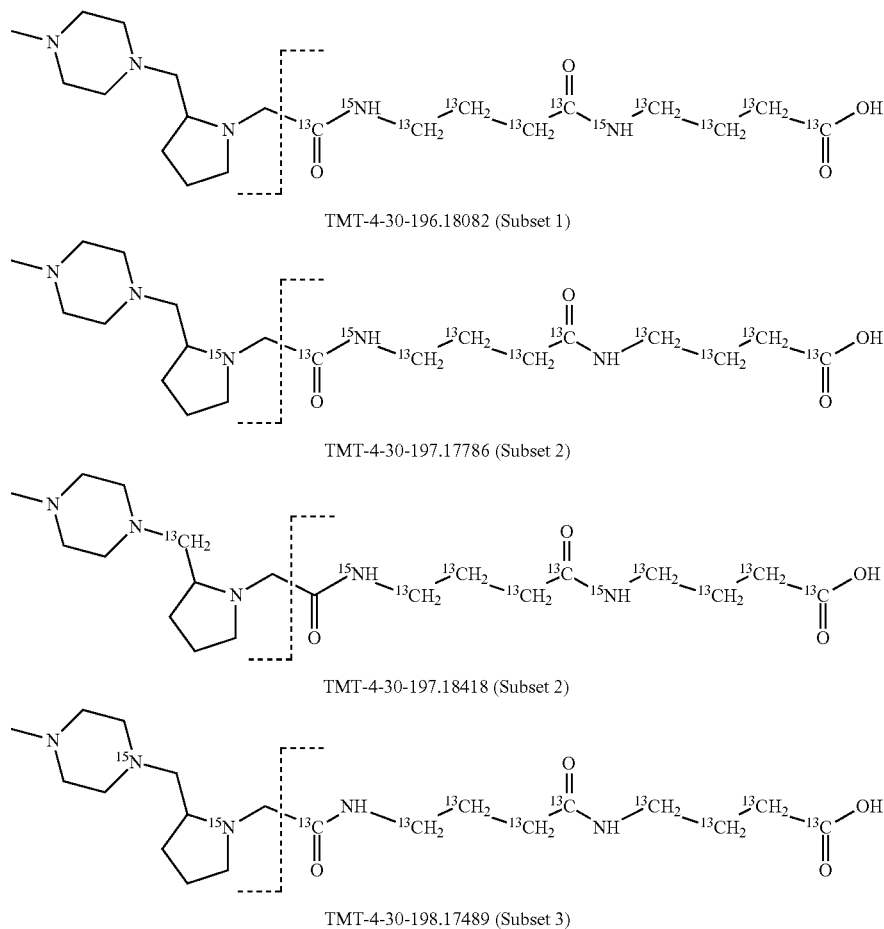

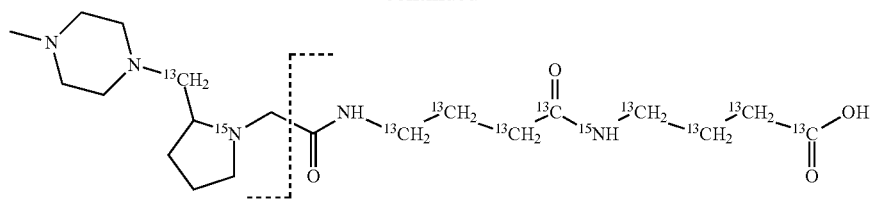
TMT-4-30-198.18121 (Subset 3)
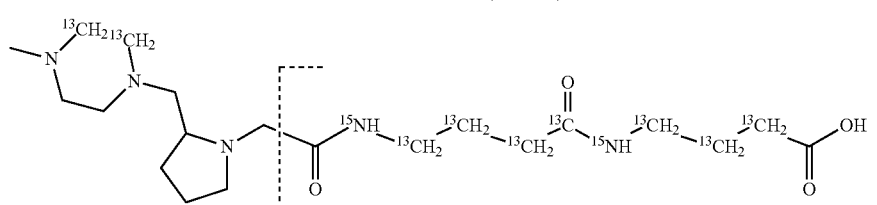
TMT-4-30-198.18753 (Subset 3)
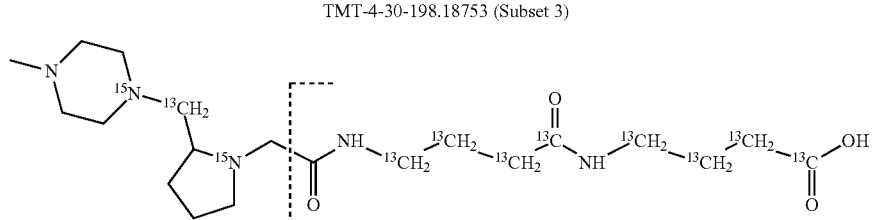
TMT-4-30-199.17825 (Subset 4)
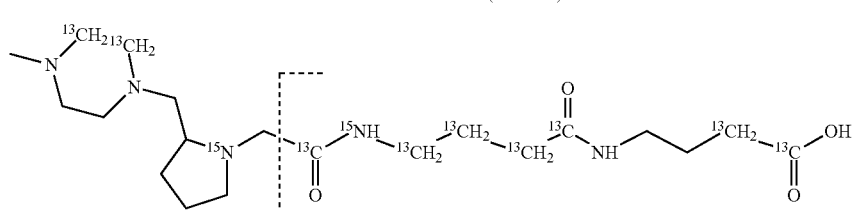
TMT-4-30-199.18457 (Subset 4)
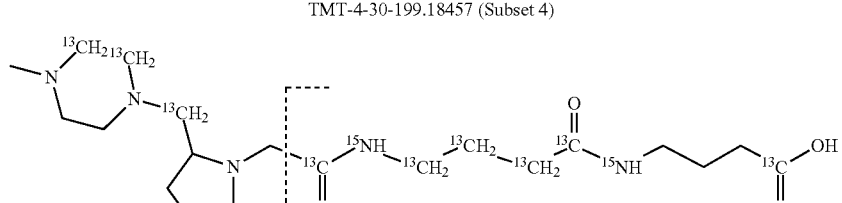
TMT-4-30-199.19089 (Subset 4)
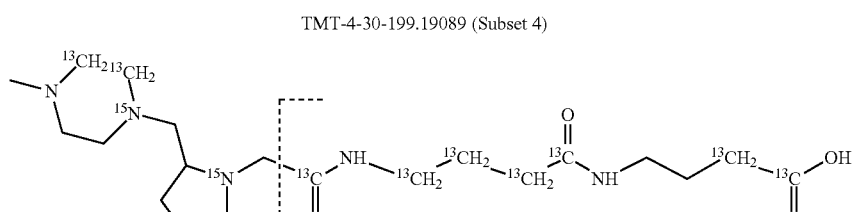
TMT-4-30-200.1816 (Subset 5)
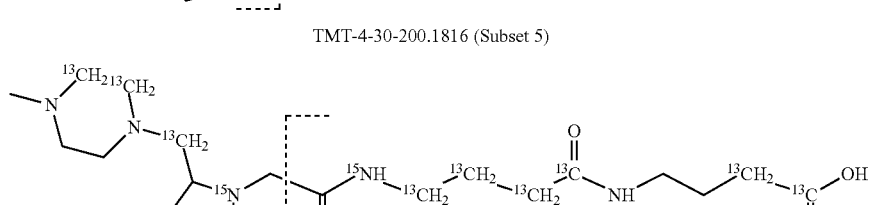
TMT-4-30-200.18792 (Subset 5)

-continued
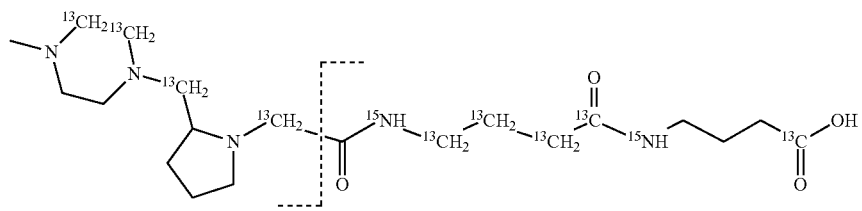
TMT-4-30-200.19424 (Subset 5)
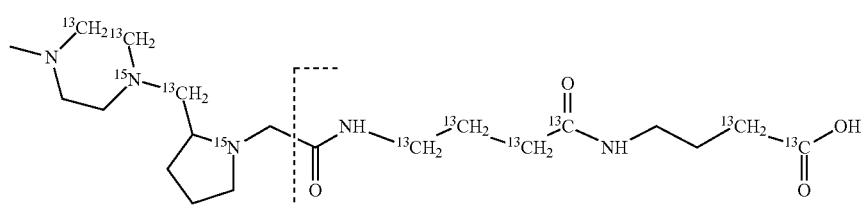
TMT-4-30-201.18496 (Subset 6)
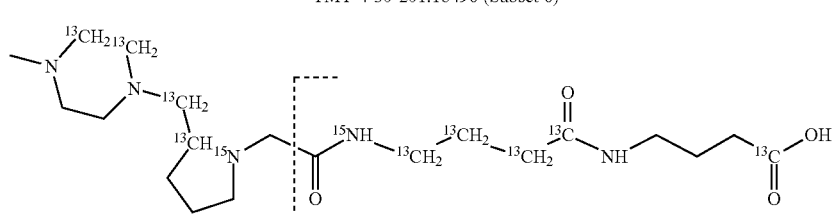
TMT-4-30-201.19128 (Subset 6)
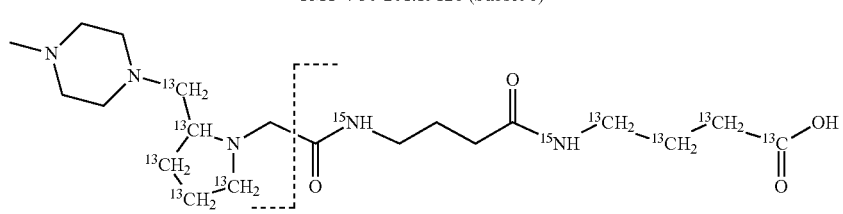
TMT-4-30-201.1976 (Subset 6)
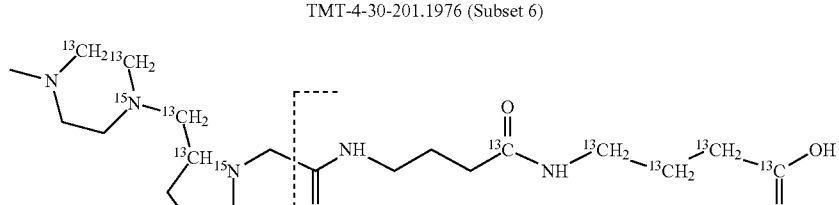
TMT-4-30-202.18831 (Subset 7)
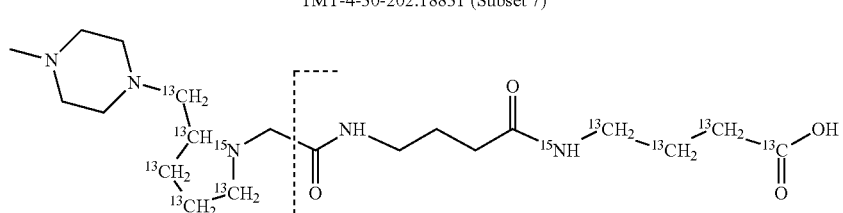
TMT-4-30-202.19463 (Subset 7)
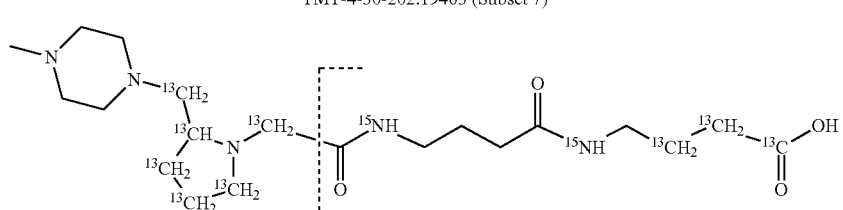
TMT-4-30-202.20095 (Subset 7)

-continued
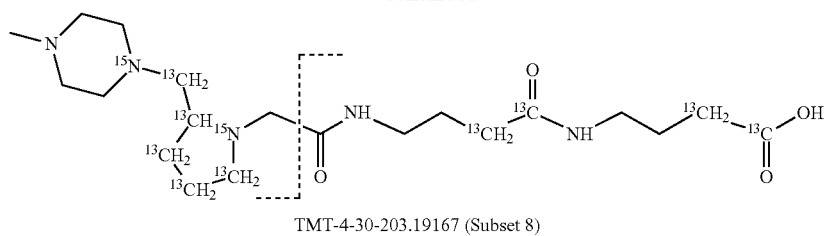
TMT-4-30-203.19167 (Subset 8)
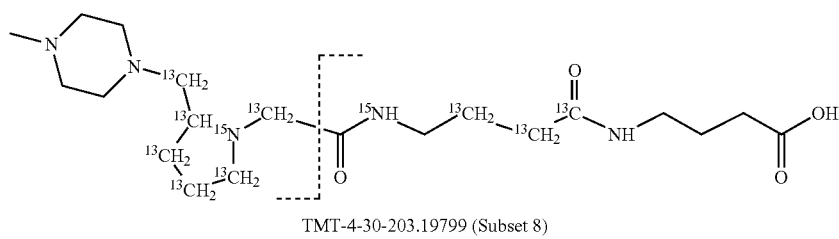
TMT-4-30-203.19799 (Subset 8)
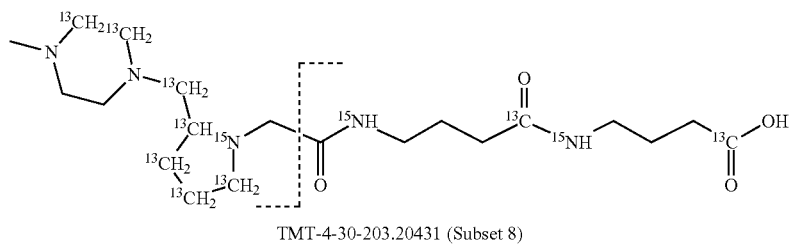
TMT-4-30-203.20431 (Subset 8)
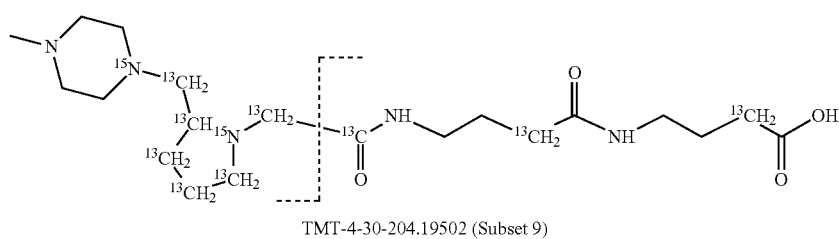
TMT-4-30-204.19502 (Subset 9)
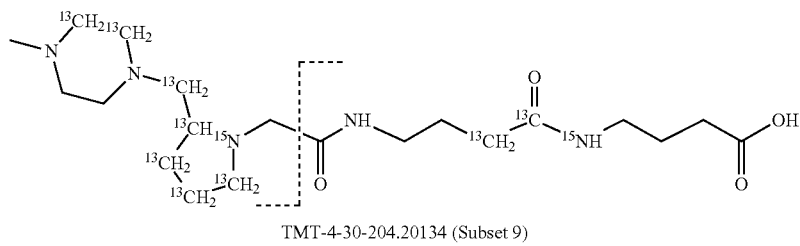
TMT-4-30-204.20134 (Subset 9)
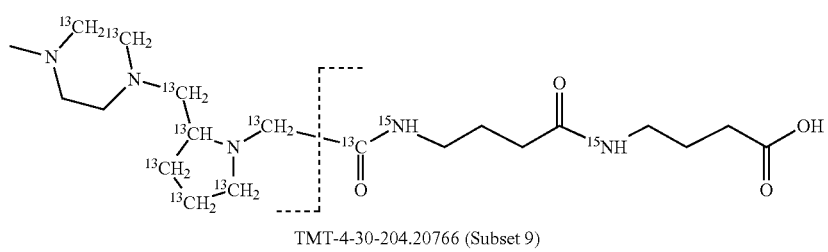
TMT-4-30-204.20766 (Subset 9)
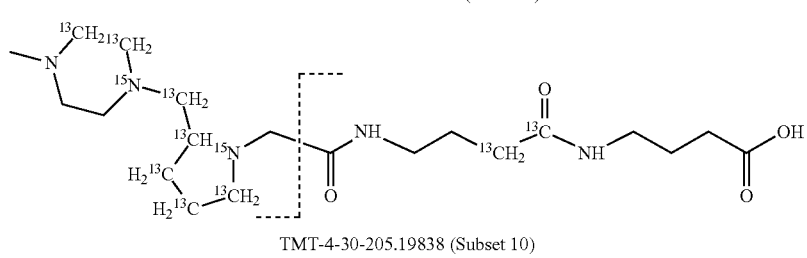
TMT-4-30-205.19838 (Subset 10)

-continued

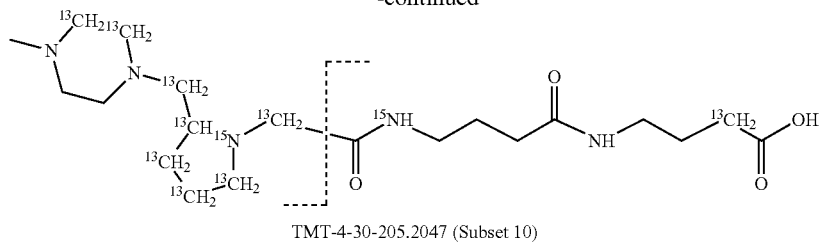
TMT-4-30-205.2047 (Subset 10)

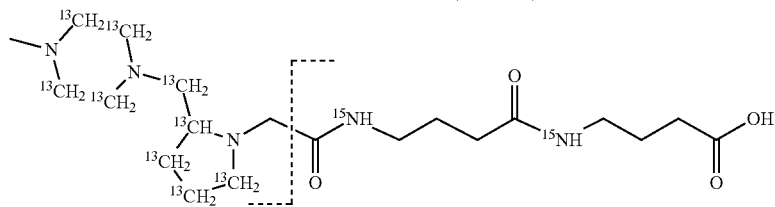
TMT-4-30-205.21102 (Subset 10)

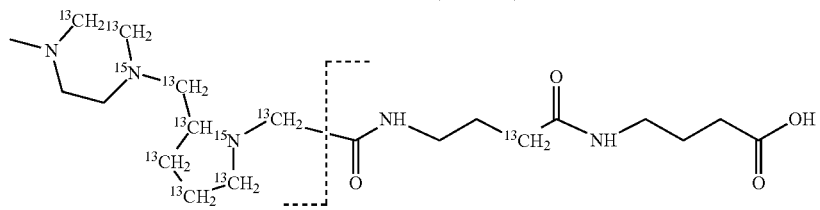
TMT-4-30-206.20173 (Subset 11)

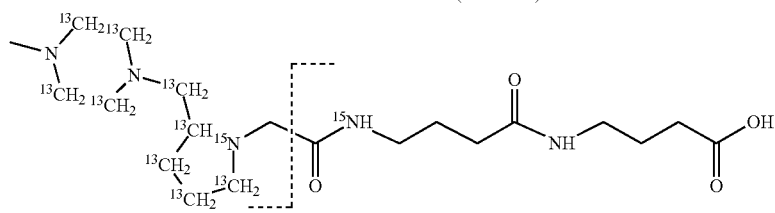
TMT-4-30-206.20805 (Subset 11)

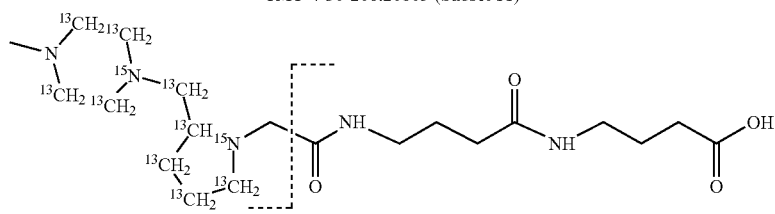
TMT-4-30-207.20509 (Subset 12)

It should be noted that although the fixed substitutions of $^2H$, $^{13}C$ and $^{15}N$ are shown in a particular location in the mass labels shown above, this has been done as a convenience for the purposes of explanation and these fixed substitutions in Set 4 could be located at any suitable position within the reporter ion if it is more convenient or cost-effective to locate them elsewhere. In this example, the fixed substituents are shown in a different location in TMT-4-30-205.21102, TMT-4-30-206.20805 and TMT-4-30-207.20509.

Set 5:

The isobaric mass labels may also have the following structure:

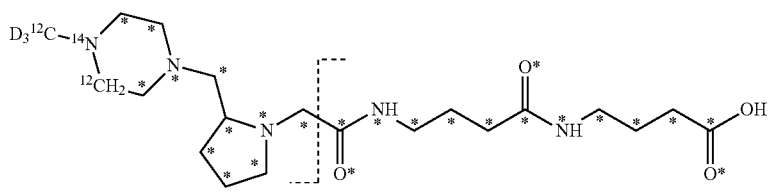

wherein the mass series modifying group * represents that oxygen is replaced (or substituted) by $^{18}O$, carbon by $^{13}C$ or nitrogen by $^{15}N$ or at sites where the hydrogen is present * represents $^{2}H$. One or more positions may be substituted in single label. Preferably more than one position is substituted.

The N-methyl group substituted into the piperazine ring has a fixed substitution of 3 deuterium atoms and a fixed substitution of $^{12}C$. In addition one of the nitrogen atoms in the piperazine ring of the reporter has a fixed substitution of $^{14}N$ and one of the carbon atoms in the piperazine ring has a fixed substitution of $^{12}C$. These fixed substitutions in this example mean that the reporter moieties of the mass labels of Set 5 have a fixed mass offset relative to the reporter moieties of the mass labels of Set 4, thus the lightest reporter moieties in Set 4 will be approximately 3 daltons lighter than the lightest reporter moieties in Set 5. The deuterium substitutions in Set 5 also mean that all the reporter moieties in Set 5 will have a different exact mass from every reporter in Set 4 despite some reporter moieties having the same mass. However, some of the mass differences will be very small.

The synthesis of the reporter moieties structure is shown in FIG. 3 using N-methylpiperazine as the secondary amine. Coupling of this reporter moiety structure to two consecutive gamma-amino butyric acid residues is shown in FIG. 15.

In a preferred embodiment of an isobaric set of mass labels, the set comprises n=30 mass labels having the following structures:

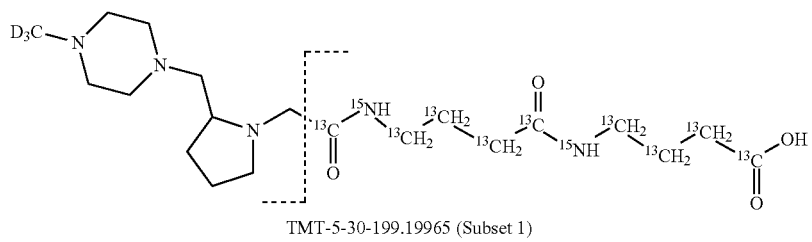
TMT-5-30-199.19965 (Subset 1)

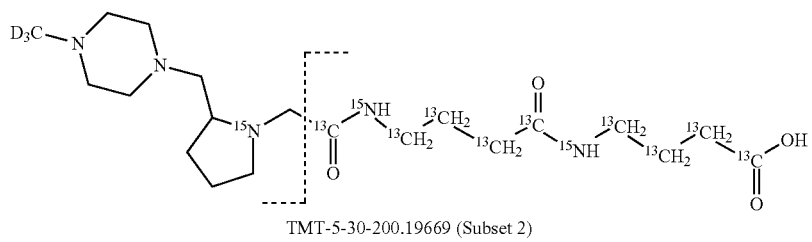
TMT-5-30-200.19669 (Subset 2)

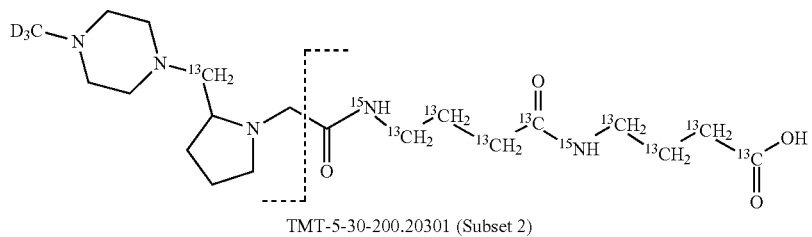
TMT-5-30-200.20301 (Subset 2)

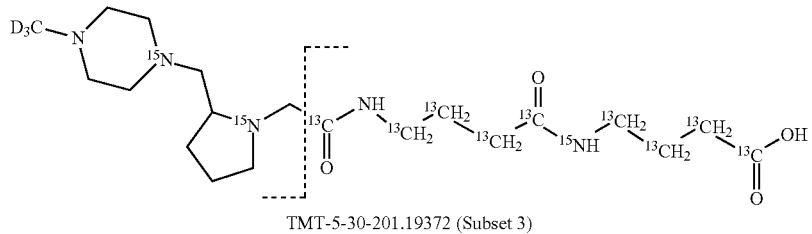
TMT-5-30-201.19372 (Subset 3)

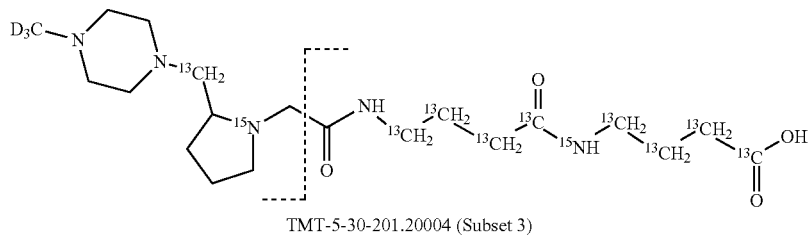
TMT-5-30-201.20004 (Subset 3)

-continued
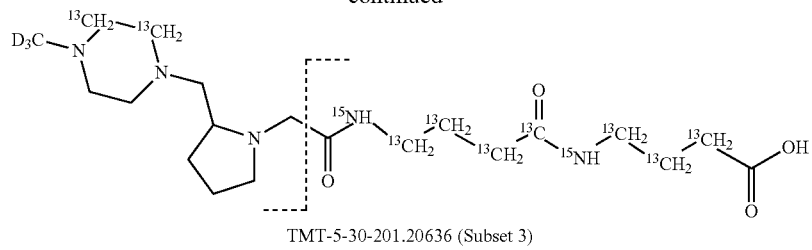
TMT-5-30-201.20636 (Subset 3)
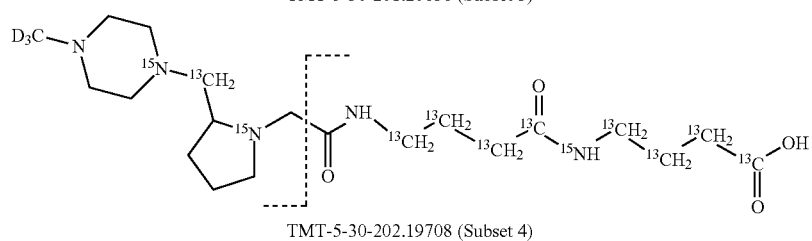
TMT-5-30-202.19708 (Subset 4)
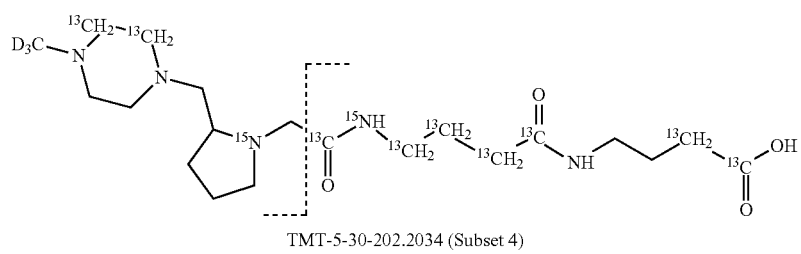
TMT-5-30-202.2034 (Subset 4)
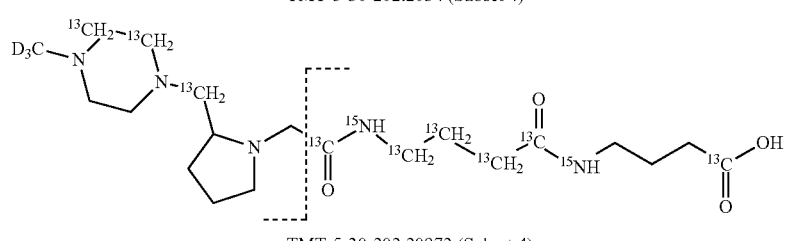
TMT-5-30-202.20972 (Subset 4)
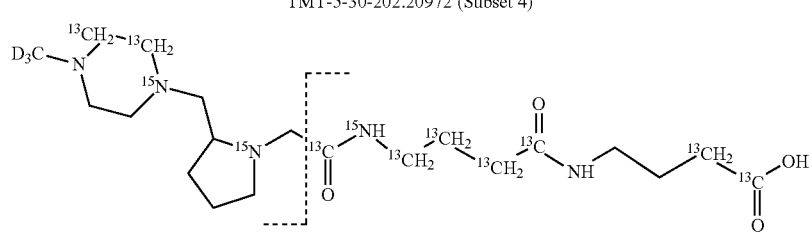
TMT-5-30-203.20043 (Subset 5)
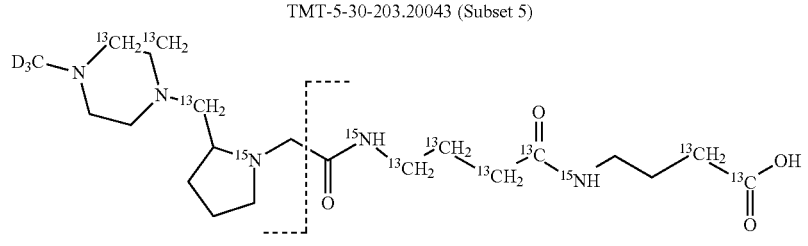
TMT-5-30-203.20675 (Subset 5)
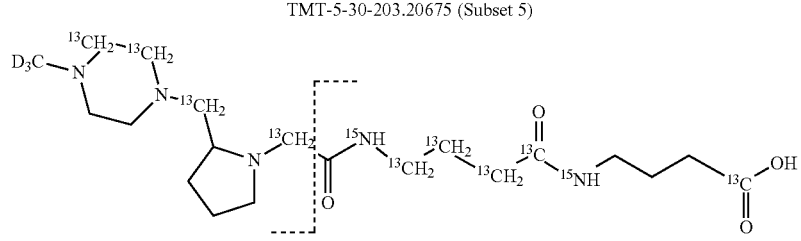
TMT-5-30-203.21307 (Subset 5)

-continued
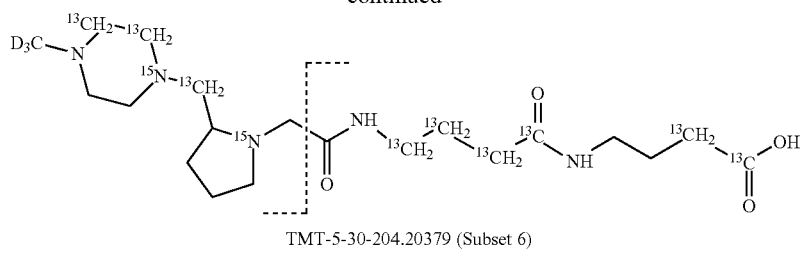
TMT-5-30-204.20379 (Subset 6)
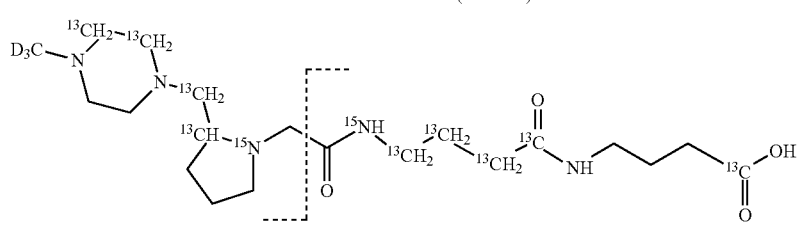
TMT-5-30-204.21066 (Subset 6)
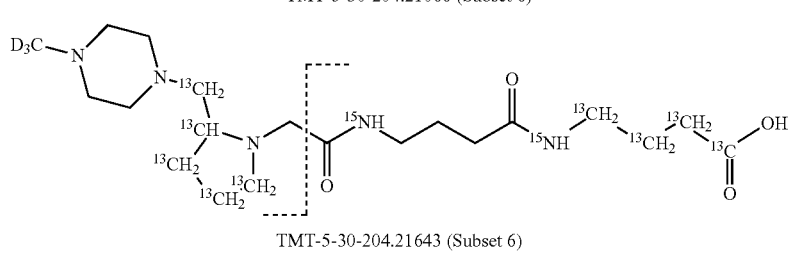
TMT-5-30-204.21643 (Subset 6)
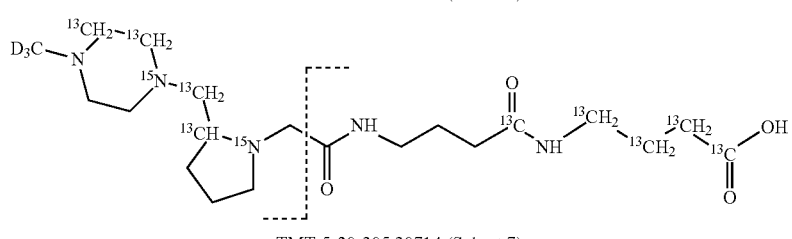
TMT-5-30-205.20714 (Subset 7)
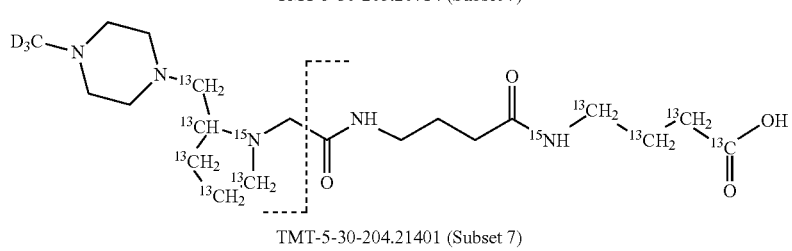
TMT-5-30-204.21401 (Subset 7)
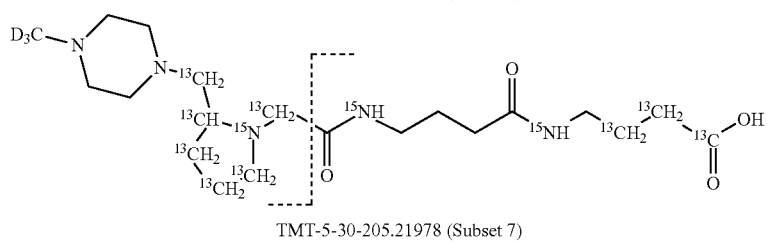
TMT-5-30-205.21978 (Subset 7)
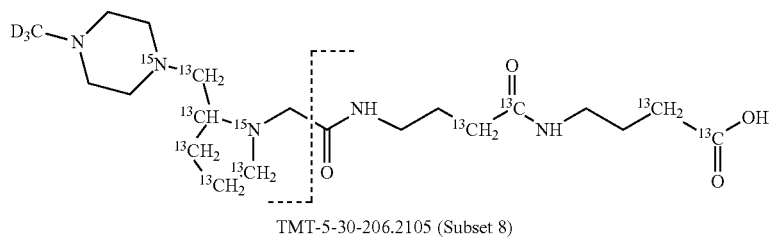
TMT-5-30-206.2105 (Subset 8)

-continued
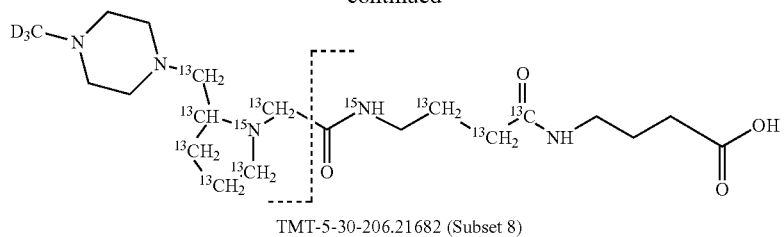
TMT-5-30-206.21682 (Subset 8)
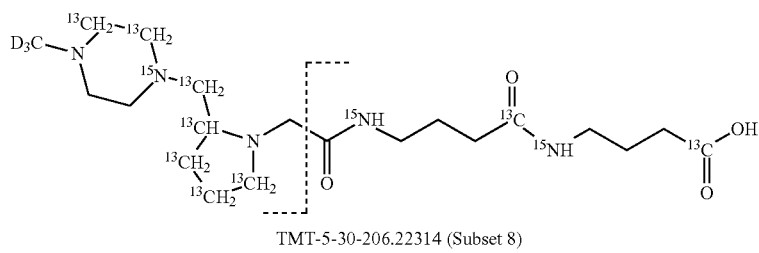
TMT-5-30-206.22314 (Subset 8)
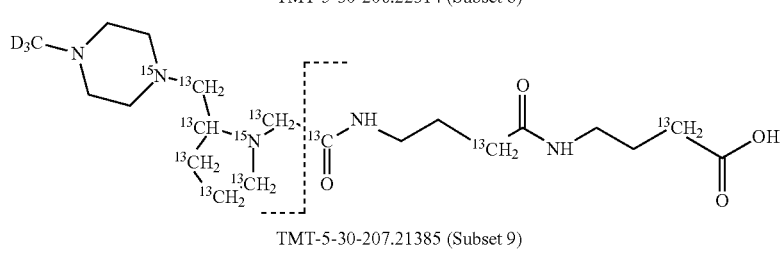
TMT-5-30-207.21385 (Subset 9)
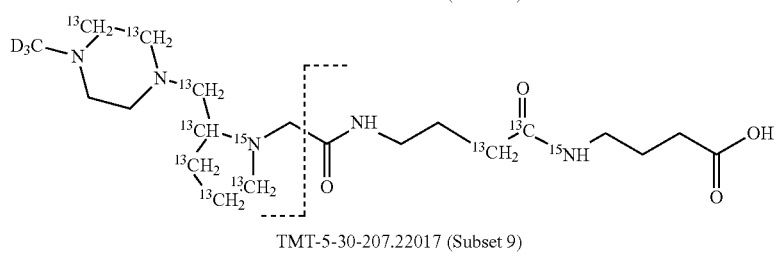
TMT-5-30-207.22017 (Subset 9)
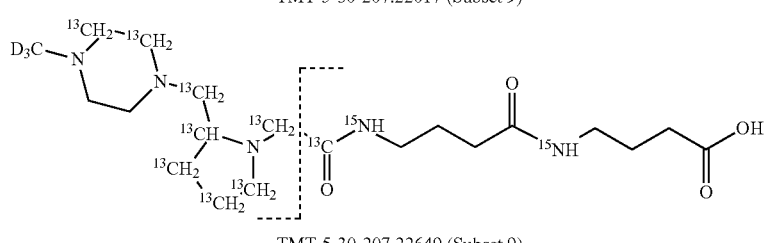
TMT-5-30-207.22649 (Subset 9)
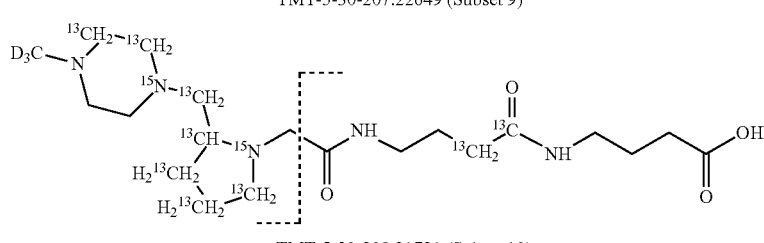
TMT-5-30-208.21721 (Subset 10)
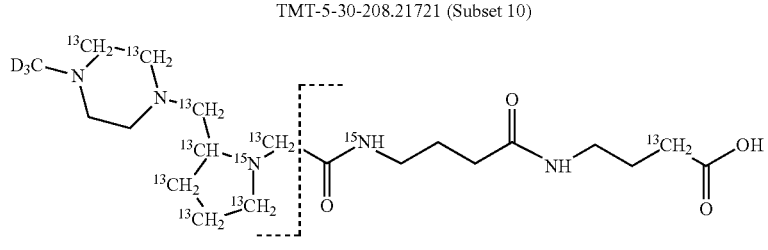
TMT-5-30-208.22353 (Subset 10)

-continued

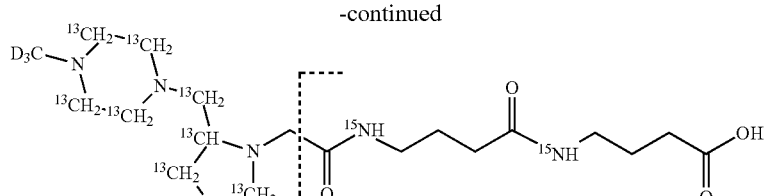

TMT-5-30-208.22985 (Subset 10)

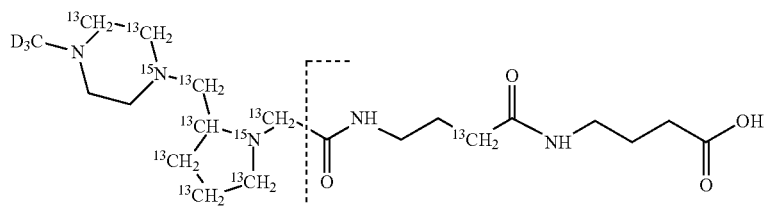

TMT-5-30-209.22056 (Subset 11)

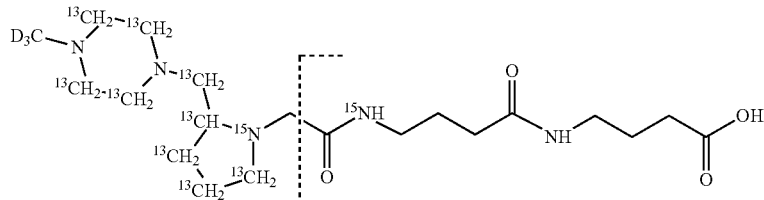

TMT-5-30-209.22688 (Subset 11)

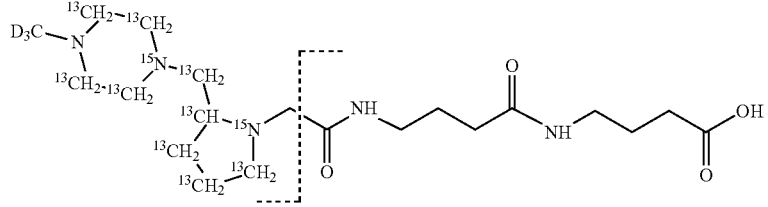

TMT-5-30-210.22392 (Subset 12)

The mass labels in Set 5 are all isotopes of the mass labels in Set 4 with mass labels in Set 5 (Parent Tag Mass: 425.32765 Daltons) being approximately 3 Daltons heavier than the mass labels in Set 4 (Parent Tag Mass: 422.30882 Daltons). More importantly, the reporter moieties' masses in Set 5 are all different from the reporter moieties' masses in Set 4. This means that the mass labels of Set 5 can be used together with the mass labels of Set 4 to label up to 60 samples for multiplexing. Peptides labelled with mass labels from Set 4 will co-elute with peptides labelled with mass labels from Set 5, although with the possibility of a small mobility shift due to the presence of deuterium in the tags of Set 5. However, it has been reported that substitution of deuterium at a basic site in a mass label does not cause significant mobility shifts (Zhang, J. et al., (2010) *Anal Chem*, 82, 7588-7595) so it would be expected that the deuterium substitutions in the mass labels of Set 5 will cause a negligible shift in the mobility of these mass labels relative to the mass labels of Set 4. Because the mass labels are isotopes of each other and will mostly co-elute, there is the possibility of co-selection of peptides labelled with Set 4 when peptides of Set 5 are analyzed and vice versa. This is a problem for previous disclosed attempts to provide isobaric mass labels with isotope substitution that are not in the reporter moiety but in the mass modifier. There is no previous report of using isotope modifications in the reporter moiety as shown in Sets 4 and 5 of the present invention. These two sets of mass labels comprise isotope substitutions in the reporter moiety, hence rendering different reporter moieties (and upon fragmentation, reporter ions) so co-selection of peptides labelled with different sets of mass labels, the different reporter moieties allow correct identification and assignment to the exact peptides. Even if some of the differences in masses between some reporter moieties in the different sets are quite small, Fourier Transform Ion Cyclotron Resonance instruments can already provide mass resolution well in excess of 1 part in 1 million. Moreover, larger mass differences can be introduced between sets of mass labels if that is desirable through the introduction of further deuterium atoms or with larger reporter moieties.

It should be noted that although the fixed substitutions of $^2H$, $^{12}C$ and $^{14}N$ are shown in a particular location in the examples shown above, this has been done as a convenience for the purposes of explanation and these fixed substitutions in Set 5 could located at any suitable position within the reporter moiety if it is more convenient or cost-effective to locate them elsewhere. In fact, one of the fixed substitutions of $^{12}C$ has not been shown in the same position in every tag but even in the heaviest reporter (Subset 12) there are 2 $^{12}C$ substitutions in the reporter. To avoid mobility shifts, it is however preferable to substitute deuterium atoms near basic sites such as an amino group that will protonate in buffers and under the acidic conditions typically used during ionisation by electrospray or MALDI.

Set 6:
The mass labels may also have the following structure:

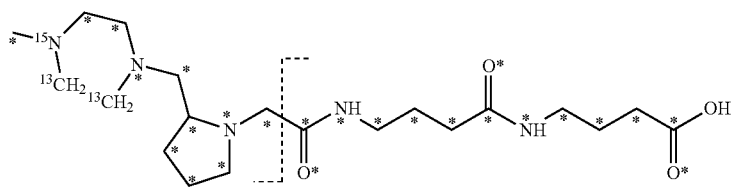

wherein the mass series modifying group * represents that oxygen is replaced (or substituted) by $^{18}O$, carbon by $^{13}C$ or nitrogen by $^{15}N$ or at sites where the hydrogen is present * represents $^2H$. One or more positions may be substituted in single label. Preferably more than one position is substituted.

One of the Nitrogen heteroatoms present in the piperazine ring has a fixed substitution of $^{15}N$ and two of the carbon atoms present in the piperazine ring has a fixed substitution of $^{13}C$ producing a fixed 3 Dalton offset in the masses of the mass labels of this set of mass labels relative to the mass labels of Set 4.

The synthesis of the reporter structure is shown in FIG. 3 using N-methylpiperazine as the secondary amine. Coupling of this reporter moiety structure to two consecutive gamma-amino butyric acid residues is shown in FIG. 15.

In a preferred embodiment of an isobaric set of mass labels, the set comprises n=30 mass labels having the following structures:

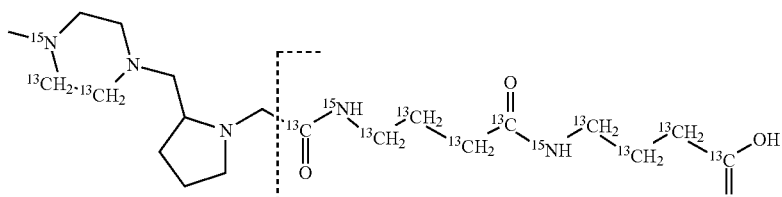

TMT-6-30-199.18457 (Subset 1)

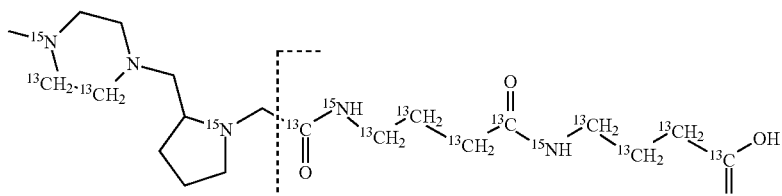

TMT-6-30-200.1816 (Subset 2)

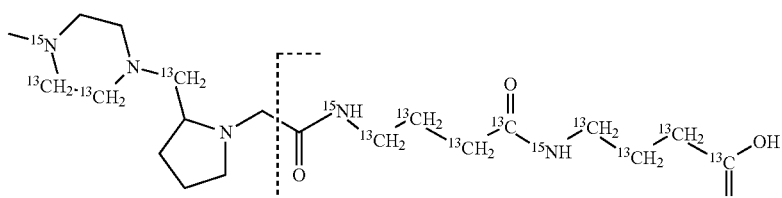

TMT-6-30-200.18792 (Subset 2)

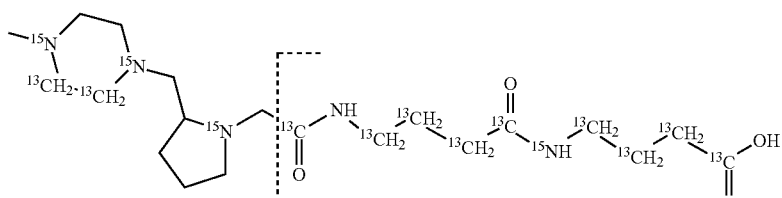

TMT-6-30-201.17864 (Subset 3)

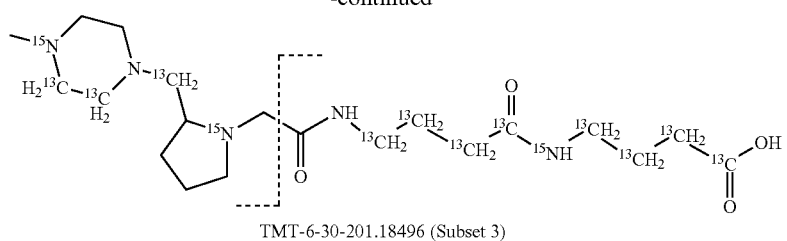
TMT-6-30-201.18496 (Subset 3)
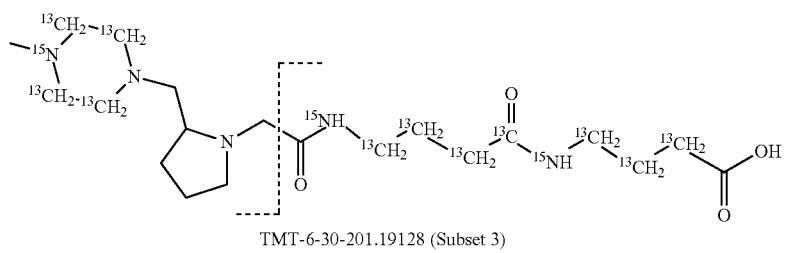
TMT-6-30-201.19128 (Subset 3)
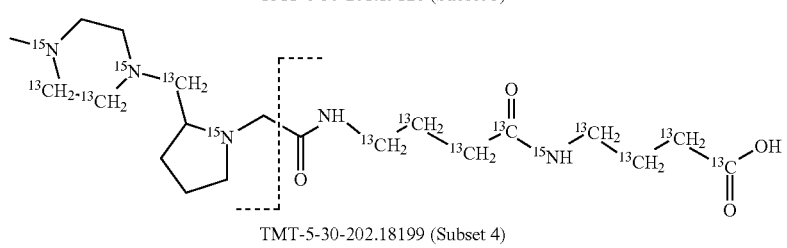
TMT-5-30-202.18199 (Subset 4)
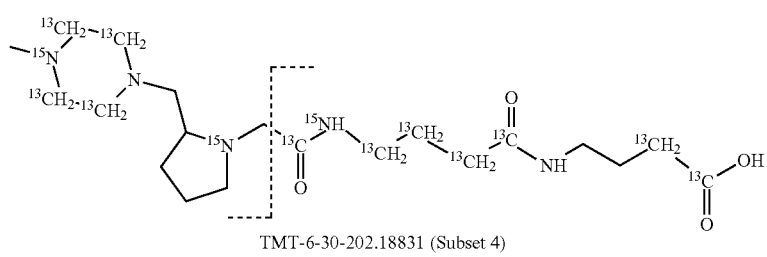
TMT-6-30-202.18831 (Subset 4)
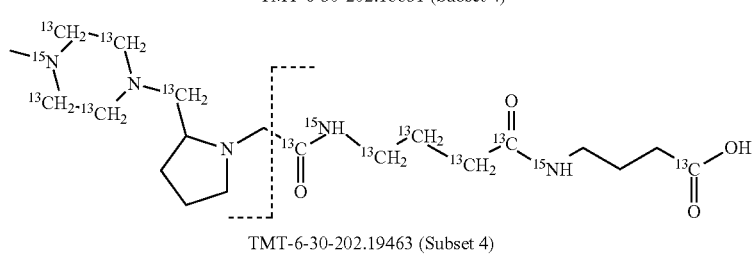
TMT-6-30-202.19463 (Subset 4)
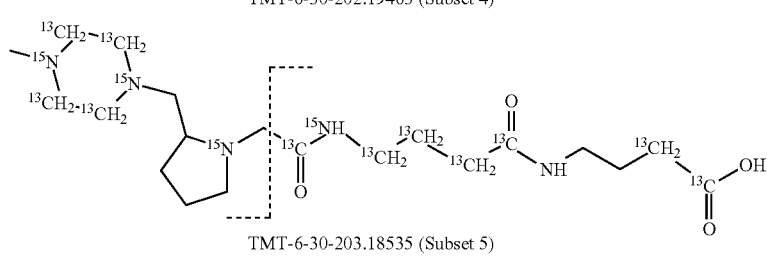
TMT-6-30-203.18535 (Subset 5)
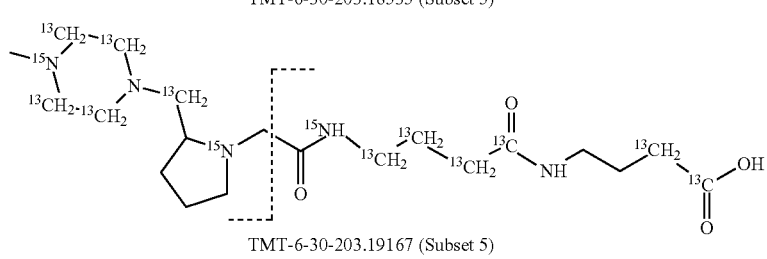
TMT-6-30-203.19167 (Subset 5)

-continued
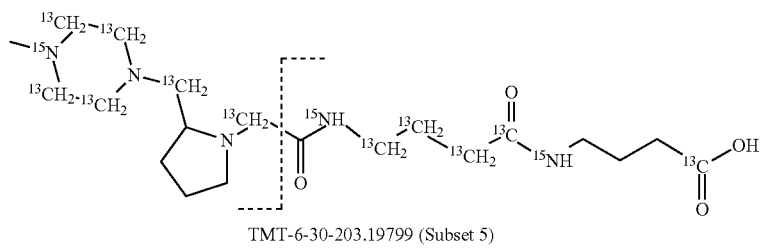
TMT-6-30-203.19799 (Subset 5)
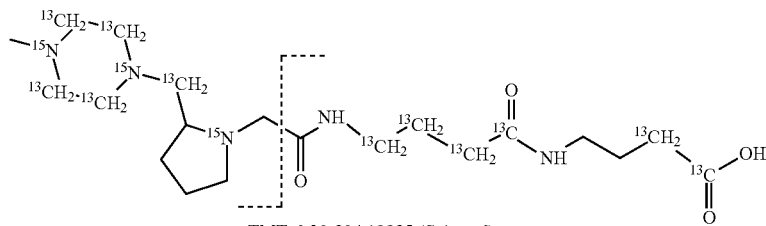
TMT-6-30-204.18925 (Subset 6)
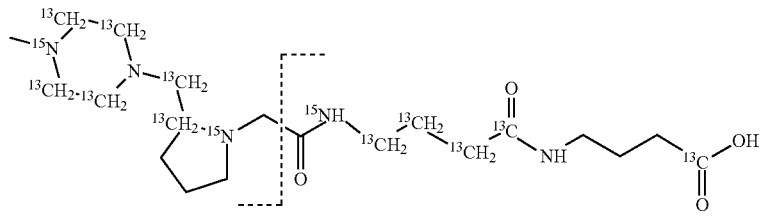
TMT-6-30-204.19557 (Subset 6)
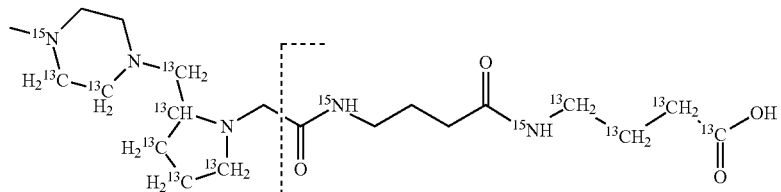
TMT-6-30-204.20189 (Subset 6)
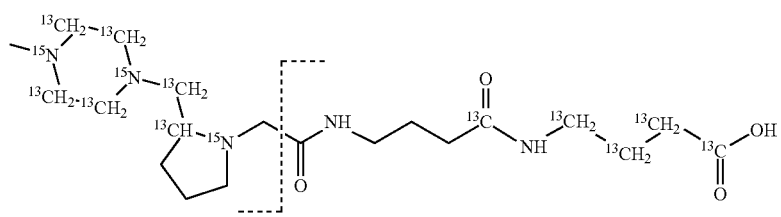
TMT-6-30-205.19261 (Subset 7)
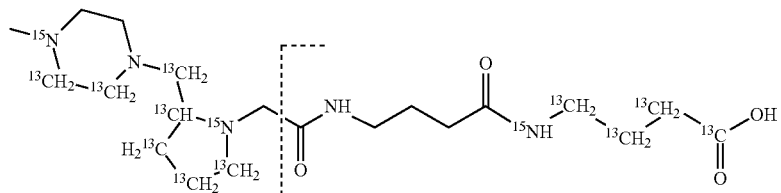
TMT-6-30-205.19893 (Subset 7)
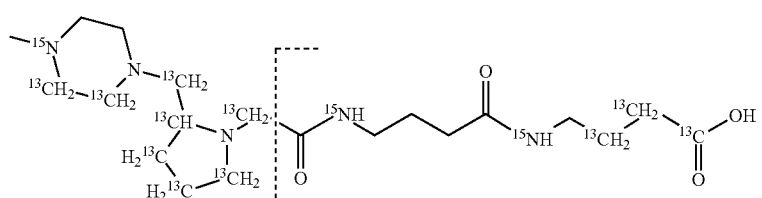
TMT-6-30-205.20525 (Subset 7)

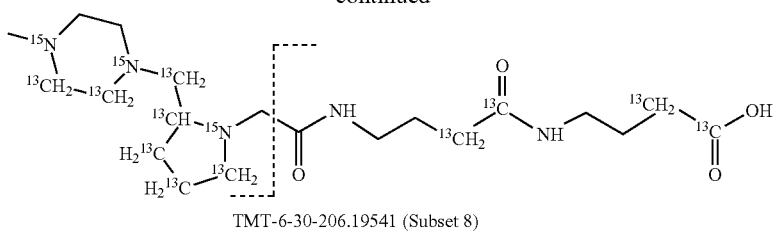
TMT-6-30-206.19541 (Subset 8)
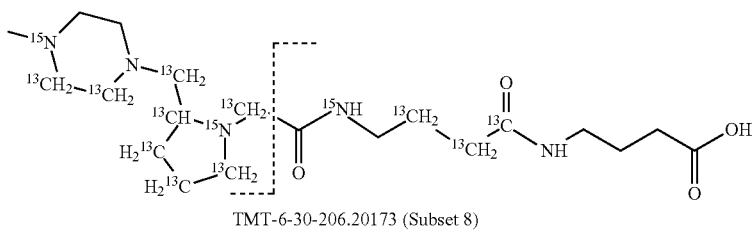
TMT-6-30-206.20173 (Subset 8)
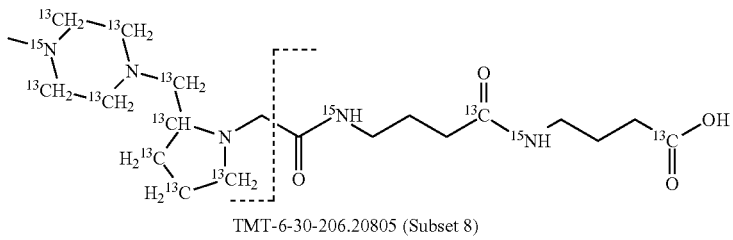
TMT-6-30-206.20805 (Subset 8)
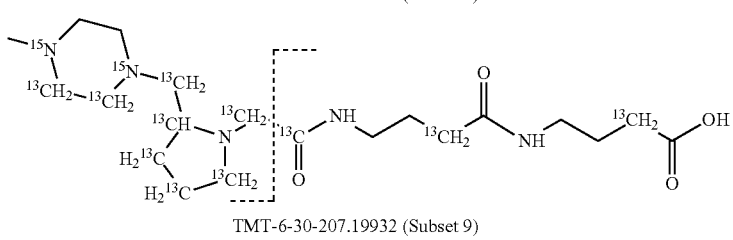
TMT-6-30-207.19932 (Subset 9)
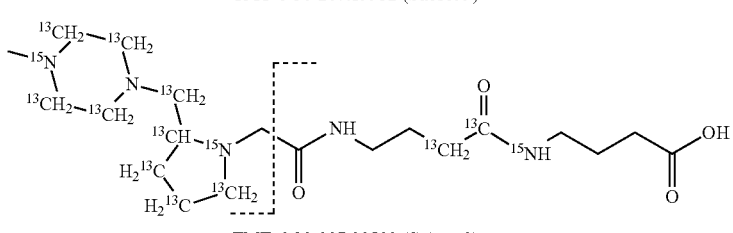
TMT-6-30-207.20509 (Subset 9)
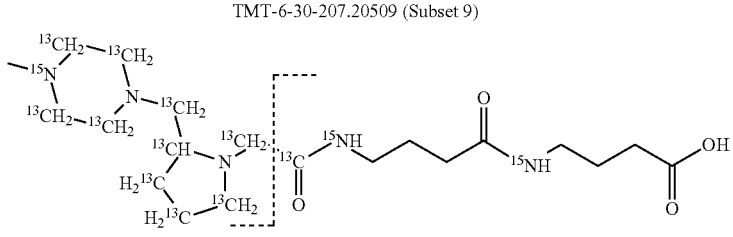
TMT-6-30-207.21196 (Subset 9)
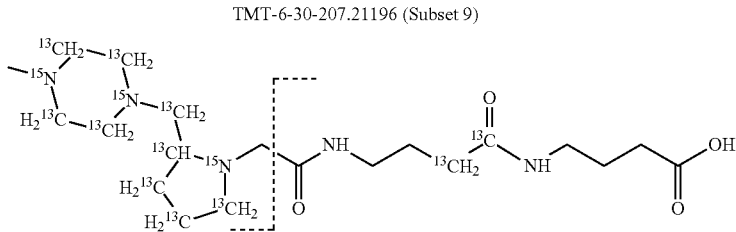
TMT-6-30-208.20267 (Subset 10)

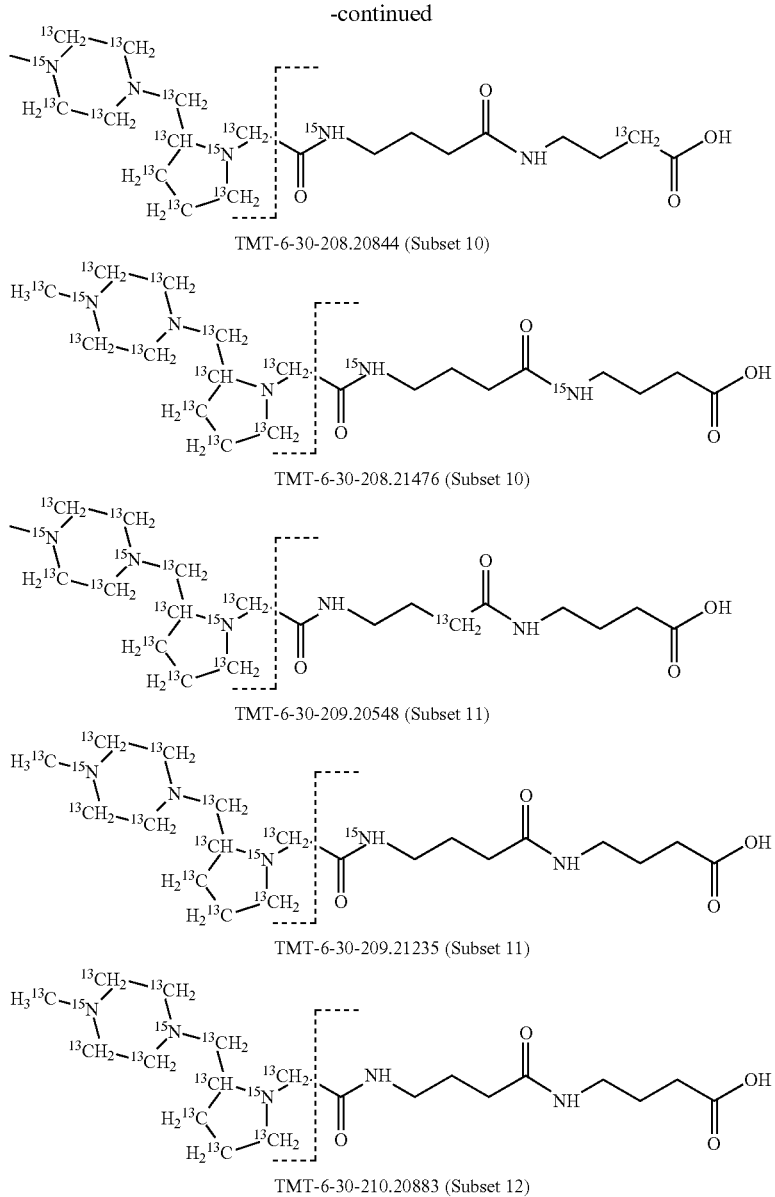

TMT-6-30-208.20844 (Subset 10)

TMT-6-30-208.21476 (Subset 10)

TMT-6-30-209.20548 (Subset 11)

TMT-6-30-209.21235 (Subset 11)

TMT-6-30-210.20883 (Subset 12)

The mass labels in Set 6 are all isotopologues of the mass labels in Set 5 with mass labels in Set 5 (Parent Tag Mass: 425.32765 Daltons) being approximately isobaric (pseudo-isobaric) with the mass labels in Set 6 (Parent Tag Mass: 425.31256 Daltons). This means that peptides labelled with the mass labels from Set 6 would be co-selectable with peptides labelled with mass labels from Set 5. However, the masses of the reporter moieties in the mass labels of Set 5 are all different from the masses of the reporter moieties of the mass labels in Set 6. In other words, the mass labels of Set 5 can be used together with the mass labels of Set 6 to label up to 60 samples for multiplexing. Peptides labelled with the mass labels from Set 6 will mostly co-elute with peptides labelled with the mass labels from Set 5 (minus the possibility of a small mobility shift due to the presence of deuterium as mentioned above). Because the mass labels are isotopes of each other and will mostly co-elute, and the mass labels are co-selectable, then peptides labelled with the mass labels of Set 6 will be analyzed simultaneously with peptides labelled with mass labels of Set 5 and the mass labels will behave as if they are single pseudo-isobaric sets of mass labels. These two sets of mass labels, however, comprise reporter moieties, which will give different reporter ions so when peptides labelled with mass labels from Sets 5 and 6, reporter ions can still be assigned to their correct peptides because the reporter moieties are all different. It should be noted that although the fixed substitutions of $^{13}C$ and $^{15}N$ are shown in a particular location in the examples shown above, this has been done as a convenience for the purposes of explanation and these fixed substitutions in Set 6 could located at any suitable location within the reporter ion if it is more convenient or cost-effective to locate them elsewhere.

When Sets 5 and 6 are used together, they may be regarded as an isotopologue array of two isotopomeric sets of isobaric mass labels. It is also worth noting, that the isotopologue array, comprising Set 5 and Set 6, with 60 tags is made of tags that are smaller than required to achieve the 48-plex isobaric tag set shown in Set 3. This is advantageous in terms of synthesis, as a large set of tags can be created from a smaller structure, i.e. a smaller mass modifier structure is required when reporter offsets are used to achieve a given number of tags, which is a key advantage of the invention presented here.

Set 7:

The isobaric mass labels may also have the following structure:

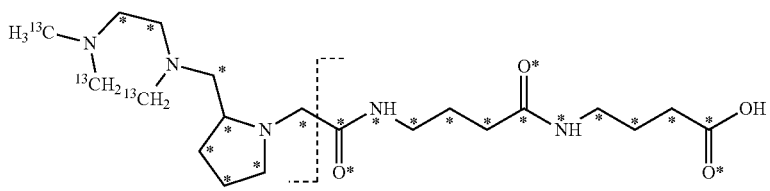

wherein the mass series modifying group * represents that oxygen is replaced (or substituted) $^{18}O$, carbon by $^{13}C$ or nitrogen by $^{15}N$ or at sites where the hydrogen is present * represents $^{2}H$. One or more positions may be substituted in single label. Preferably more than one position is substituted.

All of the nitrogen heteroatoms present in the reporter moiety structure have a fixed substitution of $^{14}N$ and three of the carbon atoms present in the reporter moiety structure have a fixed substitution of $^{13}C$ producing a fixed 3 Dalton offset in the parent tag masses of this tag set relative the mass labels of Set 4.

The synthesis of the reporter moiety structure is shown in FIG. 3 using N-methylpiperazine as the secondary amine. Coupling of this reporter moiety structure to two consecutive gamma-amino butyric acid residues is shown in FIG. 15.

In a preferred embodiment of an isobaric set of mass labels, the set comprises n=9 mass labels having the following structures:

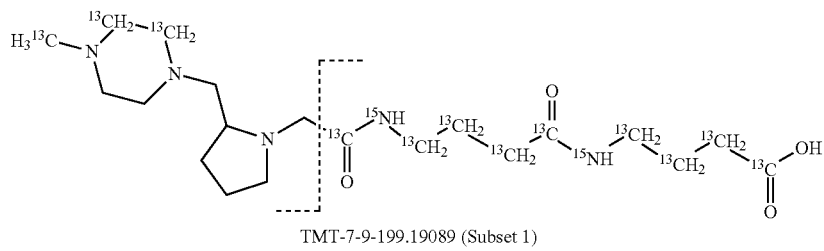

TMT-7-9-199.19089 (Subset 1)

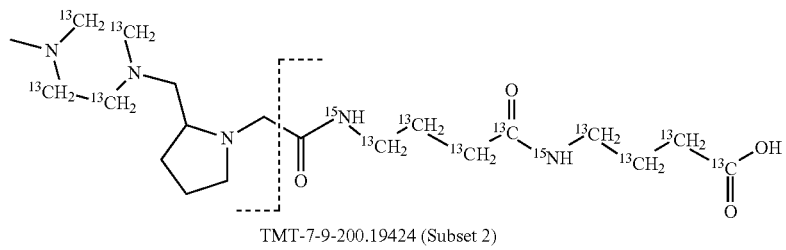

TMT-7-9-200.19424 (Subset 2)

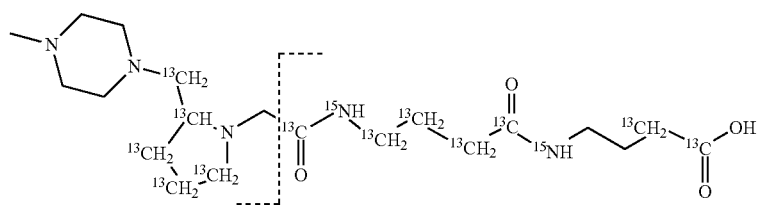

TMT-7-9-201.1976 (Subset 3)

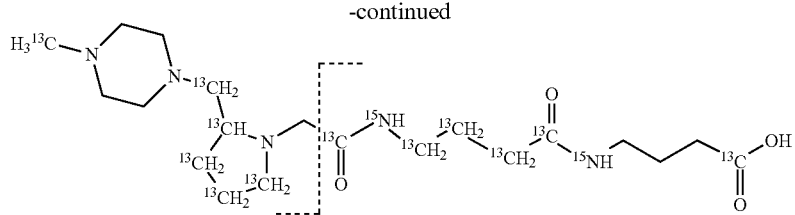

TMT-7-9-202.20095 (Subset 4)

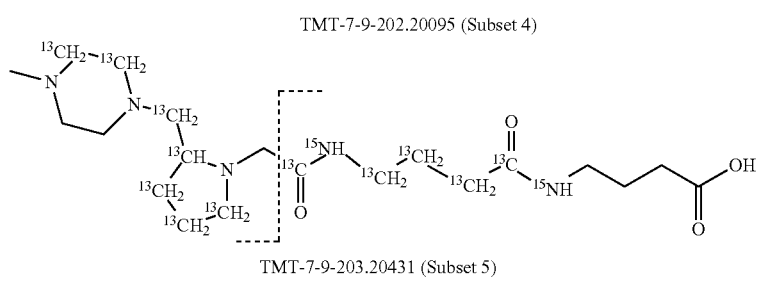

TMT-7-9-203.20431 (Subset 5)

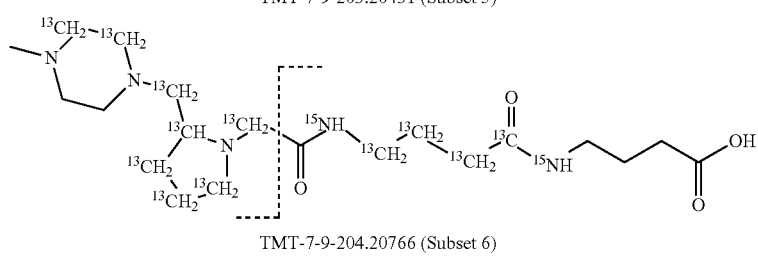

TMT-7-9-204.20766 (Subset 6)

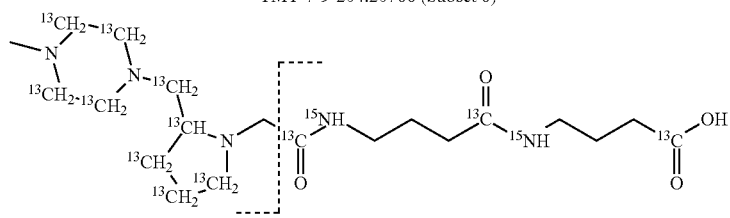

TMT-7-9-205.21102 (Subset 7)

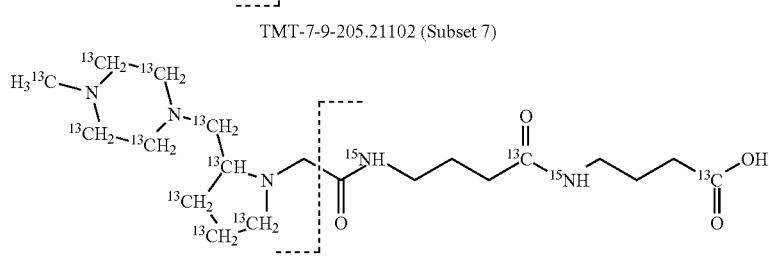

TMT-7-9-206.21437 (Subset 8)

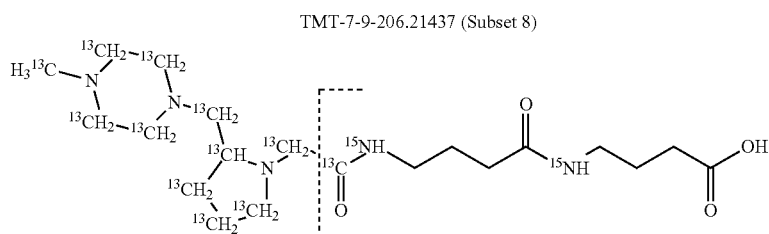

TMT-7-9-207.21773 (Subset 9)

The mass labels in Set 7 are all isotopes of the mass labels in Sets 5 and 6 with the mass labels in Set 5 (Parent Tag Mass: 425.32765 Daltons) being approximately isobaric with the mass labels in Set 6 and Set 7 (Parent Tag Masses: 425.31256 and 425.31888 Daltons, respectively). As explained above, although peptides labelled with these mass labels will co-elute, because the masses of the reporter moieties are all different, the reporter ions can still be assigned to the correct peptides.

It should be noted that although the fixed substitutions of $^{13}C$ and $^{15}N$ are shown in a particular location in the examples shown above, this has been done as a convenience for the purposes of explanation and these fixed substitutions in Set 7 could located at any suitable position within the reporter ion if it is more convenient or cost-effective to locate them elsewhere.

Set 8:

The isobaric mass labels may also have the structure below:

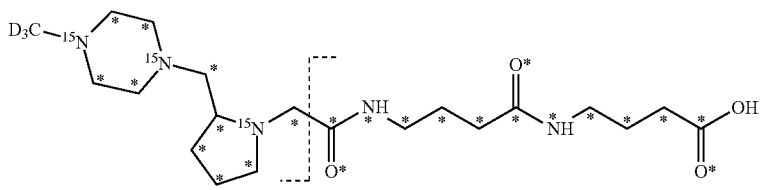

wherein the mass series modifying group * represents that oxygen is replaced (or substituted) by $^{18}O$, carbon by $^{13}C$ or nitrogen by $^{15}N$ or at sites where the hydrogen is present * represents $^2H$. One or more positions may be substituted in single label. Preferably more than one position is substituted.

All of the nitrogen heteroatoms present in the reporter moiety structure have a fixed substitution of $^{15}N$ and the N-methyl group substituted into the piperazine ring has a fixed substitution of 3 deuterium atoms.

The synthesis of the reporter moiety structure is shown in FIG. 3 using N-methylpiperazine as the secondary amine. Coupling of this reporter moiety structure to two consecutive gamma-amino butyric acid residues is shown in FIG. 15.

In a preferred embodiment of an isobaric set of mass labels, the set comprises n=9 mass labels having the following structures:

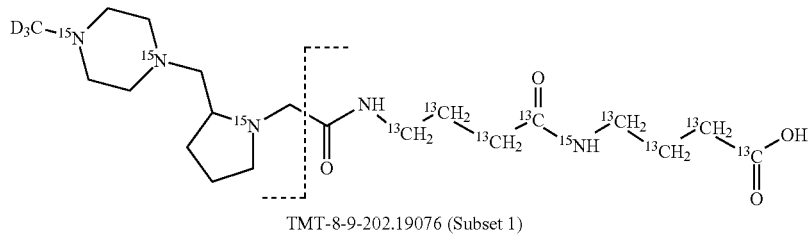

TMT-8-9-202.19076 (Subset 1)

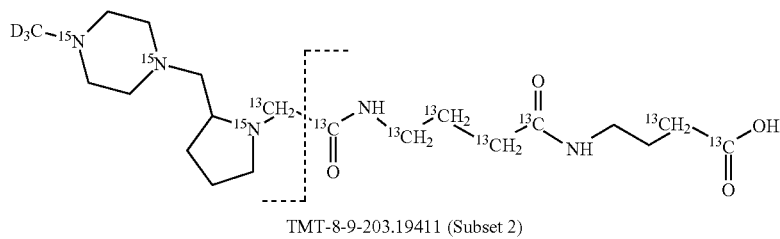

TMT-8-9-203.19411 (Subset 2)

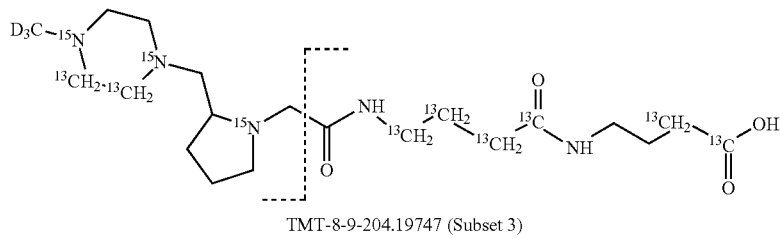

TMT-8-9-204.19747 (Subset 3)

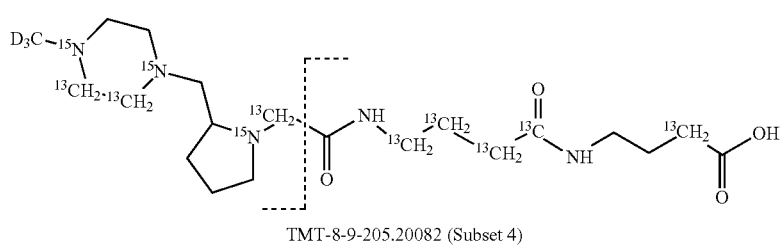

TMT-8-9-205.20082 (Subset 4)

-continued

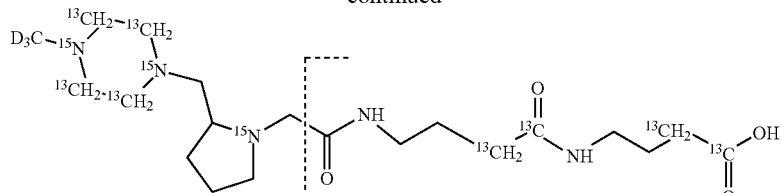
TMT-8-9-206.20418 (Subset 5)

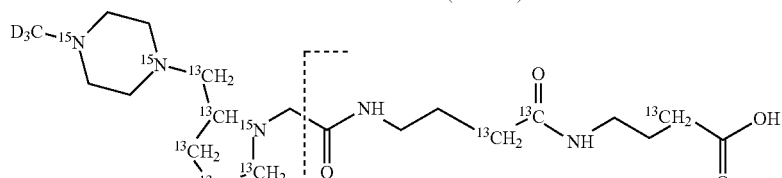
TMT-8-9-207.20753 (Subset 6)

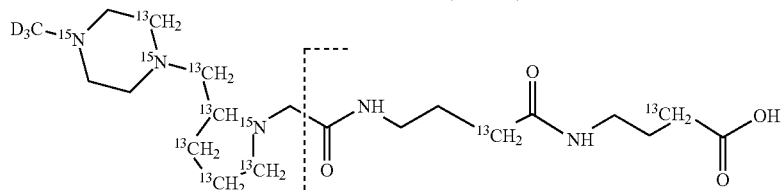
TMT-8-9-208.21089 (Subset 7)

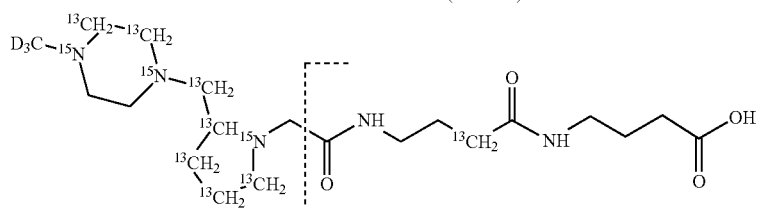
TMT-8-9-209.21424 (Subset 8)

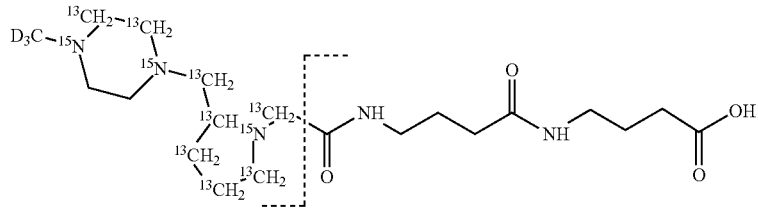
TMT-8-9-210.2176 (Subset 9)

The mass labels in Set 8 are all isotopes of the mass labels in Sets 5, 6 and 7 with the mass labels in Set 5 (Parent Tag Mass: 425.32765 Daltons) being approximately isobaric with the mass labels in Set 6 (Parent Tag Mass: 425.31256 Daltons), Set 7 (Parent Tag Mass: 425.31888 Daltons) and Set 8 (Parent Tag Mass: 425.32133 Daltons). This means that peptides labelled with mass labels from Set 8 would be co-selectable with peptides labelled with mass labels from Sets 5, 6 and 7. More importantly, the reporter moieties masses in Set 8 are all different from the reporter moieties masses in Sets 5, 6 and 7. This means that the mass labels of Set 8 can be used together with the mass labels of Sets 5, 6 and 7 to label up to 78 samples for multiplexing. Peptides labelled with mass labels from Set 8 will co-elute exactly with peptides labelled with mass labels from Set 5 and should co-elute more or less exactly with mass labels from Set 6 and 7, although with the possibility of a small mobility shift due to the presence of deuterium in the mass labels of Sets 5 and 8. Because the mass labels are isotopes of each other and will mostly co-elute, and the mass labels are co-selectable, then peptides labelled with the mass labels of Set 8 will be analysed simultaneously with peptides labelled with mass labels from Sets 5, 6 and 7 and the mass labels will behave as if they are a single pseudo-isobaric set of mass labels. However, because the reporter moieties have all different masses, they can be assigned to their correct peptides. It should be noted that although the fixed substitutions of $^2$H, $^{13}$C and $^{15}$N are shown in a particular location in the examples shown above, this has been done as a convenience for the purposes of explanation and these fixed substitutions in Example Set 8 could be located at any suitable position within the reporter ion if it is more convenient or cost-effective to locate them elsewhere.

Some further pseudo-isobaric mass labels that are isotopes of the mass labels in Sets 5, 6, 7 and 8 can be made according to the structure below:

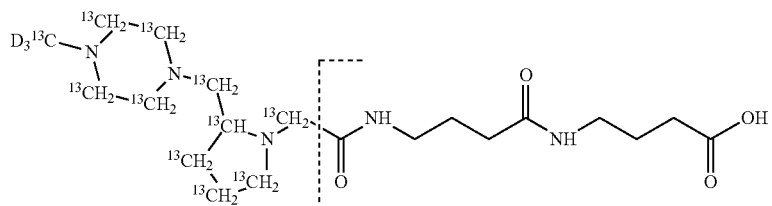
TMT-210.23656

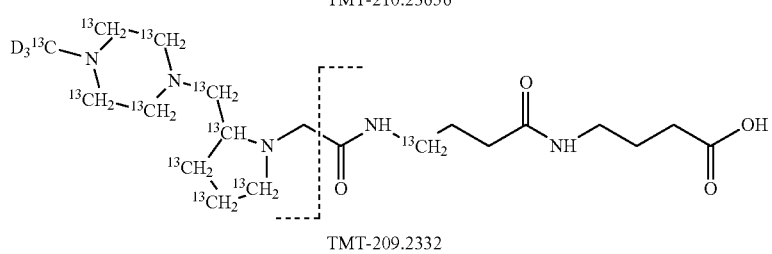
TMT-209.2332

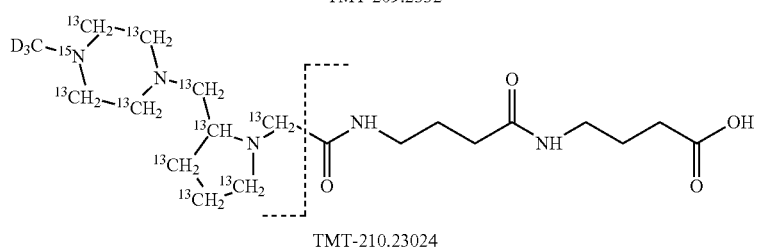
TMT-210.23024

These three mass labels are also pseudo-isobaric and co-selectable with the mass labels from Sets 5, 6, 7 and 8 enabling 81-plex multiplexing.

Further sets of mass labels can be constructed with additional fixed substitutions of hydrogen, deuterium, $^{12}C$ and $^{14}N$ as shown in the general example formulae below:

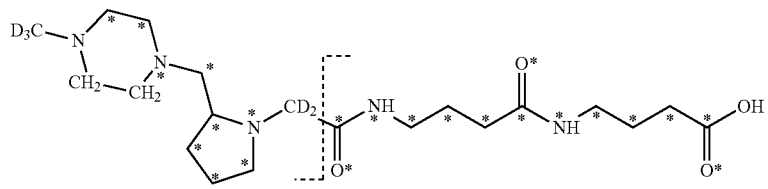

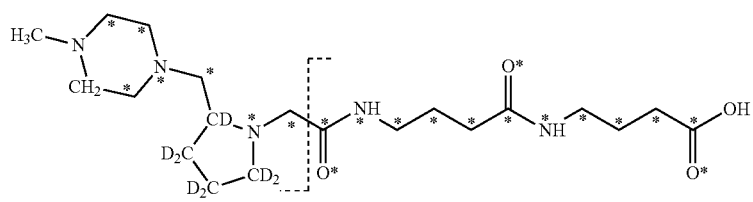

It should be apparent to one of ordinary skill in the art that a great many different combinations of Fixed Hydrogen, Deuterium, $^{12}C$, $^{13}C$, $^{14}N$ and $^{15}N$ substitution are possible and that very large arrays of sets of isobaric and pseudo-isobaric tags are possible. It should also be apparent that the same approach of fixing certain substitutions in the reporter ion ring can be readily applied to different reporter ion structures.

In some embodiments of this invention, where analytes are to be analysed by LC-MS, it may be preferable to minimise the number of deuterium substitutions to minimise the possibility of relative mobility shifts of mass labels with isotopes with different numbers of deuterium. In other embodiments, where LC is not used, the issue of mobility shifts may not be relevant in which case the use of extensive deuterium substitution may be desirable. It should be noted though, that deuterium does not always result in mobility shifts of differentially substituted isotopes as reported in the literature (Zhang, J. et al., (2010) *Anal Chem*, 82, 7588-7595 & Thompson, A. et al., (2003) *Anal Chem*, 75, 1895-1904).

In another embodiment of the invention, the mass labels correspond to isomers of the mass labels in Sets 4 to 8 with the general formula below:

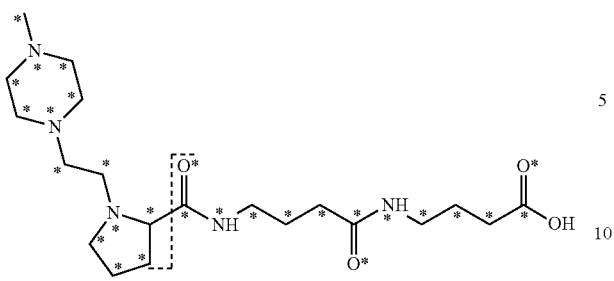

The reporter moiety structure could be synthesized according to the scheme shown in FIG. 5. The coupling of the GABA linkers would be essentially the same as that shown for the isomeric reporter in FIG. 15.

Set 9:

The isobaric mass labels may also have the structure below:

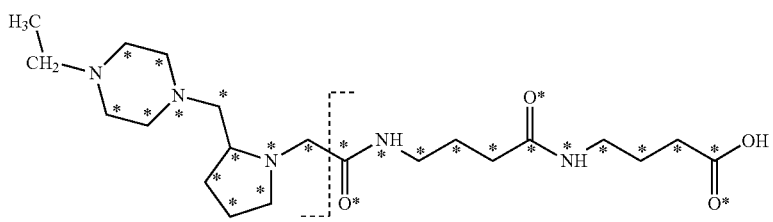

wherein the mass series modifying group * represents that oxygen is replaced (or substituted) by $^{18}O$, carbon by $^{13}C$ or nitrogen by $^{15}N$ or at sites where the hydrogen is present * represents $^{2}H$. One or more positions may be substituted in single label. Preferably more than one position is substituted. The N-ethyl group substituted into the piperazine ring has a fixed substitution of 5 hydrogen atoms and 2 $^{12}C$ atoms. The synthesis of the reporter moiety structure is shown in FIG. 3 using N-ethylpiperazine as the secondary amine. Coupling of this reporter moiety structure to two consecutive gamma-amino butyric acid residues is shown in FIG. 15.

In a preferred embodiment of an isobaric set of mass labels, the set comprises n=30 mass labels having the following structures:

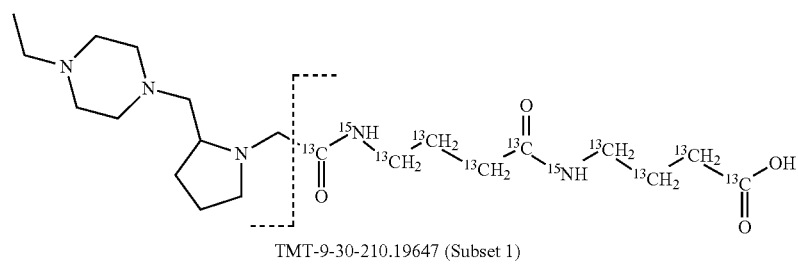

TMT-9-30-210.19647 (Subset 1)

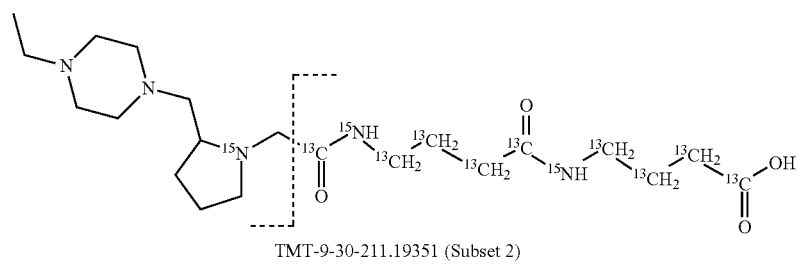

TMT-9-30-211.19351 (Subset 2)

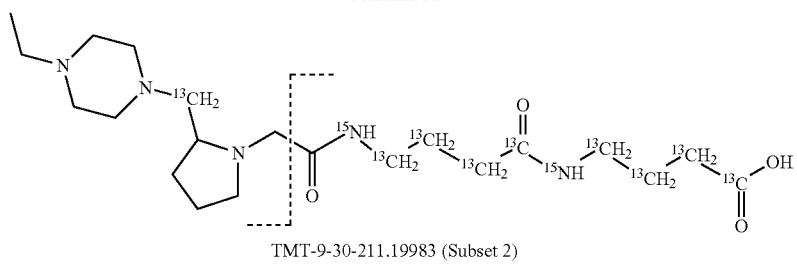
TMT-9-30-211.19983 (Subset 2)
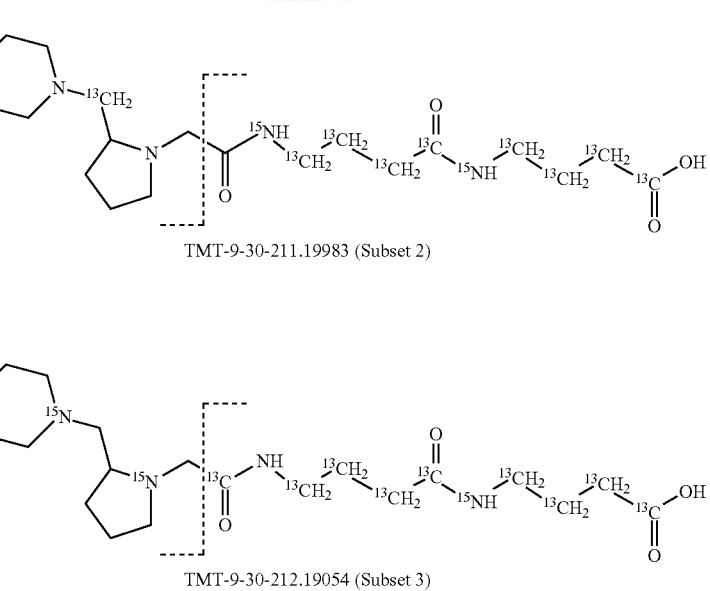
TMT-9-30-212.19054 (Subset 3)
TMT-9-30-212.19686 (Subset 3)
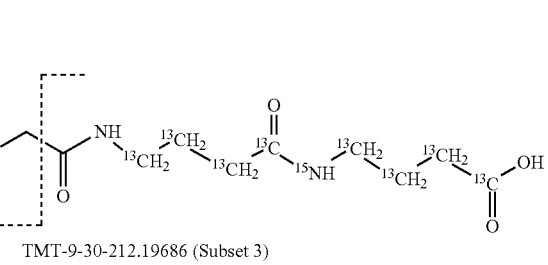
TMT-9-30-212.20318 (Subset 3)
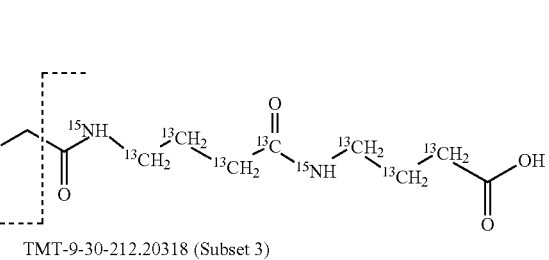
TMT-9-30-213.1939 (Subset 4)
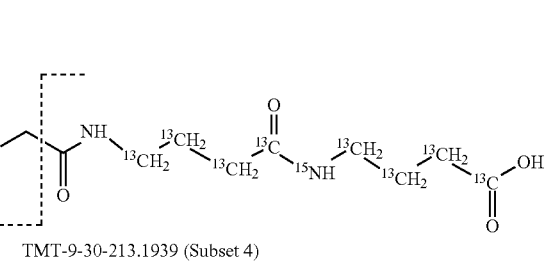
TMT-9-30-213.20022 (Subset 4)

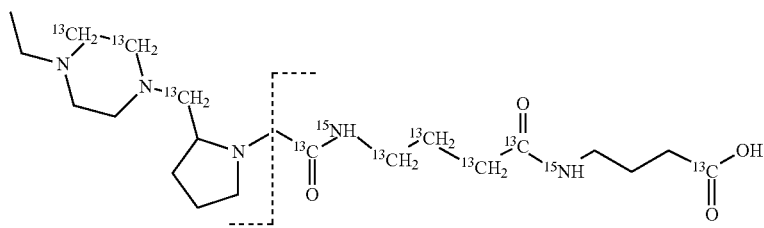
TMT-9-30-199.213.20654 (Subset 4)
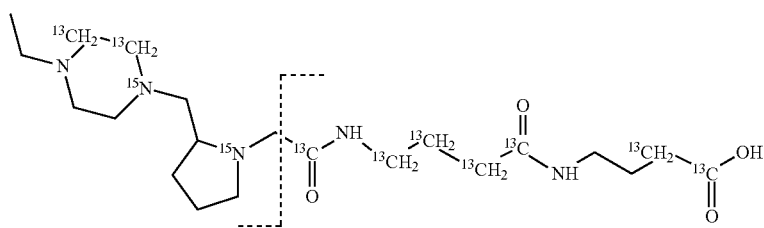
TMT-9-30-214.19725 (Subset 5)
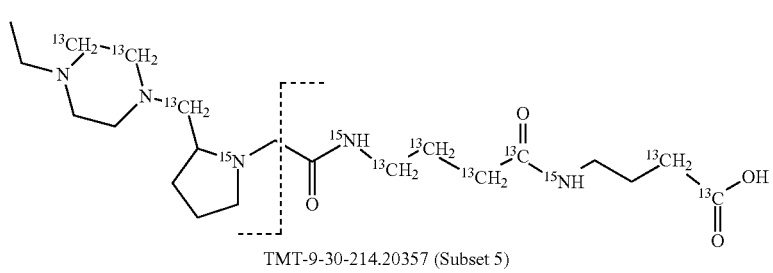
TMT-9-30-214.20357 (Subset 5)
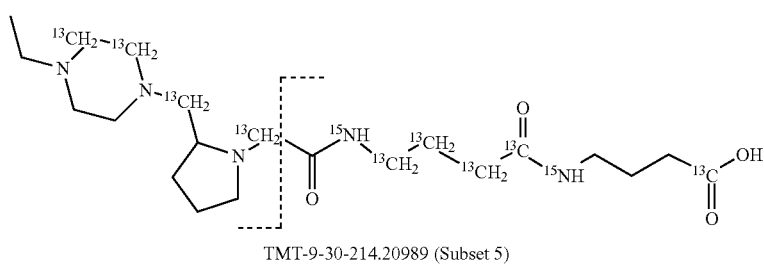
TMT-9-30-214.20989 (Subset 5)
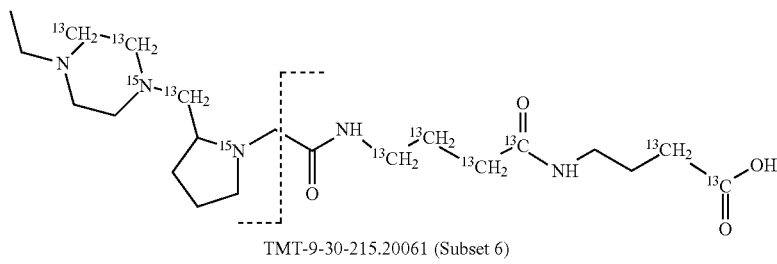
TMT-9-30-215.20061 (Subset 6)
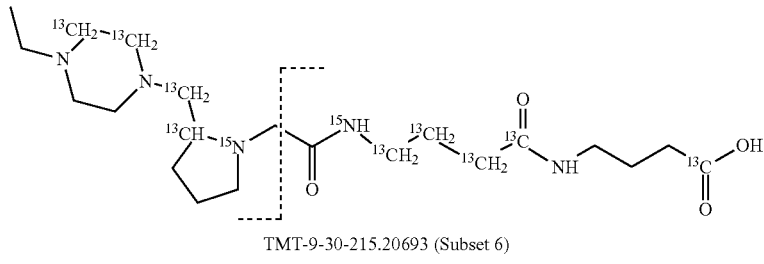
TMT-9-30-215.20693 (Subset 6)

-continued
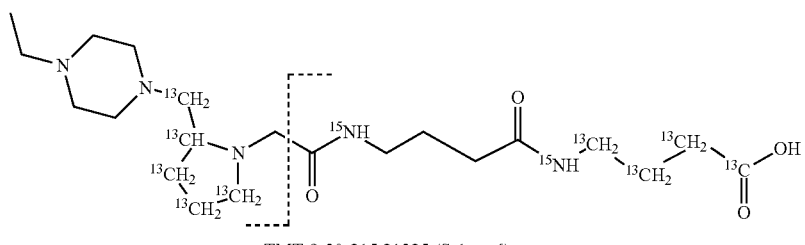
TMT-9-30-215.21325 (Subset 6)
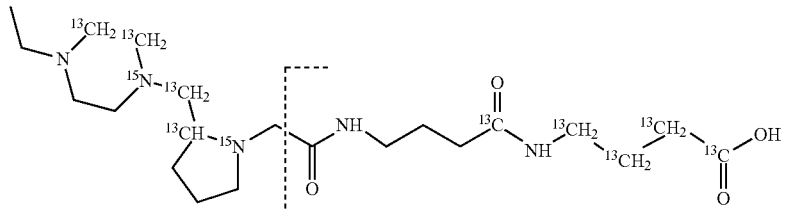
TMT-9-30-216.20396 (Subset 6)
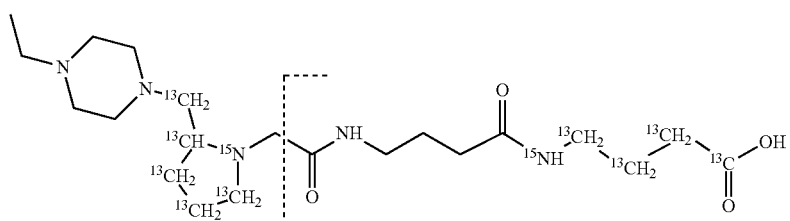
TMT-9-30-216.21028 (Subset 7)
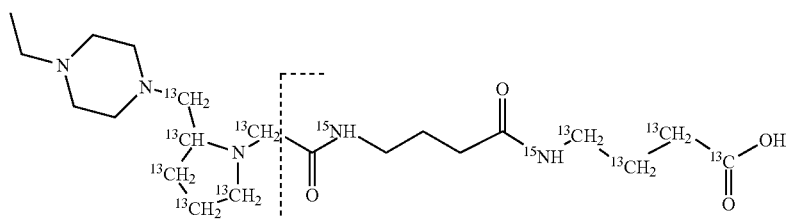
TMT-9-30-216.2166 (Subset 7)
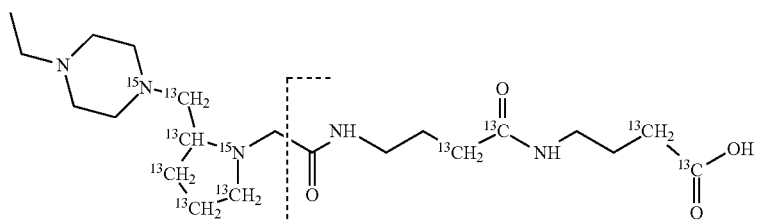
TMT-9-30-217.20732 (Subset 8)
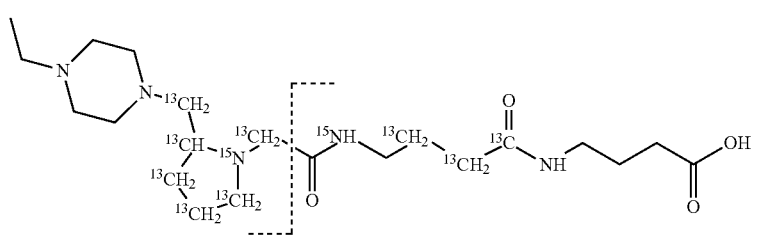
TMT-9-30-217.21364 (Subset 8)

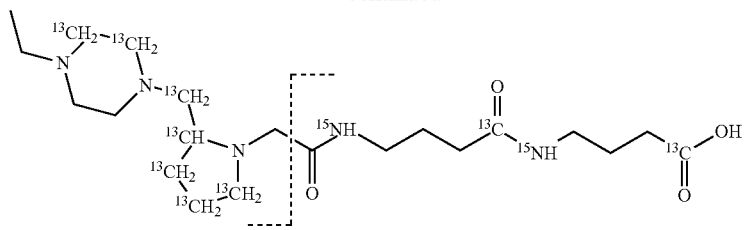
TMT-9-30-217.21996 (Subset 8)
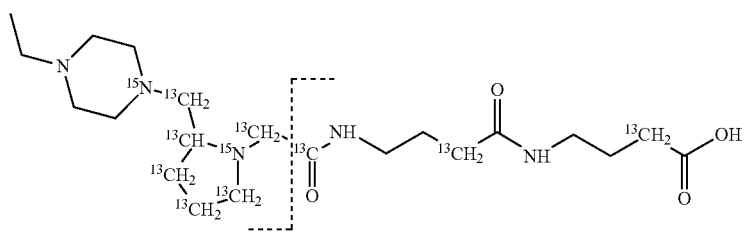
TMT-9-30-218.21067 (Subset 9)
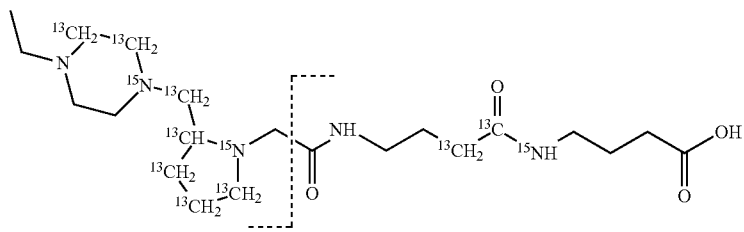
TMT-9-30-218.21699 (Subset 9)
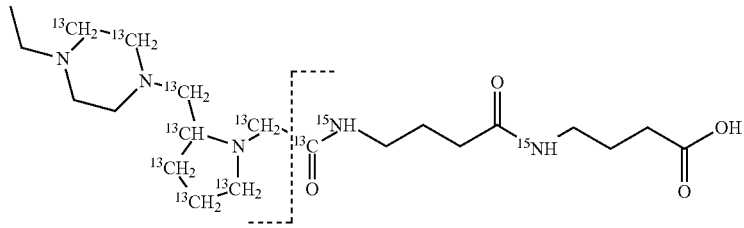
TMT-9-30-218.22331 (Subset 9)
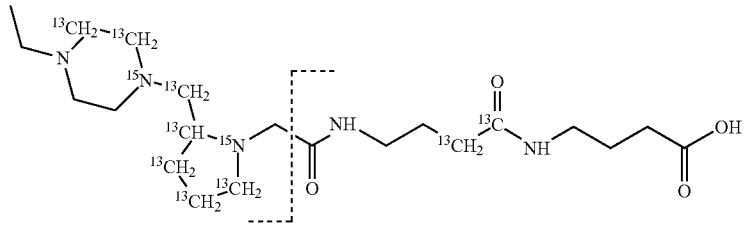
TMT-9-30-219.21403 (Subset 10)
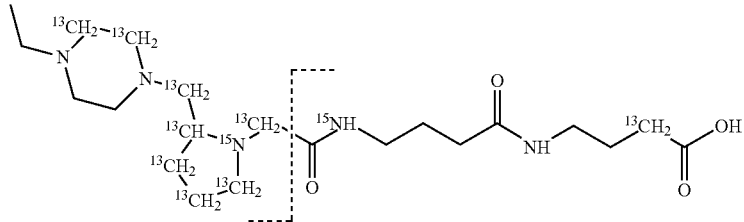
TMT-9-30-219.22035 (Subset 10)

-continued

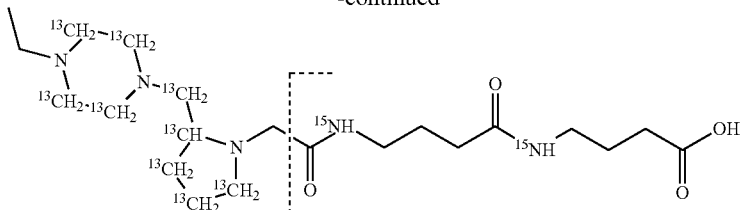

TMT-9-30-219.22667 (Subset 10)

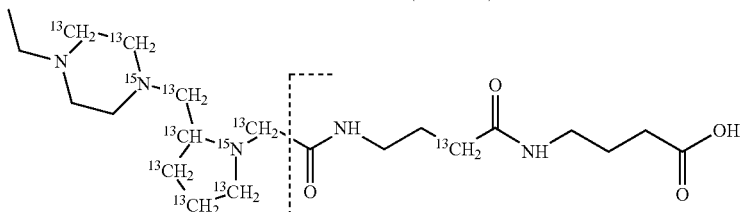

TMT-9-30-220.21738 (Subset 11)

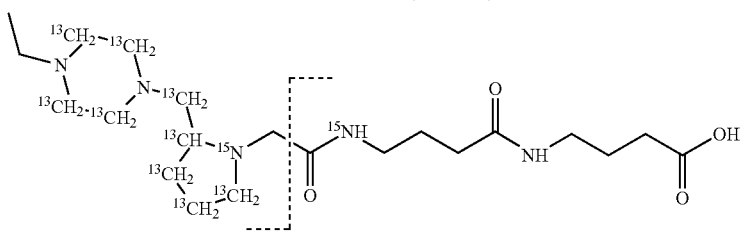

TMT-9-30-220.2237 (Subset 11)

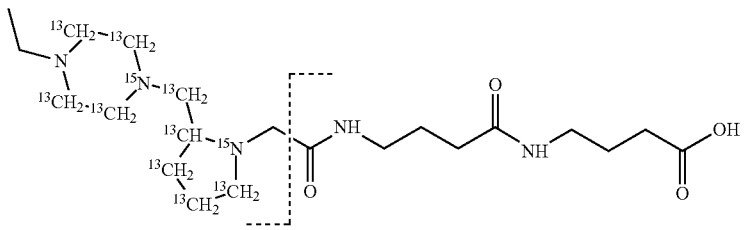

TMT-9-30-221.22074 (Subset 12)

The mass labels in Set 9 are chemically very similar to the mass labels in Sets 4 to 8, differing by the change of a methyl substitution in the piperazine ring to an ethyl substitution. Mass labels in Set 9 comprise non-isotopic modifications relative to Sets 4 to 8. Mass labels in Set 9 (Parent Tag Mass: 436.32447 Daltons) are approximately 14 Daltons heavier than the mass labels in Set 4 (Parent Tag Mass: 422.30882 Daltons). This means that the mass labels of Set 9 can be used together with the mass labels of Set 4 to label up to 60 samples for multiplexing. Peptides labelled with the mass labels from Set 9 will not elute exactly with peptides labelled with mass labels from Set 4, but the mobility shifts due to the presence of the extra —$CH_2$— function in the mass labels of Set 9 are likely to be small and it would be expected that many peptides labelled with the mass labels of Set 9 would overlap in elution with peptides labelled with the mass labels of Set 4. Because the mass labels are likely to co-elute to some extent, there is the possibility of co-selection of peptides labelled with mass labels of Set 4 when peptides labelled with mass labels of Set 9 are analysed and vice versa. This is a problem for previous disclosed attempts to provide isobaric mass tags with mass series offsets that are not in the reporter ion but in the mass normalisation function. There is no previous report of using non-isotopic mass series modifiers in the reporter moiety as shown in the mass labels of Sets 4 and 9. However, because these two sets of mass labels comprise reporter moieties which all give different reporter ions, the reporter ions can still be assigned to their correct peptides.

It should be noted that although the fixed substitutions of $^1H$, $^{12}C$ and $^{14}N$ are shown in a particular location in the examples shown above, this has been done as a convenience for the purposes of explanation and these fixed substitutions in Example Set 9 could located at any suitable position within the reporter ion if it is more convenient or cost-effective to locate them elsewhere.

One of ordinary skill in the art should also be able to design further sets of mass labels that are isotopes and pseudo-isobaric with the mass labels in Set 9.

For example, further sets of mass labels can be constructed with additional fixed substitutions of hydrogen, deuterium, $^{12}C$, $^{13}C$, $^{14}N$ and $^{15}N$ as shown in the general example formulae below:

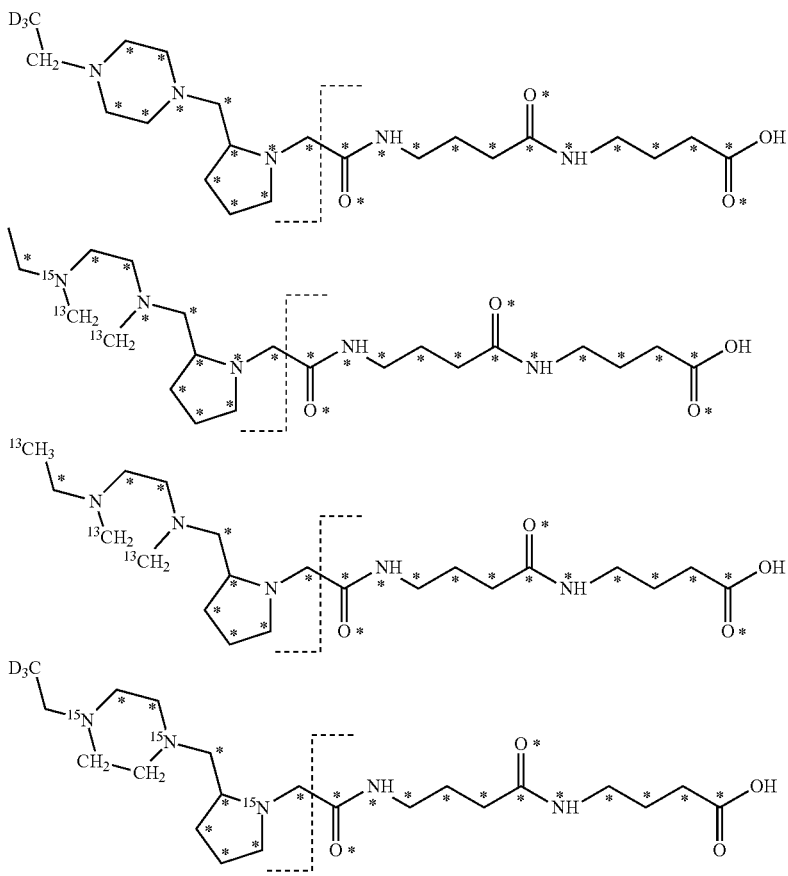

It should be apparent that the 4 general formulae correspond to the same fixed substitutions as Sets 5, 6, 7 and 8 and that corresponding sets of 30, 30, 9 and 9 mass labels, respectively, can be made supporting 78-plex multiplexing. These sets of mass labels could be used simultaneously with mass labels of Sets 5, 6, 7 and 8 to support 156-plex multiplexing. It should also be apparent that even higher levels of multiplexing are achievable using alternative fixed substitutions of hydrogen, deuterium, $^{12}C$, $^{13}C$, $^{14}N$ and $^{15}N$, if desirable. Similarly, the corresponding isomeric mass labels based on the reporter moieties from FIG. 5 can also be synthesized.

Design of Isobaric Mass Labels for Multi-Plexing

Improving multiplexing is a highly sought characteristic of isobaric mass labels as it allows labelling of a high number of sample and analysis is one single experiments thus reducing time of analysis, costs and also standardizing the analysis conditions for a higher number of samples. In order to generate mass labels for isobaric mass labelling using only $^{15}N$ and $^{13}C$ substitutions in a mass label according to the general structures disclosed in the present invention, it is necessary to consider the positions substitutable with heavy isotope mass series modifying groups comprising 2 different elements (P positions) and positions substitutable for the first element (A positions) and positions substitutable for the second element (B positions) different from the first. The number of A positions should be greater than or equal to the number of B positions. Assuming there are (P+1) subsets of mass labels and the $x^{th}$ subset of mass labels comprises C mass labels, C should be less than or equal to (B+1). Each reporter moiety comprises (x−1) positions substituted with heavy isotopes from either the first or second element and where the $w^{th}$ mass label in each subset of mass labels comprises y atoms of the first heavy isotope element and z atoms of the second heavy isotope element different from the first, x will have values from 1 to (P+1). P=(A+B) and the total number of mass labels will be (A+1) multiplied by (B+1).

In preferred embodiments B is greater than or equal to 2.

For example, a mass label where there are 7 dopable Carbons and 2 dopable Nitrogens in the reporter moiety and in the mass modifier, will support up to 24-plex isobaric sets, i.e. (7+1) multiplied by (2+1). At single Dalton resolution, these reporters will support 10-plex (P=7+2 giving (9+1) subsets of mass labels with different integer reporter masses. Obviously as the reporter moiety groups can be substituted with different R-groups different isomers of the mass labels are possible, providing options for different fragmentation behaviours.

Synthesis of N-Methyl Piperazine Ring Isotopes

Figure 12:
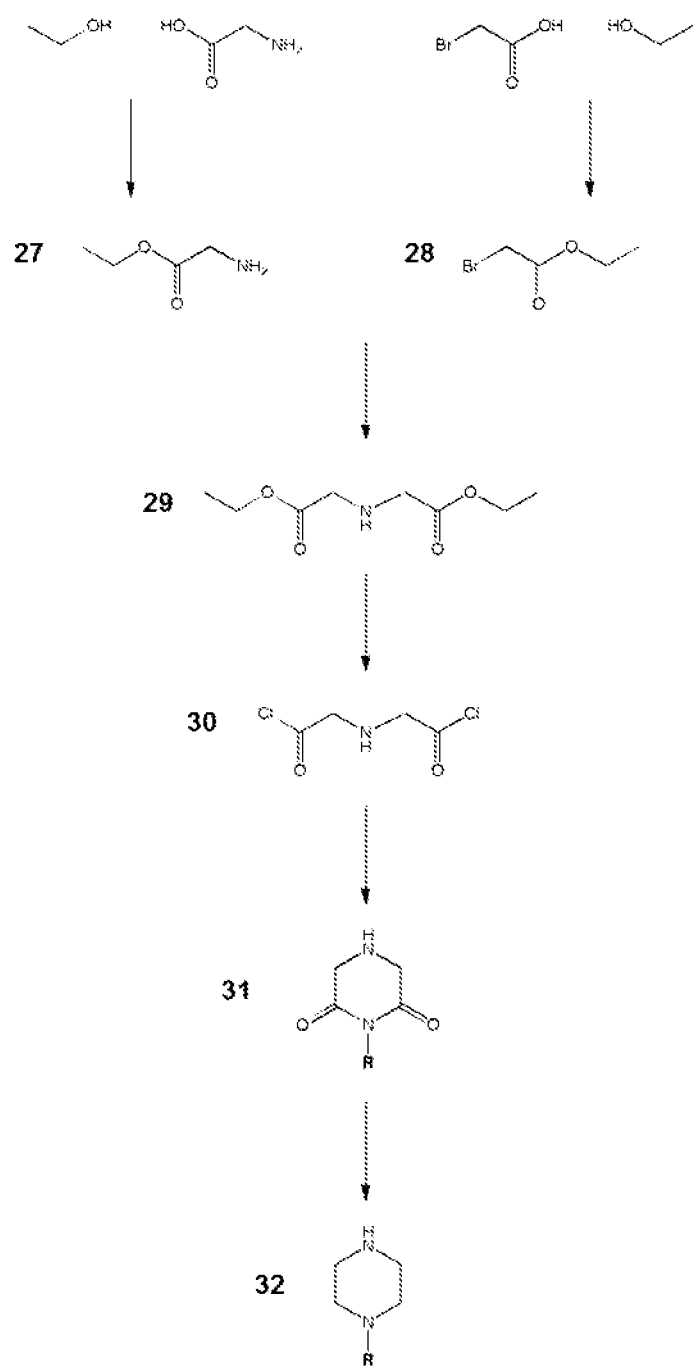
FIG. 12 illustrates how glycine, bromoacetic acid and an alkylamine such as methylamine can be used to synthesise N-alkylpiperazine.
Figure 13:
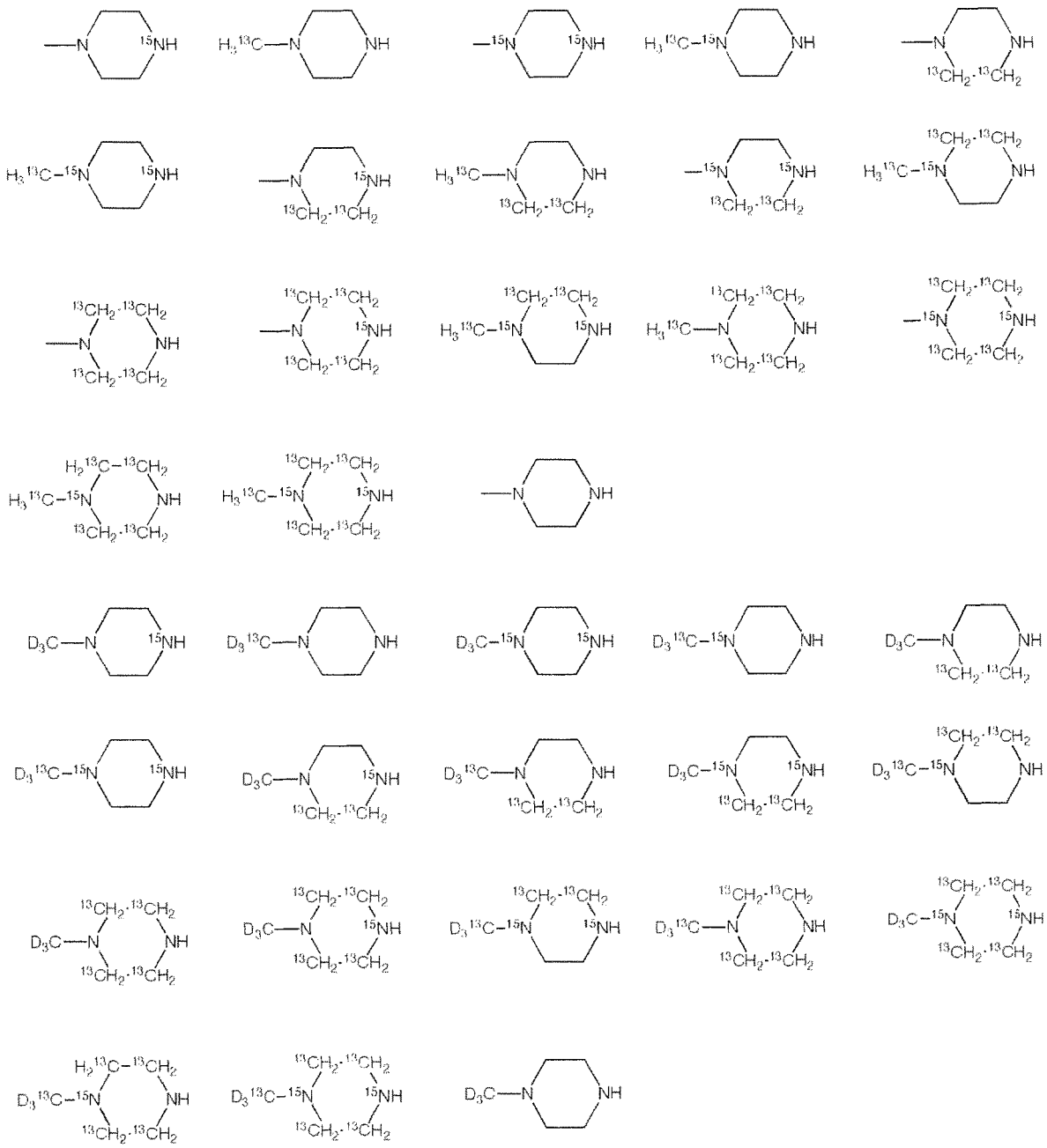
FIG. 13 shows examples of the possible heavy isotope substituted N-methylpiperazines that can be synthesised with the commercially available isotopes.

The synthesis of a large number of N-methyl piperazine isotopes has been described previously (for examples U.S. Pat. Nos. 7,947,513, 7,355,045 and 8,273,706). FIG. 12 illustrates a previously published route in which glycine, bromoacetic acid and an alkylamine such as methylamine can be used to synthesise N-alkylpiperazine. In the first step in the synthesis, glycine is reacted with ethanol to form the ethyl ester (27) protecting the carboxyl group of glycine. In parallel, bromoacetic acid is reacted with ethanol to form its corresponding ethyl ester (28). Products 27 and 28 are then coupled together to form the secondary amine (29). The diester product (29) is deprotected to give the free acid and the dicarboxylic acid is then converted to the corresponding di-acid chloride (30) by reaction with a suitable reagent (e.g. thionyl chloride). The di-acid chloride product (30) is then reacted with an alkylamine (e.g. methylamine) in a ring-closure reaction to give the N-alkyl-diketopiperazine (31). The N-alkyl-diketopiperazine (31) is then reduced with an appropriate reducing agent (e.g. Lithium Aluminium Hydride) to give the N-alkylpiperazine (32). FIG. 13 shows examples of the possible heavy isotope substituted N-methylpiperazines that can be synthesised with the commercially available isotopes although further substituted rings are possible particularly with further deuterium substitutions. The N-methylpiperazine isotopes shown in FIG. 13 are sufficient to make the Sets of Isobaric mass labels according to the invention. One of ordinary skill in the art will appreciate that the alkylamine used for the ring closure shown in FIG. 12 can be selected from molecules other than methylamine, e.g. ethylamine, propylamine, butylamine, pentylamine or hexylamine. Similarly, other alpha amino acids can be substituted for glycine, e.g. alanine, valine, leucine, isoleucine, phenylalanine, etc.

Reactive Groups

The mass labels exemplified herein have all been shown having a free carboxylic acid as a reactive functionality Re. Mass labels with carboxylic acids as reactive functionality can be coupled to amino groups with a suitable coupling agent such as a carbodiimide like N,N'-dicyclohexylcarbodiimide. More preferably, the free carboxylic acids are modified to form so-called active esters, which are stable reagents that will react readily with free amino groups without requiring an additional coupling agent. The synthesis of preferred N-hydroxysuccinimide active ester forms follows the general route of dissolving the free acid forms of the mass labels (one example shown below)

Figure 11:
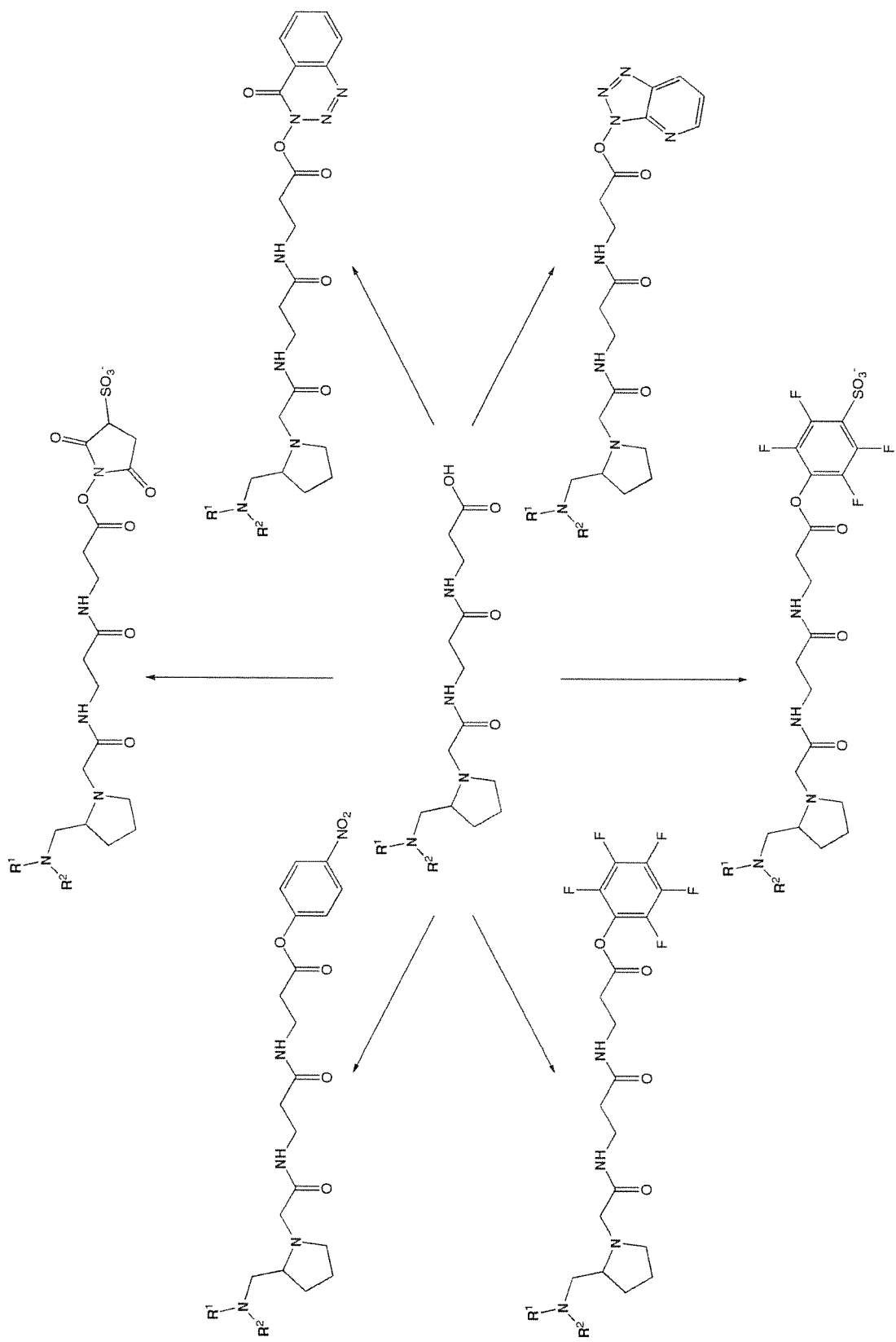
FIG. 11 shows mass labels with different active ester reactive functionalities

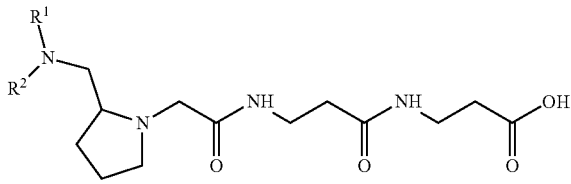

in Dimethylformamide (DMF) or Dichloromethane (DCM) and is then coupled to N-hydroxysuccinimide in the presence of N,N'-dicyclohexylcarbodiimide to give the active ester. Other preferred active esters may be prepared in a similar fashion as shown in FIG. 11. The pentafluorophenol ester is prepared by coupling the mass label with pentafluorophenol, similarly the nitrophenol is prepared by coupling the mass label with nitrophenol. The 1-hydroxy-7-azabenzotriazole ester, the N-hydroxysulphosuccinimidyl ester, the 2,3,5,6-tetrafluorophenyl ester, the sulpho-dichlorophenyl ester, the sulphotetrafluorophenyl ester and the 3,4-dehydro-4-oxo-1,2,3-benzotriazinyl (DHBT) ester can all be prepared from the corresponding alcohols.

Figure 7:
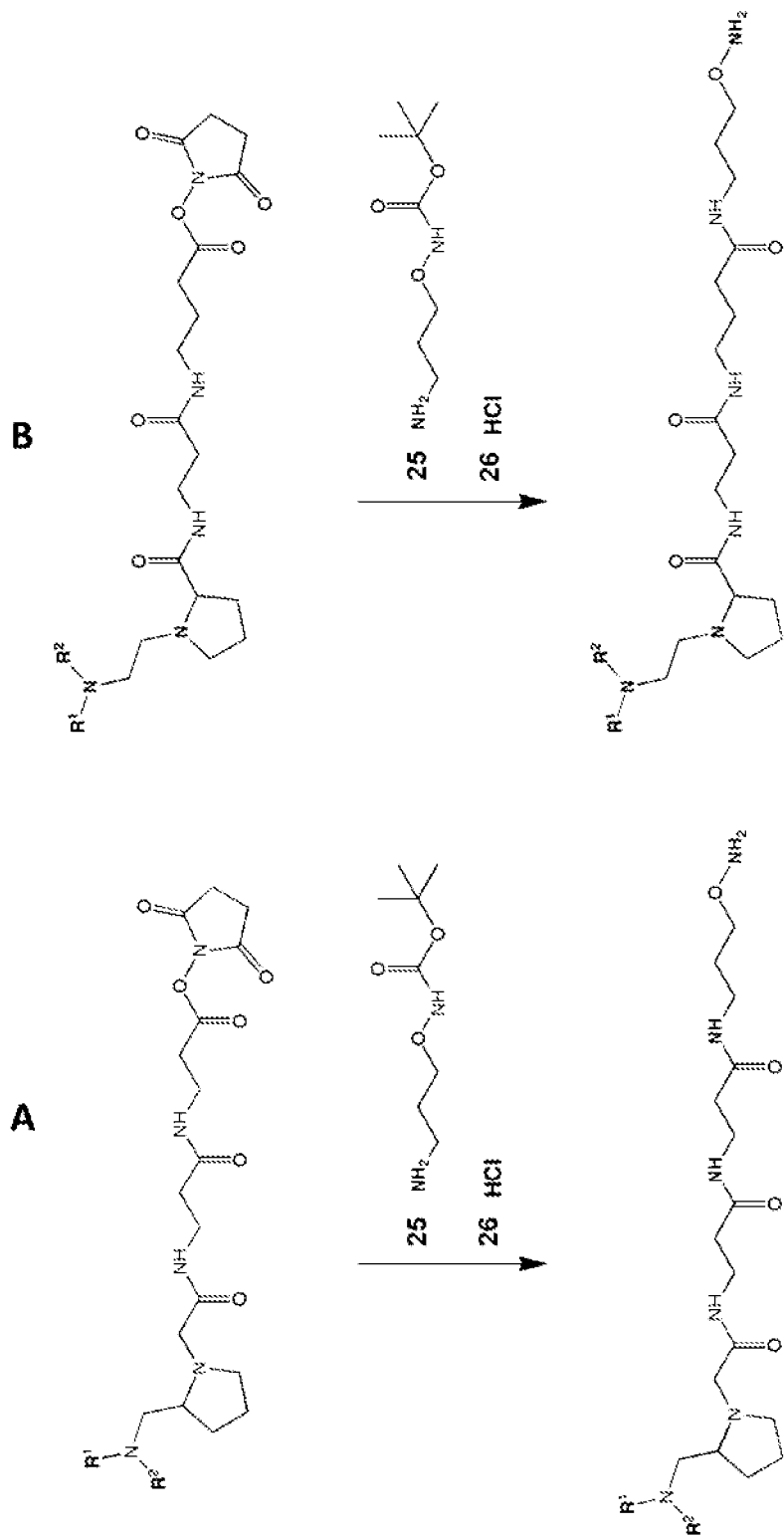
FIGS. 7A and 7B show schemes for the formation of reactive mass labels with aminoxy reactive functionalities.

FIGS. 7A and 7B illustrate the synthesis of aminoxy-activated forms of the mass labels of this invention. N-hydroxysuccinimide ester activated forms of two mass labels of this invention are coupled with Boc-protected aminoxy-propylamine (25). The BOC protecting group is then removed under acid conditions (26) to provide the aminoxy form of the mass labels. The aminoxy reacts with carbonyl functions to form an oxime bond, which is quite stable. Carbonyl functions appear in oxidised carbohydrates and steroids and various methods are known in the art for preparing steroid-containing samples, carbohydrate-containing samples or glycoprotein containing samples for labelling with aminoxy-functionalised mass labels.

Hydrazide reagents react with carbonyl groups to form a hydrazone linkage. The hydrazone is moderately stable and compounds labelled this way can be analysed directly or to avoid any chance of the coupling reaction being reversed, the hydrazone may be reduced to a secondary amine. Synthesis of hydrazide-activated forms of the mass labels of this invention is achieved by coupling hydrazine to the N-hydroxysuccinimide ester activated forms of two of the mass labels of this invention.

Figure 8:
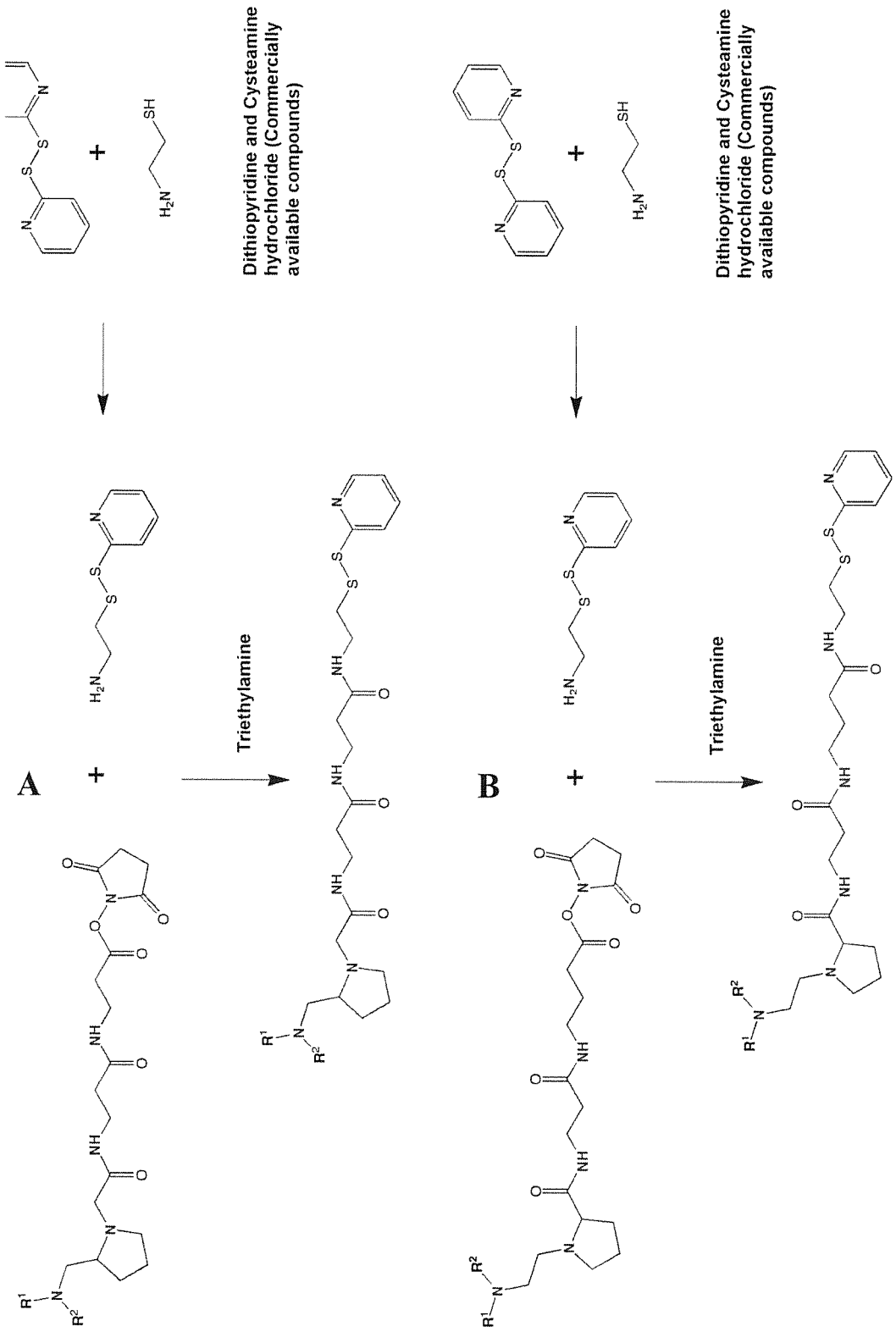
FIGS. 8A and 8B show schemes for the formation of reactive mass labels with 2-dithiopyridine reactive functionalities

FIGS. 8A and 8B illustrate the synthesis of pyridyldithio-activated forms of the mass labels of this invention. In this reaction scheme cysteamine is reacted with dithiopyridine to produce the protected amine that is then coupled to the N-hydroxysuccinimide ester activated forms of two of the mass labels of this invention to yield the pyridyldithio-activated form of the mass labels of this invention. The pyridyldithio-activated form of the mass labels of this invention may be used to couple the mass labels of this invention to thiol functions such as reduced cysteine residues in proteins or peptides. The 2-dithiopyridine group and has several advantages: it shows a high selectivity to label cysteine residues, even at increased pH as often used in buffer solutions useful in proteomic investigations (e.g. Triethylammonium bicarbonate TEAB) and it is not labile to exposure to water. Furthermore, this group can be re-cleaved from peptides easily if desired by treatment with any disulfide-reducing reagents.

Figure 9:
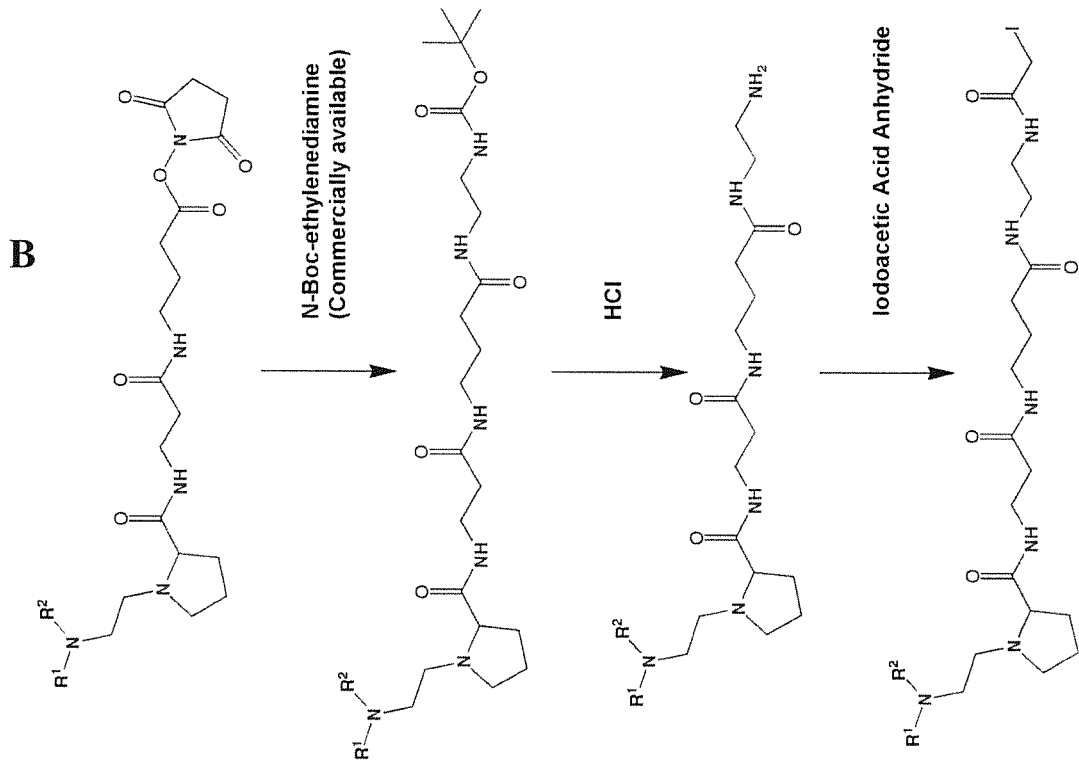
FIGS. 9A and 9B show schemes for the formation of reactive mass labels with iodoacetamide reactive functionalities
Figure 9:
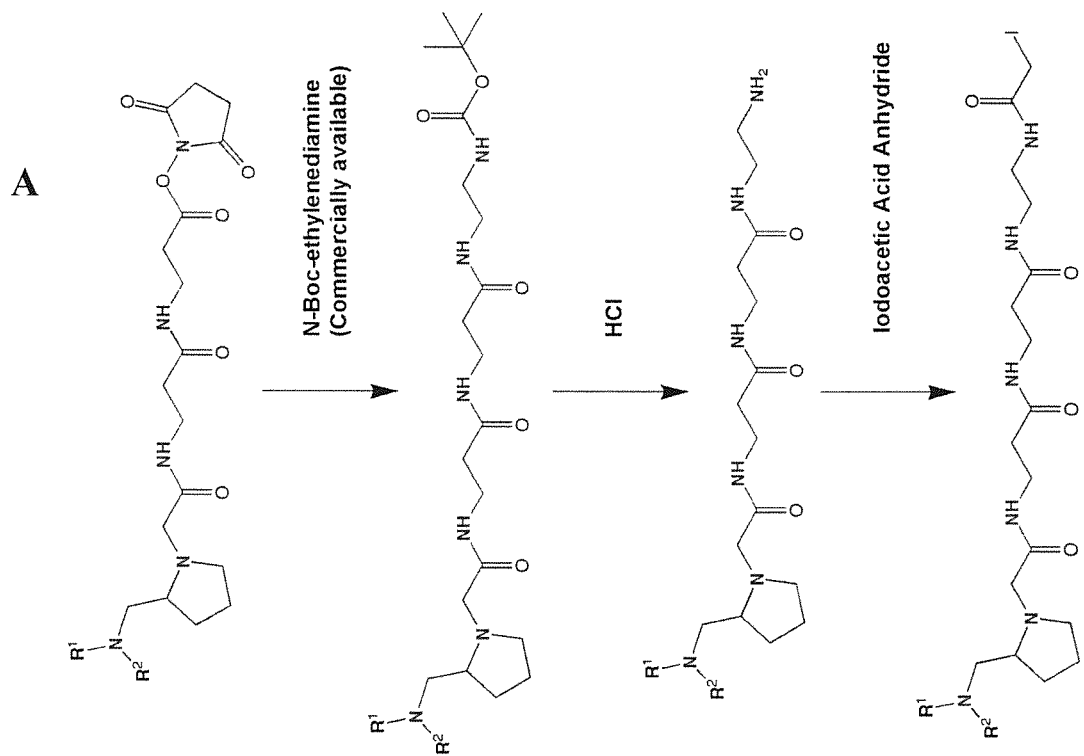

FIGS. 9A and 9B illustrate the synthesis of iodoacetamide-activated forms of the mass labels of this invention. In this reaction scheme BOC-protected ethylenediamine is reacted with the N-hydroxysuccinimide ester activated forms of two of the mass labels of this invention followed by removal of the BOC group to yield amino-functionalised form of the mass labels of this invention. Amino-functionalised mass labels are useful in their own right and may be used to couple the mass labels of this invention to carbonyl groups with reduction of the resulting imines. The amino-functionalised forms of the mass labels of this invention may be reacted further to produce haloacetyl forms of the mass tags of this invention by coupling haloacetic acid anhydrides, such as iodoacetic acid anhydride, to the amino-functionalised tags. The resulting iodoacetamide-activated form of the mass labels of this invention may be used to couple the mass labels of this invention to thiol functions such as reduced cysteine residues in proteins or peptides.

The synthesis of alkyne-activated forms of the mass tags of this invention is achieved by reacting propargylamine with the N-hydroxysuccinimide ester activated forms of two of the mass labels according to the invention to yield alkyne-functionalised form of the mass labels of this invention. Alkyne-functionalized mass labels may be reacted with azide functionalities via Copper-catalyzed Azide Alkyne Cycloaddition (CuAAC) reaction to form triazole linkages, which is sometimes referred to as the 'Sharpless Reaction' (Rostovtsev, V. V.; Green, L. G.; Fokin, V. V.; Sharpless, K. B. Angew. Chem., Int. Ed. 2002, 41, 2596-2599). A variety of azide-based reagents for metabolic labelling of live cells are commercially available and allowing azide-labelled molecules derived from such cells to be labelled with the mass labels of this invention.

Figure 10:
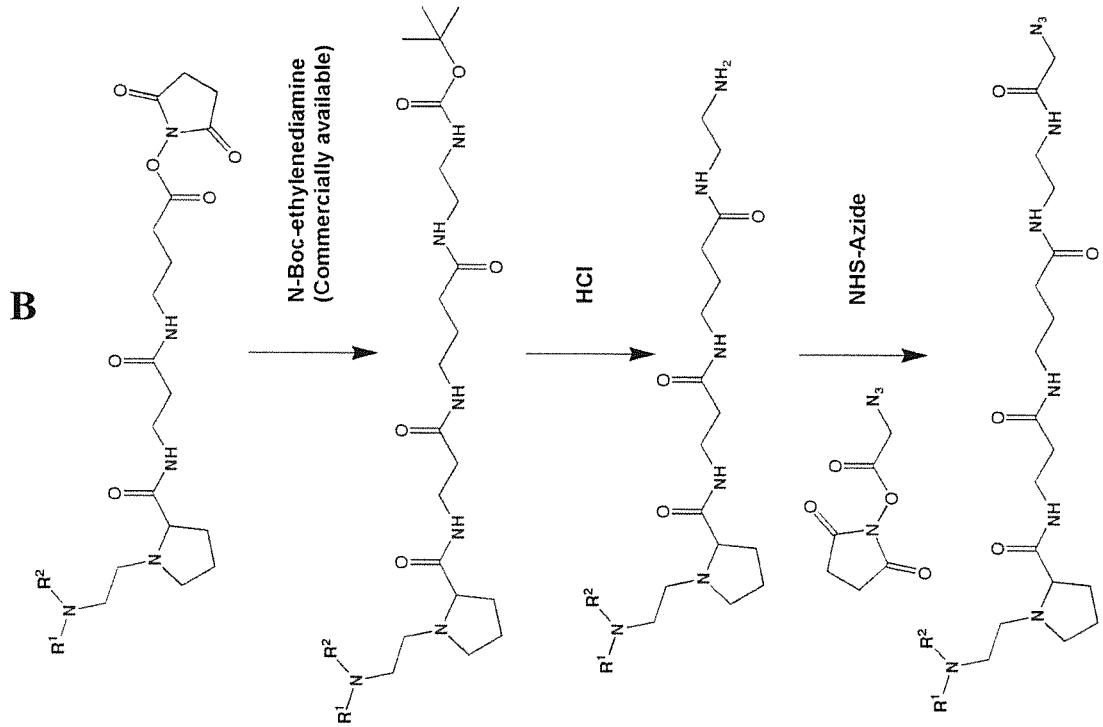
FIGS. 10A and 10B show schemes for the formation of reactive mass labels with azide reactive functionalities
Figure 10:
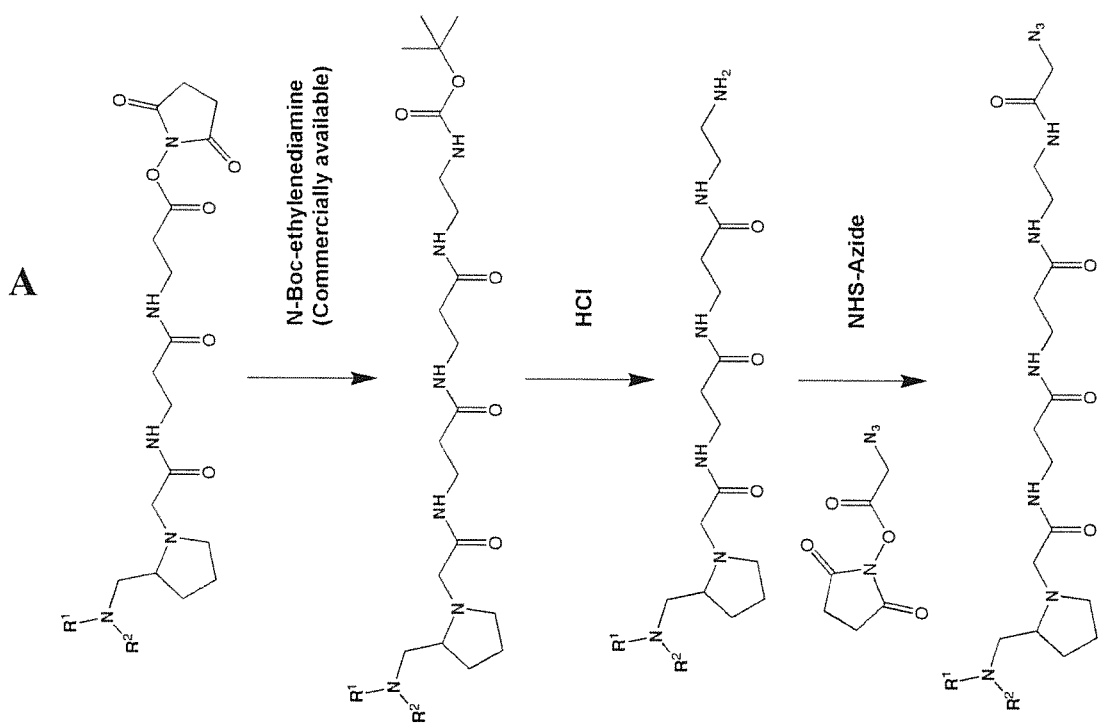

FIGS. 10A and 10B illustrate the synthesis of azide-activated forms of the mass labels of this invention. BOC-protected ethylenediamine is reacted with the NHS-ester activated forms of two of the mass label of this invention followed by removal of the BOC group to yield amino-functionalised form of the mass labels of this invention. The amino-functionalised forms of the mass labels of this invention may be reacted further to produce azide-functionalized forms of the mass labels of this invention by coupling a commercially available NHS-Azide reagent (Thermo Scientific's Pierce Biotechnology division, Rockford, Ill., USA), to the amino-functionalised mass labels. Alternatively, the amino-functionalized mass labels can be converted directly to the azide by reaction with azidification reagent imidazole-1-sulfonyl azide. Imidazole-1-sulfonyl azide is prepared by treating sulfuryl chloride with sodium azide in acetonitrile, followed by the addition of excess imidazole (Goddard-Borger, E. D. and Stick, R. V. (2007) *Org Lett,* 9, 3797-3800). Azide-functionalized tags may be reacted with alkyne functionalities via the 'Sharpless Reaction' or Copper-catalyzed Azide Alkyne Cycloaddition (CuAAC) reaction to form triazole linkages. A variety of alkyne-based reagents for metabolic labelling of live cells are commercially available and allowing alkyne-labelled molecules derived from such cells to be labelled with the tags of this invention.

Arrays of Mass Labels

The present invention also provides an array of mass labels, comprising two or more sets of mass labels as defined herein.

Preferably the integer mass of each of the mass labels of any one set in the array is different from the integer mass of each of the mass labels of every other set in the array.

More preferably each mass label in a set comprises:
 a) a mass series modifying group having the same integer mass as every other mass label in the set and
 b) a different integer mass to the mass labels of all the other sets of the array.

In a particularly preferred embodiment the reporter moiety comprises the mass series modifying group.

In one embodiment each mass label in a set comprises the same mass series modifying group. Preferably each mass label in a set comprises a mass series modifying group which is an isotopologue of the mass series modifying group of all other mass labels of the array.

Methods of Mass Spectrometry Analysis

The present invention also provides for a method of mass spectrometry analysis, which method comprises detecting an analyte by identifying by mass spectrometry a mass label or combination of mass labels relatable to the analyte, wherein the mass label is a mass label from a set or array of mass labels as defined herein.

In one embodiment the method comprises:
a. providing a plurality of samples, wherein each sample is differentially labelled with a mass label or a combination of mass labels, wherein the mass label(s) are from a set or an array of mass labels as defined herein;
b. mixing the plurality of labelled samples to form an analysis mixture comprising labelled analytes;
c. optionally detecting the labelled analytes in a mass spectrometer;
d. dissociating the labelled analytes in the mass spectrometer to form mass labels and/or analyte fragments comprising intact mass labels;
e. detecting the mass labels and/or analyte fragments comprising intact mass labels;
f. optionally dissociating the mass labels in the mass spectrometer to release the reporter moieties, and detecting the reporter moieties;
g. optionally dissociating the reporter moieties formed in step f to form fragments, and detecting the fragments;
h. identifying the analytes on the basis of the mass spectrum of the labelled analytes; and/or the mass spectrum of the mass labels and/or analyte fragments comprising an intact mass label; and/or the mass spectrum of the reporter moieties or fragments of reporter moieties.

The analytes may be identified on the basis of the mass spectrum of the labelled analytes.

The analytes may be identified on the basis of the mass spectrum of the mass labels and/or analyte fragments comprising an intact mass label. In one embodiment the analyte fragment comprising an intact mass label is a b-series ion comprising an intact mass label, preferably a b1 ion. The analytes may be identified on the basis of the mass spectrum of the reporter moieties or fragments of reporter moieties.

In another embodiment, the method comprises:
a. providing a plurality of samples, wherein each sample is differentially labelled with a mass label or a combination of mass labels, wherein the mass label(s) are from a set or an array of mass labels as defined herein;
b. mixing the plurality of labelled samples to form an analysis mixture comprising labelled analytes;
c. detecting the labelled analytes in a mass spectrometer;
d. dissociating the labelled analytes in the mass spectrometer to release the reporter moieties, and detecting the complement ions comprising the remainder of the mass label attached to the analyte or a fragment of the analyte;
e. optionally one or more further steps of dissociating the complement ions formed in step d to form fragments, and detecting the fragments;
f. identifying the analytes on the basis of the mass spectrum of the labelled analytes and/or the mass spectrum of the complement ions and/or fragments thereof.

The dissociation is, preferably, collision induced dissociation in a mass spectrometer. In some embodiments, a complement ion is formed in step d. by neutral loss of carbon monoxide from the linker L.

Preferably the methods described herein are performed in a mass spectrometer with a resolution of greater than 60,000 at a mass-to-charge ratio of 400, preferably a resolution of greater than 100,000 at a mass-to-charge ratio of 400, most preferably greater than 250,000 at a mass-to-charge ratio of 400.

Many of the mass labels of this invention are differentiated from each other by very small mass difference, sometimes of the order of only 1 milliDalton. It has already be established that current Orbitrap instrumentation can resolve reporter ions with 6.3 milliDalton mass differences (6). However, for mass labels that are differentiated from each other by the smallest mass differences, higher resolution may be necessary and this can currently be achieved routinely on commercially available Fourier Transform Ion Cyclotron Resonance mass spectrometers.

Time-of-Flight (TOF) mass spectrometers are a further example of a type of mass spectrometer from which high resolution, high mass accuracy data may be obtained depending on the length of the flight tube. Commercially available, Multi-turn (Okumura, D. et al., (2005) *Eur J Mass Spectrom* (Chichester, Eng), 11, 261-266) and Spiral TOF (Shimma, S. et al., (2012) *PLoS One*, 7, e37107) geometries can already achieve mass resolution similar to Orbitraps.

The Orbitrap mass spectrometer consists of an outer barrel-like electrode and a coaxial inner spindle-like electrode that form an electrostatic field with quadro-logarithmic potential distribution (Hu, Q. et al., (2005) *J Mass Spectrom*, 40, 430-443 & Makarov, A. (2000) *Anal Chem*, 72, 1156-1162). Image currents from dynamically trapped ions are detected, digitized and converted using Fourier transforms into frequency domain data and then into mass spectra. Ions are injected into the Orbitrap, where they settle into orbital pathways around the inner electrode. The frequencies of the orbital oscillations around the inner electrode are recorded as image currents to which Fourier Transform algorithms can be applied to convert the frequency domain signals into mass spectra with very high resolutions.

In Fourier Transform Ion Cyclotron Resonance (FTICR) mass spectrometry, a sample of ions is retained within a cavity like and ion trap but in FTICR MS the ions are trapped in a high vacuum chamber by crossed electric and magnetic fields (Marshall, A. G. et al., (1998) *Mass Spectrom Rev*, 17, 1-35 & Marshall, A. G. and Hendrickson, C. L. (2008) *Annu Rev Anal Chem* (Palo Alto Calif.), 1, 579-599). The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates', which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis. The mass resolution of FTICR instruments increases with the strength of the applied magnetic field and very high resolution (>1,000,000) analysis can be achieved (Schaub, T. M. et al., (2008) *Anal Chem*, 80, 3985-3990).

For induced fragmentation experiments, FTICR instruments can perform in a similar manner to an ion trap—all ions except a single species of interest can be ejected from the FTICR cavity. A collision gas can be introduced into the FTICR cavity and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole or Time-of-Flight instrument, for example.

In a time-of-flight mass spectrometer, pulses of ions with a narrow distribution of kinetic energy are caused to enter a field-free drift region. In the drift region of the instrument, ions with different mass-to-charge ratios in each pulse travel with different velocities and therefore arrive at an ion detector positioned at the end of the drift region at different times. The length of the drift region determines mass resolution of TOF instruments and this may be readily increased. The analogue signal generated by the detector in response to arriving ions is immediately digitised by a time-to-digital converter. Measurement of the ion flight-time determines mass-to-charge ratio of each arriving ion. There are a number of different designs for time of flight instruments. The design is determined to some extent by the nature of the ion source. In Matrix Assisted Laser Desorption Ionisation Time-of-Flight (MALDI TOF) mass spectrometry pulses of ions are generated by laser excitation of sample material crystallized on a metal target. These pulses form at one end of the flight tube from which they are accelerated.

In order to acquire a mass spectrum from an electrospray ion source, an orthogonal axis TOF (oaTOF) geometry is used. Pulses of ions, generated in the electrospray ion source, are sampled from a continuous stream by a 'pusher' plate. The pusher plate injects ions into the Time-Of-Flight mass analyser by the use of a transient potential difference that accelerates ions from the source into the orthogonally positioned flight tube. The flight times from the pusher plate to the detector are recorded to produce a histogram of the number of ion arrivals against mass-to-charge ratio. This data is recorded digitally using a time-to-digital converter.

For the purposes of resolving all of the possible tags of this invention, mass spectrometers with high resolution are required but the nature of the instruments is not particularly important to the practice of this invention. In addition, many of the tags that have been described in this application can still be resolved on instruments with only single Dalton resolution as long as subsets of the possible tags that are separated by single Dalton mass differences are used.

Syntheses of Mass Labels

Example 1

Synthesis of N-Methyl Proline—Beta-Alanine—Beta-Alanine—N-Hydroxysuccinimide Ester Mass Label The N-methyl proline—beta-alanine—beta-alanine—N-hydroxysuccinimide ester mass label structure shown below was synthesized (N-methyl proline tag).

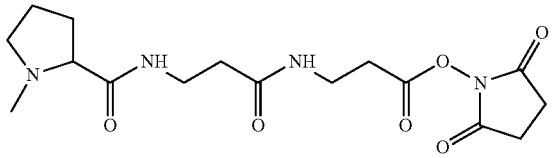 [SMILES: CN1CCCC1C(=O)NCCC(=O)NCCC(=O)ON1C(=O)CCC1=O]

Proline and N-methyl proline are commercially available in an undoped form (SigmaAldrich, St Louis, Mo., USA). Isotope doped variants of proline are available from Sigma Aldrich (St Louis, Mo., USA), Cambridge Isotope Laboratories, Inc (Tewksbury, Mass., USA) and Alsa Chim (Illkirch-Graffenstaden, Strasbourg, France)

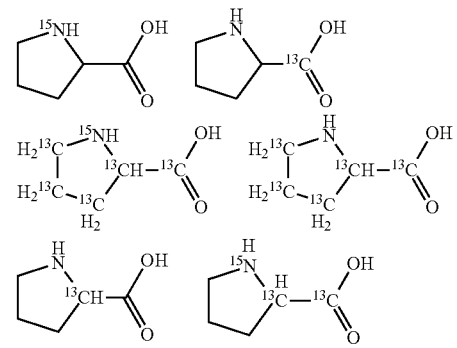

-continued

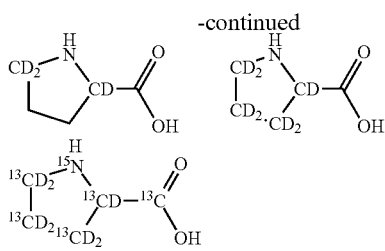

N-Boc protected proline was coupled via its carboxylic acid group to the free amino group of beta-alanine that was protected as a benzyl ester at its carboxylic acid group. After removal of the benzyl ester, a further benzyl ester protected beta-alanine molecule was coupled to the beta-alanine extended N-Boc proline structure to give the double beta-alanine extended structure. The Boc group was cleaved by treatment with trifluoroacetic acid and the N-methyl group was introduced by reaction with formaldehyde and sodium cyanoborohydride. After deprotection of the second benzyl ester, the tag structure was activated to give the N-hydroxysuccinimide ester.

Isotope doped versions of the N-methyl proline tag can be prepared using the procedure above from the commercially available proline isotopes or by following published methods (da Silva et al., Tetrahedron Letters 48(43) 7680-7682, "Reductive methylation of primary and secondary amines and amino acids by aqueous formaldehyde and zinc", 2007). Various formaldehyde isotopes are commercially available ($^{13}COH_2$, $COD_2$, $^{13}COD_2$) from SigmaAldrich (St Louis, Mo., USA) and Cambridge Isotope Laboratories, Inc (Tewksbury, Mass., USA).

The N-methyl proline tag was coupled to a synthetic peptide with the sequence VATVSLPR. This peptide sequence has one free primary amino group at the N-terminus, which couples with the N-methyl proline tag to give a labelled molecule with a mass of 1095.32. The peptide tag was dissolved in 100 mM Triethylammonium Bicarbonate (TEAB) buffer at pH 8.5 to which the tag (dissolved in acetonitrile) was added to give a final concentration of 15 mM tag and the reaction was left for 1 hour at room temperature. The sample was then quenched with a small amount hydroxylamine according to a previously published protocol for Tandem Mass Tags (Kuhn K et al., Methods Mol Biol. 799:127-41, "TMT labelling for the quantitative analysis of adaptive responses in the meningococcal proteome." 2012).

Electrospray Ionisation mass spectra for this labelled peptide structure were obtained on a Waters Q-TOF 2 instrument by direct injection of the tagged peptide solution. In the MS-mode spectrum for the labelled peptide, the $[M+2H]^{2+}$ ion were seen at m/z 548.309. The MS/MS spectrum of the tagged peptide after Collision Induced Dissociation (CID) with precursor selection of the ion at m/z 548.3 was carried out. An intense N-methylproline a-ion reporter at m/z 84 was observed. In addition, a reasonably strong 'complement ion' was seen at m/z 984.6. The complement ion is the peptide fragment ion that is left after loss of the reporter and further neutral loss of carbon monoxide. This species is singly charged. The fragmentation mechanism of this mass label is shown in FIG. 2, where the R substituent is a methyl group. The N-methyl proline tag structure will support a 12-plex set of isobaric tags based on all the possible isotopic substitutions of $^{13}C$ and $^{15}N$ according to this invention. The corresponding N-ethyl proline tag structure will support a 14-plex set of isobaric tags while the N-propyl proline tag structure will support a 16-plex set of isobaric tags based on all the possible isotopic substitutions of $^{13}C$ and $^{15}N$. Larger sets of isobaric tags can be made if all possible deuterium substitutions are included.

Example 2

Synthesis of 3-{3-[((S)-1-Isobutylpyrrolidine-2-carbonyl)-amino]-propionylamino}-propionic acid 2,5-dioxo-pyrrolidin-1-yl ester (Isobutyl-L-Pro-b-Ala-b-Ala-OSu)—Sets 10, 11 and 12

Step 1: Synthesis of 3-tert-butoxycarbonylaminopropionic acid (Boc-β-Ala-OH)

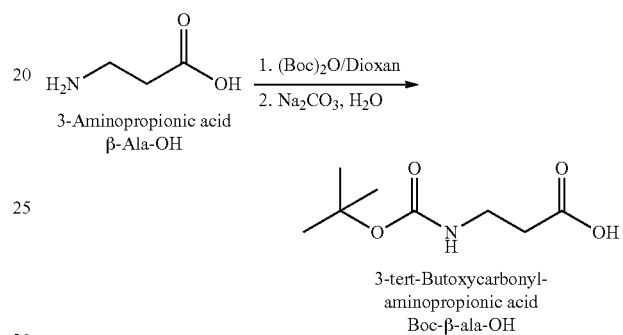

A 6L-four-headed flask was loaded with a solution of 71.3 g (0.8 mol) ß-alanine and 183.3 g (1.05 mol) di-tert-butyl dicarbonate in 800 mL dioxan at room temperature. Over a period of 30 minutes a solution of 217.3 g sodium carbonate in 800 ml water was added and after 30 minutes a solid precipitated. 3.5 L water were added, the precipitate dissolved and the solution was stirred for 3 hours at room temperature. The solution was washed with two times 1 L-portions of diisopropyl ether. The pH of the aqueous phase was set to 5 with 2 M hydrochloric acid and the solution was extracted with three 500 mL-portions of dichloromethane. The pH of the aqueous phase was set to 3-4 with 2 M hydrochloric acid and the solution was extracted with two 500 mL-portions of dichloromethane. The organic phases were combined, dried over magnesium sulfate, filtrated and evaporated in vacuo. The residue was crystallized by means of diisopropyl ether. The solid was filtrated, washed with diisopropyl ether and dried in vacuo to yield 129.9 g (0.687 mol, 86%).

Step 2: Synthesis of 3-aminopropionic acid benzyl ester (H-β-Ala-OBn)

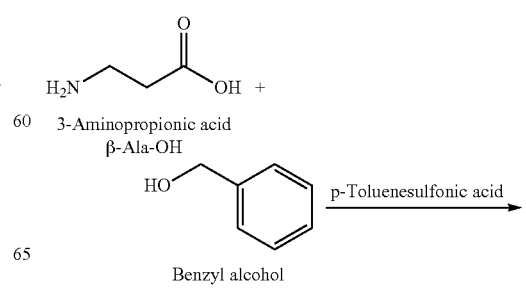

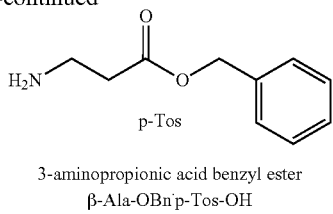

3-aminopropionic acid benzyl ester
β-Ala-OBn·p-Tos-OH

A 4-L four-necked flask equipped with a Dean-Stark apparatus and a condenser was charged with 115.8 g (1.3 mol) ß-alanine, 811 mL (7.8 mol) benzyl alcohol, 264.4 g (1.39 mol) of p-toluenesulfonic acid and 1.3 L toluene. The reaction mixture was heated 2.5 hours under reflux and ca. 54 mL of water were separated. The solution was allowed to cool down, and at 45° C. to 50° C. 1.5 L of diisopropyl ether were added slowly and the product started to crystalize. The mixture was stirred for 1.5 hours and the temperature of the solution dropped to 20° C.–25° C. and crystallization of the product finished. The solid was filtrated, washed with diisopropyl ether and dried in vacuo at 40° C.

Yield: 447.7 g (1.274 mol, 98%) as p-toluenesulfonate salt.

Step 3: Synthesis of 3-(3-tert-butoxycarbonylamino-propionylamino)-propionic acid benzyl ester (Boc-β-Ala-β-Ala-OBn)

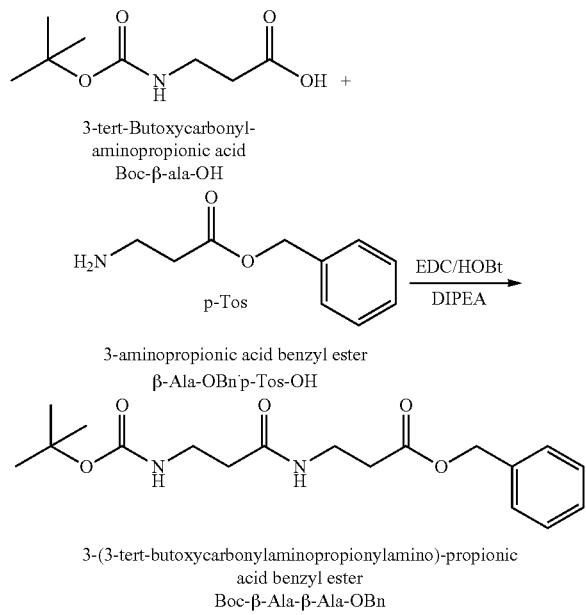

3-(3-tert-butoxycarbonylaminopropionylamino)-propionic acid benzyl ester
Boc-β-Ala-β-Ala-OBn To a suspension of 126.8 g (0.67 mol) (1) in 1.2 L tetrahydrofuran were added 227.9 mL diisopropylethylamine (DIPEA) and a clear solution was formed. Following the addition of 143.6 g (0.94 mol) 1-hydroxybenzotriazole monohydrate (HOBt) and 167.0 g (0.87 mol) 1-ethyl-3-(3-dimethylamino-propyl)-carbodiimide hydrochloride (EDC), 235.5 g (0.67 mol) (2) were added after 30 minutes. The solution was stirred for 2 hours at room temperature. The reaction was evaporated in vacuo and the residue was dissolved in 2 L ethylacetate. The ethyl acetate solution was washed with two 2 L-portion of saturated sodium bicarbonate solution and with 1 L of half-saturated sodium chloride solution. The organic layer was dried over magnesium sulfate, filtrated and evaporated in vacuo. The residue was dissolved in 250 mL dichloromethane, treated with 500 mL diisopropylether and the dichloromethane was evaporated in vacuo. The product, which crystalized during cooling off, was filtrated, washed with diisopropyl ether and n-hexane and dried in vacuo.

Yield: 125.9 g (0.359 mol; 53.6%)

Step 4: Synthesis of 3-(3-aminopropionylamino)-propionic acid benzyl ester hydrochloride (H-β-Ala-β-Ala-OBn*HCl)

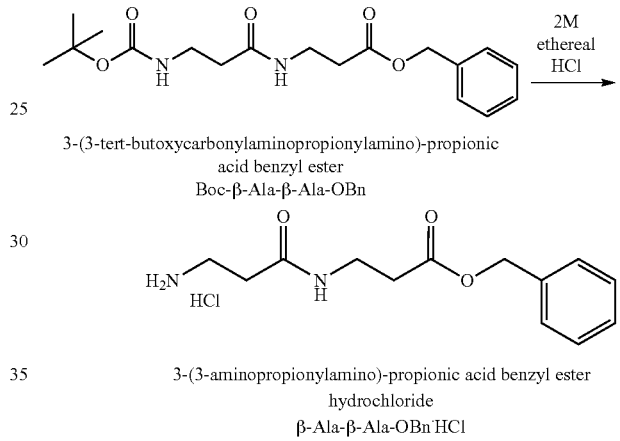

3-(3-tert-butoxycarbonylaminopropionylamino)-propionic acid benzyl ester
Boc-β-Ala-β-Ala-OBn 3-(3-aminopropionylamino)-propionic acid benzyl ester hydrochloride
β-Ala-β-Ala-OBn·HCl 125.9 g (0.36 mol) Boc-ß-Ala-ß-Ala-OBn dissolved in 450 mL dichloromethane were treated with 468 ml 2 M (0.94 mol) ethereal hydrogen chloride. The solution turned brown-orange and gas forms. After 4 hours the crystallized product was filtrated, washed with diisopropyl ether and dried in vacuo at 40° C.

Yield: 104.1 g (100%)

Since numerous isotopes of beta-Alanine are commercially available, it should be apparent to one of ordinary skill in the art that these can be substituted into the synthetic steps above to generate double beta-alanine linkers with multiple different isotopic masses.

Step 5: Synthesis of (2S)-pyrrolidine-1,2-dicarboxylic acid 1-tert-butyl ester (Boc-L-Proline, Boc-L-Pro)

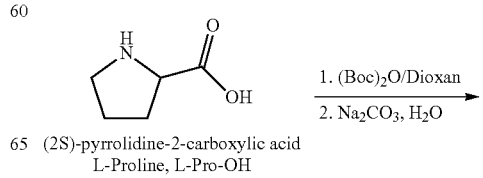

(2S)-pyrrolidine-2-carboxylic acid
L-Proline, L-Pro-OH

-continued

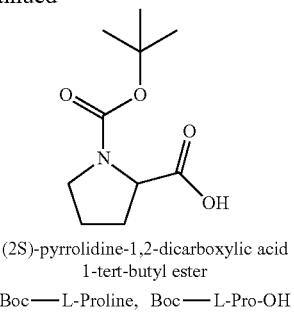

(2S)-pyrrolidine-1,2-dicarboxylic acid
1-tert-butyl ester

Boc—L-Proline, Boc—L-Pro-OH

A 6 L four-headed flask was loaded with a solution of 92.1 g (0.8 mol) L-proline and 183.3 g (1.05 mol) di-tert-butyl dicarbonate in 800 mL dioxan at room temperature. Over a period of 30 minutes a solution of 217.3 g sodium carbonate in 800 ml water was added and after 10 minutes a solid precipitated. 3.5 L water were added, the precipitate dissolved and the solution was stirred for 3 hours at room temperature. The solution was washed with two times 1 L-portions of diisopropyl ether. The pH of the aqueous phase was set to 5 with 2 M hydrochloric acid and the solution was extracted with three 500 mL-portions of dichloromethane. Then the pH of the aqueous phase was set to 3-4 with 2 M hydrochloric acid and the solution was extracted with two 500 mL-portions of dichloromethane. The organic phases were combined, dried over magnesium sulfate, filtrated and evaporated in vacuo. The residue was crystallized by means of diisopropyl ether. The solid was filtrated, washed with diisopropyl ether and dried in vacuo to yield 155.4 g (0.722 mol, 90.3%). All the commercially available isotopes discussed in Example 1 can be used at this stage in the synthesis to generate different reporter isotopes according to this invention.

Step 6: Synthesis of (S)-2-[2-(2-Benzyloxycarbonyl-ethylcarbamoyl)-ethylcarbamoyl]-pyrrolidine-1-carboxylic acid tert-butyl ester (Boc-L-Pro-β-Ala-β-Ala-OBn)

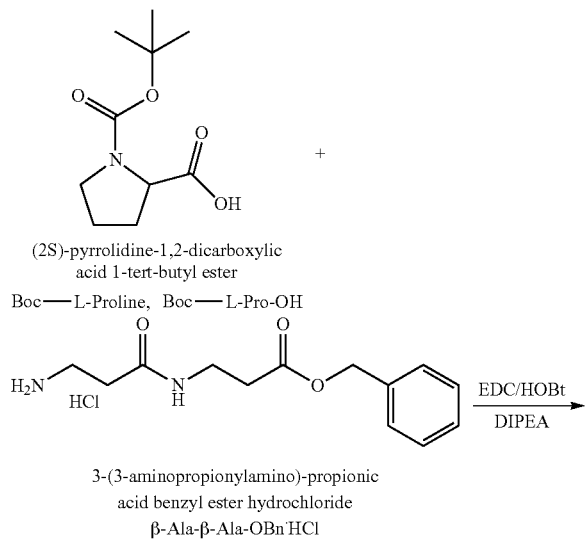

(2S)-pyrrolidine-1,2-dicarboxylic
acid 1-tert-butyl ester

Boc—L-Proline, Boc—L-Pro-OH 3-(3-aminopropionylamino)-propionic
acid benzyl ester hydrochloride β-Ala-β-Ala-OBn·HCl

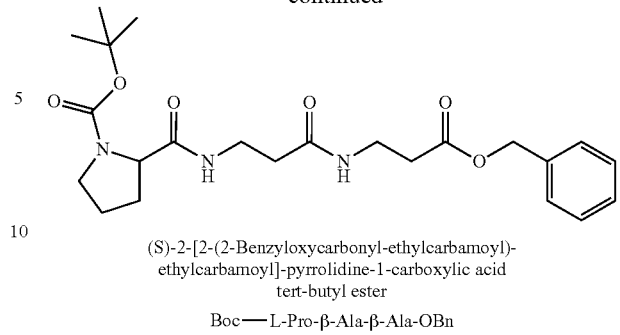

(S)-2-[2-(2-Benzyloxycarbonyl-ethylcarbamoyl)-
ethylcarbamoyl]-pyrrolidine-1-carboxylic acid
tert-butyl ester Boc—L-Pro-β-Ala-β-Ala-OBn To a suspension of 22.5 g (0.105 mol) Boc-L-proline in 400 mL tetrahydrofuran were added 63.0 mL (0.362 mol) diisopropylethylamine (DIPEA) and a clear solution was formed. Following the addition of 22.4 g (0.146 mol) 1-hydroxybenzotriazole monohydrate (HOBt) and 26.1 g (0.136 mol) 1-ethyl-3-(3-dimethylamino-propyl)-carbodiimide hydrochloride (EDC), 30.0 g (0.105 mol) H-ß-Ala-ß-Ala-OBn*HCl were added after 5 minutes. The solution was stirred for 3.5 hours at room temperature. The reaction was evaporated in vacuo and the residue was dissolved in ethyl acetate. The ethyl acetate solution was washed two times with saturated sodium bicarbonate solution and with half-saturated sodium chloride solution. The organic layer was dried over magnesium sulfate, filtrated and evaporated in vacuo. The residue was dissolved in dichloromethane, treated with diisopropyl ether and the dichloromethane was evaporated in vacuo. The product, which crystalizes during cooling off, was filtrated, washed with diisopropyl ether and dried in vacuo.

Yield: 38.3 g (0.086 mol; 82.2%)

It should be apparent to one of ordinary skill in the art that any heavy isotope of proline can be substituted into this synthesis to generate a range of isotopically differentiated reagents according to this invention.

Step 7: Synthesis of 3-{3-[((S)-Pyrrolidine-2-carbonyl)-amino]-propionylamino}-propionic acid benzyl ester hydrochloride (H-L-Pro-β-Ala-β-Ala-OBn*HCl)

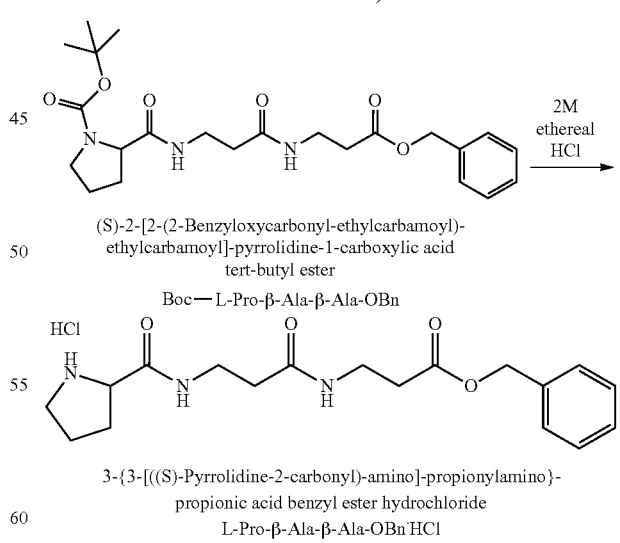

(S)-2-[2-(2-Benzyloxycarbonyl-ethylcarbamoyl)-
ethylcarbamoyl]-pyrrolidine-1-carboxylic acid
tert-butyl ester Boc—L-Pro-β-Ala-β-Ala-OBn 3-{3-[((S)-Pyrrolidine-2-carbonyl)-amino]-propionylamino}-
propionic acid benzyl ester hydrochloride L-Pro-β-Ala-β-Ala-OBn·HCl 50 g (0.11 mol) Boc-L-Pro-ß-Ala-ß-Ala-OBn dissolved in 250 mL dichloromethane were treated with 250 ml 2 M (0.50 mol) ethereal hydrogen chloride. After stirring the reaction for 2.5 hours at room temperature, the solution was evaporated in vacuo to yield a highly viscous oil.

Yield: 43.0 g (100%)

Step 8: Synthesis of 3-{3-[((S)-1-Isobutylpyrrolidine-2-carbonyl)-amino]-propionylamino}-propionic acid benzyl ester (Isobutyl-L-Pro-β-Ala-β-Ala-OBn)

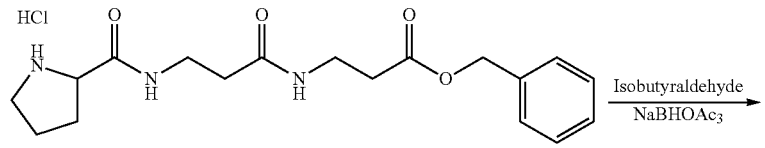

3-{3-[((S)-Pyrrolidine-2-carbonyl)-amino]-propionylamino}-propionic acid benzyl ester hydrochloride
L-Pro-β-Ala-β-Ala-OBn·HCl

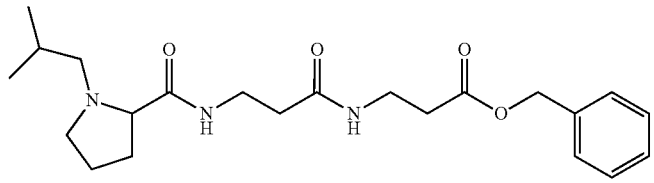

3-{3-[((S)-1-Isobutylpyrrolidine-2-carbonyl)-amino]-propionylamino}-propionic acid benzyl ester
Isobutyl-L-Pro-β-Ala-β-Ala-OBn 10 g L-Pro-ß-Ala-ß-Ala-OBn were dissolved in 150 mL 1,2-dichloroethane under an argon atmosphere and 5.8 ml diisopropylethylamine were added. Then 3.04 ml isobutyraldehyde and 7.06 g sodium triacetoxyborohydride were added with cooling and the reaction is stirred for 1 hour at room temperature. The solution was evaporated in vacuo. The residue was dissolved in ethyl acetate, washed two times with saturated sodium bicarbonate and saturated sodium chloride, dried over sodium sulfate and evaporated in vacuo. The crude product was loaded on a silica gel column and eluted by dichloromethane/methanol (20:1).

Yield: 7.8 g (74.2%)

Step 9: Synthesis of 3-{3-[((S)-1-Isobutylpyrrolidine-2-carbonyl)-amino]-propionylamino}-propionic acid (Isobutyl-L-Pro-β-Ala-β-Ala-OH)

3.2 g (7.9 mmol) Isobutyl-L-Pro-β-Ala-β-Ala-OBn in 40 mL methanol over 5%-Pd/C catalyst under an argon atmosphere was hydrogenated by passing hydrogen into the reaction mixture. After the consumption of hydrogen was finished, the reaction mixture was filtrated and the filter residue was washed with methanol. The combined methanol layers were evaporated in vacuo. The crude product was loaded on a silica gel column and eluted by dichloromethane/methanol (3:1).

Yield: 1.4 g (58.8%)

Analysis of the Isobutyl-L-Pro-β-Ala-β-Ala-OH Tag by Mass Spectrometry:

Electrospray ionisation (ESI) mass spectra for the free acid form of the tag (Isobutyl-L-Pro-β-Ala-β-Ala-OH) were obtained on a Waters Q-TOF 2 instrument by direct injection of the free acid tag solution (in 1% formic acid). In the MS-mode spectrum for the tag free acid the [M+H]$^+$ ion was seen at m/z 314.2. In the MS/MS spectrum of the tag free acid after Collision Induced Dissociation (CID) with precursor selection of the ion at m/z 314.2, an intense isobu-

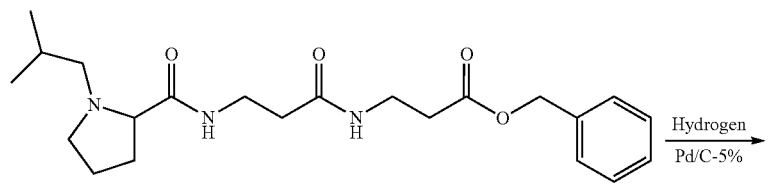

3-{3-[((S)-1-Isobutylpyrrolidine-2-carbonyl)-amino]-propionylamino}-propionic acid benzyl ester
Isobutyl-L-Pro-β-Ala-β-Ala-OBn

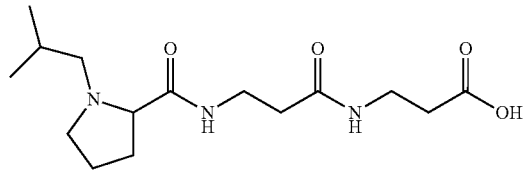

3-{3-[((S)-1-Isobutylpyrrolidine-2-carbonyl)-amino]-propionylamino}-propionic acid
Isobutyl-L-Pro-β-Ala-β-Ala-OH tylproline a-ion reporter at m/z 126.14 was observed. The fragmentation mechanism of this tag is shown in FIG. 2, where the R substituent is an isobutyl group. The Isobutyl-L-Pro-β-Ala-β-Ala-OSu will support an 18-plex set of isobaric tags as shown in Set 10. A larger set of isobaric tags can be made if deuterium substitutions are included as shown in Set 11 as these tag sets could be used in combination.

Step 10: Synthesis of 3-{3-[((S)-1-Isobutylpyrrolidine-2-carbonyl)-amino]-propionylamino}-propionic acid 2,5-dioxo-pyrrolidin-1-yl ester (Isobutyl-L-Pro-β-Ala-β-Ala-OSu)

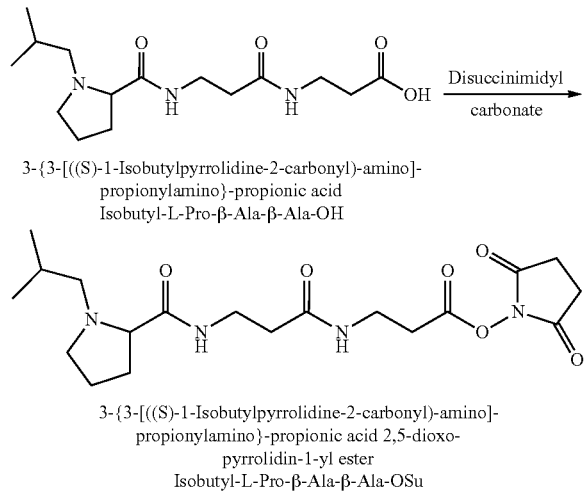

3-{3-[((S)-1-Isobutylpyrrolidine-2-carbonyl)-amino]-propionylamino}-propionic acid
Isobutyl-L-Pro-β-Ala-β-Ala-OH 3-{3-[((S)-1-Isobutylpyrrolidine-2-carbonyl)-amino]-propionylamino}-propionic acid 2,5-dioxo-pyrrolidin-1-yl ester
Isobutyl-L-Pro-β-Ala-β-Ala-OSu To a solution of 3.6 g (11.4 mmol) isobutyl-L-Pro-β-Ala-β-Ala-OH in 100 mL dichloromethane were added 3.56 g (13.7 mmol) disuccinimidyl carbonate. The suspension gave a clear solution with formation of carbon dioxide and was stirred for 2 hours at room temperature. The reaction was diluted with dichloromethane, washed with three 40 mL-portions of saturated sodium bicarbonate solution and with water, dried over sodium sulfate and evaporated in vacuo. The residue was crystallized by means of ethyl acetate/diisopropyl ether.

Yield: 3.5 g (8.5 mmol, 74.8%)

Example 3

Synthesis of 3-{3-[((S)-1-Isopropylpyrrolidine-2-carbonyl)-amino]-propionylamino}-propionic acid 2,5-dioxo-pyrrolidin-1-yl ester (Isopropyl-L-Pro-β-Ala-β-Ala-OSu)—Sets 13 and 14

Step 1: Synthesis of 3-{3-[((S)-1-Isopropylpyrrolidine-2-carbonyl)-amino]-propionylamino}-propionic acid benzyl ester (Isopropyl-L-Pro-β-Ala-β-Ala-OBn)

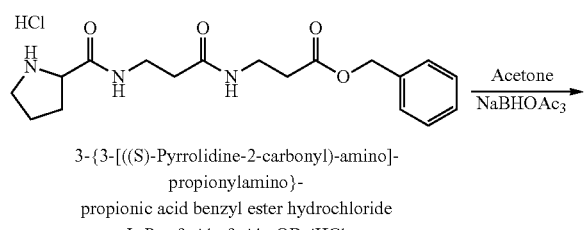

3-{3-[((S)-Pyrrolidine-2-carbonyl)-amino]-propionylamino}-propionic acid benzyl ester hydrochloride
L-Pro-β-Ala-β-Ala-OBn·HCl

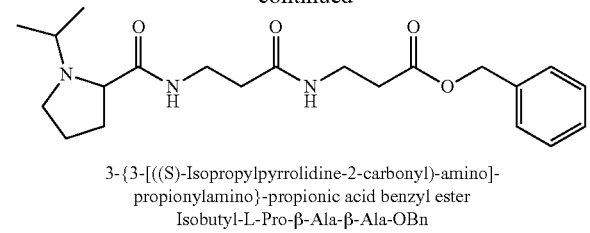

3-{3-[((S)-Isopropylpyrrolidine-2-carbonyl)-amino]-propionylamino}-propionic acid benzyl ester
Isobutyl-L-Pro-β-Ala-β-Ala-OBn 4 g (10.4 mmol) L-Pro-β-Ala-β-Ala-OBn were dissolved in 50 mL 1,2-dichloroethane under an argon atmosphere and 3.54 ml (20.8 mmol) diisopropylethylamine were added. Then 3 g (50.9 mmol) acetone and 2.65 g (12.5 mmol) sodium triacetoxyborohydride were added with cooling and the reaction was stirred for 1 hour at room temperature. The solution was evaporated in vacuo. The residue was dissolved in ethyl acetate, washed two times with saturated sodium bicarbonate and saturated sodium chloride, dried over sodium sulfate and evaporated in vacuo.

Yield: 3.4 g (8.02 mmol, 83.9%)

It should be noted that multiple reporter isotopes can be readily synthesized using commercially available isotopes of acetone. Isotopes of acetone are commercially available from SigmaAldrich (St Louis, Mo., USA) and Cambridge Isotope Laboratories, Inc (Tewksbury, Mass., USA) in addition to the commercially available isotopes of proline discussed above:

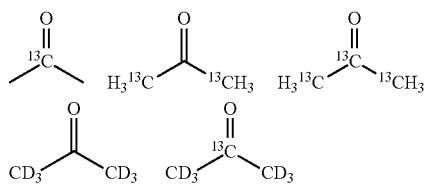

Step 2: Synthesis of 3-{3-[((S)-1-Isopropylpyrrolidine-2-carbonyl)-amino]-propionylamino}-propionic acid (Isopropyl-L-Pro-β-Ala-β-Ala-OH)

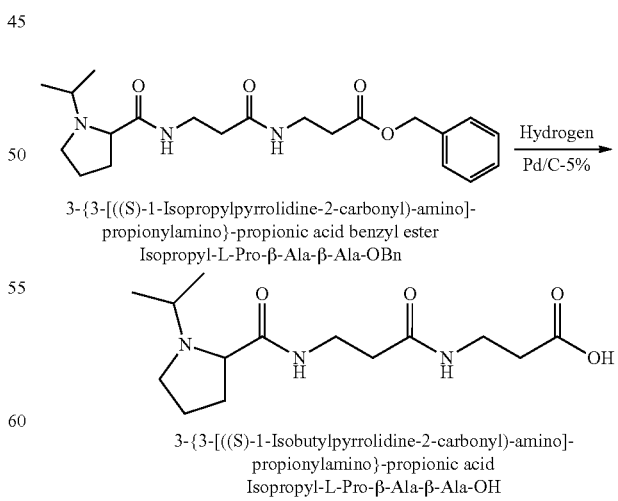

3-{3-[((S)-1-Isopropylpyrrolidine-2-carbonyl)-amino]-propionylamino}-propionic acid benzyl ester
Isopropyl-L-Pro-β-Ala-β-Ala-OBn 3-{3-[((S)-1-Isobutylpyrrolidine-2-carbonyl)-amino]-propionylamino}-propionic acid
Isopropyl-L-Pro-β-Ala-β-Ala-OH 3.4 g (8.7 mmol) Isobutyl-L-Pro-β-Ala-β-Ala-OBn in 40 mL methanol over 5%-Pd/C catalyst under an argon atmosphere was hydrogenated by passing hydrogen into the reaction mixture. After the consumption of hydrogen was finished, the reaction mixture was filtrated and the filter residue was washed with methanol. The combined methanol layers were evaporated in vacuo. The crude product was loaded on a silica gel column and eluted by dichloromethane/methanol (2:1).

Yield: 2.4 g (92.1%)

Analysis of the Isopropyl-L-Pro-β-Ala-β-Ala-OH Tag by Mass Spectrometry

Electrospray ionisation (ESI) mass spectra for the free acid form of the mass labels (Isopropyl-L-Pro-β-Ala-β-Ala-OH) were obtained on a Waters Q-TOF 2 instrument by direct injection of the free acid tag solution (in 1% formic acid). The MS-mode spectrum for the tag free acid showed [M+H]$^+$ ion at m/z 300.2. The MS/MS spectrum of the tag free acid after Collision Induced Dissociation (CID) with precursor selection of the ion at m/z 300.2 resulted in an intense isopropylproline a-ion reporter at m/z 112.12. The fragmentation mechanism of this tag is shown in FIG. 2, where the R substituent is an isopropyl group. The Isopropyl-L-Pro-β-Ala-β-Ala-OSu will support a 16-plex set of isobaric tags as shown in Sets 13 and 14. A larger set of isobaric tags can be made if deuterium substitutions are included.

Step 3: Synthesis of 3-{3-[((S)-1-Isopropylpyrrolidine-2-carbonyl)-amino]-propionylamino}-propionic acid 2,5-dioxo-pyrrolidin-1-yl ester (Isopropyl-L-Pro-β-Ala-β-Ala-OSu)

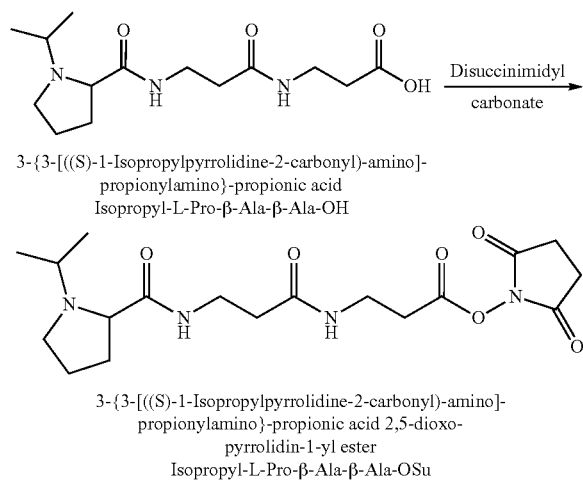

To a solution of 2.4 g (8.0 mmol) isopropyl-L-Pro-β-Ala-β-Ala-OH in 30 mL dichloromethane were added 2.46 g (9.6 mmol) disuccinimidyl carbonate. The suspension gave a clear solution with formation of carbon dioxide and was stirred for 2 hours at room temperature. The reaction was diluted with dichloromethane, washed with three 10 mL portions of saturated sodium bicarbonate solution and with water, dried over sodium sulfate and evaporated in vacuo to yield a viscous oil.

Yield: 2.8 g (7.1 mmol, 88.0%)

Step 4: 3-{3-[((S)-1-Isopropylpyrrolidine-2-carbonyl)-amino]-propionylamino}-propionic acid 2,3,5,6-tetrafluorophenyl ester (Isopropyl-L-Pro-β-Ala-β-Ala-O-TFP)

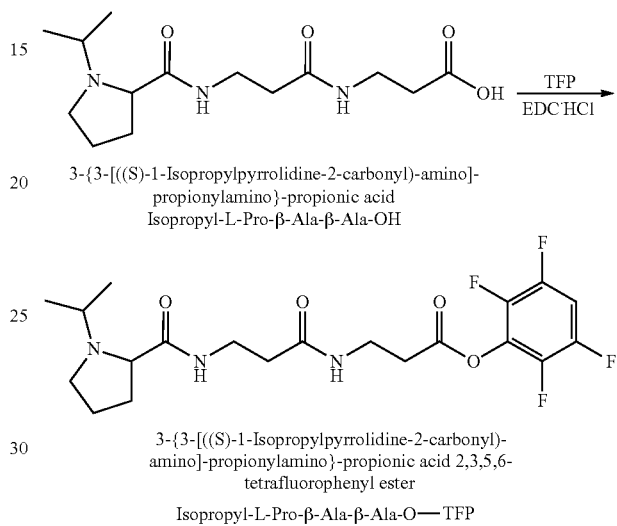

To a solution of 1 g (3.3 mmol) isopropyl-L-Pro-β-Ala-β-Ala-OH and 0.55 g (3.3 mmol) tetrafluorophenol (TFP) in 20 ml dichloromethane was added 0.64 g (3.3 mmol) of N-ethyl-N'-(3-dimethylaminopropyl)-carbodiimide hydrochloride (EDC*HCl). The reaction was stirred for 2 hours at room temperature, diluted with dichloromethane, washed with two 10 mL-portions of saturated sodium bicarbonate solution and with water, dried over sodium sulfate and evaporated in vacuo to yield a viscous oil. The oil was left at 4° C. over night and gave a solid product.

Yield: 0.93 g (2.08 mmol, 63%)

Example 4

3-{3-[((S)-1-Butylpyrrolidine-2-carbonyl)-amino]-propionylamino}-propionic acid 2,5-dioxo-pyrrolidin-1-yl ester (Butyl-L-Pro-β-Ala-β-Ala-OSu)

Step 1: Synthesis of 3-{3-[((S)-1-Butylpyrrolidine-2-carbonyl)-amino]-propionylamino}-propionic acid benzyl ester (Butyl-L-Pro-β-Ala-β-Ala-OBn)

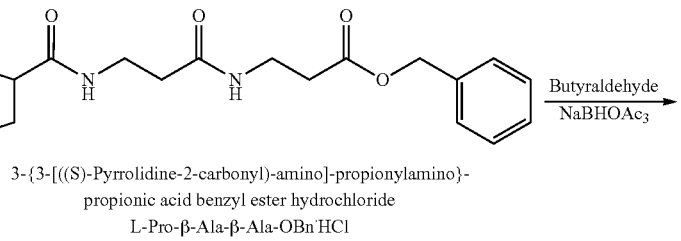

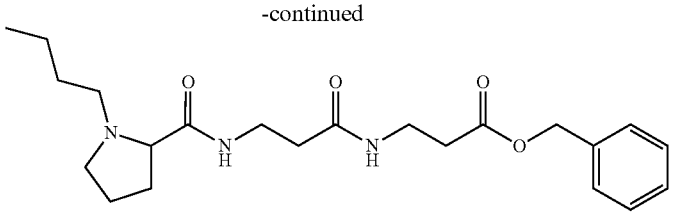

3-{3-[((S)-1-Butylpyrrolidine-2-carbonyl)-amino]-
propionylamino}-propionic acid benzyl ester
Butyl-L-Pro-β-Ala-β-Ala-OBn 5 g (13.0 mmol) L-Pro-ß-Ala-ß-Ala-OBn were dissolved in 50 mL 1,2-dichloroethane under an argon atmosphere and 3.1 ml (18.2 mmol) diisopropylethylamine were added. Then 1.4 ml (15.6 mmol) butyraldehyde and 3.3 g (15.6 mmol) sodium triacetoxyborohydride were added with cooling and the reaction was stirred for 1.5 hour at room temperature. The solution was evaporated in vacuo. The residue was dissolved in ethyl acetate, washed two times with saturated sodium bicarbonate and saturated sodium chloride, dried over sodium sulfate and evaporated in vacuo.

Yield: 2.9 g (7.19 mmol, 55.2%)

Step 2: Synthesis of 3-{3-[((S)-1-Butylpyrrolidine-
2-carbonyl)-amino]-propionylamino}-propionic acid
(n-Butyl-L-Pro-β-Ala-β-Ala-OH)

washed with methanol. The combined methanol layers were evaporated in vacua.

Yield: 2.0 g (6.38 mmol, 90.9%)

Analysis of the n-Butyl-L-Pro-β-Ala-β-Ala-OH Tag by Mass Spectrometry:

Electrospray ionisation (ESI) mass spectra for the free acid form of the tag (n-Butyl-L-Pro-β-Ala-β-Ala-OH) were obtained on a Waters Q-TOF 2 instrument by direct injection of the free acid tag solution (in 1% formic acid). The MS-mode spectrum for the tag free acid showed the $[M+H]^+$ ion at m/z 314.2. In the MS/MS spectrum of the tag free acid after Collision Induced Dissociation (CID) with precursor selection of the ion at m/z 314.2, an intense n-butylproline a-ion reporter at m/z 126.14 was observed. The fragmentation mechanism of this tag is shown in FIG. 2, where the R

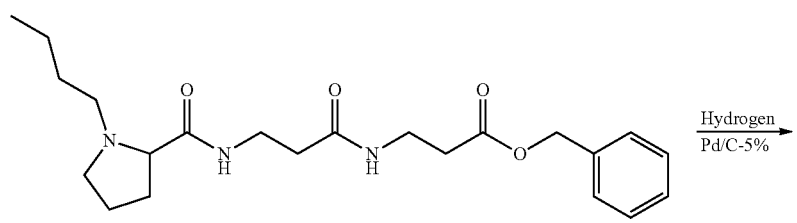

3-{3-[((S)-1-Butylpyrrolidine-2-carbonyl)-amino]-
propionylamino}-propionic acid benzyl ester
Butyl-L-Pro-β-Ala-β-Ala-OBn

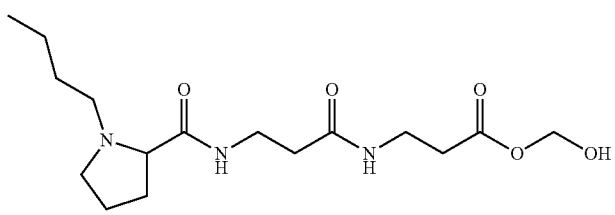

3-{3-[((S)-1-Butylpyrrolidine-2-carbonyl)-amino]-
propionylamino}-propionic acid
Butyl-L-Pro-β-Ala-β-Ala-OH 2.9 g (7.1 mmol) Butyl-L-Pro-β-Ala-β-Ala-OBn in 40 mL methanol over 5%-Pd/C catalyst under an argon atmosphere was hydrogenated by passing hydrogen into the reaction mixture. After the consumption of hydrogen ws finished, the reaction mixture was filtrated and the filter residue was substituent is a linear butyl chain. The n-Butyl-L-Pro-β-Ala-β-Ala-OSu will support an 18-plex set of isobaric tags in the same way as the isobutyl reagents. Similarly, a larger set of isobaric tags can be made if deuterium substitutions are included.

Step 3: Synthesis of 3-{3-[((S)-1-Butylpyrrolidine-2-carbonyl)-amino]-propionylamino}-propionic acid 2,5-dioxo-pyrrolidin-1-yl ester (Butyl-L-Pro-β-Ala-β-Ala-OSu)

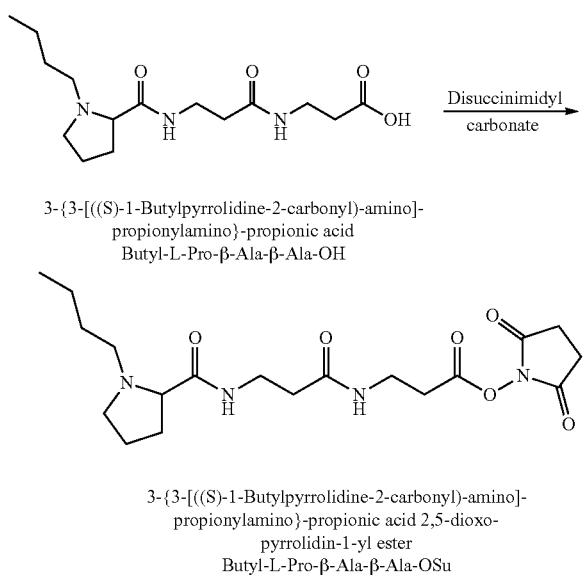

3-{3-[((S)-1-Butylpyrrolidine-2-carbonyl)-amino]-propionylamino}-propionic acid
Butyl-L-Pro-β-Ala-β-Ala-OH 3-{3-[((S)-1-Butylpyrrolidine-2-carbonyl)-amino]-propionylamino}-propionic acid 2,5-dioxo-pyrrolidin-1-yl ester
Butyl-L-Pro-β-Ala-β-Ala-OSu To a solution of 2.0 g (6.38 mmol) butyl-L-Pro-β-Ala-β-Ala-OH in 100 mL dichloromethane were added 1.96 g (7.65 mmol) disuccinimidyl carbonate. The suspension gave a clear solution under formation of carbon dioxide and was stirred for 2 hours at room temperature. The reaction was diluted with dichloromethane, washed with three 40 mL-portions of saturated sodium bicarbonate solution and with water, dried over sodium sulfate and evaporated in vacuo to yield a viscous oil.

Yield: 2.0 g (4.87 mmol, 76.4%)

Example 5

3-{3-[((S)-1-sec-Butylpyrrolidine-2-carbonyl)-amino]-propionylamino}-propionic acid 2,5-dioxo-pyrrolidin-1-yl ester (sec-Butyl-L-Pro-β-Ala-β-Ala-OSu)

Step 1: Synthesis of 3-{3-[((S)-1-sec-Butylpyrrolidine-2-carbonyl)-amino]-propionylamino}-propionic acid benzyl ester (sec-Butyl-L-Pro-β-Ala-β-Ala-OBn)

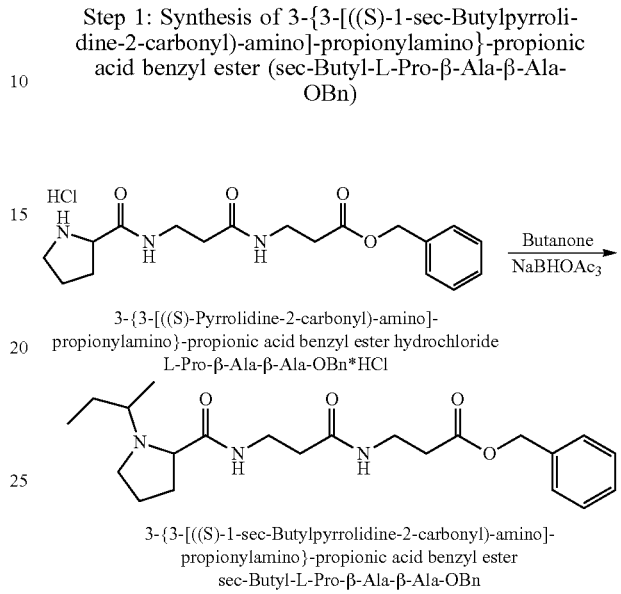

3-{3-[((S)-Pyrrolidine-2-carbonyl)-amino]-propionylamino}-propionic acid benzyl ester hydrochloride
L-Pro-β-Ala-β-Ala-OBn*HCl 3-{3-[((S)-1-sec-Butylpyrrolidine-2-carbonyl)-amino]-propionylamino}-propionic acid benzyl ester
sec-Butyl-L-Pro-β-Ala-β-Ala-OBn 5 g (13.0 mmol) L-Pro-β-Ala-β-Ala-OBn were dissolved in 50 mL 1,2-dichloroethane under an argon atmosphere and 3.1 ml (18.2 mmol) diisopropylethylamine were added. Then 1.4 ml (15.6 mmol) butanone and 3.3 g (15.6 mmol) sodium triacetoxyborohydride were added with cooling and the reaction was stirred for 1.5 hour at room temperature. The solution was evaporated in vacuo. The residue was dissolved in ethyl acetate, washed two times with saturated sodium bicarbonate and saturated sodium chloride, dried over sodium sulfate and evaporated in vacuo.

Yield: 3.7 g (9.17 mmol, 70.4%)

Step 2: Synthesis of 3-{3-[((S)-1-sec-Butylpyrrolidine-2-carbonyl)-amino]-propionylamino}-propionic acid (sec-Butyl-L-Pro-β-Ala-β-Ala-OH)

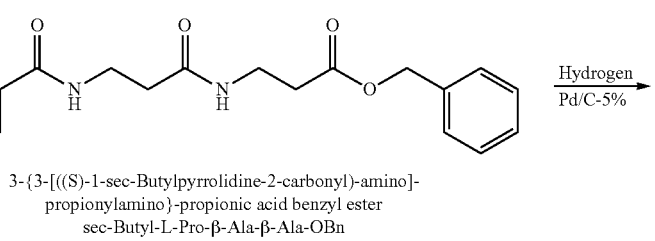

3-{3-[((S)-1-sec-Butylpyrrolidine-2-carbonyl)-amino]-propionylamino}-propionic acid benzyl ester
sec-Butyl-L-Pro-β-Ala-β-Ala-OBn

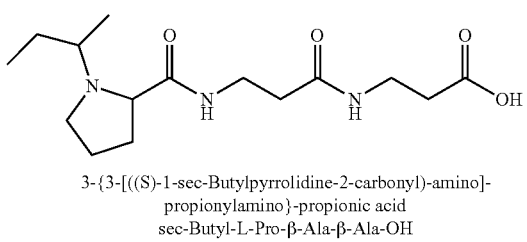

3-{3-[((S)-1-sec-Butylpyrrolidine-2-carbonyl)-amino]-propionylamino}-propionic acid
sec-Butyl-L-Pro-β-Ala-β-Ala-OH 3.7 g (9.17 mmol) sec-Butyl-L-Pro-β-Ala-β-Ala-OBn in 40 mL methanol over 5%-Pd/C catalyst under an argon atmosphere was hydrogenated by passing hydrogen into the reaction mixture. After the consumption of hydrogen was finished, the reaction mixture was filtrated and the filter residue was washed with methanol. The combined methanol layers were evaporated in vacuo.

Yield: 2.8 g (8.93 mmol, 90.9%)

Analysis of the Sec-Butyl-L-Pro-β-Ala-β-Ala-OH Tag by Mass Spectrometry:

Electrospray ionisation (ESI) mass spectra for the free acid form of the mass labels sec-Butyl-L-Pro-β-Ala-β-Ala-OH were obtained on a Waters Q-TOF 2 instrument by direct injection of the free acid tag solution (in 1% formic acid). The MS-mode spectrum for the tag free acid showed the [M+H]$^+$ ion at m/z 314.2. In the MS/MS spectrum of the tag free acid after Collision Induced Dissociation (CID) with precursor selection of the ion at m/z 314.2, an intense sec-butylproline a-ion reporter at m/z 126.14 was observed. The fragmentation mechanism of this tag is shown in FIG. 2, where the R substituent is a sec-butyl chain. The sec-Butyl-L-Pro-β-Ala-β-Ala-OSu will support an 18-plex set of isobaric tags in the same way as the isobutyl reagents shown in Set 10. Similarly, a larger set of isobaric tags can be made if deuterium substitutions are included.

Step 3: Synthesis of 3-{3-[((S)-1-sec-Butylpyrrolidine-2-carbonyl)-amino]-propionylamino}-propionic acid 2,5-dioxo-pyrrolidin-1-yl ester (sec-Butyl-L-Pro-β-Ala-β-Ala-OSu)

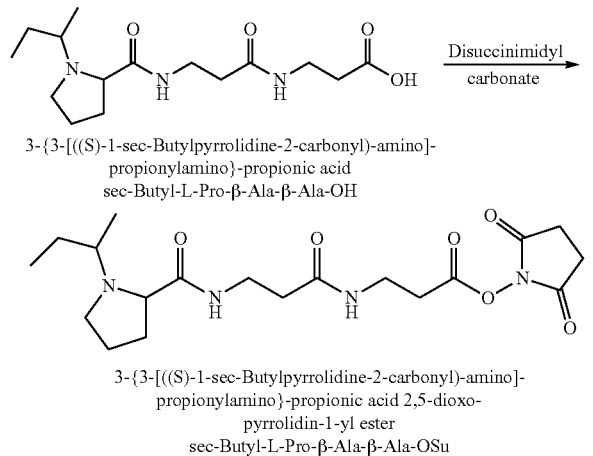

3-{3-[((S)-1-sec-Butylpyrrolidine-2-carbonyl)-amino]-propionylamino}-propionic acid
sec-Butyl-L-Pro-β-Ala-β-Ala-OH 3-{3-[((S)-1-sec-Butylpyrrolidine-2-carbonyl)-amino]-propionylamino}-propionic acid 2,5-dioxo-pyrrolidin-1-yl ester
sec-Butyl-L-Pro-β-Ala-β-Ala-OSu To a solution of 2.8 g (8.93 mmol) sec-butyl-L-Pro-β-Ala-β-Ala-OH in 100 mL dichloromethane were added 2.74 g (10.7 mmol) disuccinimidyl carbonate. The suspension gave a clear solution under formation of carbon dioxide and was stirred for 2 hours at room temperature. The reaction was diluted with dichloromethane, washed with three 40 mL-portions of saturated sodium bicarbonate solution and with water, dried over sodium sulfate and evaporated in vacuo to yield a viscous oil.

Yield: 3.0 g (7.31 mmol, 95.7%)

Example 6

3-{3-[((S)-1-(2,2-Dimethylpropyl)-pyrrolidine-2-carbonyl)-amino]-propionylamino}-propionic acid 2,5-dioxo-pyrrolidin-1-yl ester (Neopentyl-L-Pro-β-Ala-β-Ala-OSu)—Set 15

Step 1: Synthesis of 3-{3-[((S)-1-(2,2-Dimethylpropyl)-pyrrolidine-2-carbonyl)-amino]-propionylamino}-propionic acid benzyl ester (Neopentyl-L-Pro-β-Ala-β-Ala-OBn)

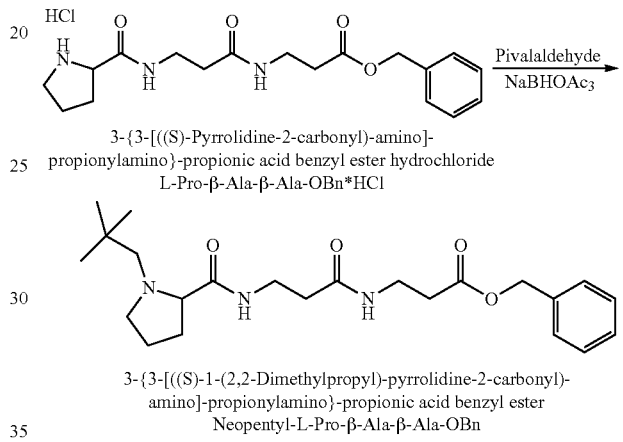

3-{3-[((S)-Pyrrolidine-2-carbonyl)-amino]-propionylamino}-propionic acid benzyl ester hydrochloride
L-Pro-β-Ala-β-Ala-OBn*HCl 3-{3-[((S)-1-(2,2-Dimethylpropyl)-pyrrolidine-2-carbonyl)-amino]-propionylamino}-propionic acid benzyl ester
Neopentyl-L-Pro-β-Ala-β-Ala-OBn 6 g (15.6 mmol) L-Pro-β-Ala-β-Ala-OBn were dissolved in 30 mL 1,2-dichloroethane under an argon atmosphere and 5.4 ml (31.1 mmol) diisopropylethylamine were added. Then 1.89 ml (17.1 mmol) pivalaldehyde and 3.6 g (17.1 mmol) sodium triacetoxyborohydride were added with cooling and the reaction was stirred for 1.5 hour at room temperature. The solution was evaporated in vacuo.

The residue was dissolved in ethyl acetate, washed two times with saturated sodium bicarbonate and saturated sodium chloride, dried over sodium sulfate and evaporated in vacuo.

Yield: 5.8 g (13.9 mmol, 80.0%)

Step 2: Synthesis of 3-{3-[((S)-1-(2,2-Dimethylpropyl)-pyrrolidine-2-carbonyl)-amino]-propionylamino}-propionic acid (Neopentyl-L-Pro-β-Ala-β-Ala-OH)

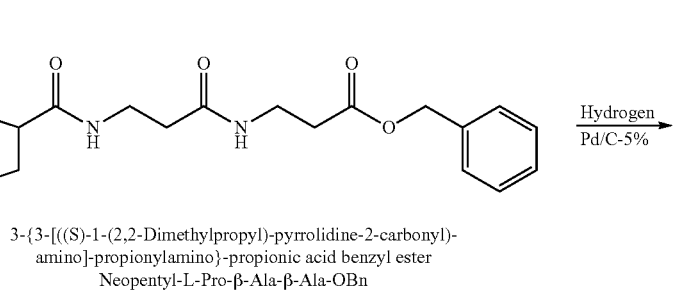

3-{3-[((S)-1-(2,2-Dimethylpropyl)-pyrrolidine-2-carbonyl)-amino]-propionylamino}-propionic acid benzyl ester
Neopentyl-L-Pro-β-Ala-β-Ala-OBn -continued

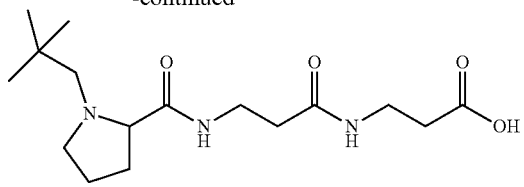

3-{3-[((S)-1-(2,2-Dimethylpropyl)-pyrrolidine-2-carbonyl)-
amino]-propionylamino}-propionic acid
Neopentyl-L-Pro-β-Ala-β-Ala-OH 5.8 g (13.9 mmol) Neopentyl-L-Pro-β-Ala-β-Ala-OBn in 100 mL methanol over 5%-Pd/C catalyst under an argon atmosphere was hydrogenated by passing hydrogen into the reaction mixture. After the consumption of hydrogen was finished, the reaction mixture was filtrated and the filter residue was washed with methanol. The combined methanol layers were evaporated in vacuo. The crude product was loaded on a silica gel column and eluted by dichloromethane/methanol (2:1).

Yield: 4.0 g (12.2 mmol, 87.8%)

Analysis of the Neopentyl-L-Pro-β-Ala-β-Ala-OH Tag by Mass Spectrometry:

Electrospray ionisation (ESI) mass spectra for the free acid form of the tag (Neopentyl-L-Pro-β-Ala-β-Ala-OH) were obtained on a Waters Q-TOF 2 instrument by direct injection of the free acid tag solution (in 1% formic acid). In the MS-mode spectrum for the tag free acid the [M+H]$^+$ ion was seen at m/z 328.2. In the MS/MS spectrum of the tag free acid after Collision Induced Dissociation (CID) with precursor selection of the ion at m/z 328.2, an intense sec-butylproline a-ion reporter at m/z 126.14 was observed. The fragmentation mechanism of this tag is shown in FIG. 2, where the R substituent is a neopentyl chain. The Neopentyl-L-Pro-β-Ala-β-Ala-OSu will support a 20-plex set of isobaric tags as shown in Set 15. Similarly, a larger set of isobaric tags can be made if deuterium substitutions are included.

Step 3: Synthesis of 3-{3-[((S)-1-(2,2-Dimethylpropyl)-pyrrolidine-2-carbonyl)-amino]-propionylamino}-propionic acid 2,5-dioxo-pyrrolidin-1-yl ester (Neopentyl-L-Pro-β-Ala-β-Ala-OSu)

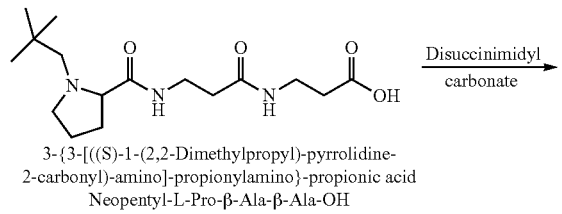

3-{3-[((S)-1-(2,2-Dimethylpropyl)-pyrrolidine-
2-carbonyl)-amino]-propionylamino}-propionic acid
Neopentyl-L-Pro-β-Ala-β-Ala-OH → Disuccinimidyl carbonate -continued

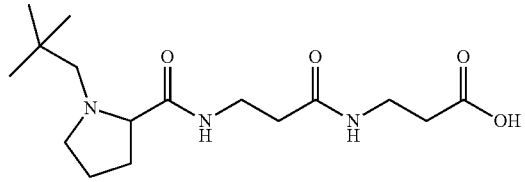

3-{3-[((S)-1-(2,2-Dimethylpropyl)-pyrrolidine-2-carbonyl)-
amino]-propionylamino}-propionic acid 2,5-dioxo-
pyrrolidin-1-yl ester
Neopentyl-L-Pro-β-Ala-β-Ala-OSu To a solution of 4.0 g (12.2 mmol) neopentyl-L-Pro-β-Ala-β-Ala-OH in 50 mL dichloromethane were added 3.75 g (14.6 mmol) disuccinimidyl carbonate. The suspension gave a clear solution under formation of carbon dioxide and was stirred for 2 hours at room temperature. The reaction was diluted with dichloromethane, washed with three 10 mL-portions of saturated sodium bicarbonate solution and with water, dried over sodium sulfate and evaporated in vacuo to yield a viscous oil.

Yield: 4.92 g (11.6 mmol, 95.0%)

Example 7

Synthesis of Deuterated Forms of Alkyl-Proline Tags

The mass labels exemplified herein were all prepared by reductive alkylation of the proline nitrogen using the relevant aldehyde or ketone with the reducing agent sodium triacetoxyborohydride. The sodium triacetoxyborodeuteride reagent can also be prepared from the corresponding sodium borodeuteride (Commercially available from SigmaAldrich, St Louis, Mo., USA) using a published procedure (Evans D. A. et al., J. Am. Chem. Soc. 110, 3560-3578, 1988).

In brief, a 100 ml flask was charged with 206 mg (4.92 mmol) of sodium borodeuteride and 50 mL of toluene. The slurry was cooled to 10° C. and 8604 (15.0 mmol, 3.05 equiv) of acetic acid was added dropwise. After addition of acetic acid was complete the mixture was allowed to warm to room temperature and stirred for 5 h. The colourless slurry was filtered and the resultant white powder washed with three 20-mL portions of ether. The powder was held under vacuum over night to afford 961 mg (92%) of sodium triacetoxyborohydride as a white solid.

The use of sodium triacetoxyborodeuteride enables the synthesis of deuterated forms of the proline mass labels disclosed herein.

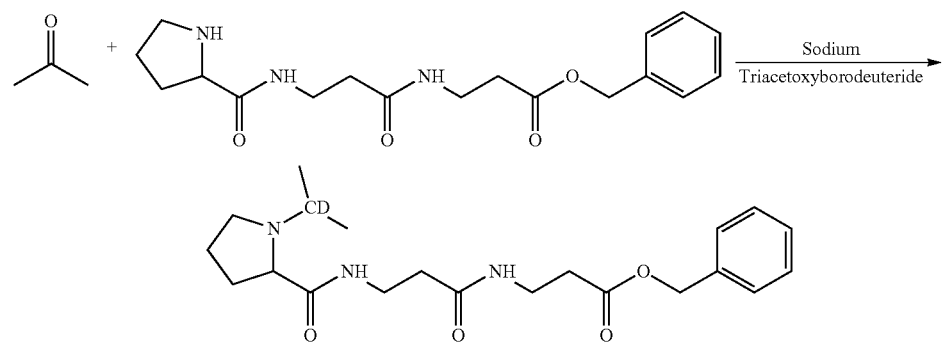
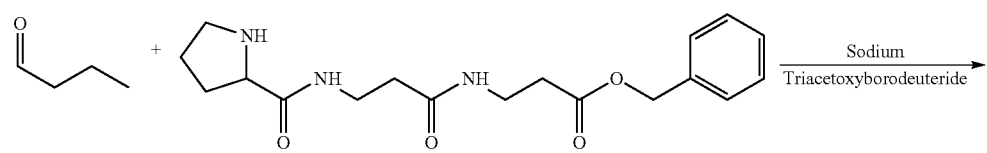
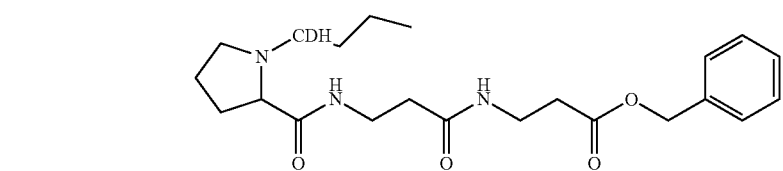
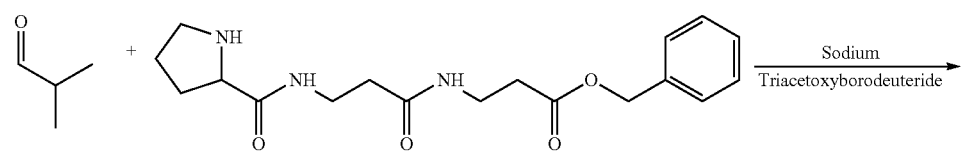
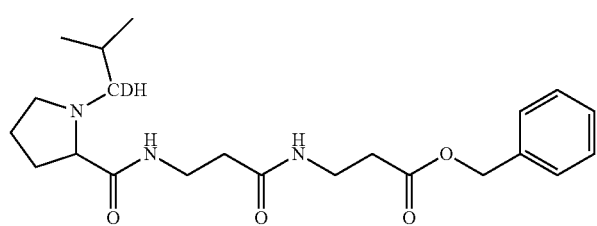

Example 8

3-{3-[(1,4-Diethyl-piperazine-2-carbonyl)-amino]-propionylamino}-propionic acid 2,5-dioxo-pyrrolidin-1-yl ester

Step 1: Synthesis of piperazine-1,2,4-tricarboxylic acid 1,4-di-tert-butyl ester

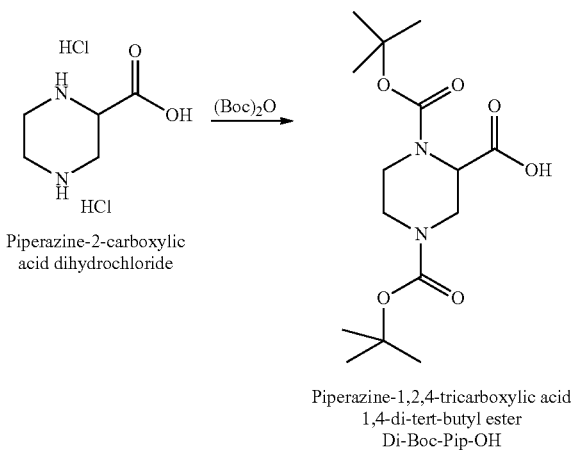 [SMILES: "(Boc)2O" ; O=C(O)C1CNCCN1 ; Cl ; Cl ; CC(C)(C)OC(=O)N1CCN(C(=O)OC(C)(C)C)C(C(=O)O)C1]

Piperazine-2-carboxylic acid dihydrochloride

Piperazine-1,2,4-tricarboxylic acid 1,4-di-tert-butyl ester
Di-Boc-Pip-OH

A 1 L flask was loaded with 10 g (49.2 mmol) piperazine-2-carboxylic acid dihydrochloride in 300 ml water and 200 ml dioxan. After addition of 13 g sodium carbonate to the suspension a clear solution forms, 32.2 g (147 mmol) di-tert-butyl dicarbonate were added and the solution was stirred at room temperature. After 1 hour the pH was set to 10 by addition of sodium carbonate and the reaction was stirred for 5 more hours. The solution was diluted with 200 ml water and washed with two 200 ml portions diisopropyl ether. The aqueous phase was set to pH 5 with 2 M hydrogen chloride, extracted three times with dichloromethane, and the organic phase is dried over sodium sulfate and evaporated in vacuo. The residue was suspended in diethyl ether, filtrated and dried in vacuo.

Yield: 13.5 g (40.9 mmol, 83.3%)

Step 2: 2-[2-(2-Benzyloxycarbonyl-ethylcarbamoyl)-ethylcarbamoyl]-piperazine-1,4-dicarboxylic acid di-tert-butyl ester

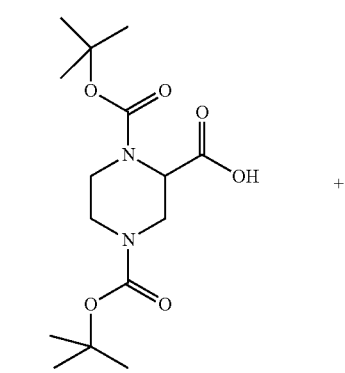

Piperazine-1,2,4-tricarboxylic acid 1,4-di-tert-butyl ester
Di-Boc-Pip-OH

+

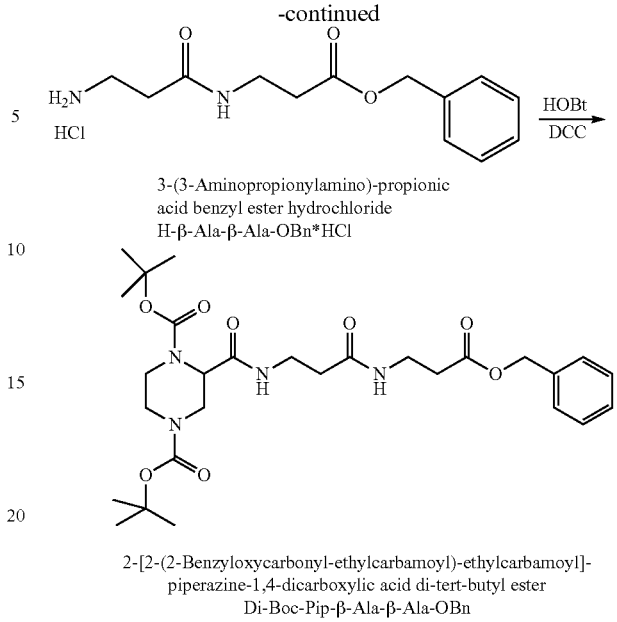

3-(3-Aminopropionylamino)-propionic acid benzyl ester hydrochloride
H-β-Ala-β-Ala-OBn*HCl 2-[2-(2-Benzyloxycarbonyl-ethylcarbamoyl)-ethylcarbamoyl]-piperazine-1,4-dicarboxylic acid di-tert-butyl ester
Di-Boc-Pip-β-Ala-β-Ala-OBn To a solution of 5 g (15.1 mmol) Di-Boc-Pip-OH in 150 ml dimethylformamide were added 7.8 ml (45.4 mmol) Huenig's base, 3.2 g (21 mmol) hydroxybenzotriazole monohydrate and 4.05 g (19.6 mmol) N,N'-dicyclohexylcarbodiimide and the reaction was stirred for 30 minutes. 4.3 g (15.1 mmol) H-β-Ala-β-Ala-OBn*HCl were added and after stirring 2.5 hours at room temperature the precipitated solid was filtrated, recrystallized from methanol and washed with ether.

Yield: 7.1 g (12.6 mmol, 83.5%)

Step 3: Synthesis of 3-{3-[(Piperazine-2-carbonyl)-amino]-propionylamino}-propionic acid benzyl ester dihydrochloride

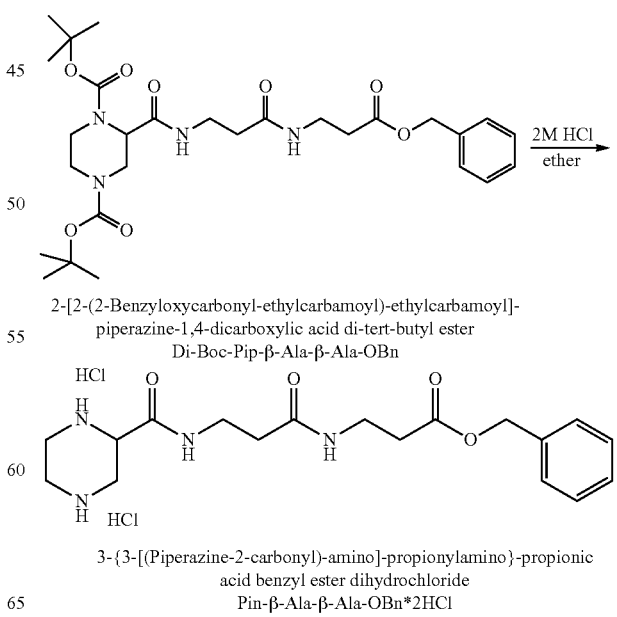

2-[2-(2-Benzyloxycarbonyl-ethylcarbamoyl)-ethylcarbamoyl]-piperazine-1,4-dicarboxylic acid di-tert-butyl ester
Di-Boc-Pip-β-Ala-β-Ala-OBn 3-{3-[(Piperazine-2-carbonyl)-amino]-propionylamino}-propionic acid benzyl ester dihydrochloride
Pin-β-Ala-β-Ala-OBn*2HCl 3 g (5.3 mmol) Di-Boc-Pip-β-Ala-β-Ala-OBn were dissolved in 30 ml dichloromethane and 30 ml 2 M ethereal hydrogen chloride. After stirring for one hour at room temperature the precipitated solid was filtrated and washed with diethyl ether.

Yield: 2.3 g (5.2 mmol, 98%)

Step 4: Synthesis of 3-{3-[(1,4-Diethylpiperazine-2-carbonyl)amino]-propionylamino}-propionic acid benzyl ester

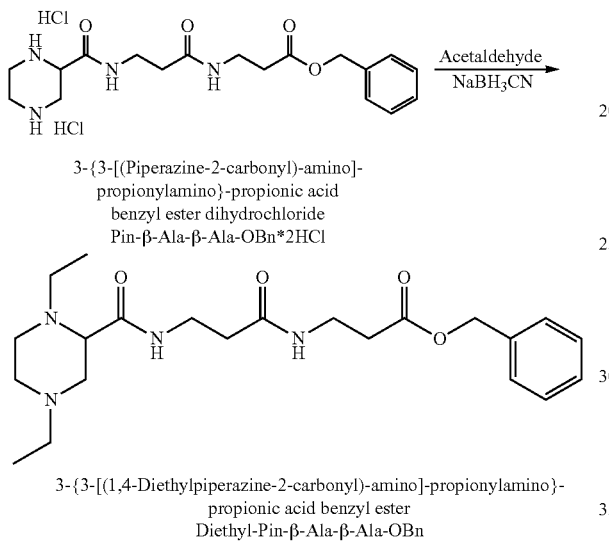

3-{3-[(Piperazine-2-carbonyl)-amino]-propionylamino}-propionic acid benzyl ester dihydrochloride
Pin-β-Ala-β-Ala-OBn*2HCl 3-{3-[(1,4-Diethylpiperazine-2-carbonyl)-amino]-propionylamino}-propionic acid benzyl ester
Diethyl-Pin-β-Ala-β-Ala-OBn To a solution of 1 g (2.2 mmol) Pip-β-Ala-β-Ala-OBn*2HCl and 1.36 ml (8 mmol) Huenig's base in 10 m 1,2-dimethoxyethane were added 0.28 ml (5 mmol) acetaldehyde and 0.31 g (5 mmol) sodium cyanoborohydride and the reaction was stirred for one hour at room temperature. The solution was diluted with sodium carbonate solution and extracted with ethyl acetate. The organic phase was washed with sodium carbonate solution and saturated sodium chloride solution, dried over sodium sulfate and evaporated in vacuo.

Yield: 0.8 g (1.19 mmol, 86.9%)

Analysis of 3-{3-[(1,4-Diethylpiperazine-2-carbonyl)-amino]-propionylamino}-Propionic Acid Benzyl Ester by Mass Spectrometry Electrospray ionisation (ESI) mass spectra for 3-{3-[(1,4-Diethylpiperazine-2-carbonyl)-amino]-propionylamino}-propionic acid benzyl ester (the benzyl ester protected form of the mass label) were obtained on a Waters Q-TOF 2 instrument by direct injection of the benzyl ester mass label solution (in 1% formic acid). In the MS-mode spectrum for the tag free acid, the [M+H]$^+$ ion was seen at m/z 328.2. In the MS/MS spectrum of the tag free acid after Collision Induced Dissociation (CID) with precursor selection of the ion at m/z 419.24 an intense diethylpiperazine reporter at m/z 140.137 was observed. The diethyl-piperazine-2-carboxylic acid-β-Ala-β-Ala-OSu structure will support a 27-plex set of isobaric tags. Similarly, a larger set of isobaric tags can be made if deuterium substitutions were included.

Step 5: Synthesis of 3-{3-[(1,4-Diethylpiperazine-2-carbonyl)-amino]-propionylamino}-propionic acid

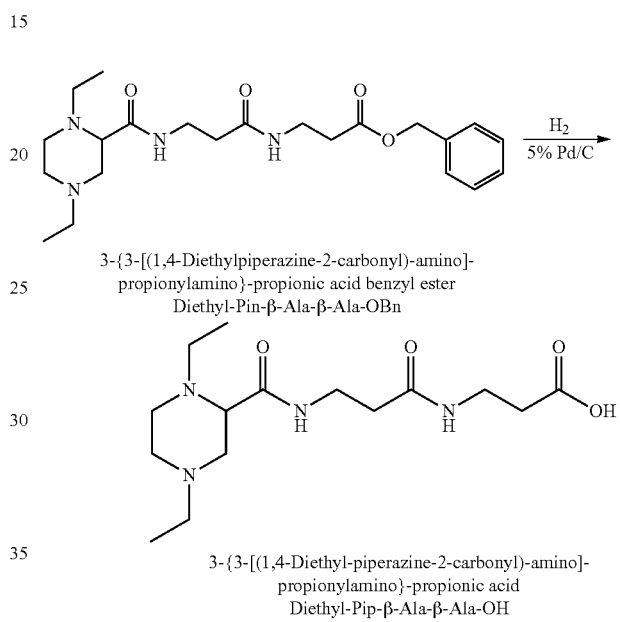

3-{3-[(1,4-Diethylpiperazine-2-carbonyl)-amino]-propionylamino}-propionic acid benzyl ester
Diethyl-Pin-β-Ala-β-Ala-OBn 3-{3-[(1,4-Diethyl-piperazine-2-carbonyl)-amino]-propionylamino}-propionic acid
Diethyl-Pip-β-Ala-β-Ala-OH 0.45 g (1.07 mmol) Diethyl-Pip-β-Ala-β-Ala-OBn were hydrogenated over 5%-Pd/C under an argon atmosphere by passing hydrogen into the reaction mixture. After the consumption of hydrogen was finished, the reaction mixture was filtered and the filter residue was washed with methanol. The combined methanol layers were evaporated in vacuo.

Yield: 250 mg (0.76 mmol, 71.1%)

Step 6: Synthesis of 3-{3-[(1,4-Diethyl-piperazine-2-carbonyl)-amino]-propionylamino}-propionic acid 2,5-dioxo-pyrrolidin-1-yl ester

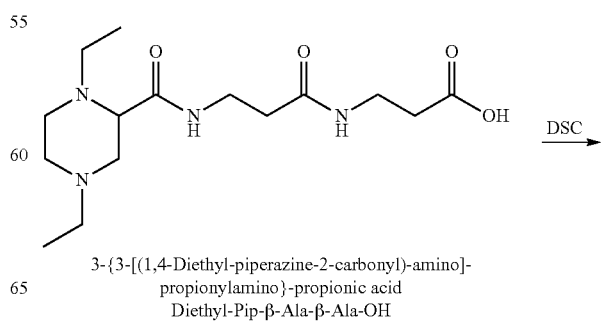

3-{3-[(1,4-Diethyl-piperazine-2-carbonyl)-amino]-propionylamino}-propionic acid
Diethyl-Pip-β-Ala-β-Ala-OH

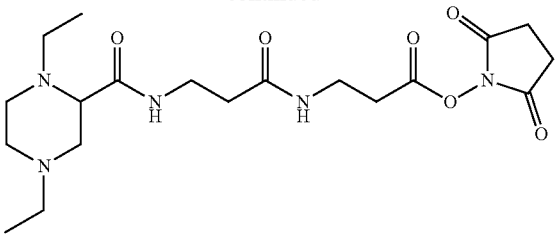

3-{3-[(1,4-Diethyl-piperazine-2-carbonyl)-amino]-propionylamino}-propionic acid 2,5-dioxo-pyrrolidin-1-yl ester
Diethyl-Pip-β-Ala-β-Ala-OSu To a solution of 0.25 g (0.76 mmol) diethyl-Pip-β-Ala-β-Ala-OH in 20 mL dichloromethane were added 0.23 g (0.91 mmol) disuccinimidyl carbonate. The suspension gave a clear solution under formation of carbon dioxide and was stirred for 2 hours at room temperature. The reaction was diluted with dichloromethane, washed with three 10 mL-portions of saturated sodium bicarbonate solution and with water, dried over sodium sulfate and evaporated in vacuo to yield a viscous oil.

Yield: 120 mg (0.28 mmol, 37.1%).

The invention claimed is:

1. A set of two or more mass labels, wherein each label comprises the formula:

X-L-M-Re wherein X is a reporter moiety having an exact mass, L is a bond cleavable by collision in a mass spectrometer, M is a mass modifier, and Re is (a) a reactive functionality for attaching the mass label to an analyte or (b) the analyte, and X comprises the following general formula:

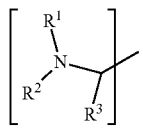

wherein:
i) $R^1$ is a substituted or unsubstituted straight or branched $C_1$-$C_{10}$ alkyl group, a substituted or unsubstituted aliphatic cyclic group, a substituted or unsubstituted aromatic group or a substituted or unsubstituted heterocyclic group; or a structure selected from methyl, ethyl, propyl, isopropyl, butyl, isobutyl, sec-butyl, pentyl or neopentyl,

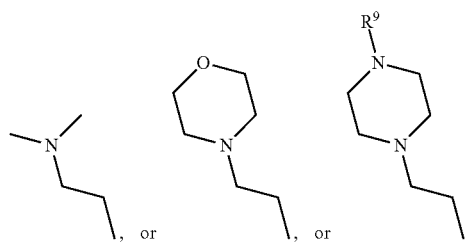

and $R^9$ is selected from a substituted or unsubstituted straight or branched $C_1$-$C_{10}$ alkyl group or hydrogen, and $R^2$ and $R^3$ together comprise:

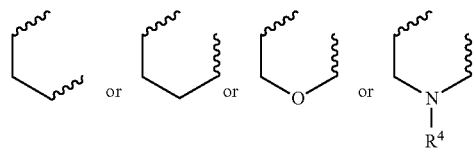

wherein $R^4$ is a H or a substituted or unsubstituted linear or branched $C_1$-$C_{10}$ alkyl group; or
ii) $R^3$ is H; and
$R^1$ and $R^2$ together comprise:

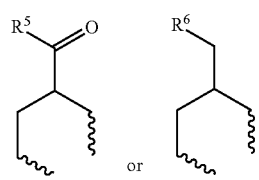

and wherein $R^5$ and $R^6$ are each independently a substituted or unsubstituted straight or branched $C_1$-$C_{10}$ alkyl group, a substituted or unsubstituted aliphatic cyclic group, a substituted or unsubstituted aromatic group or a substituted or unsubstituted heterocyclic group, or a substituted or unsubstituted amine group, or

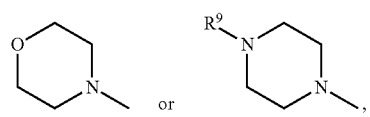

and each $R^9$ is independently selected from a substituted or unsubstituted straight or branched $C_1$-$C_{10}$ alkyl group or hydrogen.

2. The set of claim 1, wherein each mass label in the set has an integer mass, wherein each mass label in the set has the same integer mass, and wherein the set comprises two or more subsets of mass labels, each subset comprising one, two or more mass labels, and wherein, when the subset comprises two or more mass labels, the exact mass of the reporter moiety X of each mass label in the subset is different from the exact mass of the reporter moiety X of the mass labels in the same subset and in all other subsets, and wherein each mass label is distinguishable by mass spectrometry.

3. The set of claim 1, wherein each mass label comprises a mass series modifying group, wherein the mass series modifying group is part of the reporter moiety X or part of the mass modifier M.

4. The set of claim 3, wherein the mass series modifying group is part of the reporter moiety X.

5. The set of claim 3, wherein the mass series modifying group is selected from:
a) a heavy isotope $^2H$, $^{13}C$, $^{15}N$ or $^{18}O$;
b) a substituted or unsubstituted straight or branched $C_1$-$C_{10}$ alkyl group optionally comprising one or more heavy isotope substitutions; or
c) a combination of a) and b).

6. The set of claim 5, wherein the mass series modifying group is
—$CH_3$, —$^{13}CH_3$, —$^{13}CD_3$ or —$CD_3$.

7. The set of claim 1, wherein when Re is the analyte, and the analyte comprises one or more analytes selected from the group consisting of amino acids, peptides, polypeptides, nucleotides, oligonucleotides, polynucleotides, carbohydrates, lipids, phospholipids, or a combination thereof.

8. The set of two or more mass labels of claim 1, wherein $R^4$ is methyl, ethyl, propyl, isopropyl, butyl, isobutyl, sec-butyl, pentyl, neopentyl or (dimethylamino)methyl.

9. The set of two or more mass labels of claim 1, further comprising wherein each mass label has a reporter moiety X selected from:

a)
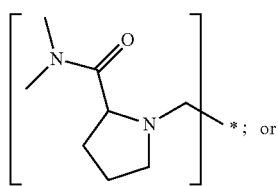

b)
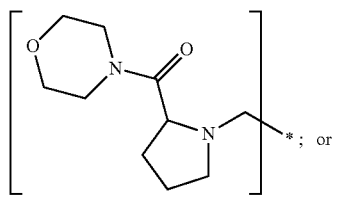

c)
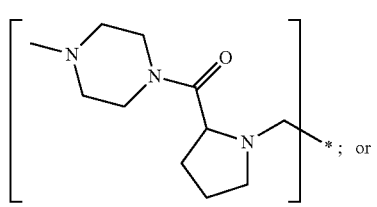

d)
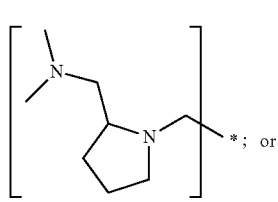

e)
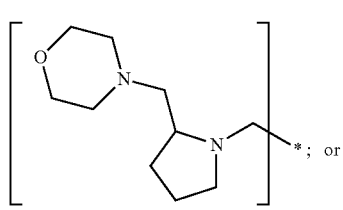

f)
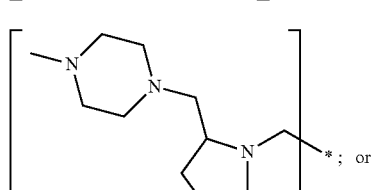

g)
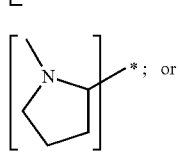

-continued h)
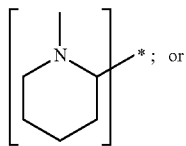

i)
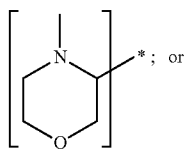

j)
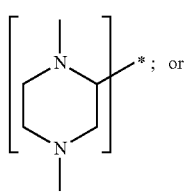

k)
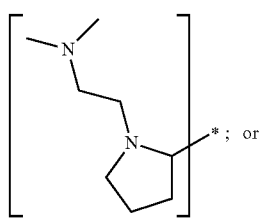

l)
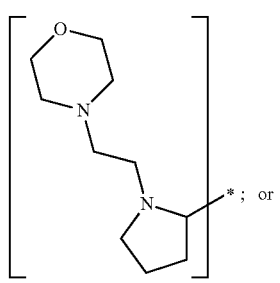

m)
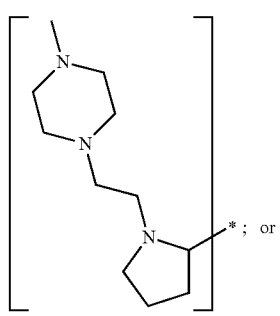

n)
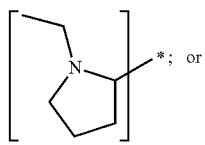

o)

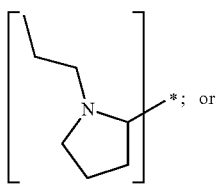

p)

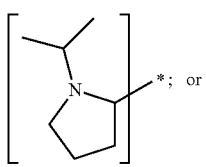

q)

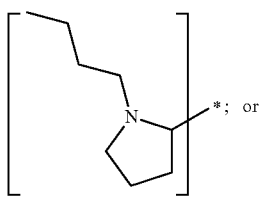

r)

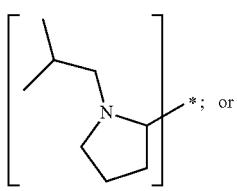

s)

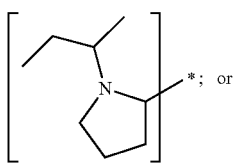

t)

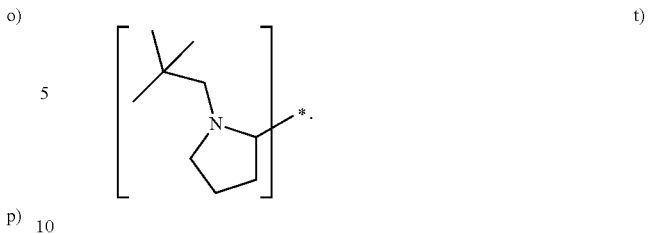

10. The set of two or more mass labels of claim 1, wherein each mass label has the following structure:

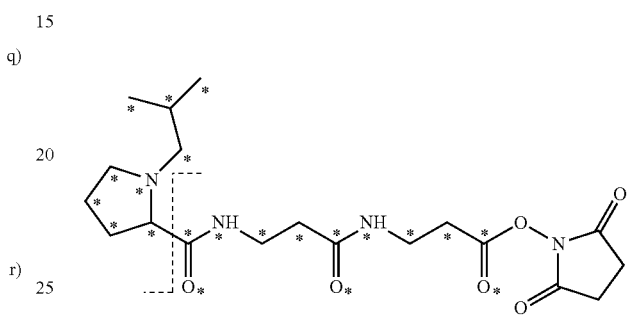

wherein each * represents that oxygen is $^{18}O$ carbon is $^{13}C$, nitrogen is $^{15}N$ or hydrogen is $^{2}H$, and wherein one or more * may be present, said structure being independently selected for each mass label in the set.

11. The set of two or more mass labels of claim 10, wherein each * is $^{13}C$ or $^{15}N$ and the set comprises eighteen mass labels, each having one of the following structures:

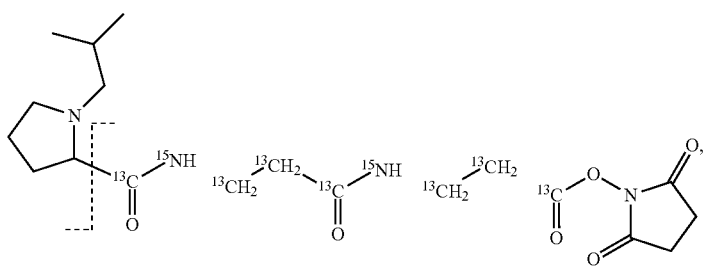

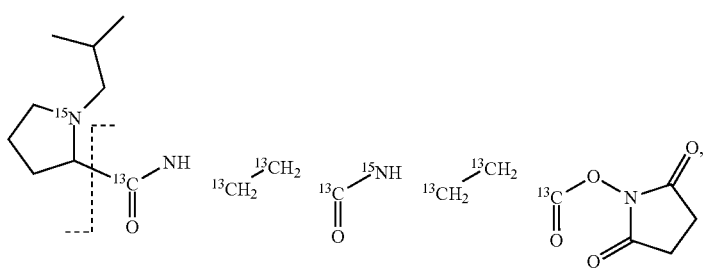

-continued
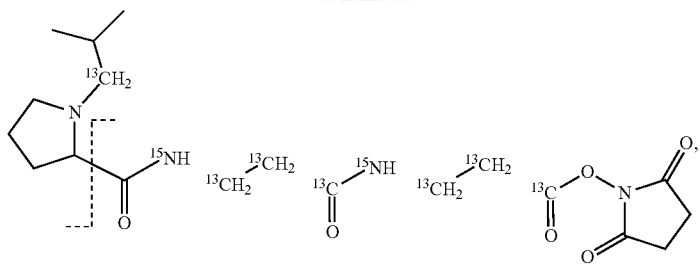
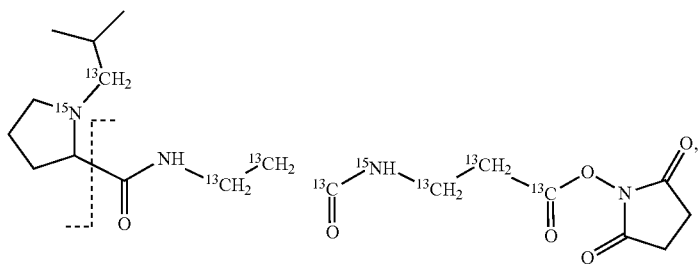
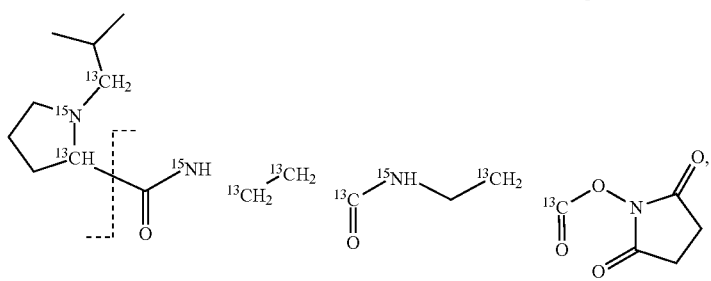
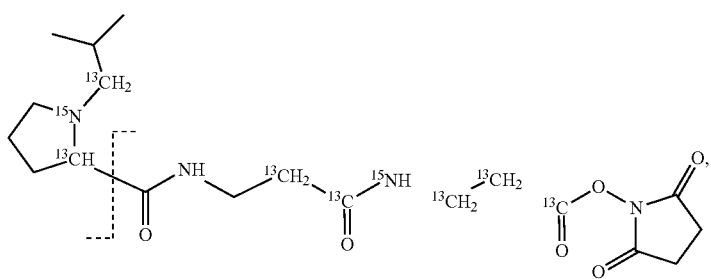
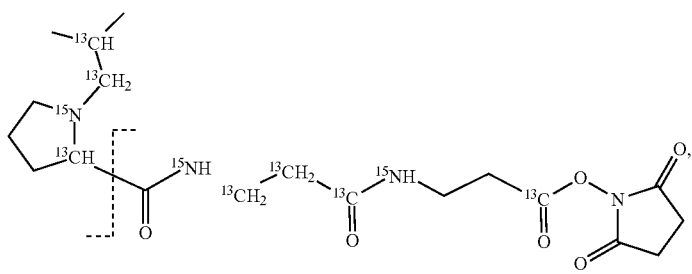
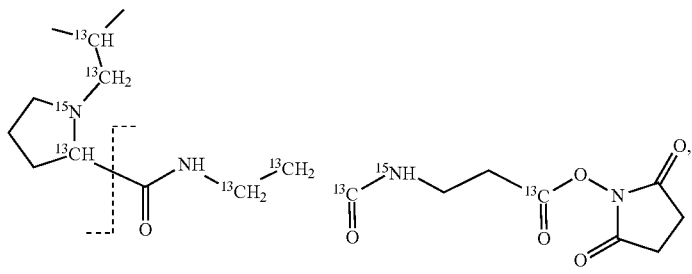

-continued
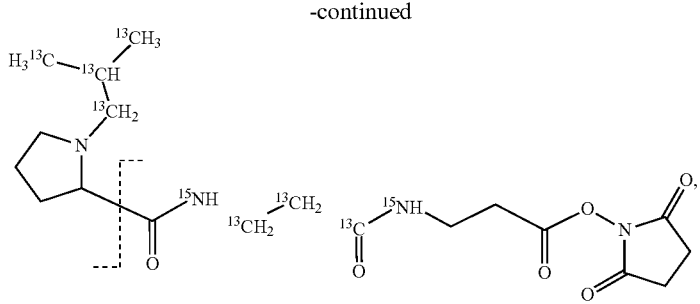
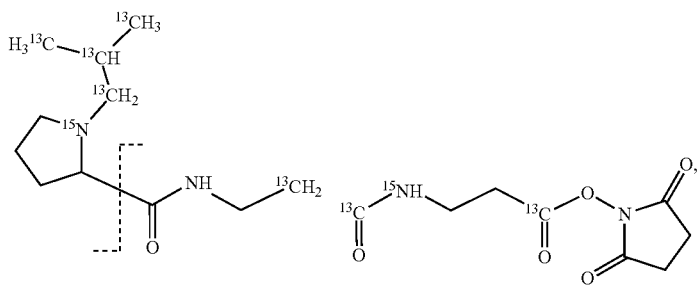
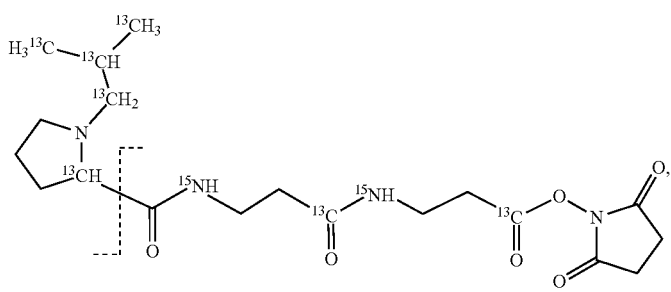
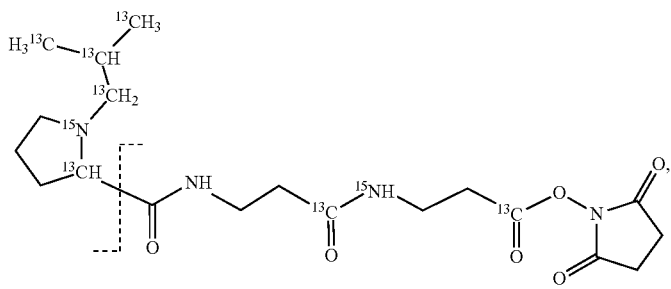
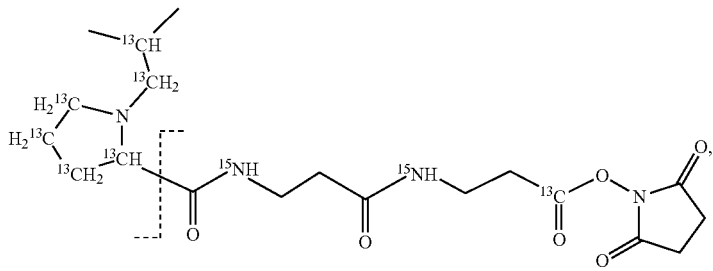
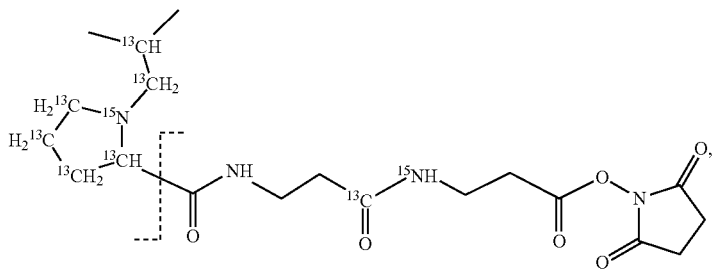

-continued

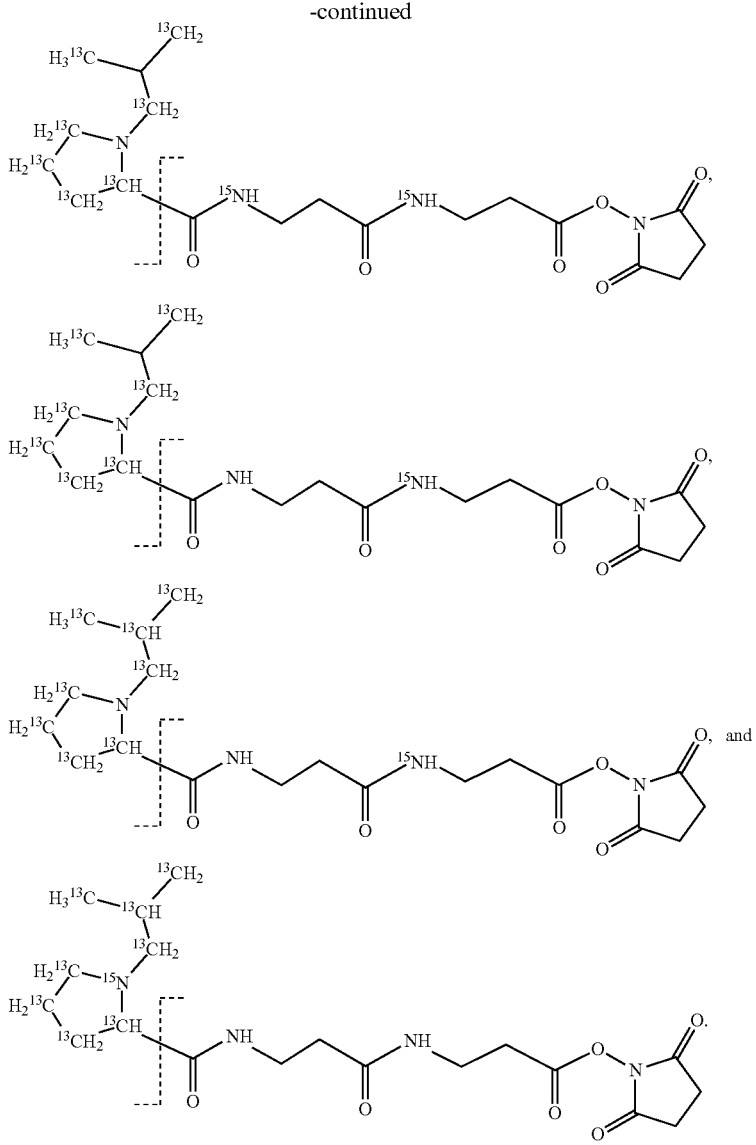

12. The set of two or more mass labels of claim 1, wherein each mass label has the following structure:

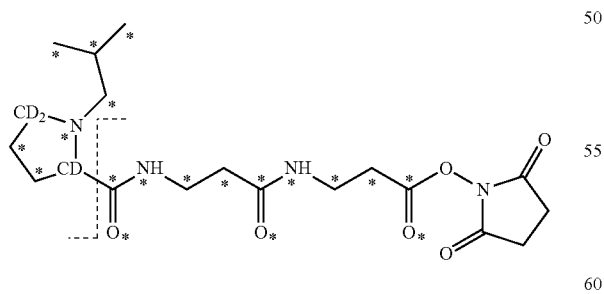

wherein each * represents that oxygen is $^{18}O$, carbon is $^{13}C$, nitrogen is $^{15}N$ or hydrogen is $^{2}H$, and one or more * may be present, said structure being independently selected for each mass label in the set.

13. The set of two or more mass labels of claim 12, wherein each * is $^{13}C$ or $^{15}N$ and the set comprises five mass labels, each having one of the following structures:

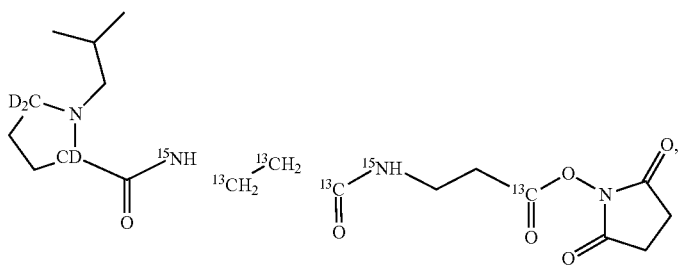
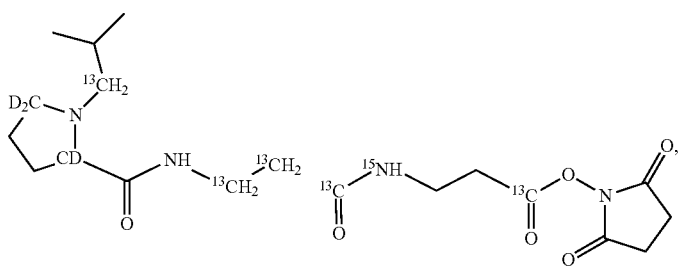
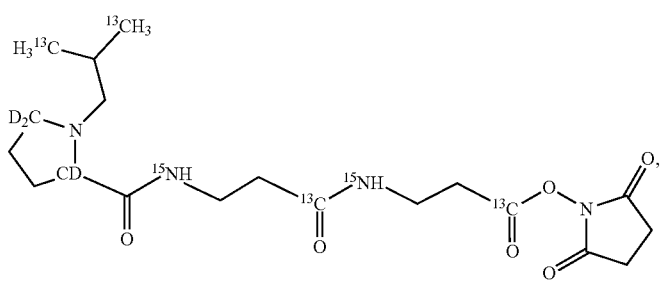
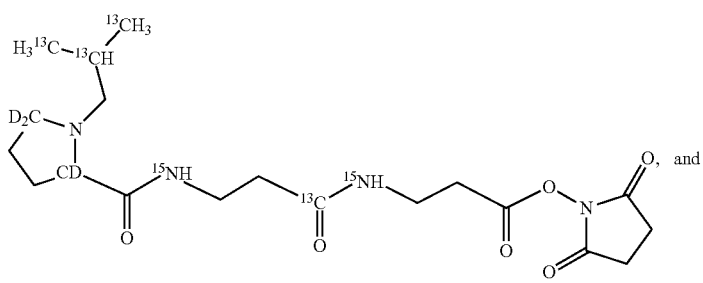
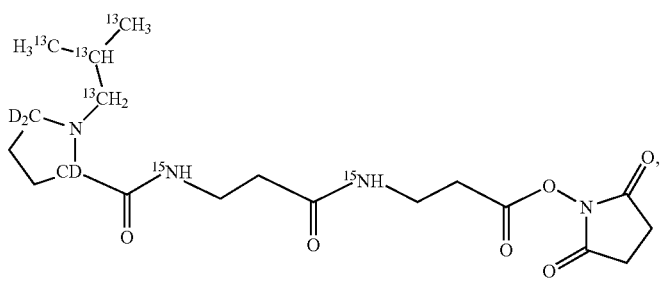

14. The set of two or more mass labels of claim 1, wherein each mass label has the following structure:

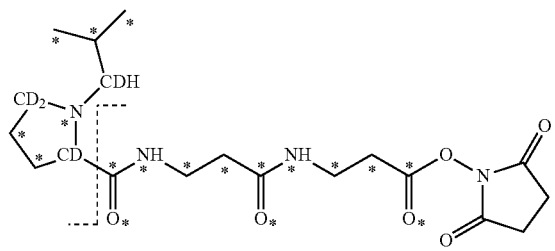

wherein each * represents that oxygen is $^{18}O$, carbon is $^{13}C$, nitrogen is $^{15}N$ or hydrogen is $^{2}H$, and one or more * may be present, said structure being independently selected for each mass label in the set.

15. The set of two or more mass labels of claim 14, wherein each * is $^{13}C$ or $^{15}N$ and the set comprises two mass labels having the following structures:

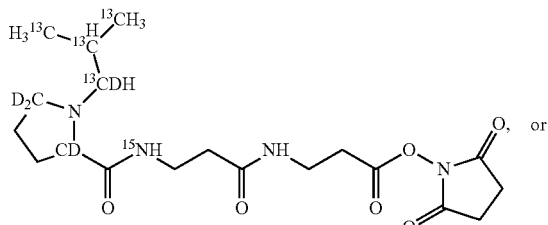

or

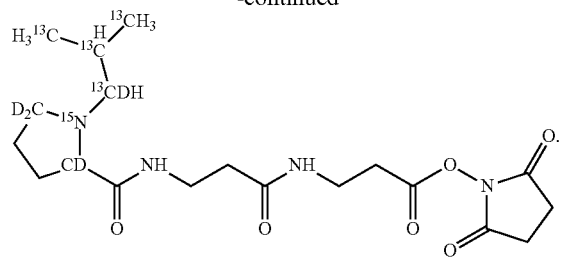

16. The set of two or more mass labels of claim 1, wherein each mass label has the following structure:

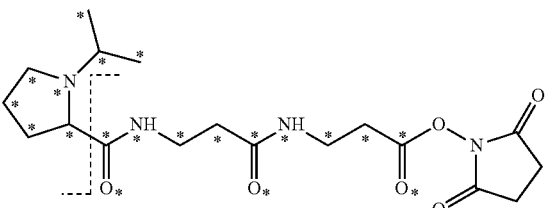

wherein each * represents that oxygen is $^{18}O$ carbon is $^{13}C$, nitrogen is $^{15}N$ or hydrogen is $^{2}H$, and one or more * may be present, said structure being independently selected for each mass label in the set.

17. The set of two or more mass labels of claim 16, wherein * is $^{13}C$ or $^{15}N$ and each mass label in the set has one of the following structures:

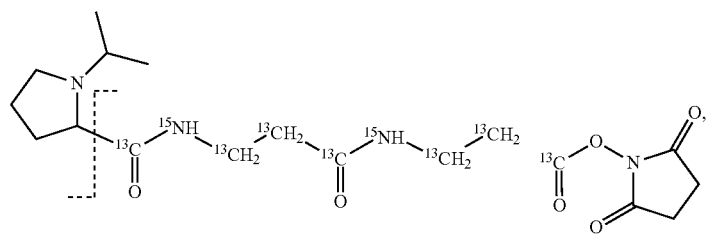

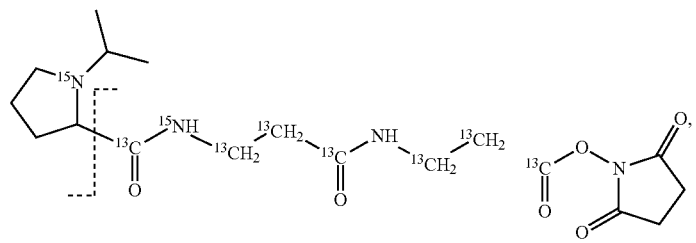

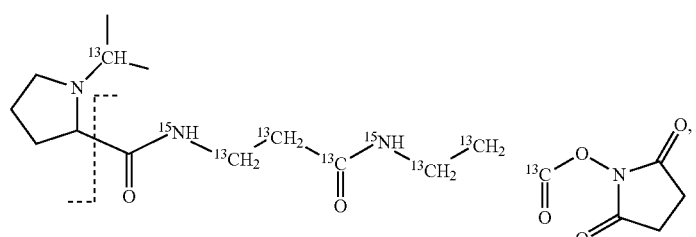

-continued
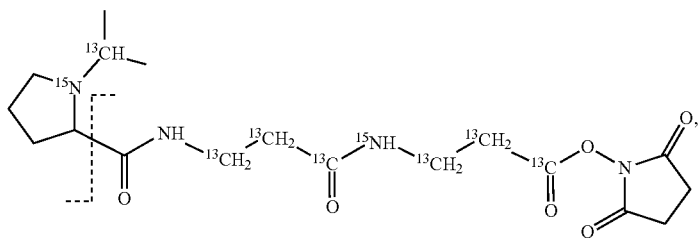
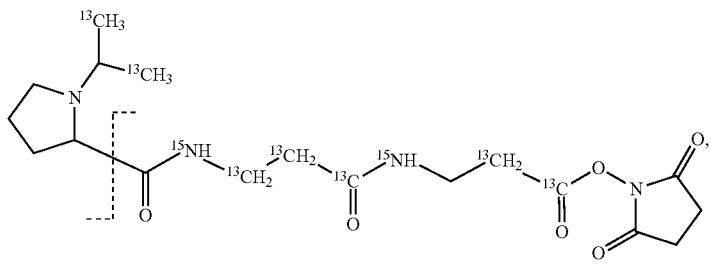
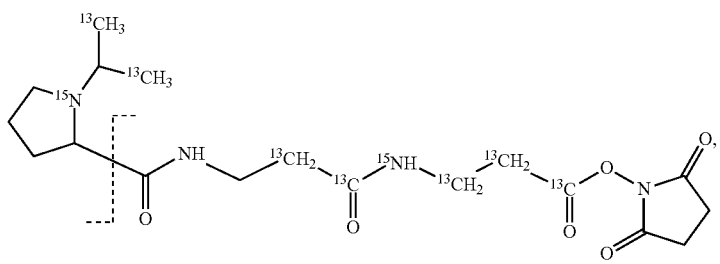
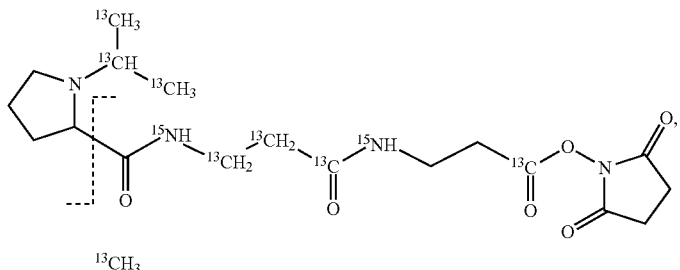
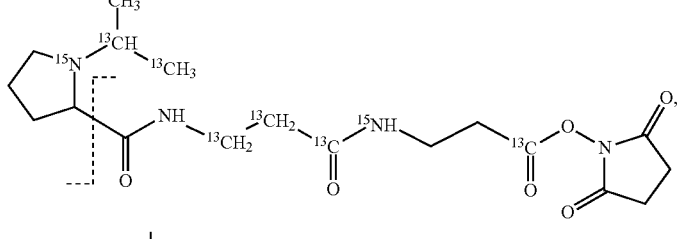
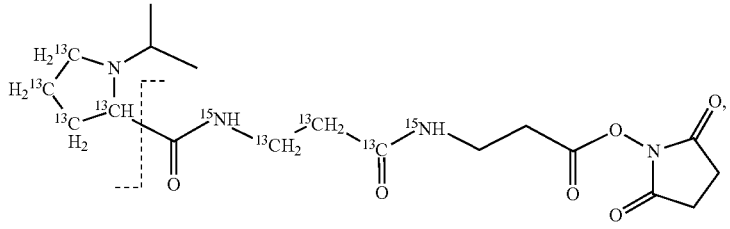
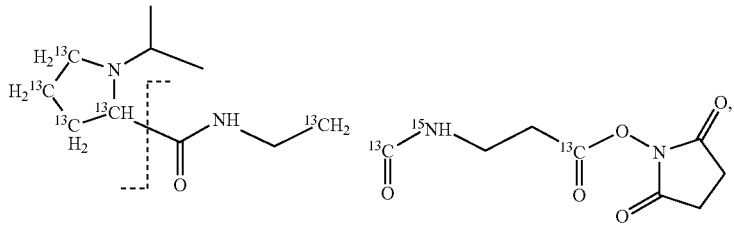

-continued
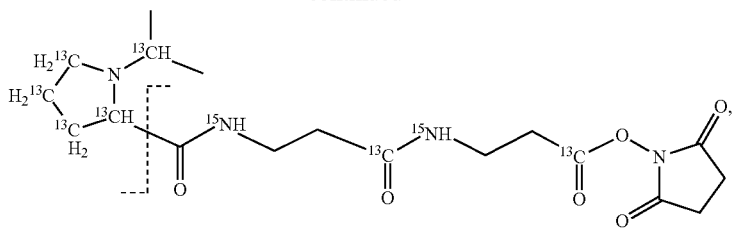
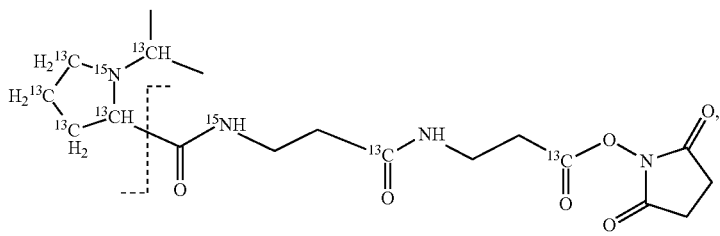
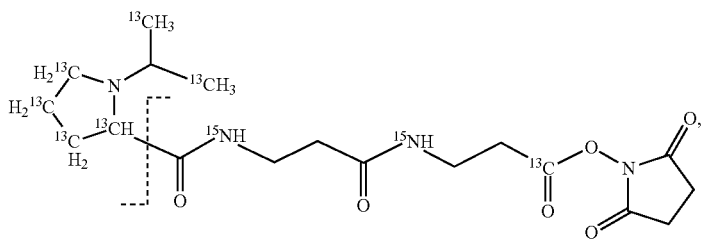
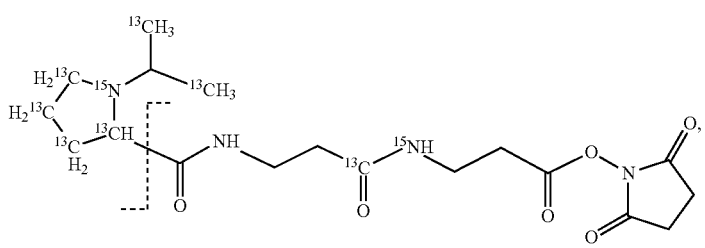
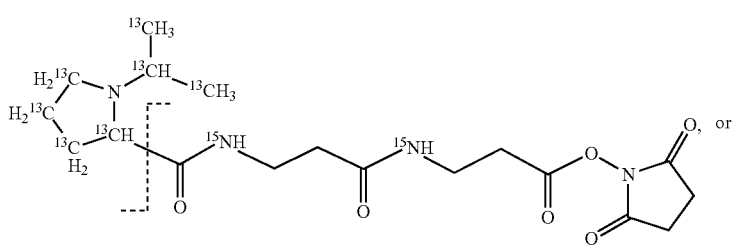
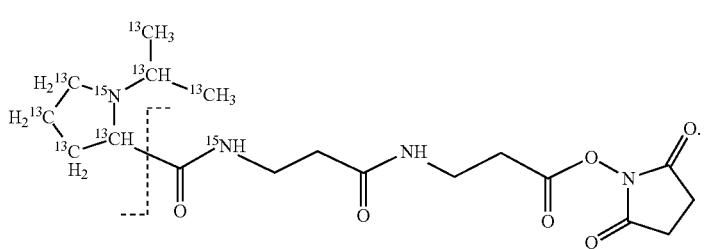

18. The set of two or more mass labels of claim 1, wherein each mass label has the following structure:

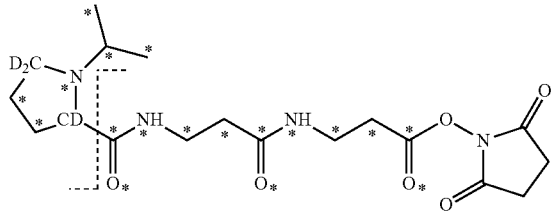

wherein each * represents that oxygen is $^{18}O$, carbon is $^{13}C$, nitrogen is $^{15}N$ or hydrogen is $^{2}H$, and one or more * may be present, said structure being independently selected for each mass label in the set.

19. The set of two or more mass labels of claim 18, wherein each * is $^{13}C$ or $^{15}N$ and each mass label in the set has one of the following structures:

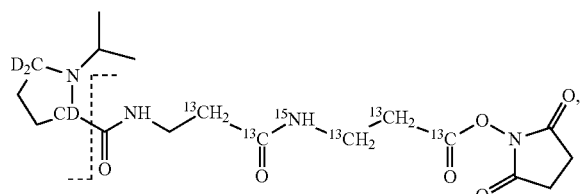

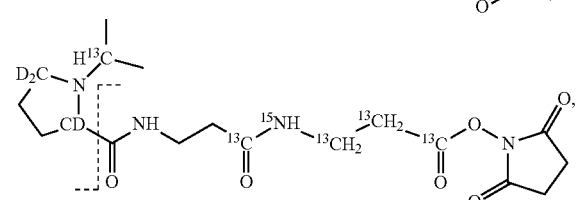

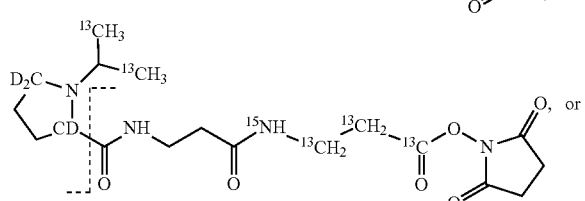

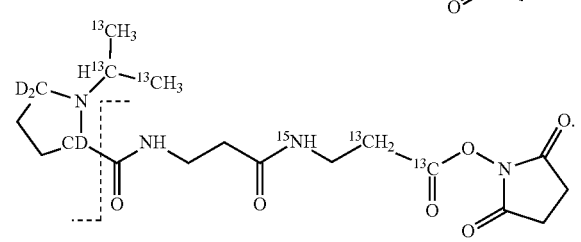

20. The set of two or more mass labels of claim 1, wherein each mass label has one of the following structures:

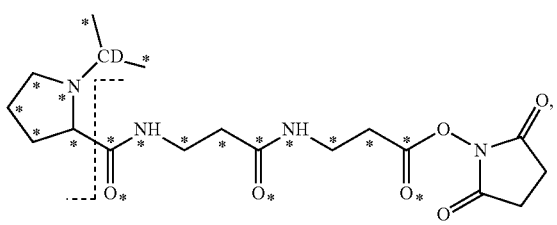

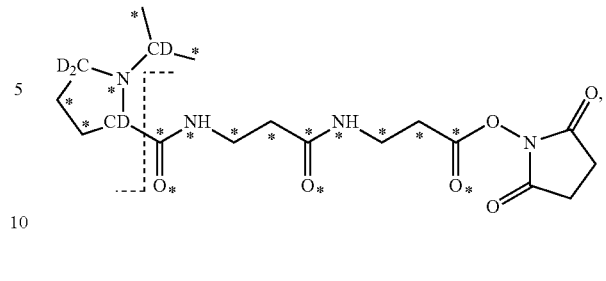

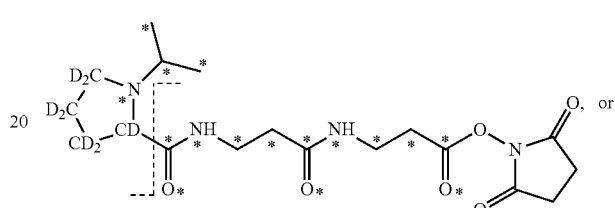

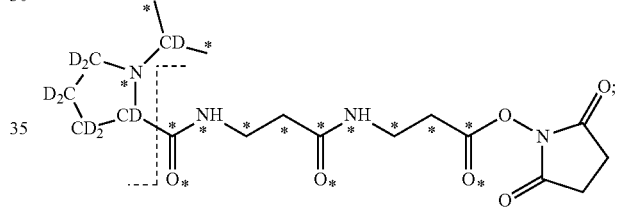

wherein each * represents that oxygen is $^{18}O$, carbon is $^{13}C$, nitrogen is $^{15}N$ or hydrogen is $^{2}H$, and one or more * may be present, said structure being independently selected for each mass label in the set.

21. The set of two or more mass labels of claim 1, wherein each mass label has the following structure:

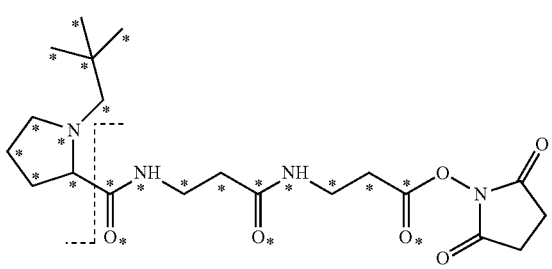 [SMILES: CC(C)(C)CN1CCCC1C(=O)NCCC(=O)NCCC(=O)ON1C(=O)CCC1=O]

wherein each * represents that oxygen is $^{18}O$ carbon is $^{13}C$, nitrogen is $^{15}N$ or hydrogen is $^{2}H$, and one or more * may be present, said structure being independently selected for each mass label in the set.

22. The set of two or more mass labels of claim 21, wherein each * is $^{13}C$ or $^{15}N$ and the set comprises eighteen mass labels, each having one of the following structures:

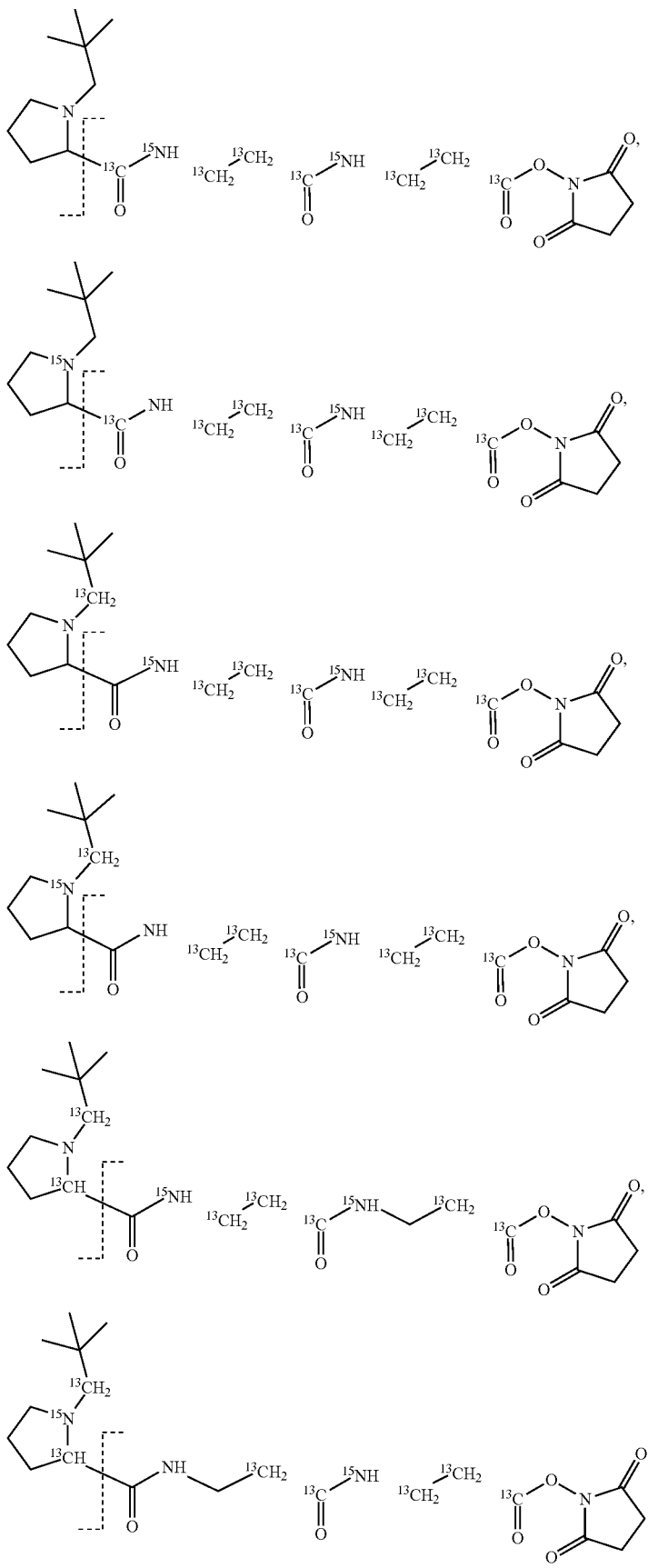

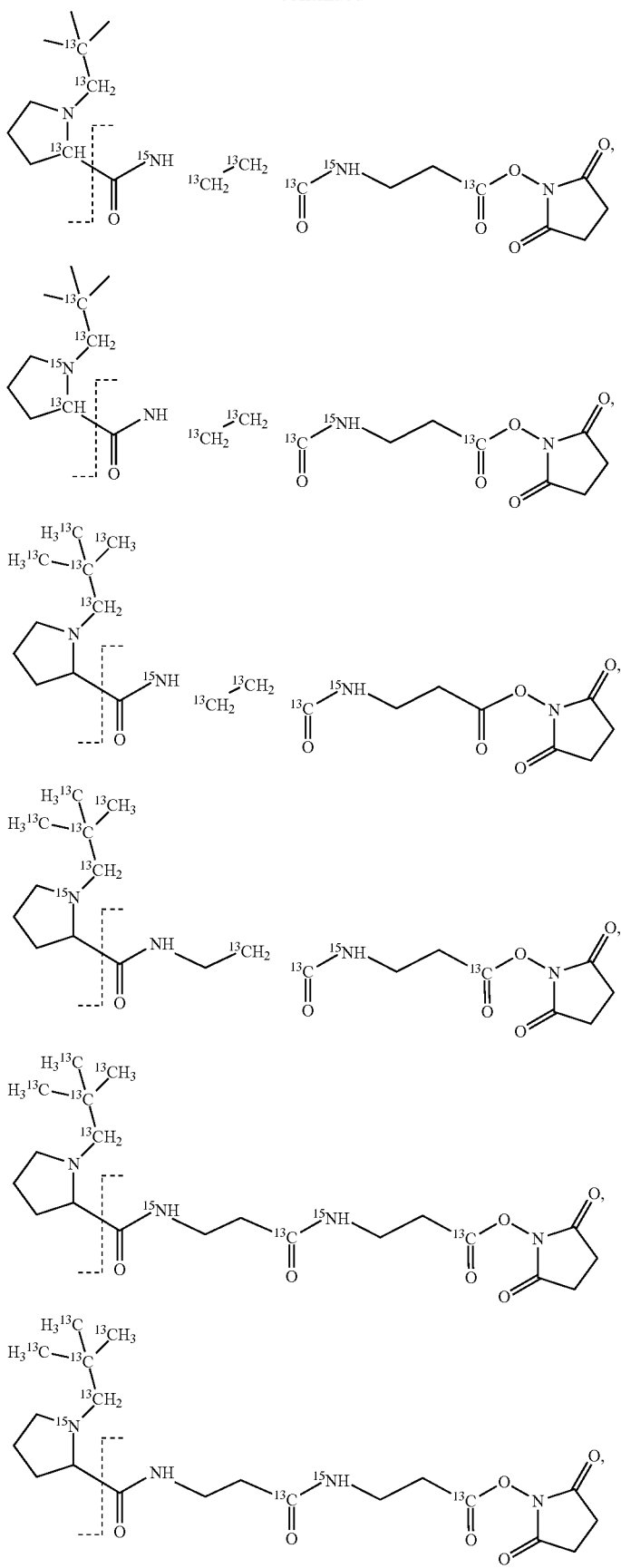

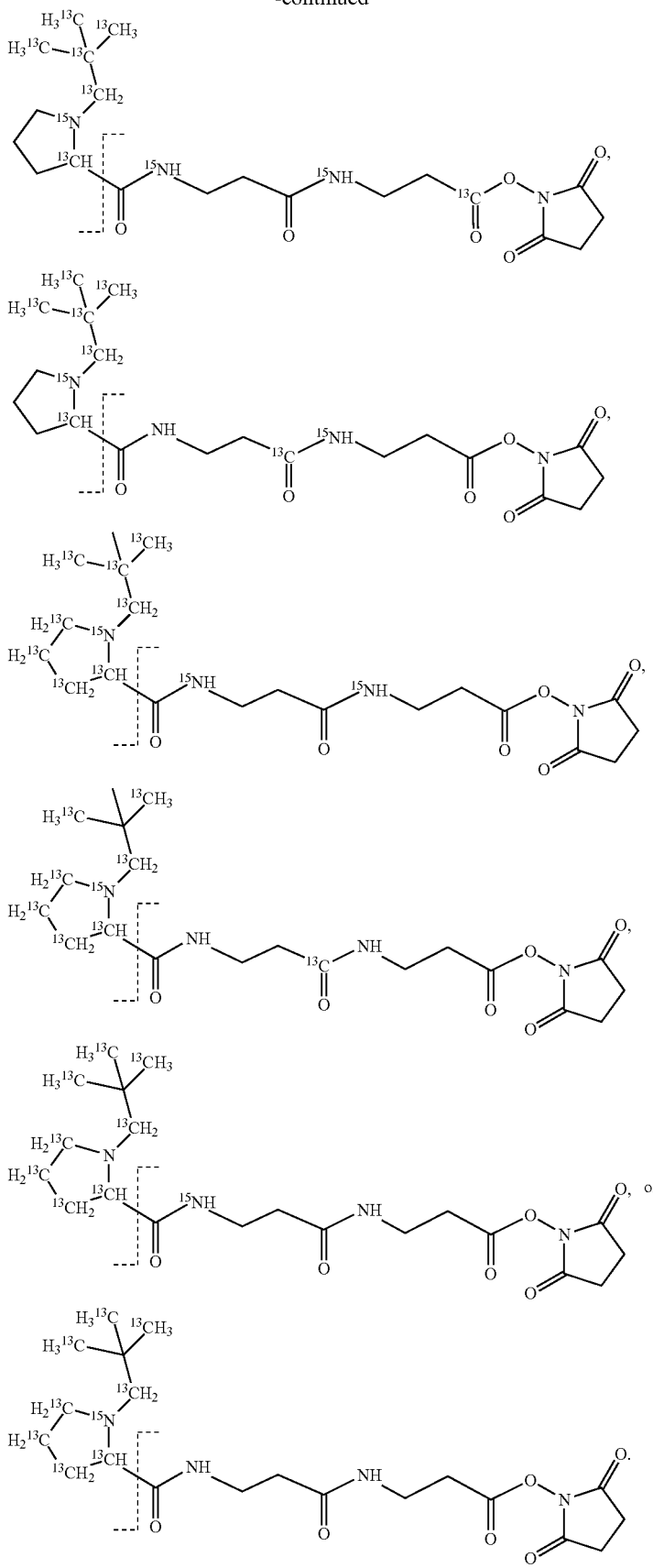

23. The set of two or more mass labels of claim 1, wherein each mass label has one of the following structures:

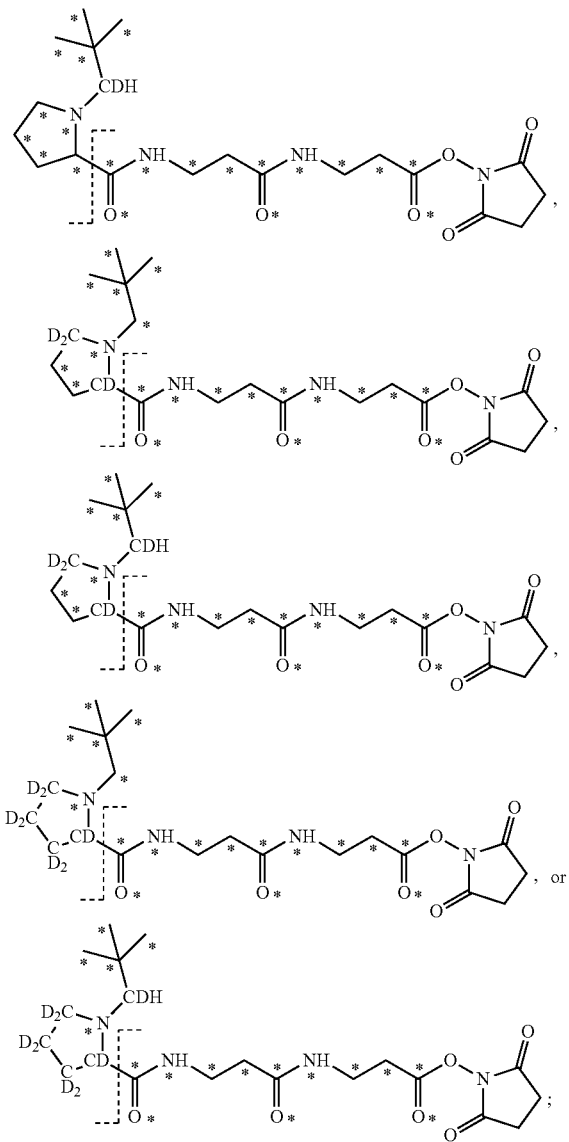

wherein each * represents that oxygen is $^{18}O$, carbon is $^{13}C$, nitrogen is $^{15}N$ or hydrogen is $^2H$, and one or more * may be present, said structure being independently selected for each mass label in the set.

24. An array of mass labels, comprising two or more sets of mass labels as defined in claim 1.

25. The array of mass labels of claim 24, wherein the integer mass of each of the mass labels of any one set in the array is different from the integer mass of each of the mass labels in every other set in the array.

26. The array of mass labels of claim 24, wherein each mass label in at least one of the two or more sets comprises:
   a) a mass series modifying group having the same integer mass as every other mass label in the set; and
   b) a different integer mass compared to the mass labels in all of the other sets in the array.

27. The array of claim 24, wherein each mass label in a set comprises the same mass series modifying group.

28. The array of claim 24, wherein each mass label in at least one of the sets comprises a mass series modifying group which is an isotopologue of the mass series modifying group of all of the other mass labels in the array.

29. A method of mass spectrometry analysis, comprising: detecting an analyte by identifying by mass spectrometry a mass label or combination of mass labels relatable to the analyte, wherein the mass label or each mass label in the combination of mass labels is a mass label from a set of mass labels defined in claim 1.

30. A method of detecting one or more analytes by identifying by mass spectrometry a mass label or combination of mass labels relatable to the analyte, comprising:
   a) providing a plurality of samples, each sample comprising the one or more analytes, wherein each sample is differentially labelled with the mass label or a combination of mass labels, resulting in one or more labelled analytes;
   wherein each of the mass label(s) are from a set of mass labels as defined in claim 1;
   b) mixing the plurality of differentially labelled samples to form an analysis mixture comprising the labelled analytes;
   c) optionally, detecting the labelled analytes in a mass spectrometer;
   d) dissociating the labelled analytes in the mass spectrometer to form mass labels and/or analyte fragments comprising intact mass labels;
   e) detecting the mass labels and/or analyte fragments comprising intact mass labels;
   f) optionally, dissociating the mass labels in the mass spectrometer to release the reporter moieties, and detecting the reporter moieties;
   g) optionally, dissociating the reporter moieties formed in step (f) to form fragments, and detecting the fragments; and
   h) identifying the analytes on the basis of the mass spectrum of the labelled analytes; and/or the mass spectrum of the mass labels and/or analyte fragments comprising an intact mass label; and/or the mass spectrum of the reporter moieties or fragments of reporter moieties.

31. A method of detecting one or more analytes by identifying by mass spectrometry a mass label or combination of mass labels relatable to the analyte, comprising:
   a) providing a plurality of samples, each sample comprising the one or more analytes, wherein each sample is differentially labelled with the mass label or a combination of mass labels, resulting in one or more labelled analytes, wherein each of the mass label(s) are from a set of mass labels as defined in claim 1;
   b) mixing the plurality of differentially labelled samples to form an analysis mixture comprising the labelled analytes;
   c) detecting the labelled analytes in a mass spectrometer;
   d) dissociating the labelled analytes in the mass spectrometer to release the reporter moieties, and detecting complement ions comprising the remainder of the mass label attached to the analyte or a fragment of the analyte;
   e) optionally, one or more further steps of dissociating the complement ions formed in step (d) to form fragments, and detecting the fragments; and
   f) identifying the analytes on the basis of the mass spectrum of the labelled analytes and/or the mass spectrum of the complement ions and/or fragments thereof.

* * * * *